US009321764B2

(12) United States Patent
Wang et al.

(10) Patent No.: US 9,321,764 B2
(45) Date of Patent: Apr. 26, 2016

(54) DIHYDRO-PYRROLOPYRIDINONE INHIBITORS

(71) Applicant: AbbVie Inc., North Chicago, IL (US)

(72) Inventors: Le Wang, Vernon Hills, IL (US); John Pratt, Kenosha, WI (US); Lisa A. Hasvold, Grayslake, IL (US); Dachun Liu, Vernon Hills, IL (US); Yujia Dai, Gurnee, IL (US); Steven D. Fidanze, Grayslake, IL (US); James H. Holms, Gurnee, IL (US); Robert A. Mantei, Franklin, WI (US); Keith F. McDaniel, Wauconda, IL (US); George S. Sheppard, Wilmette, IL (US); William J. McClellan, Waukegan, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/206,028

(22) Filed: Mar. 12, 2014

(65) Prior Publication Data

US 2014/0275026 A1  Sep. 18, 2014

Related U.S. Application Data

(60) Provisional application No. 61/777,699, filed on Mar. 12, 2013.

(51) Int. Cl.
*C07D 401/04* (2006.01)
*A61K 31/4353* (2006.01)
*C07D 471/04* (2006.01)

(52) U.S. Cl.
CPC .................................... *C07D 471/04* (2013.01)

(58) Field of Classification Search
CPC .......................... C07D 401/04; A61K 31/4353
USPC .......................................... 546/113; 514/300
See application file for complete search history.

(56) References Cited

U.S. PATENT DOCUMENTS 7,446,199 B2 * 11/2008 Aronov et al. ................ 546/113
8,980,879 B2 *  3/2015 Liu et al. ..................... 514/211.1

FOREIGN PATENT DOCUMENTS

JP          3465827     *  8/2003
WO    2006129623 A1    12/2006

OTHER PUBLICATIONS

Thomae et al., European Journal of Organic Chemistry (2013), 2013(16), 3328-3336.*
DeWitte et al., Journal of the American Chemical Society (1996), 118(47), 11733-11744.*
Banerjee C., et al., "BET Bromodomain Inhibition as a Novel Strategy for Reactivation of HIV-1," Journal of Leukocyte Biology, 2012, vol. 92 (6), pp. 1147-1154.

Berge, S. M. et al., "Pharmaceutical Salts," Journal of Pharmaceutical Sciences, 1977, vol. 66 (1), pp. 1-19.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Green, et al., "Protecting Groups in Organic Synthesis" in: Antibodies, 3rd Edition, John Wiley & Sons, NY, 1999, pp. 20.
Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Leroy G., et al., "The Double Bromodomain Proteins Brd2 and Brd3 Couple Histone Acetylation to Transcription," Molecular Cell, 2008, vol. 30 (1), pp. 51-60.
Matzuk M.M., et al., "Small-molecule Inhibition of BRDT for Male Contraception," Cell, 2012, vol. 150 (4), pp. 673-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Miyaura N., et al., "Palladium-Catalyzed Cross-Coupling Reactions of Organoboron Compounds," Chemical Reviews, 1995, vol. 95 (7), pp. 2457-2483.
Nicodeme E., et al., "Suppression of Inflammation by a Synthetic Histone Mimic," Nature, 2010, vol. 468 (7327), pp. 1119-1123.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

(Continued)

*Primary Examiner* — Niloofar Rahmani
(74) *Attorney, Agent, or Firm* — Glen J. Gesicki

(57) ABSTRACT

The present invention provides for compounds of formula (I)

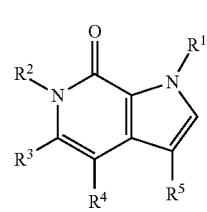

(I)

wherein $R^1$, $R^2$, $R^3$, $R^4$, and $R^5$ have any of the values defined in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

25 Claims, No Drawings

(56) References Cited

OTHER PUBLICATIONS

Suzuki A, "Recent Advances in the Cross-Coupling Reactions of Organoboron Derivatives with Organic Electrophiles," Journal of Organometallic Chemistry, 1999, vol. 576, pp. 147-168.

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zhang G., et al., "Down-regulation of NF-κb Transcriptional Activity in HIV-associated Kidney Disease by BRD4 Inhibition," Journal of Biological Chemistry, 2012, vol. 287 (34), pp. 28840-28851.

Zuber J., et al., "RNAi Screen Identifies Brd4 as a Therapeutic Target in Acute Myeloid Leukaemia," Nature, 2011, vol. 478 (7370), pp. 524-528.

* cited by examiner

DIHYDRO-PYRROLOPYRIDINONE INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell. 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-κB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or a salt thereof,

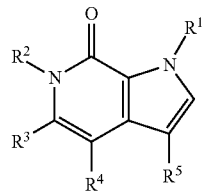

(I)

wherein
$R^1$ is H, $C_1$-$C_3$ alkyl, or $C_1$-$C_3$ haloalkyl;
$R^2$ is H, $C_1$-$C_3$ alkyl, or $C_1$-$C_3$ haloalkyl;
$R^3$ is H, $C_1$-$C_6$ alkyl, $C_2$-$C_6$ alkenyl, $C_2$-$C_6$ alkynyl, halogen, —$OR^{3a}$, —$NR^{3b}R^{3c}$, —$N(R^{3b})C(O)R^{3d}$, —$N(R^{3b})C(O)NR^{3b}R^{3c}$, —$N(R^{3b})S(O)_2NR^{3b}R^{3c}$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of halogen, $G^1$, —$OR^{3a}$, and —$NR^{3b}R^{3c}$;
$R^{3a}$, $R^{3b}$, and $R^{3c}$, at each occurrence, are each independently H, $C_1$-$C_6$ alkyl, $C_1$-$C_6$ haloalkyl, $G^1$, —($C_1$-$C_6$ alkylenyl)-$G^1$, —($C_1$-$C_6$ alkylenyl)-CN, —($C_1$-$C_6$ alkylenyl)-$OR^{z1}$, or —($C_1$-$C_6$ alkylenyl)-$NR^{z3}R^{z4}$;
$R^{3d}$, at each occurrence, is independently $C_1$-$C_6$ alkyl, $C_1$-$C_6$ haloalkyl, $G^1$, or —($C_1$-$C_6$ alkylenyl)-$G^1$;
$G^1$, at each occurrence, is independently aryl, heteroaryl, heterocycle, cycloalkyl, or cycloalkenyl; and each $G^1$ is optionally substituted with 1, 2, 3, 4, or 5 $R^{1g}$ groups;
$R^4$ is H, $C_1$-$C_6$ alkyl, halogen, or $C_1$-$C_6$ haloalkyl;
$R^5$ is a monocyclic or bicyclic ring selected from the group consisting of aryl and heteroaryl; each of which is substituted with 1, 2, or 3 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^2$, —$OR^a$, —$OC(O)R^b$, —$OC(O)NR^cR^d$, —$SR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)C(O)R^b$, —$N(R^e)S(O)_2R^b$, —$N(R^e)C(O)O(R^b)$, —$N(R^e)C(O)NR^cR^d$, —$N(R^e)S(O)_2NR^cR^d$, —($C_1$-$C_6$ alkylenyl)-$G^2$, —($C_1$-$C_6$ alkylenyl)-$OR^a$, —($C_1$-$C_6$ alkylenyl)-$OC(O)R^b$, —($C_1$-$C_6$ alkylenyl)-$OC(O)NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, —($C_1$-$C_6$ alkylenyl)-$N(R^e)S(O)_2NR^cR^d$, and —($C_1$-$C_6$ alkylenyl)-CN;
$R^a$, $R^c$, $R^d$, and $R^e$, at each occurrence, are each independently H, $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y2}$, —$C(O)NR^{y3}R^{y4}$, —$S(O)_2R^{y1}$, —$S(O)_2NR^{y3}R^{y4}$, and $G^2$;
$R^b$, at each occurrence, is independently $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y2}$, —$S(O)_2NR^{y3}R^{y4}$, and $G^2$;
$G^2$, at each occurrence, are each independently aryl, heteroaryl, heterocycle, cycloalkyl, or cycloalkenyl; and each $G^2$ group is optionally substituted with 1, 2, 3, 4, or 5 $R^{2g}$ groups;
$R^{1g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)(C_3$-$C_6$ cycloalkyl), —$C(O)R^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —($C_1$-$C_6$ alkylenyl)-$OR^{z1}$, —($C_1$-$C_6$ alkylenyl)-$OC(O)R^{z2}$, —($C_1$-$C_6$ alkylenyl)-$OC(O)NR^{z3}R^{z4}$, —($C_1$-$C_6$ alkylenyl)-$S(O)_2R^{z1}$, —($C_1$-$C_6$ alkylenyl)-$S(O)_2NR^{z3}R^{z4}$, —($C_1$-$C_6$ alkylenyl)-C(O)$R^{z1}$, —($C_1$-$C_6$ alkylenyl)-C(O)O$R^{z1}$, —($C_1$-$C_6$ alkylenyl)-C(O)N$R^{z3}R^{z4}$, —($C_1$-$C_6$ alkylenyl)-N$R^{z3}R^{z4}$, —($C_1$-$C_6$ alkylenyl)-N($R^{z3}$)C(O)$R^{z2}$, —($C_1$-$C_6$ alkylenyl)-N($R^{z3}$)S(O)$_2R^{z2}$, —($C_1$-$C_6$ alkylenyl)-N($R^{z3}$)C(O)O($R^{z2}$), —($C_1$-$C_6$ alkylenyl)-N($R^{z3}$)C(O)N$R^{z3}R^{z4}$, —($C_1$-$C_6$ alkylenyl)-N($R^{z3}$)S(O)$_2$N$R^{z3}R^{z4}$, —($C_1$-$C_6$ alkylenyl)-CN, or —O(phenyl); wherein the phenyl moiety and the $C_3$-$C_6$ cycloalkyl moiety are each optionally substituted with 1, 2, 3, or 4 substituents independently selected from the group consisting of $C_1$-$C_6$ alkyl, halogen, $C_1$-$C_6$ haloalkyl, —OH, —O(alkyl), —O(haloalkyl), CN, and $NO_2$;

$R^{2g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, oxo, —CN, $NO_2$, —$OR^{y1}$, —OC(O)$R^{y2}$, —OC(O)N$R^{y3}R^{y4}$, —$SR^{y1}$, —S(O)$_2R^{y1}$, —S(O)$_2$N$R^{y3}R^{y4}$, —C(O)$R^{y1}$, —C(O)O$R^{y1}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, —N($R^{y3}$)S(O)$_2$N$R^{y3}R^{y4}$, $G^{2b}$, —($C_1$-$C_6$ alkylenyl)-$OR^{y1}$, —($C_1$-$C_6$ alkylenyl)-OC(O)$R^{y2}$, —($C_1$-$C_6$ alkylenyl)-OC(O)N$R^{y3}R^{y4}$, —($C_1$-$C_6$ alkylenyl)-S(O)$_2R^{y1}$, —($C_1$-$C_6$ alkylenyl)-S(O)$_2$N$R^{y3}R^{y4}$, —($C_1$-$C_6$ alkylenyl)-C(O)$R^{y1}$, —($C_1$-$C_6$ alkylenyl)-C(O)O$R^{y1}$, —($C_1$-$C_6$ alkylenyl)-C(O)N$R^{y3}R^{y4}$, —($C_1$-$C_6$ alkylenyl)-N$R^{y3}R^{y4}$, —($C_1$-$C_6$ alkylenyl)-N($R^{y3}$)C(O)$R^{y2}$, —($C_1$-$C_6$ alkylenyl)-N($R^{y3}$)S(O)$_2R^{y2}$, —($C_1$-$C_6$ alkylenyl)-N($R^{y3}$)C(O)O($R^{y2}$), —($C_1$-$C_6$ alkylenyl)-N($R^{y3}$)C(O)N$R^{y3}R^{y4}$, —($C_1$-$C_6$ alkylenyl)-N($R^{y3}$)S(O)$_2$N$R^{y3}R^{y4}$, —($C_1$-$C_6$ alkylenyl)-CN, or —($C_1$-$C_6$ alkylenyl)-$G^{2b}$;

$R^{y1}$, $R^{y3}$, and $R^{y4}$, at each occurrence, are each independently H, $C_1$-$C_6$ alkyl, $C_1$-$C_6$ haloalkyl, $G^{2b}$, or —($C_1$-$C_6$ alkylenyl)-$G^{2b}$;

$R^{y2}$, at each occurrence, is independently $C_1$-$C_6$ alkyl, $C_1$-$C_6$ haloalkyl, $G^{2b}$, or —($C_1$-$C_6$ alkylenyl)-$G^{2b}$;

$G^{2b}$, at each occurrence, is independently aryl, heteroaryl, cycloalkyl, cycloalkenyl, or heterocycle; and each $G^{2b}$ group is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —OC(O)$R^{z2}$, —OC(O)N$R^{z3}R^{z4}$, —$SR^{z1}$, —S(O)$_2R^{z1}$, —S(O)$_2$N$R^{z3}R^{z4}$, —C(O)$R^{z1}$, —C(O)O$R^{z1}$, —C(O)N$R^{z3}R^{z4}$, —N$R^{z3}R^{z4}$, —N($R^{z3}$)C(O)$R^{z2}$, —N($R^{z3}$)S(O)$_2R^{z2}$, —N($R^{z3}$)C(O)O($R^{z2}$), —N($R^{z3}$)C(O)N$R^{z3}R^{z4}$, —N($R^{z3}$)S(O)$_2$N$R^{z3}R^{z4}$, —($C_1$-$C_6$ alkylenyl)-$OR^{z1}$, —($C_1$-$C_6$ alkylenyl)-OC(O)$R^{z2}$, —($C_1$-$C_6$ alkylenyl)-OC(O)N$R^{z3}R^{z4}$, —($C_1$-$C_6$ alkylenyl)-S(O)$_2R^{z1}$, —($C_1$-$C_6$ alkylenyl)-S(O)$_2$N$R^{z3}R^{z4}$, —($C_1$-$C_6$ alkylenyl)-C(O)$R^{z1}$, —($C_1$-$C_6$ alkylenyl)-C(O)O$R^{z1}$, —($C_1$-$C_6$ alkylenyl)-C(O)N$R^{z3}R^{z4}$, —($C_1$-$C_6$ alkylenyl)-N$R^{z3}R^{z4}$, —($C_1$-$C_6$ alkylenyl)-N($R^{z3}$)C(O)$R^{z2}$, —($C_1$-$C_6$ alkylenyl)-N($R^{z3}$)S(O)$_2R^{z2}$, —($C_1$-$C_6$ alkylenyl)-N($R^{z3}$)C(O)O($R^{z2}$), —($C_1$-$C_6$ alkylenyl)-N($R^{z3}$)C(O)N$R^{z3}R^{z4}$, —($C_1$-$C_6$ alkylenyl)-N($R^{z3}$)S(O)$_2$N$R^{z3}R^{z4}$, and —($C_1$-$C_6$ alkylenyl)-CN;

$R^{z1}$, $R^{z3}$, and $R^{z4}$, at each occurrence, are each independently H, $C_1$-$C_6$ alkyl, or $C_1$-$C_6$ haloalkyl; and $R^{z2}$, at each occurrence, is independently $C_1$-$C_6$ alkyl or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced kidney disease. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention provides for methods for contraception in a male subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided. In certain embodiments, pharmaceutical compositions comprise a therapeutically effective amount of a compound of formula (I), or a pharmaceutically acceptable salt thereof, and a pharmaceutically acceptable carrier.

DETAILED DESCRIPTION

Disclosed herein are compounds of formula (I)

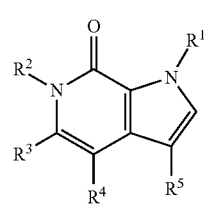

(I)

wherein $R^1$, $R^2$, $R^3$, $R^4$, and $R^5$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a). DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$," wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms, or of 1 to 6 carbon atoms ($C_1$-$C_6$ alkylenyl), or of 1 to 4 carbon atoms, or of 2 to 3 carbon atoms ($C_2$-$C_3$ alkylenyl). Examples of alkylene and alkylenyl include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon radical containing from 2 to 10 carbon atoms and containing at least one carbon-carbon triple bond. The term "$C_2$-$C_6$ alkynyl" means an alkynyl group of 2 to 6 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (indanyl), indenyl, naphthyl, dihydronaphthalenyl, and tetrahydronaphthalenyl. The aryls are attached to the parent molecular moiety through any carbon atom contained within the bicyclic ring systems and can be unsubstituted or substituted.

The term "cycloalkyl" as used herein, means a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups can be unsubstituted or substituted, and are attached to the parent molecular moiety through any substitutable atom contained within the ring system.

The term "$C_3$-$C_6$ cycloalkyl" as used herein, means cyclopropyl, cyclobutyl, cyclopentyl, and cyclohexyl.

The term "cycloalkenyl" as used herein, means a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, six, or seven hydrogen atoms are replaced by halogen. The term "$C_1$-$C_3$ haloalkyl" means a $C_1$-$C_3$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, trifluoropropyl, 2,2,3,3,3-pentafluoropropyl, and 2,2,3,3,4,4,4-heptafluorobutyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1-thiopyranyl, 1,1-dioxo-1$\lambda^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 3,4-dihydro-2H-chromenyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H,4H-spiro[1,3-benzodioxine-2,4'-piperidin]-1'-yl, 1'H,3H-spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized.

The term "$C_4$-$C_6$ heterocycle" as used herein, means a four-, five-, or six-membered monocyclic heterocycle as defined herein. Examples of $C_4$-$C_6$ heterocycle include azetidinyl, tetrahydrofuranyl, piperazinyl, piperidinyl, and morpholinyl.

The term "heteroaryl" as used herein, means a monocyclic heteroaryl and a bicyclic heteroaryl. The monocyclic heteroaryl is a five- or six-membered monocyclic ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, 6,7-dihydro-5H-pyrrolo[1,2-a]imidazolyl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen atom in the heteroaryl rings may optionally be oxidized and may optionally be quarternized.

The term "$C_5$-$C_6$ heteroaryl" as used herein, means a monocyclic heteroaryl ring as described above. Examples of $C_5$-$C_6$ heteroaryl include, but are not limited to, furanyl, thienyl, pyrrolyl, oxazolyl, pyrazolyl, imidazolyl, 1,3-thiadiazolyl, pyridinyl, pyridazinyl, pyrimidinyl, and pyrazinyl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

b. COMPOUNDS

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $R^1$ is H, $C_1$-$C_3$ alkyl, or $C_1$-$C_3$ haloalkyl.

In certain embodiments, $R^1$ is $C_1$-$C_3$ alkyl. In some such embodiments, $R^1$ is methyl.

In certain embodiments of formula (I), $R^2$ is H, $C_1$-$C_3$ alkyl, or $C_1$-$C_3$ haloalkyl.

In certain embodiments, $R^2$ is H or $C_1$-$C_3$ alkyl. In some such embodiments, $R^2$ is H or methyl.

In certain embodiments, $R^2$ is H.

In certain embodiments, $R^2$ is $C_1$-$C_3$ alkyl. In some such embodiments, $R^2$ is methyl.

In certain embodiments of formula (I), $R^3$ is H, $C_1$-$C_6$ alkyl, $C_2$-$C_6$ alkenyl, $C_2$-$C_6$ alkynyl, halogen, —$OR^{3a}$, $NR^{3b}R^{3c}$, —$N(R^{3b})C(O)R^{3d}$, —$N(R^{3b})C(O)NR^{3b}R^{3c}$, —$N(R^{3b})S(O)_2NR^{3b}R^{3c}$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, or $G^1$; wherein the $C_1$-$C_6$ alkyl, $C_2$-$C_6$ alkenyl, $C_2$-$C_6$ and alkynyl are each independently unsubstituted or substituted with 1 or 2 substituents independently selected from the group consisting of halogen, $G^1$, —$OR^{3a}$, and —$NR^{3b}R^{3c}$.

For example, in certain embodiments, $R^3$ is H, $C_1$-$C_6$ alkyl, $C_2$-$C_6$ alkenyl, halogen, —$C(O)R^{3a}$, —$C(O)OR^{3a}$, —$C(O)NR^{3b}R^{3c}$ or $G^1$; wherein the $C_1$-$C_6$ alkyl and the $C_2$-$C_6$ alkenyl are each independently unsubstituted or substituted with 1 or 2 substituents independently selected from the group consisting of halogen, $G^1$, —$OR^{3a}$, and —$NR^{3b}R^{3c}$.

In certain embodiments, $R^3$ is H, $C_1$-$C_3$ alkyl, $C_2$-$C_4$ alkenyl, halogen, or $G^1$; wherein the $C_1$-$C_3$ alkyl and the $C_2$-$C_4$ alkenyl are each independently unsubstituted or substituted with 1 or 2 substituents independently selected from the group consisting of halogen, —OH, —O($C_1$-$C_3$ alkyl), —$NH_2$, —N(H)($C_1$-$C_3$ alkyl), and —N($C_1$-$C_3$ alkyl)$_2$.

In certain embodiments, $R^3$ is H, halogen, unsubstituted $C_1$-$C_3$ alkyl, optionally substituted phenyl, optionally substituted 1,2-oxazolyl, or $C_2$-$C_4$ alkenyl which is substituted with 2 substituents independently selected from the group consisting of halogen and —OH. In some such embodiments, $R^3$ is H, Cl, ethyl, $C_4$ alkenyl, optionally substituted phenyl, or optionally substituted 1,2-oxazolyl; wherein the $C_4$ alkenyl is substituted with 2 substituents independently selected from the group consisting of Cl and —OH.

In certain embodiments, $R^3$ is H, unsubstituted $C_1$-$C_3$ alkyl, or halogen. In some such embodiments, $R^3$ is H, unsubstituted $C_1$-$C_3$ alkyl, F, or Cl. In some such embodiments, $R^3$ is H, unsubstituted $C_1$-$C_3$ alkyl, or Cl. In some such embodiments, $R^3$ is H, ethyl, or Cl.

In certain embodiments, $R^3$ is H.

In certain embodiments, $R^3$ is unsubstituted $C_1$-$C_3$ alkyl or halogen. In some such embodiments, $R^3$ is unsubstituted $C_1$-$C_3$ alkyl, F, or Cl. In some such embodiments, $R^3$ is unsubstituted $C_1$-$C_3$ alkyl or F. In some such embodiments, $R^3$ is unsubstituted $C_1$-$C_3$ alkyl or Cl. In further such embodiments, $R^3$ is ethyl or Cl.

In certain embodiments, $R^3$ is —$C(O)R^{3a}$, —$C(O)NR^{3b}R^{3c}$, $C_4$-$C_6$ heterocycle, or $C_1$-$C_3$ alkyl which is substituted with $C_4$-$C_6$ heterocycle; wherein each of the $C_4$-$C_6$ heterocycle moieties is optionally substituted with 1, 2, 3, 4, or 5 $R^{1g}$; $R^{3a}$ is $C_4$-$C_6$ heterocycle which is optionally substituted with 1, 2, 3, 4, or 5 $R^{1g}$; $R^{3b}$ is H or $C_1$-$C_6$ alkyl; and $R^{3c}$ is H, $C_1$-$C_6$ alkyl, —($C_1$-$C_6$ alkylenyl)-$OR^{z1}$, —($C_1$-$C_6$ alkylenyl)-$NR^{z3}R^{z4}$, —($C_1$-$C_6$ alkylenyl)-CN, or —($C_1$-$C_6$ alkylenyl)-$G^1$; wherein $G^1$ is $C_4$-$C_6$ heterocycle, $C_5$-$C_6$ heteroaryl, $C_3$-$C_6$ cycloalkyl, or phenyl; each of which is optionally substituted with 1, 2, 3, 4, or 5 $R^{1g}$;

In certain embodiments, $R^3$ is —$C(O)R^{3a}$ or —$C(O)NR^{3b}R^{3c}$. In some such embodiments, $R^{3a}$ is optionally substituted $C_4$-$C_6$ heterocycle. In some such embodiments, $R^{3a}$ is piperidinyl, morpholinyl, or piperazinyl, each of which is optionally substituted. In some such embodiments, $R^{3b}$ is H or $C_1$-$C_3$ alkyl; and $R^{3c}$ is H, $C_1$-$C_3$ alkyl, —($C_1$-$C_6$ alkylenyl)-$OR^{z1}$, —($C_1$-$C_6$ alkylenyl)-$NR^{z3}R^{z4}$, —($C_1$-$C_6$ alkylenyl)-CN, or —($C_1$-$C_6$ alkylenyl)-$G^1$; wherein $G^1$ is $C_4$-$C_6$ heterocycle, $C_5$-$C_6$ heteroaryl, $C_3$-$C_6$ cycloalkyl, or phenyl; each of which is optionally substituted.

In certain embodiments of formula (I), $R^4$ is H, $C_1$-$C_6$ alkyl, halogen, or $C_1$-$C_6$ haloalkyl.

In certain embodiments, $R^4$ is H, $C_1$-$C_3$ alkyl, or halogen. In some such embodiments, $R^4$ is H, $C_1$-$C_3$ alkyl, F, or Cl. In some such embodiments, $R^4$ is H, $C_1$-$C_3$ alkyl, or Cl. In some such embodiments, $R^4$ is H, methyl, or Cl.

In certain embodiments, $R^4$ is H.

In certain embodiments, $R^4$ is $C_1$-$C_3$ alkyl or halogen. In some such embodiments, $R^4$ is $C_1$-$C_3$ alkyl, F, or Cl. In some such embodiments, $R^4$ is $C_1$-$C_3$ alkyl or Cl. In some such embodiments, $R^4$ is methyl or Cl.

In certain embodiments of formula (I), $R^5$ is a monocyclic or bicyclic ring selected from the group consisting of aryl and heteroaryl; each of which is independently substituted with 1, 2, or 3 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^2$, —$OR^a$, —$OC(O)R^b$, —$OC(O)NR^cR^d$, —$SR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)C(O)R^b$, —$N(R^e)S(O)_2R^b$, —$N(R^e)C(O)O(R^b)$, —$N(R^e)C(O)NR^cR^d$, —$N(R^e)S(O)_2NR^cR^d$, —($C_1$-$C_6$ alkylenyl)-$G^2$, —($C_1$-$C_6$ alkylenyl)-$OR^a$, —($C_1$-$C_6$ alkylenyl)-$OC(O)R^b$, —($C_1$-$C_6$ alkylenyl)-$OC(O)NR^cR^d$, —($C_1$-$C_6$ alkylenyl)-S (O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, —(C$_1$-C$_6$ alkylenyl)-N(R$^e$)S(O)$_2$NR$^c$R$^d$, and —(C$_1$-C$_6$ alkylenyl)-CN. In some such embodiments, R$^5$ is substituted aryl. In some such embodiments, R$^5$ is substituted phenyl. In some such embodiments, R$^5$ is substituted heteroaryl. In some such embodiments, R$^5$ is substituted pyridinyl or substituted indolyl. In some such embodiments, R$^5$ is phenyl, pyridinyl, or indolyl, each of which is substituted. In some such embodiments, R$^5$ is substituted phenyl or substituted pyridinyl. In some such embodiments, R$^5$ is substituted indolyl.

In certain embodiments, R$^5$ is a monocyclic or bicyclic ring selected from the group consisting of aryl and heteroaryl; each of which is independently substituted with 1, 2, or 3 substituents independently selected from the group consisting of C$_1$-C$_3$ alkyl, halogen, C$_1$-C$_3$ haloalkyl, —CN, NO$_2$, G$^2$, —OR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)S(O)$_2$R$^b$, —(C$_1$-C$_3$ alkylenyl)-G$^2$ wherein G$^2$ is optionally substituted heterocycle, —(C$_1$-C$_3$ alkylenyl)-S(O)$_2$R$^a$, —(C$_1$-C$_3$ alkylenyl)-S(O)$_2$NR$^c$R$^d$, —(C$_1$-C$_3$ alkylenyl)-NR$^c$R$^d$, and —(C$_1$-C$_3$ alkylenyl)-N(R$^e$)S(O)$_2$R$^b$. In some such embodiments, R$^5$ is substituted aryl. In some such embodiments, R$^5$ is substituted phenyl. In some such embodiments, R$^5$ is substituted heteroaryl. In some such embodiments, R$^5$ is substituted pyridinyl or substituted indolyl. In some such embodiments, R$^5$ is phenyl, pyridinyl, or indolyl, each of which is substituted. In some such embodiments, R$^5$ is substituted phenyl or substituted pyridinyl. In some such embodiments, R$^5$ is substituted indolyl.

In certain embodiments, R$^5$ is indolyl substituted with 1 or 2 substituents independently selected from the group consisting of —OR$^a$, —C(O)OR$^a$, and —C(O)NR$^c$R$^d$. In some such embodiments, R$^5$ is indolyl substituted with an —OR$^a$ group and optionally further substituted with another substituent selected from the group consisting of —C(O)OR$^a$ and —C(O)NR$^c$R$^d$.

In certain embodiments, R$^5$ is phenyl or pyridinyl; each of which is substituted with 1, 2, or 3 substituents independently selected from the group consisting of C$_1$-C$_3$ alkyl, halogen, C$_1$-C$_3$ haloalkyl, —CN, NO$_2$, G$^2$, —OR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)S(O)$_2$R$^b$, —(C$_1$-C$_3$ alkylenyl)-G$^2$ wherein G$^2$ is optionally substituted heterocycle, —(C$_1$-C$_3$ alkylenyl)-S(O)$_2$R$^a$, —(C$_1$-C$_3$ alkylenyl)-S(O)$_2$NR$^c$R$^d$, —(C$_1$-C$_3$ alkylenyl)-NR$^c$R$^d$, and —(C$_1$-C$_3$ alkylenyl)-N(R$^e$)S(O)$_2$R$^b$. In some such embodiments, R$^5$ is substituted phenyl. In some such embodiments, R$^5$ is substituted pyridinyl.

In certain embodiments, R$^5$ is phenyl or pyridinyl; each of which is substituted with 1, 2, or 3 substituents, wherein one substituent is selected from the group consisting of —OR$^a$ and —NR$^c$R$^d$, and the other optional substituents are selected from the group consisting of C$_1$-C$_3$ alkyl, halogen, C$_1$-C$_3$ haloalkyl, —S(O)$_2$R$^a$, —S(O)$_2$NR$^c$R$^d$, —N(R$^e$)S(O)$_2$R$^b$, —(C$_1$-C$_3$ alkylenyl)-G$^2$ wherein G$^2$ is optionally substituted heterocycle, —(C$_1$-C$_3$ alkylenyl)-S(O)$_2$R$^a$, —(C$_1$-C$_3$ alkylenyl)-S(O)$_2$NR$^c$R$^d$, —(C$_1$-C$_3$ alkylenyl)-NR$^c$R$^d$, and —(C$_1$-C$_3$ alkylenyl)-N(R$^e$)S(O)$_2$R$^b$. In some such embodiments, R$^5$ is substituted phenyl. In some such embodiments, R$^5$ is substituted pyridinyl.

In certain embodiments, R$^5$ is phenyl or pyridinyl; each of which is substituted with two substituents, wherein one substituent is —OR$^a$, and the other substituent is selected from the group consisting of —S(O)$_2$R$^a$, —S(O)$_2$NR$^c$R$^d$, —N(R$^e$)S(O)$_2$R$^b$, —(C$_1$-C$_3$ alkylenyl)-G$^2$ wherein G$^2$ is optionally substituted C$_4$-C$_6$ heterocycle, —(C$_1$-C$_3$ alkylenyl)-S(O)$_2$R$^a$, —(C$_1$-C$_3$ alkylenyl)-S(O)$_2$NR$^c$R$^d$, —(C$_1$-C$_3$ alkylenyl)-NR$^c$R$^d$, and —(C$_1$-C$_3$ alkylenyl)-N(R$^e$)S(O)$_2$R$^b$. In some such embodiments, R$^5$ is substituted phenyl. In some such embodiments, R$^5$ is substituted pyridinyl.

In certain embodiments, R$^5$ is phenyl or pyridinyl; each of which is substituted with two substituents, wherein one substituent is —NR$^c$R$^d$, and the other substituent is selected from the group consisting of —S(O)$_2$R$^a$, —S(O)$_2$NR$^c$R$^d$, —N(R$^e$)S(O)$_2$R$^b$, —(C$_1$-C$_3$ alkylenyl)-G$^2$ wherein G$^2$ is optionally substituted C$_4$-C$_6$ heterocycle, —(C$_1$-C$_3$ alkylenyl)-S(O)$_2$R$^a$, —(C$_1$-C$_3$ alkylenyl)-S(O)$_2$NR$^c$R$^d$, —(C$_1$-C$_3$ alkylenyl)-NR$^c$R$^d$, and —(C$_1$-C$_3$ alkylenyl)-N(R$^e$)S(O)$_2$R$^b$. In some such embodiments, R$^5$ is substituted phenyl. In some such embodiments, R$^5$ is substituted pyridinyl.

The compounds of formula (I) wherein R$^5$ is phenyl or pyridinyl correspond in structure to the following formula (i.e. formula (IA)).

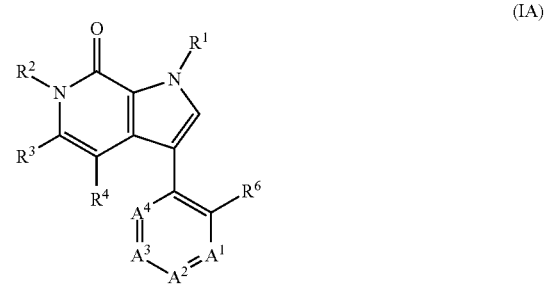

(IA)

wherein
A$^1$ is C(R$^7$), A$^2$ is C(R$^8$), A$^3$ is C(R$^9$), and A$^4$ is C(R$^{10}$); or
A$^1$ is N, A$^2$ is C(R$^8$), A$^3$ is C(R$^9$), and A$^4$ is C(R$^{10}$); or
A$^1$ is C(R$^7$), A$^2$ is N, A$^3$ is C(R$^9$), and A$^4$ is C(R$^{10}$); or
A$^1$ is C(R$^7$), A$^2$ is C(R$^8$), A$^3$ is N, and A$^4$ is C(R$^{10}$); or
A$^1$ is C(R$^7$), A$^2$ is C(R$^8$), A$^3$ is C(R$^9$), and A$^4$ is N;

In certain embodiments of compounds of formula (IA), A$^1$ is C(R$^7$), A$^2$ is C(R$^8$), A$^3$ is C(R$^9$), and A$^4$ is C(R$^{10}$). In these embodiments, the compounds of formula (IA) correspond in structure to formula (IA-a).

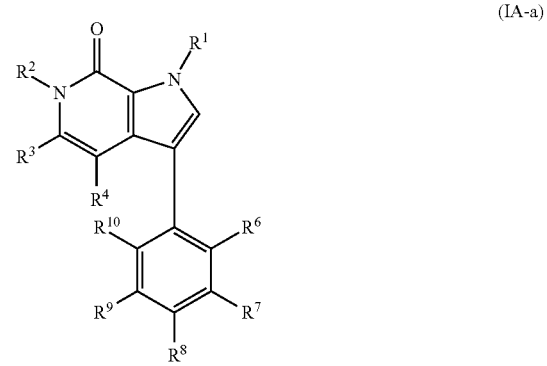

(IA-a)

In certain embodiments of compounds of formula (IA), A$^1$ is N, A$^2$ is C(R$^8$), A$^3$ is C(R$^9$), and A$^4$ is C(R$^{10}$). In these embodiments, the compounds of formula (IA) correspond in structure to formula (IA-b).

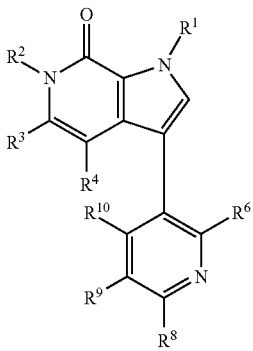

(IA-b)

In certain embodiments of compounds of formula (IA), $A^1$ is $C(R^7)$, $A^2$ is N, $A^3$ is $C(R^9)$, and $A^4$ is $C(R^{10})$. In these embodiments, the compounds of formula (IA) correspond in structure to formula (IA-c).

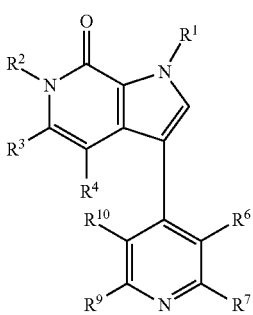

(IA-c)

In certain embodiments of compounds of formula (IA), $A^1$ is $C(R^7)$, $A^2$ is $C(R^8)$, $A^3$ is N, and $A^4$ is $C(R^{10})$. In these embodiments, the compounds of formula (IA) correspond in structure to formula (IA-d).

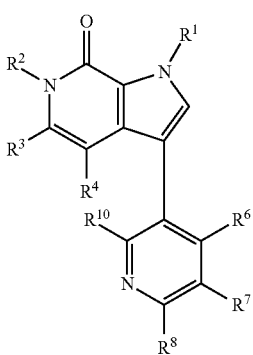

(IA-d)

In certain embodiments of compounds of formula (IA), $A^1$ is $C(R^7)$, $A^2$ is $C(R^8)$, $A^3$ is $C(R^9)$, and $A^4$ is N. In these embodiments, the compounds of formula (IA) correspond in structure to formula (IA-e).

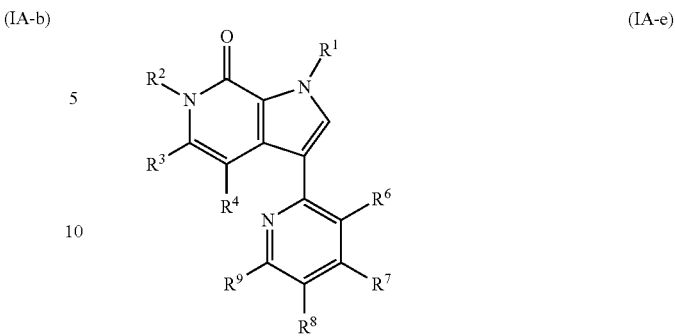

(IA-e)

In certain embodiments of formula (IA), (IA-a), (IA-b), (IA-c), (IA-d), and (IA-e), $R^6$ is halogen, —$OR^a$, or —$NR^cR^d$;

$R^7$ is H, $C_1$-$C_6$ alkyl, $C_2$-$C_6$ alkenyl, $C_2$-$C_6$ alkynyl, halogen, $C_1$-$C_6$ haloalkyl, —CN, $NO_2$, or $C_3$-$C_6$ cycloalkyl optionally substituted 1, 2, 3, 4, or 5 substituents independently selected from the group consisting of halogen, $C_1$-$C_3$ alkyl, and CN.

$R^8$ is H, halogen, —$OR^a$, —$NR^cR^d$, —$C(O)R^a$, —$C(O)NR^cR^d$, $G^2$, —($C_1$-$C_6$ alkylenyl)-$G^2$, or —($C_1$-$C_6$ alkylenyl)-$NR^cR^d$;

$R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$; and $R^{10}$ is H, $C_1$-$C_6$ alkyl, $C_2$-$C_6$ alkenyl, $C_2$-$C_6$ alkynyl, halogen, $C_1$-$C_6$ haloalkyl, —CN, or $NO_2$;

$R^1$, $R^2$, $R^3$, and $R^4$ in compounds of formula (IA), (IA-a), (IA-b), (IA-c), (IA-d), and (IA-e) are as set forth in formula (I). Various embodiments of $R^1$, $R^2$, $R^3$, and $R^4$ of formula (I) as discussed above are also contemplated for compounds of formula (IA), (IA-a), (IA-b), (IA-c), (IA-d), and (IA-e).

In certain embodiments of compounds of formula (IA), (IA-a), (IA-b), (IA-c), (IA-d), and (IA-e), $R^6$ is halogen (e.g. F, Cl), —$OR^a$, or —$NR^cR^d$. In some such embodiments, $R^6$ is F, —$OR^a$, or —$NR^cR^d$.

In certain embodiments of compounds of formula (IA), (IA-a), (IA-b), (IA-c), (IA-d), and (IA-e), $R^6$ is —$OR^a$ or —$NR^cR^d$; wherein $R^a$ is $C_1$-$C_6$ haloalkyl, $G^2$, or $C_1$-$C_6$ alkyl wherein the $C_1$-$C_6$ alkyl is optionally substituted with one $G^2$ group;

$R^c$ is H or unsubstituted $C_1$-$C_6$ alkyl; and $R^d$ is $C_1$-$C_6$ haloalkyl, $G^2$, or $C_1$-$C_6$ alkyl wherein the $C_1$-$C_6$ alkyl is optionally substituted with one $G^2$ group.

In certain embodiments of compounds of formula (IA), (IA-a), (IA-b), (IA-c), (IA-d), and (IA-e), $R^6$ is —$OR^a$ or —$NR^cR^d$; wherein $R^a$ is $C_1$-$C_6$ haloalkyl or unsubstituted $C_1$-$C_6$ alkyl;

$R^c$ is H or unsubstituted $C_1$-$C_3$ alkyl; and $R^d$ is $C_1$-$C_6$ haloalkyl or unsubstituted $C_1$-$C_6$ alkyl.

In certain embodiments of compounds of formula (IA), (IA-a), (IA-b), (IA-c), (IA-d), and (IA-e), $R^6$ is —$OR^a$ or —$NR^cR^d$; wherein $R^a$ is methyl, 2,2-dimethylpropyl, 3,3-dimethylbutyl, or 2,2,3,3,3-pentafluoropropyl;

$R^c$ is H or methyl; and $R^d$ is 2,2,2-trifluoroethyl or 2,2,3,3,4,4,4-heptafluorobutyl.

In certain embodiments of compounds of formula (IA), (IA-a), (IA-b), (IA-c), (IA-d), and (IA-e), $R^6$ is —$OR^a$ or —$NR^cR^d$; wherein $R^a$ is $G^2$ or $C_1$-$C_6$ alkyl wherein the $C_1$-$C_6$ alkyl is substituted with one $G^2$ group;
$R^c$ is H or unsubstituted $C_1$-$C_3$ alkyl; and
$R^d$ is $G^2$ or $C_1$-$C_6$ alkyl wherein the $C_1$-$C_6$ alkyl is substituted with one $G^2$ group.

In certain embodiments, of compounds of formula (IA), (IA-a), (IA-b), (IA-c), (IA-d), and (IA-e), $R^6$ is —$OR^a$ or —$NR^cR^d$; wherein
- $R^a$ and $R^d$ are each independently $G^2$ or $C_1$-$C_6$ alkyl substituted with a $G^2$ group; wherein $G^2$ is phenyl, $C_3$-$C_6$ cycloalkyl, $C_4$-$C_6$ heterocycle, or $C_5$-$C_6$ heteroaryl; each of which is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —OC(O)$R^{y2}$, —OC(O)N$R^{y3}R^{y4}$, —S$R^{y1}$, —S(O)$_2R^{y1}$, —S(O)$_2$N$R^{y3}R^{y4}$, —C(O)$R^{y1}$, —C(O)O$R^{y1}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, and —N($R^{y3}$)S(O)$_2$N$R^{y3}R^{y4}$;
- $R^c$ is hydrogen or unsubstituted $C_1$-$C_6$ alkyl;
- $R^{y1}$, $R^{y3}$, and $R^{y4}$, at each occurrence, are each independently H, $C_1$-$C_6$ alkyl, or $C_1$-$C_6$ haloalkyl; and
- $R^{y2}$, at each occurrence, is independently $C_1$-$C_6$ alkyl or $C_1$-$C_6$ haloalkyl.

In certain embodiments of compounds of formula (IA), (IA-a), (IA-b), (IA-c), (IA-d), and (IA-e), $R^6$ is —$OR^a$ or —$NR^cR^d$; wherein
- $R^a$ is $G^2$ or $C_1$-$C_3$ alkyl wherein the $C_1$-$C_3$ alkyl is substituted with one $G^2$ group; wherein $G^2$ is aryl, $C_4$-$C_6$ heterocycle, $C_3$-$C_6$ cycloalkyl, $C_5$-$C_6$ heteroaryl, or adamantyl, each of which is optionally substituted;
- $R^c$ is H or unsubstituted $C_1$-$C_3$ alkyl; and
- $R^d$ is optionally substituted phenyl or $C_1$-$C_3$ alkyl wherein the $C_1$-$C_3$ alkyl is substituted with one $G^2$ group, wherein $G^2$ is phenyl, $C_3$-$C_6$ cycloalkyl, or bicyclo[2.2.1]heptyl, each of which is optionally substituted.

In certain embodiments of compounds of formula (IA), (IA-a), (IA-b), (IA-c), (IA-d), and (IA-e), $R^6$ is —$OR^a$ or —$NR^cR^d$; wherein
- $R^a$ is phenyl, naphthyl, indanyl, pyrazolyl, pyridinyl, pyrazinyl, pyridazinyl, pyrimidinyl, cyclohexyl, oxetanyl, tetrahydrofuranyl, piperidinyl, tetrahydropyranyl, each of which is optionally substituted; or $C_1$-$C_3$ alkyl wherein the $C_1$-$C_3$ alkyl is substituted with one $G^2$ group, wherein $G^2$ is phenyl, thienyl, $C_3$-$C_6$ cycloalkyl, adamantyl, oxetanyl, tetrahydrofuranyl, tetrahydropyranyl, each of which is optionally substituted;
- $R^c$ is H or methyl; and
- $R^d$ is optionally substituted phenyl or $C_1$-$C_3$ alkyl wherein the $C_1$-$C_3$ alkyl is substituted with one $G^2$ group, wherein $G^2$ is phenyl, $C_3$-$C_6$ cycloalkyl, or bicyclo[2.2.1]heptyl, each of which is optionally substituted.

In certain embodiments of compounds of formula (IA), (IA-a), (IA-b), (IA-c), (IA-d), and (IA-e), $R^6$ is —$OR^a$ or —$NR^cR^d$; wherein
- $R^a$ and $R^d$ are each independently phenyl, pyridinyl, or $C_1$-$C_3$ alkyl substituted with a $C_3$-$C_6$ cycloalkyl; wherein the phenyl, pyridinyl, and the $C_3$-$C_6$ cycloalkyl are optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —OC(O)$R^{y2}$, —OC(O)N$R^{y3}R^{y4}$, —S$R^{y1}$, —S(O)$_2R^{y1}$, —S(O)$_2$N$R^{y3}R^{y4}$, —C(O)$R^{y1}$, —C(O)O$R^{y1}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, and —N($R^{y3}$)S(O)$_2$N$R^{y3}R^{y4}$;
- $R^c$ is hydrogen or unsubstituted $C_1$-$C_3$ alkyl;
- $R^{y1}$, $R^{y3}$, and $R^{y4}$, at each occurrence, are each independently H, $C_1$-$C_6$ alkyl, or $C_1$-$C_6$ haloalkyl; and
- $R^{y2}$, at each occurrence, is independently $C_1$-$C_6$ alkyl or $C_1$-$C_6$ haloalkyl.

In certain embodiments of compounds of formula (IA), (IA-a), (IA-b), (IA-c), (IA-d), and (IA-e), $R^6$ is —$OR^a$ wherein $R^a$ is $G^2$, and $G^2$ is optionally substituted phenyl or optionally substituted $C_3$-$C_6$ cycloalkyl. In some such embodiments, $G^2$ is optionally substituted phenyl or optionally substituted cyclohexyl.

In certain embodiments of compounds of formula (IA), (IA-a), (IA-b), (IA-c), (IA-d), and (IA-e), $R^6$ is —$OR^a$ wherein $R^a$ is $G^2$, and $G^2$ is phenyl or cyclohexyl; each of which is optionally substituted with 1 or 2 substituents independently selected from the group consisting of —CN, —$OR^{z1}$, and halogen. In some such embodiments, the optional substituents are selected from —CN, —OH, —O($C_1$-$C_3$ alkyl), F, and Cl. In some such embodiments, the optional substituents are selected from —CN, —OH, —O($CH_3$), and F.

In certain embodiments of compounds of formula (IA), (IA-a), (IA-b), (IA-c), (IA-d), and (IA-e), $R^6$ is —$OR^a$ wherein $R^a$ is $G^2$, and $G^2$ is phenyl optionally substituted with 1 or 2 substituents selected from the group consisting of CN and halogen. In some such embodiments, $G^2$ is phenyl substituted with 1 or 2 substituents. In some such embodiments, $G^2$ is unsubstituted phenyl. In some such embodiments, the substituents are selected from —CN, F, and Cl. In some such embodiments, the substituents are selected from CN and F.

In certain embodiments of compounds of formula (IA), (IA-a), (IA-b), (IA-c), (IA-d), and (IA-e), $R^6$ is —$OR^a$ wherein $R^a$ is $G^2$, and $G^2$ is phenyl substituted with 1 or 2 substituents selected from halogen. In some such embodiments, $G^2$ is phenyl substituted with two halogen substituents. In some such embodiments, the halogen is F.

In certain embodiments of compounds of formula (IA), (IA-a), (IA-b), (IA-c), (IA-d), and (IA-e), $R^6$ is —$OR^a$ wherein $R^a$ is $G^2$, and $G^2$ is cyclohexyl optionally substituted with 1 or 2 substituents selected from the group consisting of —$OR^{z1}$ and halogen. In some such embodiments, the substituents are selected from —OH, —O($C_1$-$C_3$ alkyl), F, and Cl. In some such embodiments, the substituents are selected from —OH, —O($CH_3$), and F. In some such embodiments, $G^2$ is cyclohexyl substituted with one substituent selected from the group consisting of —OH, —O($CH_3$), and F. In some such embodiments, $G^2$ is cyclohexyl substituted with two halogen substituents. In some such embodiments, $G^2$ is cyclohexyl substituted with two F.

In certain embodiments of compounds of formula (IA), (IA-a), (IA-b), (IA-c), (IA-d), and (IA-e), $R^6$ is —$NR^cR^d$; wherein $R^c$ is H or unsubstituted $C_1$-$C_3$ alkyl; and $R^d$ is optionally substituted phenyl or $C_1$-$C_3$ alkyl wherein the $C_1$-$C_3$ alkyl is substituted with one $G^2$ group, wherein $G^2$ is optionally substituted $C_3$-$C_6$ cycloalkyl. In some such embodiments, $G^2$ is optionally substituted cyclopropyl.

In certain embodiments of compounds of formula (IA), (IA-a), (IA-b), (IA-c), (IA-d), and (IA-e), $R^6$ is —$NR^cR^d$; wherein $R^c$ is H or methyl; and $R^d$ is phenyl substituted with 1 or 2 halogen groups, or $R^d$ is $C_1$-$C_3$ alkyl wherein the $C_1$-$C_3$ alkyl is substituted with one $G^2$ group, wherein $G^2$ is optionally substituted $C_3$-$C_6$ cycloalkyl. In some such embodiments, $G^2$ is optionally substituted cyclopropyl. In some such embodiments, $G^2$ is unsubstituted cyclopropyl. In some such embodiments, the halogen substituents of the phenyl group are selected from fluoro or chloro. In some such embodiments, the halogen is fluoro.

In certain embodiments of compounds of formula (IA), (IA-a), (IA-b), (IA-c), (IA-d), and (IA-e), $R^6$ is —$NR^cR^d$; wherein $R^c$ is H and $R^d$ is phenyl substituted with 1 or 2 halogen groups. In some such embodiments, the halogen is selected from fluoro or chloro. In some such embodiments, the halogen is fluoro.

In certain embodiments of compounds of formula (IA), (IA-a), (IA-b), (IA-c), (IA-d), and (IA-e), $R^6$ is —$NR^cR^d$; wherein $R^c$ is H and $R^d$ is cyclopropylmethyl wherein the cyclopropyl is optionally substituted. In some such embodiments, the cyclopropyl is unsubstituted.

In certain embodiments of formula (IA), (IA-a), (IA-c), (IA-d), and (IA-e), $R^7$ is H, $C_1$-$C_6$ alkyl, $C_2$-$C_6$ alkenyl, $C_2$-$C_6$ alkynyl, halogen, $C_1$-$C_6$ haloalkyl, —CN, $NO_2$, or $C_3$-$C_6$ cycloalkyl optionally substituted with 1, 2, 3, 4, or 5 substituents independently selected from the group consisting of halogen, $C_1$-$C_3$ alkyl, and CN.

In certain embodiments of compounds of formula (IA), (IA-a), (IA-c), (IA-d), and (IA-e), $R^7$ is H.

In certain embodiments of formula (IA), (IA-a), (IA-b), (IA-d), and (IA-e), $R^8$ is H, halogen, —$OR^a$, —$NR^cR^d$, —$C(O)R^a$, —$C(O)NR^cR^d$, $G^2$, —($C_1$-$C_6$ alkylenyl)-$G^2$, or —($C_1$-$C_6$ alkylenyl)-$NR^cR^d$.

In certain embodiments of compounds of formula (IA), (IA-a), (IA-b), (IA-d), and (IA-e), $R^8$ is H, halogen, or —$OR^a$ wherein $R^a$ is optionally substituted phenyl. In some such embodiments, $R^8$ is H or fluoro.

In certain embodiments of compounds of formula (IA), (IA-a), (IA-b), (IA-d), and (IA-e), $R^8$ is H.

In certain embodiments of compounds of formula (IA), (IA-a), (IA-b), (IA-d), and (IA-e), $R^8$ is halogen. In some such embodiments, $R^8$ is fluoro.

In certain embodiments of formula (IA), (IA-a), (IA-b), (IA-c), and (IA-e), $R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$.

In certain embodiments of compounds of formula (IA), (IA-a), (IA-b), (IA-c), and (IA-e), $R^9$ is —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$.

In certain embodiments of compounds of formula (IA), (IA-a), (IA-b), (IA-c), and (IA-e), $R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$; wherein $R^c$, $R^d$, and $R^e$, at each occurrence, are each independently H or unsubstituted $C_1$-$C_6$ alkyl; and $R^a$ and $R^b$, at each occurrence, is independently $C_1$-$C_6$ haloalkyl, or unsubstituted $C_1$-$C_6$ alkyl.

In certain embodiments of compounds of formula (IA), (IA-a), (IA-b), (IA-c), and (IA-e), $R^9$ is —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted $C_4$-$C_6$ heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$. In some such embodiments, $R^a$ and $R^b$ are each independently $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted; $R^e$ and $R^c$ are each independently H or unsubstituted $C_1$-$C_3$ alkyl; and $R^d$ is H, $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted.

In certain embodiments of compounds of formula (IA), (IA-a), (IA-b), (IA-c), and (IA-e), $R^9$ is —($C_1$-$C_3$ alkylenyl)-$G^2$ wherein $G^2$ is optionally substituted monocyclic heterocycle, or $R^9$ is —($C_1$-$C_3$ alkylenyl)-$NR^cR^d$. In some such embodiments, $R^9$ is —($C_1$-$C_3$ alkylenyl)-$G^2$ wherein $G^2$ is optionally substituted $C_4$-$C_6$ heterocycle (e.g. morpholinyl, piperidinyl, or piperazinyl, each of which is optionally substituted), or $R^9$ is —($C_1$-$C_3$ alkylenyl)-$NR^cR^d$ wherein $R^c$ is H or unsubstituted $C_1$-$C_3$ alkyl, and $R^d$ is H, $G^2$, or $C_1$-$C_6$ alkyl which is optionally substituted with one $G^2$; wherein $G^2$ is $C_5$-$C_6$ heteroaryl, $C_3$-$C_6$ cycloalkyl, or $C_4$-$C_6$ heterocycle, each of which is optionally substituted. In some such embodiments, $R^9$ is —($C_1$-$C_3$ alkylenyl)-$NR^cR^d$ wherein $R^c$ is H or unsubstituted $C_1$-$C_3$ alkyl, and $R^d$ is H, $G^2$, or $C_1$-$C_6$ alkyl which is optionally substituted with one $G^2$; wherein $G^2$ is cyclopropyl, cyclopentyl, piperidinyl, piperazinyl, morpholinyl, imidazolyl, furanyl, thienyl, thiazolyl, or oxazolyl, wherein each of which is optionally substituted.

In certain embodiments of compounds of formula (IA), (IA-a), (IA-b), (IA-c), and (IA-e), $R^9$ is —$N(R^e)S(O)_2R^b$, —$S(O)_2R^a$, —($C_1$-$C_3$ alkylenyl)-$S(O)_2R^a$, —($C_1$-$C_3$ alkylenyl)-$S(O)_2NR^cR^d$, or —($C_1$-$C_3$ alkylenyl)-$N(R^e)S(O)_2R^b$. In some such embodiments, $R^a$ is unsubstituted $C_1$-$C_3$ alkyl or optionally substituted $C_4$-$C_6$ heterocycle, $R^b$ is unsubstituted $C_1$-$C_3$ alkyl or optionally substituted benzyl, $R^c$ is H or unsubstituted $C_1$-$C_3$ alkyl, $R^d$ is H or unsubstituted $C_1$-$C_3$ alkyl, and $R^e$ is H.

In certain embodiments of compounds of formula (IA), (IA-a), (IA-b), (IA-c), and (IA-e), $R^9$ is —$N(R^e)S(O)_2R^b$ or —($C_1$-$C_6$ alkylenyl)-$S(O)_2R^a$; wherein $R^e$ is H or unsubstituted $C_1$-$C_3$ alkyl; and $R^a$ and $R^b$, are each independently $C_1$-$C_3$ alkyl.

In certain embodiments of compounds of formula (IA), (IA-a), (IA-b), (IA-c), and (IA-e), $R^9$ is —$N(R^e)S(O)_2R^b$. In some such embodiments, $R^e$ is H and $R^b$ is unsubstituted $C_1$-$C_3$ alkyl. In some such embodiments, $R^e$ is H and $R^b$ is methyl, ethyl, or isopropyl.

In certain embodiments of compounds of formula (IA), (IA-a), (IA-b), (IA-c), and (IA-e), $R^9$ is —($C_1$-$C_3$ alkylenyl)-$N(R^e)S(O)_2R^b$. In some such embodiments, $R^9$ is —($CH_2$)—$N(R^e)S(O)_2R^b$. In some such embodiments, $R^e$ is H or unsubstituted $C_1$-$C_3$ alkyl, and $R^b$ is $C_1$-$C_6$ haloalkyl, $G^2$, or $C_1$-$C_6$ alkyl which is optionally substituted with one $G^2$ group, and $G^2$ is, phenyl, $C_3$-$C_6$ cycloalkyl, $C_5$-$C_6$ heteroaryl or $C_4$-$C_6$ heterocycle, each of which is optionally substituted. In some such embodiments, $R^e$ is H or methyl, and $R^b$ is $C_1$-$C_3$ haloalkyl, unsubstituted $C_1$-$C_3$ alkyl, phenyl, benzyl, $C_3$-$C_6$ cycloalkyl, $C_5$-$C_6$ heteroaryl, wherein the phenyl, benzyl, $C_3$-$C_6$ cycloalkyl, and $C_5$-$C_6$ heteroaryl are optionally substituted. In some such embodiments, $R^e$ is H and $R^b$ is unsubstituted $C_1$-$C_3$ alkyl, $C_1$-$C_3$ haloalkyl, phenyl, benzyl, cyclopentyl, 1,2-oxazolyl, or thienyl, wherein the phenyl, benzyl, cyclopentyl, 1,2-oxazolyl, and thienyl are optionally substituted. In some such embodiments, $R^e$ is H and $R^b$ is unsubstituted $C_1$-$C_3$ alkyl or optionally substituted benzyl. In some such embodiments, $R^9$ is —($CH_2$)—$N(R^e)S(O)_2R^b$ wherein $R^e$ is H and $R^b$ is optionally substituted benzyl.

In certain embodiments of compounds of formula (IA), (IA-a), (IA-b), (IA-c), and (IA-e), $R^9$ is —$S(O)_2R^a$ or —($C_1$-

$C_3$ alkylenyl)-$S(O)_2R^a$. In some such embodiments, $R^a$ is unsubstituted $C_1$-$C_3$ alkyl or optionally substituted heterocycle. In some such embodiments, $R^a$ is unsubstituted $C_1$-$C_3$ alkyl or optionally substituted $C_4$-$C_6$ heterocycle. In some such embodiments, $R^a$ is unsubstituted $C_1$-$C_3$ alkyl. In some such embodiments, $R^a$ is optionally substituted heterocycle. In some such embodiments, $R^9$ is —$S(O)_2R^a$ or —$(CH_2)$—$S(O)_2R^a$ wherein $R^a$ is unsubstituted $C_1$-$C_3$ alkyl. In some such embodiments, $R^9$ is —$S(O)_2R^a$ or —$(CH_2)$—$S(O)_2R^a$ wherein $R^a$ is optionally substituted $C_4$-$C_6$ heterocycle. In some further embodiments, the unsubstituted $C_1$-$C_3$ alkyl is methyl or ethyl. In some further embodiments, the $C_4$-$C_6$ heterocycle is azetidinyl, piperidinyl, piperazinyl, or morpholinyl, each of which is optionally substituted. In some further embodiments, the $C_4$-$C_6$ heterocycle is morpholinyl.

In certain embodiments of compounds of formula (IA), (IA-a), (IA-b), (IA-c), and (IA-e), $R^9$ is —($C_1$-$C_6$ alkylenyl)-$S(O)_2NR^cR^d$. In some such embodiments, $R^c$ is H or unsubstituted $C_1$-$C_3$ alkyl, and $R^d$ is H, unsubstituted $C_1$-$C_3$ alkyl, optionally substituted $C_3$-$C_6$ cycloalkyl, or optionally substituted $C_5$-$C_6$ heteroaryl. In some such embodiments, $R^9$ is —$(CH_2)$—$S(O)_2NR^cR^d$ wherein $R^c$ and $R^d$ are each independently H or unsubstituted $C_1$-$C_3$ alkyl. In some such embodiments, $R^9$ is —$(CH_2)$—$S(O)_2NR^cR^d$ wherein $R^c$ and $R^d$ are each independently H, methyl, or ethyl.

In certain embodiments of compounds of formula (IA), (IA-a), (IA-b), (IA-c), and (IA-e), $R^9$ is $S(O)_2NR^cR^d$. In some such embodiments, $R^c$ and $R^d$ are each independently H or unsubstituted $C_1$-$C_3$ alkyl. In some such embodiments, $R^c$ and $R^d$ are each independently H, methyl, or ethyl.

In certain embodiments of formula (IA), (IA-a), (IA-b), (IA-c), and (IA-d), $R^{10}$ is H, $C_1$-$C_6$ alkyl, $C_2$-$C_6$ alkenyl, $C_2$-$C_6$ alkynyl, halogen, $C_1$-$C_6$ haloalkyl, —CN, or $NO_2$.

In certain embodiments of compounds of formula (IA), (IA-a), (IA-b), (IA-c), and (IA-d), $R^{10}$ is H or $C_1$-$C_6$ alkyl. In some such embodiments, $R^{10}$ is H or $C_1$-$C_3$ alkyl. In some such embodiments, $R^{10}$ is H or methyl.

In certain embodiments of compounds of formula (IA), (IA-a), (IA-b), (IA-c), and (IA-d), $R^{10}$ is H.

In certain embodiments of compounds of formula (IA), (IA-a), (IA-b), (IA-c), and (IA-d), $R^{10}$ is $C_1$-$C_6$ alkyl. In some such embodiments, $R^{10}$ is $C_1$-$C_3$ alkyl. In some such embodiments, $R^{10}$ is methyl.

Various embodiments of substituents $R^1$, $R^2$, $R^3$, $R^4$, $R^5$, $R^6$, $R^7$, $R^8$, $R^9$ and $R^{10}$ have been discussed above. These substituents embodiments can be combined to form various embodiments of compounds of formula (I), (IA), (IA-a), (IA-b), (IA-d), and (IA-e). All embodiments of compounds of formula (I), (IA), (IA-a), (IA-b), (IA-c), (IA-d), and (IA-e) formed by combining the substituent embodiments discussed above are within the scope of Applicant's invention, and some illustrative embodiments of the compounds of formula (I), (IA), (IA-a), (IA-b), (IA-d), and (IA-e) are provided below.

In certain embodiments,
$R^1$ is $C_1$-$C_3$ alkyl; and
$R^2$ is H or $C_1$-$C_3$ alkyl.

In certain embodiments,
$R^1$ is $C_1$-$C_3$ alkyl;
$R^2$ is H or $C_1$-$C_3$ alkyl; and
$R^5$ is phenyl, pyridinyl, or indolyl, each of which is substituted.

In certain embodiments,
$R^1$ is $C_1$-$C_3$ alkyl;
$R^2$ is H or $C_1$-$C_3$ alkyl; and
$R^3$ is H, $C_1$-$C_6$ alkyl, $C_2$-$C_6$ alkenyl, halogen, —$C(O)R^{3a}$, —$C(O)OR^{3a}$, —$C(O)NR^{3b}R^{3c}$ or $G^1$; wherein the $C_1$-$C_6$ alkyl and the $C_2$-$C_6$ alkenyl are each independently unsubstituted or substituted with 1 or 2 substituents independently selected from the group consisting of halogen, $G^1$, —$OR^{3a}$, and —$NR^{3b}R^{3c}$.

In certain embodiments,
$R^1$ is $C_1$-$C_3$ alkyl;
$R^2$ is H or $C_1$-$C_3$ alkyl;
$R^3$ is H, $C_1$-$C_3$ alkyl, $C_2$-$C_4$ alkenyl, halogen, or $G^1$; wherein the $C_1$-$C_3$ alkyl and the $C_2$-$C_4$ alkenyl are each independently unsubstituted or substituted with 1 or 2 substituents independently selected from the group consisting of halogen, —OH, —$O(C_1$-$C_3$ alkyl), —$NH_2$, —$N(H)(C_1$-$C_3$ alkyl), or —$N(C_1$-$C_3$ alkyl)$_2$; and
$R^5$ is phenyl, pyridinyl, or indolyl, each of which is substituted.

In a further embodiment, $R^5$ is substituted phenyl or substituted pyridinyl. In some further embodiments, $R^5$ is substituted phenyl. In some further embodiments, $R^5$ is substituted pyridinyl. In some further embodiments, $R^5$ is substituted indolyl.

In certain embodiments,
$R^1$ is $C_1$-$C_3$ alkyl;
$R^2$ is H or $C_1$-$C_3$ alkyl;
$R^3$ is H, halogen, unsubstituted $C_1$-$C_3$ alkyl, optionally substituted phenyl, optionally substituted 1,2-oxazolyl, or $C_2$-$C_4$ alkenyl which is substituted with 2 substituents independently selected from the group consisting of halogen and —OH; and
$R^5$ is phenyl or pyridinyl, each of which is substituted with 1, 2, or 3 substituents independently selected from the group consisting of $C_1$-$C_3$ alkyl, halogen, $C_1$-$C_3$ haloalkyl, —CN, $NO_2$, $G^2$, —$OR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)S(O)_2R^b$, —($C_1$-$C_3$ alkylenyl)-$G^2$ wherein $G^2$ is optionally substituted heterocycle, —($C_1$-$C_3$ alkylenyl)-$S(O)_2R^a$, —($C_1$-$C_3$ alkylenyl)-$S(O)_2NR^cR^d$, —($C_1$-$C_3$ alkylenyl)-$NR^cR^d$, and —($C_1$-$C_3$ alkylenyl)-$N(R^e)S(O)_2R^b$.

In some further embodiments, $R^5$ is substituted phenyl. In some further embodiments, $R^5$ is substituted pyridinyl.

In certain embodiments,
$R^1$ is $C_1$-$C_3$ alkyl;
$R^2$ is H or $C_1$-$C_3$ alkyl;
$R^3$ is H, unsubstituted $C_1$-$C_3$ alkyl, or halogen;
$R^4$ is H, $C_1$-$C_3$ alkyl, or halogen; and
$R^5$ is phenyl or pyridinyl; each of which is substituted with 1, 2, or 3 substituents, wherein one substituent is selected from the group consisting of —$OR^a$ and —$NR^cR^d$, and the other optional substituents are selected from the group consisting of $C_1$-$C_3$ alkyl, halogen, $C_1$-$C_3$ haloalkyl, —$S(O)_2R^a$, —$S(O)_2NR^cR^d$, —$N(R^e)S(O)_2R^b$, —($C_1$-$C_3$ alkylenyl)-$G^2$ wherein $G^2$ is optionally substituted heterocycle, —($C_1$-$C_3$ alkylenyl)-$S(O)_2R^a$, —($C_1$-$C_3$ alkylenyl)-$S(O)_2NR^cR^d$, —($C_1$-$C_3$ alkylenyl)-$NR^cR^d$, and —($C_1$-$C_3$ alkylenyl)-$N(R^e)S(O)_2R^b$.

In some further embodiments, $R^5$ is substituted phenyl. In some further embodiments, $R^5$ is substituted pyridinyl.

In certain embodiments,
$R^1$ is $C_1$-$C_3$ alkyl;
$R^2$ is H or $C_1$-$C_3$ alkyl;
$R^3$ is H, unsubstituted $C_1$-$C_3$ alkyl, or halogen;
$R^4$ is H, $C_1$-$C_3$ alkyl, or halogen; and
$R^5$ is indolyl substituted with 1 or 2 substituents independently selected from the group consisting of —$OR^a$, —$C(O)OR^a$, and —$C(O)NR^cR^d$.

In certain embodiments
$R^1$ is H, $C_1$-$C_3$ alkyl, or $C_1$-$C_3$ haloalkyl;
$R^2$ is H, $C_1$-$C_3$ alkyl, or $C_1$-$C_3$ haloalkyl;

R³ is H, C₁-C₆ alkyl, C₂-C₆ alkenyl, C₂-C₆ alkynyl, halogen, —OR$^{3a}$, —NR$^{3b}$R$^{3c}$, —N(R$^{3b}$)C(O)R$^{3d}$, —N(R$^{3b}$)C(O)NR$^{3b}$R$^{3c}$, —N(R$^{3b}$)S(O)₂NR$^{3b}$R$^{3c}$, —C(O)R$^{3a}$, —C(O)OR$^{3a}$, —C(O)NR$^{3b}$R$^{3c}$, —S(O)R$^{3d}$, —S(O)₂R$^{3a}$, —S(O)₂NR$^{3b}$R$^{3c}$, or G¹; wherein the C₁-C₆ alkyl, C₂-C₆ alkenyl, and C₂-C₆ alkynyl are each independently unsubstituted or substituted with 1 or 2 substituents independently selected from the group consisting of halogen, G¹, —OR$^{3a}$, and —NR$^{3b}$R$^{3c}$;

R$^{3a}$, R$^{3b}$, and R$^{3c}$, at each occurrence, are each independently H, C₁-C₆ alkyl, C₁-C₆ haloalkyl, G¹, or —(C₁-C₆ alkylenyl)-G¹;

R$^{3d}$, at each occurrence, is independently C₁-C₆ alkyl, C₁-C₆ haloalkyl, G¹, or —(C₁-C₆ alkylenyl)-G¹;

G¹, at each occurrence, is independently aryl, heteroaryl, heterocycle, cycloalkyl, or cycloalkenyl; and each G¹ is optionally substituted with 1, 2, 3, 4, or 5 R$^{1g}$ groups;

R⁴ is H, C₁-C₆ alkyl, halogen, or C₁-C₆ haloalkyl;

R⁵ is a monocyclic or bicyclic ring selected from the group consisting of aryl and heteroaryl; each of which is substituted with 1, 2, or 3 substituents independently selected from the group consisting of C₁-C₆ alkyl, C₂-C₆ alkenyl, C₂-C₆ alkynyl, halogen, C₁-C₆ haloalkyl, —CN, NO₂, G², —OR$^a$, —OC(O)R$^b$, —OC(O)NR$^c$R$^d$, —SR$^a$, —S(O)₂R$^a$, —S(O)₂NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)₂R$^b$, —N(R$^e$)C(O)O(R$^b$), —N(R$^e$)C(O)NR$^c$R$^d$, —N(R$^e$)S(O)₂NR$^c$R$^d$, —(C₁-C₆ alkylenyl)-G², —(C₁-C₆ alkylenyl)-OR$^a$, —(C₁-C₆ alkylenyl)-OC(O)R$^b$, —(C₁-C₆ alkylenyl)-OC(O)NR$^c$R$^d$, —(C₁-C₆ alkylenyl)-S(O)₂R$^a$, —(C₁-C₆ alkylenyl)-S(O)₂NR$^c$R$^d$, —(C₁-C₆ alkylenyl)-C(O)R$^a$, —(C₁-C₆ alkylenyl)-C(O)OR$^a$, —(C₁-C₆ alkylenyl)-C(O)NR$^c$R$^d$, —(C₁-C₆ alkylenyl)-NR$^c$R$^d$, —(C₁-C₆ alkylenyl)-N(R$^e$)C(O)R$^b$, —(C₁-C₆ alkylenyl)-N(R$^e$)S(O)₂R$^b$, —(C₁-C₆ alkylenyl)-N(R$^e$)C(O)O(R$^b$), —(C₁-C₆ alkylenyl)-N(R$^e$)C(O)NR$^c$R$^d$, —(C₁-C₆ alkylenyl)-N(R$^e$)S(O)₂NR$^c$R$^d$, and —(C₁-C₆ alkylenyl)-CN;

R$^a$, R$^c$, R$^d$, and R$^e$, at each occurrence, are each independently H, C₂-C₆ alkenyl, C₂-C₆ alkynyl, C₁-C₆ haloalkyl, G², or C₁-C₆ alkyl wherein the C₁-C₆ alkyl is optionally substituted with one substituent selected from the group consisting of —OR$^{y1}$, —NR$^{y3}$R$^{y4}$, —C(O)OR$^{y2}$, —C(O)NR$^{y3}$R$^{y4}$, —S(O)₂R$^{y1}$, —S(O)₂NR$^{y3}$R$^{y4}$, and G²;

R$^b$, at each occurrence, is independently C₂-C₆ alkenyl, C₂-C₆ alkynyl, C₁-C₆ haloalkyl, G², or C₁-C₆ alkyl wherein the C₁-C₆ alkyl is optionally substituted with one substituent selected from the group consisting of —OR$^{y1}$, —NR$^{y3}$R$^{y4}$, —C(O)OR$^{y1}$, —C(O)NR$^{y3}$R$^{y4}$, —S(O)₂R$^{y1}$, —S(O)₂NR$^{y3}$R$^{y4}$, and G²;

G², at each occurrence, are each independently aryl, heteroaryl, heterocycle, cycloalkyl, or cycloalkenyl; and each G² group is optionally substituted with 1, 2, 3, 4, or 5 R$^{2g}$ groups;

R$^{1g}$, at each occurrence, is independently C₁-C₆ alkyl, C₂-C₆ alkenyl, C₂-C₆ alkynyl, halogen, C₁-C₆ haloalkyl, —CN, NO₂, —OR$^{z1}$, —OC(O)R$^{z2}$, —OC(O)NR$^{z3}$R$^{z4}$, —SR$^{z1}$, —S(O)₂R$^{z1}$, —S(O)₂NR$^{z3}$R$^{z4}$, —C(O)R$^{z1}$, —C(O)R$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)₂R$^{z2}$, —N(R$^{z3}$)C(O)O(R$^{z2}$), —N(R$^{z3}$)C(O)NR$^{z3}$R$^{z4}$, —N(R$^{z3}$)S(O)₂NR$^{z3}$R$^{z4}$, —(C₁-C₆ alkylenyl)-OR$^{z1}$, —(C₁-C₆ alkylenyl)-OC(O)R$^{z2}$, —(C₁-C₆ alkylenyl)-OC(O)NR$^{z3}$R$^{z4}$, —(C₁-C₆ alkylenyl)-S(O)₂R$^{z1}$, —(C₁-C₆ alkylenyl)-S(O)₂NR$^{z3}$R$^{z4}$, —(C₁-C₆ alkylenyl)-C(O)R$^{z1}$, —(C₁-C₆ alkylenyl)-C(O)NR$^{z3}$R$^{z4}$, —(C₁-C₆ alkylenyl)-NR$^{z3}$R$^{z4}$, —(C₁-C₆ alkylenyl)-N(R$^{z3}$)C(O)R$^{z2}$, —(C₁-C₆ alkylenyl)-N(R$^{z3}$)S(O)₂R$^{z2}$, —(C₁-C₆ alkylenyl)-N(R$^{z3}$)C(O)O(R$^{z2}$), —(C₁-C₆ alkylenyl)-N(R$^{z3}$)C(O)NR$^{z3}$R$^{z4}$, —(C₁-C₆ alkylenyl)-N(R$^{z3}$)S(O)₂NR$^{z3}$R$^{z4}$, —(C₁-C₆ alkylenyl)-CN, or —O(phenyl) wherein the phenyl moiety is optionally substituted with 1, 2, 3, or 4 substituents independently selected from the group consisting of C₁-C₆ alkyl, halogen, C₁-C₆ haloalkyl, —OH, —O(alkyl), —O(haloalkyl), CN, and NO₂;

R$^{2g}$, at each occurrence, is independently C₁-C₆ alkyl, C₂-C₆ alkenyl, C₂-C₆ alkynyl, halogen, C₁-C₆ haloalkyl, —CN, NO₂, —OR$^{y1}$, —OC(O)R$^{y2}$, —OC(O)NR$^{y3}$R$^{y4}$, —SR$^{y1}$, —S(O)₂R$^{y1}$, —S(O)₂NR$^{y3}$R$^{y4}$, —C(O)R$^{y1}$, —C(O)OR$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)₂R$^{y2}$, —N(R$^{y3}$)C(O)O(R$^{y2}$), —N(R$^{y3}$)C(O)NR$^{y3}$R$^{y4}$, —N(R$^{y3}$)S(O)₂NR$^{y3}$R$^{y4}$, G$^{2b}$, —(C₁-C₆ alkylenyl)-OR$^{y1}$, —(C₁-C₆ alkylenyl)-OC(O)R$^{y2}$, —(C₁-C₆ alkylenyl)-OC(O)NR$^{y3}$R$^{y4}$, —(C₁-C₆ alkylenyl)-S(O)₂R$^{y1}$, —(C₁-C₆ alkylenyl)-S(O)₂NR$^{y3}$R$^{y4}$, —(C₁-C₆ alkylenyl)-C(O)R$^{y1}$, —(C₁-C₆ alkylenyl)-C(O)OR$^{y1}$, —(C₁-C₆ alkylenyl)-C(O)NR$^{y3}$R$^{y4}$, —(C₁-C₆ alkylenyl)-NR$^{y3}$R$^{y4}$, —(C₁-C₆ alkylenyl)-N(R$^{y3}$)C(O)R$^{y2}$, —(C₁-C₆ alkylenyl)-N(R$^{y3}$)S(O)₂R$^{y2}$, —(C₁-C₆ alkylenyl)-N(R$^{y3}$)C(O)O(R$^{y2}$), —(C₁-C₆ alkylenyl)-N(R$^{y3}$)C(O)NR$^{y3}$R$^{y4}$, —(C₁-C₆ alkylenyl)-N(R$^{y3}$)S(O)₂NR$^{y3}$R$^{y4}$, —(C₁-C₆ alkylenyl)-CN, or —(C₁-C₆ alkylenyl)-G$^{2b}$;

R$^{y1}$, R$^{y3}$, and R$^{y4}$, at each occurrence, are each independently H, C₁-C₆ alkyl, C₁-C₆ haloalkyl, G$^{2b}$, or —(C₁-C₆ alkylenyl)-G$^{2b}$;

R$^{y2}$, at each occurrence, is independently C₁-C₆ alkyl, C₁-C₆ haloalkyl, G$^{2b}$, or —(C₁-C₆ alkylenyl)-G$^{2b}$;

G$^{2b}$, at each occurrence, is independently aryl, heteroaryl, cycloalkyl, cycloalkenyl, or heterocycle; and each G$^{2b}$ group is optionally substituted with 1, 2, 3, 4, or 5 substituents independently selected from the group consisting of C₁-C₆ alkyl, C₂-C₆ alkenyl, C₂-C₆ alkynyl, halogen, C₁-C₆ haloalkyl, —CN, NO₂, —OR$^{z1}$, —OC(O)R$^{z2}$, —OC(O)NR$^{z3}$R$^{z4}$, —SR$^{z1}$, —S(O)₂R$^{z1}$, —S(O)₂NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)₂R$^{z2}$, —N(R$^{z3}$)C(O)O(R$^{z2}$), —N(R$^{z3}$)C(O)NR$^{z3}$R$^{z4}$, —N(R$^{z3}$)S(O)₂NR$^{z3}$R$^{z4}$, —(C₁-C₆ alkylenyl)-OR$^{z1}$, —(C₁-C₆ alkylenyl)-OC(O)R$^{z2}$, —(C₁-C₆ alkylenyl)-OC(O)NR$^{z3}$R$^{z4}$, —(C₁-C₆ alkylenyl)-S(O)₂R$^{z1}$, —(C₁-C₆ alkylenyl)-S(O)₂NR$^{z3}$R$^{z4}$, —(C₁-C₆ alkylenyl)-C(O)R$^{z1}$, —(C₁-C₆ alkylenyl)-C(O)OR$^{z1}$, —(C₁-C₆ alkylenyl)-C(O)NR$^{z3}$R$^{z4}$, —(C₁-C₆ alkylenyl)-NR$^{z3}$R$^{z4}$, —(C₁-C₆ alkylenyl)-N(R$^{z3}$)C(O)R$^{z2}$, —(C₁-C₆ alkylenyl)-N(R$^{z3}$)S(O)₂R$^{z2}$, —(C₁-C₆ alkylenyl)-N(R$^{z3}$)C(O)O(R$^{z2}$), —(C₁-C₆ alkylenyl)-N(R$^{z3}$)C(O)NR$^{z3}$R$^{z4}$, —(C₁-C₆ alkylenyl)-N(R$^{z3}$)S(O)₂NR$^{z3}$R$^{z4}$, and —(C₁-C₆ alkylenyl)-CN;

R$^{z1}$, R$^{z3}$, and R$^{z4}$, at each occurrence, are each independently H, C₁-C₆ alkyl, or C₁-C₆ haloalkyl; and R$^{z2}$, at each occurrence, is independently C₁-C₆ alkyl or C₁-C₆ haloalkyl.

In certain embodiments are provided compounds of formula (IA)

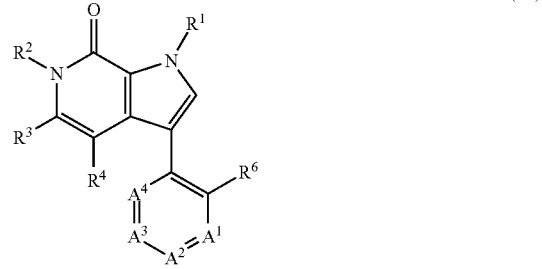

(IA)

wherein $A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is $C(R^7)$, $A^2$ is $C(R^8)$, $A^3$ is N, and $A^4$ is $C(R^{10})$; or
$A^1$ is $C(R^7)$, $A^2$ is $C(R^8)$, $A^3$ is $C(R^9)$, and $A^4$ is N;

$R^1$ is H, $C_1$-$C_3$ alkyl, or $C_1$-$C_3$ haloalkyl;

$R^2$ is H, $C_1$-$C_3$ alkyl, or $C_1$-$C_3$ haloalkyl;

$R^3$ is H, $C_1$-$C_6$ alkyl, $C_2$-$C_6$ alkenyl, $C_2$-$C_6$ alkynyl, halogen, —$OR^{3a}$, —$NR^{3b}R^{3c}$, —$N(R^{3b})C(O)R^{3d}$, —$N(R^{3b})C(O)NR^{3b}R^{3c}$, —$N(R^{3b})S(O)_2NR^{3b}R^{3c}$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of halogen, $G^1$, —$OR^{3a}$, and —$NR^{3b}R^{3c}$;

$R^{3a}$, $R^{3b}$, and $R^{3c}$, at each occurrence, are each independently H, $C_1$-$C_6$ alkyl, $C_1$-$C_6$ haloalkyl, $G^1$, —($C_1$-$C_6$ alkylenyl)-$G^1$, —($C_1$-$C_6$ alkylenyl)-CN, —($C_1$-$C_6$ alkylenyl)-$OR^{z1}$, or —($C_1$-$C_6$ alkylenyl)-$NR^{z3}R^{z4}$;

$R^{3d}$, at each occurrence, is independently $C_1$-$C_6$ alkyl, $C_1$-$C_6$ haloalkyl, $G^1$, or —($C_1$-$C_6$ alkylenyl)-$G^1$;

$G^1$, at each occurrence, is independently aryl, heteroaryl, heterocycle, cycloalkyl, or cycloalkenyl; and each $G^1$ is optionally substituted with 1, 2, 3, 4, or 5 $R^{1g}$ groups;

$R^4$ is H, $C_1$-$C_6$ alkyl, halogen, or $C_1$-$C_6$ haloalkyl;

$R^6$ is halogen, —$OR^a$, or —$NR^cR^d$;

$R^7$ is H, $C_1$-$C_6$ alkyl, $C_2$-$C_6$ alkenyl, $C_2$-$C_6$ alkynyl, halogen, $C_1$-$C_6$ haloalkyl, —CN, $NO_2$, or $C_3$-$C_6$ cycloalkyl optionally substituted with 1, 2, 3, 4, or 5 substituents independently selected from the group consisting of halogen, $C_1$-$C_3$ alkyl, or CN;

$R^8$ is H, halogen, —$OR^a$, —$NR^cR^d$, —$C(O)R^a$, —$C(O)NR^cR^d$, $G^2$, —($C_1$-$C_6$ alkylenyl)-$G^2$, or —($C_1$-$C_6$ alkylenyl)-$NR^cR^d$;

$R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$;

$R^{10}$ is H, $C_1$-$C_6$ alkyl, $C_2$-$C_6$ alkenyl, $C_2$-$C_6$ alkynyl, halogen, $C_1$-$C_6$ haloalkyl, —CN, or $NO_2$;

$R^a$, $R^c$, $R^d$, and $R^e$, at each occurrence, are each independently H, $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;

$R^b$, at each occurrence, is independently $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;

$G^2$, at each occurrence, are each independently aryl, heteroaryl, heterocycle, cycloalkyl, or cycloalkenyl; and each $G^2$ group is optionally substituted with 1, 2, 3, 4, or 5 $R^{2g}$ groups;

$R^{1g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)OR^{z1}$, —$C(O)(C_3$-$C_6$ cycloalkyl), —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —($C_1$-$C_6$ alkylenyl)-$OR^{z1}$, —($C_1$-$C_6$ alkylenyl)-$OC(O)R^{z2}$, —($C_1$-$C_6$ alkylenyl)-$OC(O)NR^{z3}R^{z4}$, —($C_1$-$C_6$ alkylenyl)-$S(O)_2R^{z1}$, —($C_1$-$C_6$ alkylenyl)-$S(O)_2NR^{z3}R^{z4}$, —($C_1$-$C_6$ alkylenyl)-$C(O)R^{z1}$, —($C_1$-$C_6$ alkylenyl)-$C(O)OR^{z1}$, —($C_1$-$C_6$ alkylenyl)-$C(O)NR^{z3}R^{z4}$, —($C_1$-$C_6$ alkylenyl)-$NR^{z3}R^{z4}$, —($C_1$-$C_6$ alkylenyl)-$N(R^{z3})C(O)R^{z2}$, —($C_1$-$C_6$ alkylenyl)-$N(R^{z3})S(O)_2R^{z2}$, —($C_1$-$C_6$ alkylenyl)-$N(R^{z3})C(O)O(R^{z2})$, —($C_1$-$C_6$ alkylenyl)-$N(R^{z3})C(O)NR^{z3}R^{z4}$, —($C_1$-$C_6$ alkylenyl)-$N(R^{z3})S(O)_2NR^{z3}R^{z4}$, —($C_1$-$C_6$ alkylenyl)-CN, or —O(phenyl); wherein the phenyl moiety and the $C_3$-$C_6$ cycloalkyl moiety are each optionally substituted with 1, 2, 3, or 4 substituents independently selected from the group consisting of $C_1$-$C_6$ alkyl, halogen, $C_1$-$C_6$ haloalkyl, —OH, —O(alkyl), —O(haloalkyl), CN, and $NO_2$;

$R^{2g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, oxo, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, —$N(R^{y3})S(O)_2NR^{y3}R^{y4}$, $G^{2b}$, —($C_1$-$C_6$ alkylenyl)-$OR^{y1}$, —($C_1$-$C_6$ alkylenyl)-$OC(O)R^{y2}$, —($C_1$-$C_6$ alkylenyl)-$OC(O)NR^{y3}R^{y4}$, —($C_1$-$C_6$ alkylenyl)-$S(O)_2R^{y1}$, —($C_1$-$C_6$ alkylenyl)-$S(O)_2NR^{y3}R^{y4}$, —($C_1$-$C_6$ alkylenyl)-$C(O)R^{y1}$, —($C_1$-$C_6$ alkylenyl)-$C(O)OR^{y1}$, —($C_1$-$C_6$ alkylenyl)-$C(O)NR^{y3}R^{y4}$, —($C_1$-$C_6$ alkylenyl)-$NR^{y3}R^{y4}$, —($C_1$-$C_6$ alkylenyl)-$N(R^{y3})C(O)R^{y2}$, —($C_1$-$C_6$ alkylenyl)-$N(R^{y3})S(O)_2R^{y2}$, —($C_1$-$C_6$ alkylenyl)-$N(R^{y3})C(O)O(R^{y2})$, —($C_1$-$C_6$ alkylenyl)-$N(R^{y3})C(O)NR^{y3}R^{y4}$, —($C_1$-$C_6$ alkylenyl)-$N(R^{y3})S(O)_2NR^{y3}R^{y4}$, —($C_1$-$C_6$ alkylenyl)-CN, or —($C_1$-$C_6$ alkylenyl)-$G^{2b}$;

$R^{y1}$, $R^{y3}$, and $R^{y4}$, at each occurrence, are each independently H, $C_1$-$C_6$ alkyl, $C_1$-$C_6$ haloalkyl, $G^{2b}$, or —($C_1$-$C_6$ alkylenyl)-$G^{2b}$;

$R^{y2}$, at each occurrence, is independently $C_1$-$C_6$ alkyl, $C_1$-$C_6$ haloalkyl, $G^{2b}$, or —($C_1$-$C_6$ alkylenyl)-$G^{2b}$;

$G^{2b}$, at each occurrence, is independently aryl, heteroaryl, cycloalkyl, cycloalkenyl, or heterocycle; and each $G^{2b}$ group is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$—$S(O)_2NR^{z3}R^{z4}$, —$C(O)R^{z1}$, —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —($C_1$-$C_6$ alkylenyl)-$OR^{z1}$, —($C_1$-$C_6$ alkylenyl)-$OC(O)R^{z2}$, —($C_1$-$C_6$ alkylenyl)-$OC(O)NR^{z3}R^{z4}$, —($C_1$-$C_6$ alkylenyl)-$S(O)_2R^{z1}$, —($C_1$-$C_6$ alkylenyl)-$S(O)_2NR^{z3}R^{z4}$, —($C_1$-$C_6$ alkylenyl)-$C(O)R^{z1}$, —($C_1$-$C_6$ alkylenyl)-$C(O)OR^{z1}$, —($C_1$-$C_6$ alkylenyl)-$C(O)NR^{z3}R^{z4}$, —($C_1$-$C_6$ alkylenyl)-$NR^{z3}R^{z4}$, —($C_1$-$C_6$ alkylenyl)-$N(R^{z3})C(O)R^{z2}$, —($C_1$-$C_6$ alkylenyl)-$N(R^{z3})S(O)_2R^{z2}$, —($C_1$-$C_6$ alkylenyl)-$N(R^{z3})C(O)O(R^{z2})$, —($C_1$-$C_6$ alkylenyl)-$N(R^{z3})C(O)NR^{z3}R^{z4}$, —($C_1$-$C_6$ alkylenyl)-$N(R^{z3})S(O)_2NR^{z3}R^{z4}$, and —($C_1$-$C_6$ alkylenyl)-CN;

$R^{z1}$, $R^{z3}$, and $R^{z4}$, at each occurrence, are each independently H, $C_1$-$C_6$ alkyl, or $C_1$-$C_6$ haloalkyl; and $R^{z2}$, at each occurrence, is independently $C_1$-$C_6$ alkyl or $C_1$-$C_6$ haloalkyl.

In some further embodiments, $A^1$ is $C(R^7)$, $A^2$ is $C(R^8)$, $A^3$ is $C(R^9)$, and $A^4$ is $C(R^{10})$;

In some further embodiments, $A^1$ is N, $A^2$ is $C(R^8)$, $A^3$ is $C(R^9)$, and $A^4$ is $C(R^{10})$.

In certain embodiments are provided compounds of formula (IA), wherein
$R^1$ is methyl; and
$R^2$ is H or methyl.

In certain embodiments are provided compounds of formula (IA), wherein
$R^1$ is methyl;
$R^2$ is H;
$R^3$ is H, unsubstituted $C_1$-$C_3$ alkyl, or halogen; and
$R^4$ is H, $C_1$-$C_3$ alkyl, or halogen.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen; and
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen; and
$R^{10}$ is H or $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$OR^a$ or $NR^cR^d$, wherein
　$R^a$ and $R^d$ are each independently $C_1$-$C_6$ haloalkyl, $G^2$, or $C_1$-$C_6$ alkyl wherein the $C_1$-$C_6$ alkyl is optionally substituted with one $G^2$ group; and
　$R^c$ is H or unsubstituted $C_1$-$C_6$ alkyl; and
$R^9$ is —$N(R^e)S(O)_2R^b$, —$S(O)_2R^a$, —$S(O)_2NR^cR^d$, —($C_1$-$C_6$ alkylenyl)-$G^2$ wherein $G^2$ is optionally substituted heterocycle, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$OR^a$ or $NR^cR^d$, wherein
　$R^a$ and $R^d$ are each independently $C_1$-$C_6$ haloalkyl or unsubstituted $C_1$-$C_6$ alkyl; and
　$R^c$ is H or unsubstituted $C_1$-$C_3$ alkyl; and
$R^9$ is —$S(O)_2R^a$ or $(CH_2)$—$SO_2R^a$, wherein $R^a$, at each occurrence, is independently unsubstituted $C_1$-$C_3$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$OR^a$ or $NR^cR^d$, wherein
　$R^a$ is $G^2$ or $C_1$-$C_3$ alkyl wherein the $C_1$-$C_3$ alkyl is substituted with one $G^2$ group; and $G^2$ is aryl, $C_4$-$C_6$ heterocycle, $C_3$-$C_6$ cycloalkyl, $C_5$-$C_6$ heteroaryl, or adamantyl, each of which is optionally substituted;
　$R^c$ is H or unsubstituted $C_1$-$C_3$ alkyl; and
　$R^d$ is optionally substituted phenyl or $C_1$-$C_3$ alkyl wherein the $C_1$-$C_3$ alkyl is substituted with one $G^2$ group; and $G^2$ is phenyl, $C_3$-$C_6$ cycloalkyl, or bicyclo[2.2.1]heptyl, each of which is optionally substituted; and
$R^9$ is —$N(R^e)S(O)_2R^b$, —$S(O)_2R^a$, —$S(O)_2NR^cR^d$, —($C_1$-$C_3$ alkylenyl)-$G^2$ wherein $G^2$ is optionally substituted $C_4$-$C_6$ heterocycle; —($C_1$-$C_3$ alkylenyl)-$S(O)_2R^a$, —($C_1$-$C_3$ alkylenyl)-$S(O)_2NR^cR^d$, —($C_1$-$C_3$ alkylenyl)-$NR^cR^d$, or —($C_1$-$C_3$ alkylenyl)-$N(R^e)S(O)_2R^b$; wherein
　$R^a$ and $R^b$ are each independently $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted;
　$R^e$ and $R^c$ are each independently H or unsubstituted $C_1$-$C_3$ alkyl; and
　$R^d$ is H, $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;

$R^6$ is —$OR^a$; wherein
  $R^a$ is $G^2$, and
  $G^2$ is optionally substituted phenyl or optionally substituted $C_3$-$C_6$ cycloalkyl; and
$R^9$ is —$N(R^e)S(O)_2R^b$, —$S(O)_2R^a$, —$(C_1$-$C_3$ alkylenyl)-$S(O)_2R^a$, —$(C_1$-$C_3$ alkylenyl)-$S(O)_2NR^cR^d$, or —$(C_1$-$C_3$ alkylenyl)-$N(R^e)S(O)_2R^b$; wherein
  $R^a$ is unsubstituted $C_1$-$C_3$ alkyl or optionally substituted $C_4$-$C_6$ heterocycle,
  $R^b$ is unsubstituted $C_1$-$C_3$ alkyl or optionally substituted benzyl;
  $R^c$ is H or unsubstituted $C_1$-$C_3$ alkyl;
  $R^d$ is H or unsubstituted $C_1$-$C_3$ alkyl; and
  $R^e$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H;
$R^4$ is H;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$OR^a$; wherein
  $R^a$ is $G^2$, and
  $G^2$ is phenyl substituted with 1 or 2 halogen; and
$R^9$ is —$N(R^e)S(O)_2R^b$, —$S(O)_2R^a$, or —$(CH_2)$—$S(O)_2R^a$, wherein
  $R^a$ and $R^b$ are each independently unsubstituted $C_1$-$C_3$ alkyl, and
  $R^e$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H;
$R^4$ is H;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$OR^a$; wherein
  $R^a$ is $G^2$, and
  $G^2$ is cyclohexyl substituted with one or two substituents selected from the group consisting of —OH, —$O(CH_3)$, and F; and
$R^9$ is —$N(R^e)S(O)_2R^b$, —$S(O)_2R^a$, or —$(CH_2)$—$S(O)_2R^a$, wherein
  $R^a$ and $R^b$ are each independently unsubstituted $C_1$-$C_3$ alkyl, and
  $R^e$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H, unsubstituted $C_1$-$C_3$ alkyl, or halogen;
$R^4$ is H, $C_1$-$C_3$ alkyl, or halogen;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$NR^cR^d$, wherein
  $R^c$ is H or unsubstituted $C_1$-$C_3$ alkyl; and
  $R^d$ is optionally substituted phenyl or $C_1$-$C_3$ alkyl wherein the $C_1$-$C_3$ alkyl is substituted with one $G^2$ group, wherein $G^2$ is optionally substituted $C_3$-$C_6$ cycloalkyl, and
$R^9$ is —$N(R^e)S(O)_2R^b$, —$S(O)_2R^a$, —$(C_1$-$C_3$ alkylenyl)-$S(O)_2R^a$, —$(C_1$-$C_3$ alkylenyl)-$S(O)_2NR^cR^d$, or —$(C_1$-$C_3$ alkylenyl)-$N(R^e)S(O)_2R^b$; wherein
  $R^a$ is unsubstituted $C_1$-$C_3$ alkyl or optionally substituted $C_4$-$C_6$ heterocycle,
  $R^b$ is unsubstituted $C_1$-$C_3$ alkyl or optionally substituted benzyl;
  $R^c$ is H or unsubstituted $C_1$-$C_3$ alkyl;
  $R^d$ is H or unsubstituted $C_1$-$C_3$ alkyl; and
  $R^e$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is H;
$R^4$ is H;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$;
$R^7$ is H;
$R^8$ is H or halogen;
$R^{10}$ is H or $C_1$-$C_6$ alkyl;
$R^6$ is —$NR^cR^d$, wherein
  $R^c$ is H or methyl; and
  $R^d$ is phenyl substituted with 1 or 2 halogen, or $R^d$ is $C_1$-$C_3$ alkyl wherein the $C_1$-$C_3$ alkyl is substituted with one $G^2$ group, and $G^2$ is optionally substituted cyclopropyl, and
$R^9$ is —$(CH_2)$—$S(O)_2R^a$; wherein $R^a$ is unsubstituted $C_1$-$C_3$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein
$R^1$ is methyl;
$R^2$ is H;
$R^3$ is —$C(O)R^{3a}$, —$C(O)NR^{3b}R^{3c}$, $C_4$-$C_6$ heterocycle, or $C_1$-$C_3$ alkyl which is substituted with $C_4$-$C_6$ heterocycle; wherein each of the $C_4$-$C_6$ heterocycle moieties is optionally substituted with 1, 2, 3, 4, or 5 $R^{1g}$;
$R^{3a}$ is $C_4$-$C_6$ heterocycle which is optionally substituted with 1, 2, 3, 4, or 5 $R^{1g}$;
$R^{3b}$ is H or $C_1$-$C_6$ alkyl;
$R^{3c}$ is H, $C_1$-$C_6$ alkyl, —$(C_1$-$C_6$ alkylenyl)-$OR^{z1}$, —$(C_1$-$C_6$ alkylenyl)-$NR^{z3}R^{z4}$, —$(C_1$-$C_6$ alkylenyl)-CN, or —$(C_1$-

$C_6$ alkylenyl)-$G^1$; wherein $G^1$ is $C_4$-$C_6$ heterocycle, $C_5$-$C_6$ heteroaryl, $C_3$-$C_6$ cycloalkyl, or phenyl; each of which is optionally substituted with 1, 2, 3, 4, or 5 $R^{1g}$;

$R^6$ is —$OR^a$ or —$NR^cR^d$; wherein $R^a$ and $R^d$ are each independently $G^2$ or $C_1$-$C_6$ alkyl substituted with a $G^2$ group; wherein $G^2$ is phenyl, $C_3$-$C_6$ cycloalkyl, $C_4$-$C_6$ heterocycle, or $C_5$-$C_6$ heteroaryl; each of which is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, and —$N(R^{y3})S(O)_2NR^{y3}R^{y4}$;

$R^c$ is hydrogen or unsubstituted $C_1$-$C_6$ alkyl;

$R^{y1}$, $R^{y3}$, and $R^{y4}$, at each occurrence, are each independently H, $C_1$-$C_6$ alkyl, or $C_1$-$C_6$ haloalkyl; and $R^{y2}$, at each occurrence, is independently $C_1$-$C_6$ alkyl or $C_1$-$C_6$ haloalkyl; and $R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-$N(R^e)S(O)_2R^b$; wherein $R^c$, $R^d$, and $R^e$, at each occurrence, are each independently H or unsubstituted $C_1$-$C_6$ alkyl; and $R^a$ and $R^b$, at each occurrence, are independently $C_1$-$C_6$ haloalkyl, or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In certain embodiments are provided compounds of formula (IA) wherein $R^1$ is methyl;

$R^2$ is H;

$R^3$ is —$C(O)R^{3a}$ or —$C(O)NR^{3b}R^{3c}$;

$R^{3a}$ is $C_4$-$C_6$ heterocycle which is optionally substituted with 1, 2, 3, 4, or 5 $R^{1g}$;

$R^{3b}$ is H or $C_1$-$C_6$ alkyl;

$R^{3c}$ is H, $C_1$-$C_6$ alkyl, —($C_1$-$C_6$ alkylenyl)-$OR^{z1}$, —($C_1$-$C_6$ alkylenyl)-$NR^{z3}R^{z4}$, —($C_1$-$C_6$ alkylenyl)-CN, or —($C_1$-$C_6$ alkylenyl)-$G^1$; wherein $G^1$ is $C_4$-$C_6$ heterocycle, $C_5$-$C_6$ heteroaryl, $C_3$-$C_6$ cycloalkyl, or phenyl; each of which is optionally substituted with 1, 2, 3, 4, or 5 $R^{1g}$;

$A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$;

$R^6$ is —$OR^a$ or —$NR^cR^d$; wherein $R^a$ and $R^d$ are each independently phenyl, pyridinyl, or $C_1$-$C_3$ alkyl substituted with a $C_3$-$C_6$ cycloalkyl; wherein the phenyl, pyridinyl, and the $C_3$-$C_6$ cycloalkyl are optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, and —$N(R^{y3})S(O)_2NR^{y3}R^{y4}$;

$R^c$ is hydrogen or unsubstituted $C_1$-$C_3$ alkyl;

$R^{y1}$, $R^{y3}$, and $R^{y4}$, at each occurrence, are each independently H, $C_1$-$C_6$ alkyl, or $C_1$-$C_6$ haloalkyl; and $R^{y2}$, at each occurrence, is independently $C_1$-$C_6$ alkyl or $C_1$-$C_6$ haloalkyl;

$R^7$ is H;

$R^8$ is H or halogen;

$R^{10}$ is H or $C_1$-$C_6$ alkyl; and $R^9$ is —$N(R^e)S(O)_2R^b$ or —($C_1$-$C_6$ alkylenyl)-$S(O)_2R^a$; wherein $R^e$ is H or unsubstituted $C_1$-$C_3$ alkyl; and $R^a$ and $R^b$, are each independently $C_1$-$C_3$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:

1-methyl-3-(2-phenoxyphenyl)-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)phenyl]methanesulfonamide;

N-[4-(2,4-difluorophenoxy)-3-(1-methyl-7-oxo-6,7-dihydro-1H-pyrrolo[2,3-c]pyridin-3-yl)phenyl]propane-2-sulfonamide;

N-[4-(2,4-difluorophenoxy)-3-(1-methyl-7-oxo-6,7-dihydro-1H-pyrrolo[2,3-c]pyridin-3-yl)phenyl]ethanesulfonamide;

N-[4-(4-chlorophenoxy)-3-(1-methyl-7-oxo-6,7-dihydro-1H-pyrrolo[2,3-c]pyridin-3-yl)phenyl]ethanesulfonamide;

N-{4-[(trans-4-methoxycyclohexyl)oxy]-3-(1-methyl-7-oxo-6,7-dihydro-1H-pyrrolo[2,3-c]pyridin-3-yl)phenyl}ethanesulfonamide;
N-[3-(1-methyl-7-oxo-6,7-dihydro-1H-pyrrolo[2,3-c]pyridin-3-yl)-4-(tetrahydro-2H-pyran-4-yloxy)phenyl]ethanesulfonamide;
N-{4-[(4,4-difluorocyclohexyl)oxy]-3-(1-methyl-7-oxo-6,7-dihydro-1H-pyrrolo[2,3-c]pyridin-3-yl)phenyl}ethanesulfonamide;
N-{4-[(cis-4-methoxycyclohexyl)oxy]-3-(1-methyl-7-oxo-6,7-dihydro-1H-pyrrolo[2,3-c]pyridin-3-yl)phenyl}ethanesulfonamide;
N-[3-(1-methyl-7-oxo-6,7-dihydro-1H-pyrrolo[2,3-c]pyridin-3-yl)-4-(oxetan-3-yloxy)phenyl]ethanesulfonamide;
N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide;
N-[2-(2,4-difluorophenoxy)-4-fluoro-5-(1-methyl-7-oxo-6,7-dihydro-1H-pyrrolo[2,3-c]pyridin-3-yl)phenyl]methanesulfonamide;
N-[2,4-bis(2,4-difluorophenoxy)-5-(1-methyl-7-oxo-6,7-dihydro-1H-pyrrolo[2,3-c]pyridin-3-yl)phenyl]methanesulfonamide;
N-[4-(cyclopropylmethoxy)-2-methyl-3-(1-methyl-7-oxo-6,7-dihydro-1H-pyrrolo[2,3-c]pyridin-3-yl)phenyl]ethanesulfonamide;
N-[4-(4-fluorophenoxy)-3-(1-methyl-7-oxo-6,7-dihydro-1H-pyrrolo[2,3-c]pyridin-3-yl)phenyl]ethanesulfonamide;
N-[4-(4-cyanophenoxy)-3-(1-methyl-7-oxo-6,7-dihydro-1H-pyrrolo[2,3-c]pyridin-3-yl)phenyl]methanesulfonamide;
3-[2-(2,4-difluorophenoxy)-5-(methylsulfonyl)phenyl]-1-methyl-1,6-dihydro-7H-pyrrolo[2,3-c]pyridin-7-one;
1-methyl-3-[5-(methylsulfonyl)-2-phenoxyphenyl]-1,6-dihydro-7H-pyrrolo[2,3-c]pyridin-7-one;
3-[2-(3,4-difluorophenoxy)-5-(methylsulfonyl)phenyl]-1-methyl-1,6-dihydro-7H-pyrrolo[2,3-c]pyridin-7-one;
3-[2-methoxy-5-(methylsulfonyl)phenyl]-1-methyl-1,6-dihydro-7H-pyrrolo[2,3-c]pyridin-7-one;
3-[2-(cyclopropylmethoxy)-5-(methylsulfonyl)phenyl]-1-methyl-1,6-dihydro-7H-pyrrolo[2,3-c]pyridin-7-one;
1-methyl-3-[5-(methylsulfonyl)-2-(tetrahydrofuran-3-yloxy)phenyl]-1,6-dihydro-7H-pyrrolo[2,3-c]pyridin-7-one;
1-methyl-3-[5-(methylsulfonyl)-2-(tetrahydrofuran-3-ylmethoxy)phenyl]-1,6-dihydro-7H-pyrrolo[2,3-c]pyridin-7-one;
1-methyl-3-[5-(methylsulfonyl)-2-(tetrahydro-2H-pyran-4-yloxy)phenyl]-1,6-dihydro-7H-pyrrolo[2,3-c]pyridin-7-one;
3-{2-[(4,4-difluorocyclohexyl)oxy]-5-(methylsulfonyl)phenyl}-1-methyl-1,6-dihydro-7H-pyrrolo[2,3-c]pyridin-7-one;
1-methyl-3-[5-(methylsulfonyl)-2-(tetrahydro-2H-pyran-3-yloxy)phenyl]-1,6-dihydro-7H-pyrrolo[2,3-c]pyridin-7-one;
3-[2-(2,2-dimethylpropoxy)-5-(methylsulfonyl)phenyl]-1-methyl-1,6-dihydro-7H-pyrrolo[2,3-c]pyridin-7-one;
3-[2-(cyclobutylmethoxy)-5-(methylsulfonyl)phenyl]-1-methyl-1,6-dihydro-7H-pyrrolo[2,3-c]pyridin-7-one;
1-methyl-3-{2-[(1-methylcyclopropyl)methoxy]-5-(methylsulfonyl)phenyl}-1,6-dihydro-7H-pyrrolo[2,3-c]pyridin-7-one;
1-methyl-3-[5-(methylsulfonyl)-2-(oxetan-3-ylmethoxy)phenyl]-1,6-dihydro-7H-pyrrolo[2,3-c]pyridin-7-one;
1-methyl-3-[5-(methylsulfonyl)-2-(tetrahydro-2H-pyran-4-ylmethoxy)phenyl]-1,6-dihydro-7H-pyrrolo[2,3-c]pyridin-7-one;
3-[2-(2-cyclopropylethoxy)-5-(methylsulfonyl)phenyl]-1-methyl-1,6-dihydro-7H-pyrrolo[2,3-c]pyridin-7-one;
3-{2-[(cis-4-hydroxycyclohexyl)oxy]-5-(methylsulfonyl)phenyl}-1-methyl-1,6-dihydro-7H-pyrrolo[2,3-c]pyridin-7-one;
3-{2-[(trans-4-hydroxycyclohexyl)oxy]-5-(methylsulfonyl)phenyl}-1-methyl-1,6-dihydro-7H-pyrrolo[2,3-c]pyridin-7-one;
3-[2-(2-cyclopentylethoxy)-5-(methylsulfonyl)phenyl]-1-methyl-1,6-dihydro-7H-pyrrolo[2,3-c]pyridin-7-one;
3-[2-(2-cyclohexylethoxy)-5-(methylsulfonyl)phenyl]-1-methyl-1,6-dihydro-7H-pyrrolo[2,3-c]pyridin-7-one;
1-methyl-3-[5-(methylsulfonyl)-2-(2-phenylethoxy)phenyl]-1,6-dihydro-7H-pyrrolo[2,3-c]pyridin-7-one;
3-[2-(2,3-dihydro-1H-inden-2-yloxy)-5-(methylsulfonyl)phenyl]-1-methyl-1,6-dihydro-7H-pyrrolo[2,3-c]pyridin-7-one;
1-methyl-3-{5-(methylsulfonyl)-2-[2-(thiophen-2-yl)ethoxy]phenyl}-1,6-dihydro-7H-pyrrolo[2,3-c]pyridin-7-one;
3-[2-(3,3-dimethylbutoxy)-5-(methylsulfonyl)phenyl]-1-methyl-1,6-dihydro-7H-pyrrolo[2,3-c]pyridin-7-one;
3-{2-[(4,4-difluorocyclohexyl)methoxy]-5-(methylsulfonyl)phenyl}-1-methyl-1,6-dihydro-7H-pyrrolo[2,3-c]pyridin-7-one;
3-{2-[(2,2-difluorocyclopropyl)methoxy]-5-(methylsulfonyl)phenyl}-1-methyl-1,6-dihydro-7H-pyrrolo[2,3-c]pyridin-7-one;
3-{2-[(2,2-difluorocyclopropyl)methoxy]-5-(methylsulfonyl)phenyl}-1,6-dimethyl-1,6-dihydro-7H-pyrrolo[2,3-c]pyridin-7-one;
3-{2-[(cyclopropylmethyl)amino]-5-(methylsulfonyl)phenyl}-1-methyl-1,6-dihydro-7H-pyrrolo[2,3-c]pyridin-7-one;
3-{2-[(cyclopropylmethyl)(methyl)amino]-5-(methylsulfonyl)phenyl}-1-methyl-1,6-dihydro-7H-pyrrolo[2,3-c]pyridin-7-one;
4-({[2-(1-methyl-7-oxo-6,7-dihydro-1H-pyrrolo[2,3-c]pyridin-3-yl)-4-(methylsulfonyl)phenyl]amino}methyl)benzonitrile;
3-{2-[(cyclohexylmethyl)amino]-5-(methylsulfonyl)phenyl}-1-methyl-1,6-dihydro-7H-pyrrolo[2,3-c]pyridin-7-one;
3-[2-(4-chlorophenoxy)-5-(ethylsulfonyl)phenyl]-1-methyl-1,6-dihydro-7H-pyrrolo[2,3-c]pyridin-7-one;
3-[2-(2,4-difluorophenoxy)-5-(ethylsulfonyl)phenyl]-1-methyl-1,6-dihydro-7H-pyrrolo[2,3-c]pyridin-7-one;
3-[2-(cyclopropylmethoxy)-6-methylphenyl]-1-methyl-1,6-dihydro-7H-pyrrolo[2,3-c]pyridin-7-one;
4-(2,4-difluorophenoxy)-3-(1-methyl-7-oxo-6,7-dihydro-1H-pyrrolo[2,3-c]pyridin-3-yl)benzenesulfonamide;
3-{2-(2,4-difluorophenoxy)-5-[(methylsulfonyl)methyl]phenyl}-1-methyl-1,6-dihydro-7H-pyrrolo[2,3-c]pyridin-7-one;
3-{2-(2,4-difluorophenoxy)-5-[(ethylsulfonyl)methyl]phenyl}-1-methyl-1,6-dihydro-7H-pyrrolo[2,3-c]pyridin-7-one;
3-{2-(2,4-difluorophenoxy)-5-[2-(ethylsulfonyl)propan-2-yl]phenyl}-1-methyl-1,6-dihydro-7H-pyrrolo[2,3-c]pyridin-7-one;
3-{2-(2,4-difluorophenoxy)-5-[1-(ethylsulfonyl)ethyl]phenyl}-1-methyl-1,6-dihydro-7H-pyrrolo[2,3-c]pyridin-7-one;

3-{2-(2,4-difluorophenoxy)-5-[(1R)-1-(ethylsulfonyl)ethyl]phenyl}-1-methyl-1,6-dihydro-7H-pyrrolo[2,3-c]pyridin-7-one;

3-{2-(2,4-difluorophenoxy)-5-[(1S)-1-(ethylsulfonyl)ethyl]phenyl}-1-methyl-1,6-dihydro-7H-pyrrolo[2,3-c]pyridin-7-one;

3-{2-(2,4-difluorophenoxy)-5-[(phenylsulfonyl)methyl]phenyl}-1-methyl-1,6-dihydro-7H-pyrrolo[2,3-c]pyridin-7-one;

3-[2-(2,4-difluorophenoxy)-5-(ethylsulfonyl)pyridin-3-yl]-1-methyl-1,6-dihydro-7H-pyrrolo[2,3-c]pyridin-7-one;

3-{2-(2,4-difluorophenoxy)-5-[(methylsulfonyl)methyl]pyridin-3-yl}-1-methyl-1,6-dihydro-7H-pyrrolo[2,3-c]pyridin-7-one;

3-[2-(4-fluorophenoxy)-5-(methylsulfonyl)phenyl]-1-methyl-1,6-dihydro-7H-pyrrolo[2,3-c]pyridin-7-one;

3-[2-(4-tert-butylphenoxy)-5-(methylsulfonyl)phenyl]-1-methyl-1,6-dihydro-7H-pyrrolo[2,3-c]pyridin-7-one;

1-methyl-3-[5-(methylsulfonyl)-2-(naphthalen-2-yloxy)phenyl]-1,6-dihydro-7H-pyrrolo[2,3-c]pyridin-7-one;

1-methyl-3-[5-(methylsulfonyl)-2-(2,2,3,3,3-pentafluoropropoxy)phenyl]-1,6-dihydro-7H-pyrrolo[2,3-c]pyridin-7-one;

1-methyl-3-[5-(methylsulfonyl)-2-{2-[tricyclo[3.3.1.1$^{3,7}$]dec-1-yl]ethoxy}phenyl]-1,6-dihydro-7H-pyrrolo[2,3-c]pyridin-7-one;

3-[2-(3-cyclopentylpropoxy)-5-(methylsulfonyl)phenyl]-1-methyl-1,6-dihydro-7H-pyrrolo[2,3-c]pyridin-7-one;

3-{2-[(1-acetylpiperidin-4-yl)oxy]-5-(methylsulfonyl)phenyl}-1-methyl-1,6-dihydro-7H-pyrrolo[2,3-c]pyridin-7-one;

3-{2-[(cyclopentylmethyl)amino]-5-(methylsulfonyl)phenyl}-1-methyl-1,6-dihydro-7H-pyrrolo[2,3-c]pyridin-7-one;

1-methyl-3-[5-(methylsulfonyl)-2-[(2,2,2-trifluoroethyl)amino]phenyl]-1,6-dihydro-7H-pyrrolo[2,3-c]pyridin-7-one;

3-{2-[(2,2,3,3,4,4,4-heptafluorobutyl)amino]-5-(methylsulfonyl)phenyl}-1-methyl-1,6-dihydro-7H-pyrrolo[2,3-c]pyridin-7-one;

3-[2-{[(1S,4R)-bicyclo[2.2.1]hept-2-ylmethyl]amino}-5-(methylsulfonyl)phenyl]-1-methyl-1,6-dihydro-7H-pyrrolo[2,3-c]pyridin-7-one;

3-{2-[(2-cyclopentylethyl)amino]-5-(methylsulfonyl)phenyl}-1-methyl-1,6-dihydro-7H-pyrrolo[2,3-c]pyridin-7-one;

3-[2-(2-chloro-4-methylphenoxy)-5-(ethylsulfonyl)phenyl]-1-methyl-1,6-dihydro-7H-pyrrolo[2,3-c]pyridin-7-one;

3-[(5-(ethylsulfonyl)-2-(pyridin-4-yloxy)phenyl]-1-methyl-1,6-dihydro-7H-pyrrolo[2,3-c]pyridin-7-one;

3-{2-[(4,6-dimethylpyridin-3-yl)oxy]-5-(ethylsulfonyl)phenyl}-1-methyl-1,6-dihydro-7H-pyrrolo[2,3-c]pyridin-7-one;

3-[2-(3,4-dichlorophenoxy)-5-(ethylsulfonyl)phenyl]-1-methyl-1,6-dihydro-7H-pyrrolo[2,3-c]pyridin-7-one;

3-{5-(ethylsulfonyl)-2-[4-(trifluoromethyl)phenoxy]phenyl}-1-methyl-1,6-dihydro-7H-pyrrolo[2,3-c]pyridin-7-one;

4-[(4-(ethylsulfonyl)-2-(1-methyl-7-oxo-6,7-dihydro-1H-pyrrolo[2,3-c]pyridin-3-yl)phenoxy]benzonitrile;

3-[2-(4-chloro-3-ethylphenoxy)-5-(ethylsulfonyl)phenyl]-1-methyl-1,6-dihydro-7H-pyrrolo[2,3-c]pyridin-7-one;

4-[4-(ethylsulfonyl)-2-(1-methyl-7-oxo-6,7-dihydro-1H-pyrrolo[2,3-c]pyridin-3-yl)phenoxy]-3-methoxybenzonitrile;

3-[(5-(ethylsulfonyl)-2-(pyridin-3-yloxy)phenyl]-1-methyl-1,6-dihydro-7H-pyrrolo[2,3-c]pyridin-7-one;

3-[2-(2,4-dichlorophenoxy)-5-(ethylsulfonyl)phenyl]-1-methyl-1,6-dihydro-7H-pyrrolo[2,3-c]pyridin-7-one;

2-[4-(ethylsulfonyl)-2-(1-methyl-7-oxo-6,7-dihydro-1H-pyrrolo[2,3-c]pyridin-3-yl)phenoxy]benzonitrile;

3-[2-(2,3-dichlorophenoxy)-5-(ethylsulfonyl)phenyl]-1-methyl-1,6-dihydro-7H-pyrrolo[2,3-c]pyridin-7-one;

3-[2-(2-chloro-4-methoxyphenoxy)-5-(ethylsulfonyl)phenyl]-1-methyl-1,6-dihydro-7H-pyrrolo[2,3-c]pyridin-7-one;

3-{5-(ethylsulfonyl)-2-[(6-methylpyrazin-2-yl)oxy]phenyl}-1-methyl-1,6-dihydro-7H-pyrrolo[2,3-c]pyridin-7-one;

3-[(5-(ethylsulfonyl)-2-(pyridazin-4-yloxy)phenyl]-1-methyl-1,6-dihydro-7H-pyrrolo[2,3-c]pyridin-7-one;

3-[(5-(ethylsulfonyl)-2-(pyrimidin-5-yloxy)phenyl]-1-methyl-1,6-dihydro-7H-pyrrolo[2,3-c]pyridin-7-one;

3-{5-(ethylsulfonyl)-2-[(3-methylpyrazin-2-yl)oxy]phenyl}-1-methyl-1,6-dihydro-7H-pyrrolo[2,3-c]pyridin-7-one;

3-{5-(ethylsulfonyl)-2-[(1,3,5-trimethyl-1H-pyrazol-4-yl)oxy]phenyl}-1-methyl-1,6-dihydro-7H-pyrrolo[2,3-c]pyridin-7-one;

5-chloro-3-{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one;

3,5-bis{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-(3,5-dimethyl-1,2-oxazol-4-yl)-1-methyl-1,6-dihydro-7H-pyrrolo[2,3-c]pyridin-7-one;

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]methanesulfonamide;

3-[2-(cyclopropylmethoxy)-5-(2,3-dihydro-1H-indol-1-ylsulfonyl)phenyl]-1-methyl-1,6-dihydro-7H-pyrrolo[2,3-c]pyridin-7-one;

3-[6-(cyclopropylmethoxy)-1H-indol-7-yl]-1-methyl-1,6-dihydro-7H-pyrrolo[2,3-c]pyridin-7-one;

ethyl 5-(cyclopropylmethoxy)-4-(1-methyl-7-oxo-6,7-dihydro-1H-pyrrolo[2,3-c]pyridin-3-yl)-1H-indole-2-carboxylate;

1-[4-(2,4-difluorophenoxy)-3-(1-methyl-7-oxo-6,7-dihydro-1H-pyrrolo[2,3-c]pyridin-3-yl)phenyl]-N-methylmethanesulfonamide;

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide;

N-cyclohexyl-1-[4-(2,4-difluorophenoxy)-3-(1-methyl-7-oxo-6,7-dihydro-1H-pyrrolo[2,3-c]pyridin-3-yl)phenyl]methanesulfonamide;

3-{2-(2,4-difluorophenoxy)-5-[(piperidin-1-ylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]-N-(1,3-thiazol-2-yl)methanesulfonamide;

3-[2-(2,4-difluorophenoxy)-5-(piperazin-1-ylmethyl)phenyl]-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)benzyl]ethanesulfonamide;

5-(cyclopropylmethoxy)-N-methyl-4-(1-methyl-7-oxo-6,7-dihydro-1H-pyrrolo[2,3-c]pyridin-3-yl)-1H-indole-2-carboxamide;

4-chloro-3-[2-(2,4-difluorophenoxy)-5-(methylsulfonyl)phenyl]-1-methyl-1,6-dihydro-7H-pyrrolo[2,3-c]pyridin-7-one;

4-chloro-3-[2-(2-cyclopropylethoxy)-5-(methylsulfonyl)phenyl]-1-methyl-1,6-dihydro-7H-pyrrolo[2,3-c]pyridin-7-one;

3-{2-[(cyclopropylmethyl)amino]-5-[(methylsulfonyl)methyl]phenyl}-1-methyl-1,6-dihydro-7H-pyrrolo[2,3-c]pyridin-7-one;

3-{5-[(4-aminopiperidin-1-yl)methyl]-2-(2,4-difluorophenoxy)phenyl}-1-methyl-1,6-dihydro-7H-pyrrolo[2,3-c]pyridin-7-one;

3-{2-(2,4-difluorophenoxy)-5-[(piperidin-4-ylamino)methyl]phenyl}-1-methyl-1,6-dihydro-7H-pyrrolo[2,3-c]pyridin-7-one;

3-[2-(2,4-difluorophenoxy)-5-{[4-(dimethylamino)piperidin-1-yl]methyl}phenyl]-1-methyl-1,6-dihydro-7H-pyrrolo[2,3-c]pyridin-7-one;

3-[2-(2,4-difluorophenoxy)-5-{[(3,3-dimethylbutyl)amino]methyl}phenyl]-1-methyl-1,6-dihydro-7H-pyrrolo[2,3-c]pyridin-7-one;

3-{2-(2,4-difluorophenoxy)-5[(4-methoxypiperidin-1-yl)methyl]phenyl}-1-methyl-1,6-dihydro-7H-pyrrolo[2,3-c]pyridin-7-one;

3-{2-(2,4-difluorophenoxy)-5[(4-methylpiperazin-1-yl)methyl]phenyl}-1-methyl-1,6-dihydro-7H-pyrrolo[2,3-c]pyridin-7-one;

3-[2-(2,4-difluorophenoxy)-5-{[(3-methylbutyl)amino]methyl}phenyl]-1-methyl-1,6-dihydro-7H-pyrrolo[2,3-c]pyridin-7-one;

3-[5-{[(cyclopropylmethyl)amino]methyl]-2-(2,4-difluorophenoxy)phenyl}-1-methyl-1,6-dihydro-7H-pyrrolo[2,3-c]pyridin-7-one;

3-[2-(2,4-difluorophenoxy)-5-{[(1H-imidazol-4-ylmethyl)amino]methyl}phenyl]-1-methyl-1,6-dihydro-7H-pyrrolo[2,3-c]pyridin-7-one;

3-[(5-(chloromethyl)-2-(2,4-difluorophenoxy)phenyl]-1-methyl-1,6-dihydro-7H-pyrrolo[2,3-c]pyridin-7-one;

3-{2-[(4-fluorophenyl)amino]-5-[(methylsulfonyl)methyl]phenyl}-1-methyl-1,6-dihydro-7H-pyrrolo[2,3-c]pyridin-7-one;

3-{2-[(2,4-difluorophenyl)amino]-5-[(methylsulfonyl)methyl]phenyl}-1-methyl-1,6-dihydro-7H-pyrrolo[2,3-c]pyridin-7-one;

3-[2-(2,4-difluorophenoxy)-5-(methylsulfonyl)phenyl]-1,4-dimethyl-1,6-dihydro-7H-pyrrolo[2,3-c]pyridin-7-one;

3-[2-(2-cyclopropylethoxy)-5-(methylsulfonyl)phenyl]-1,4-dimethyl-1,6-dihydro-7H-pyrrolo[2,3-c]pyridin-7-one;

3-{2-(cyclopropylmethoxy)-5-[(3,3-difluoroazetidin-1-yl)sulfonyl]phenyl}-1-methyl-1,6-dihydro-7H-pyrrolo[2,3-c]pyridin-7-one;

5-[(1Z)-2-chloro-4-hydroxybut-1-en-1-yl]-3-[2-(2,4-difluorophenoxy)-5-(ethylsulfonyl)phenyl]-1-methyl-1,6-dihydro-7H-pyrrolo[2,3-c]pyridin-7-one;

3-[2-(2,4-difluorophenoxy)-5-{[(furan-3-ylmethyl)amino]methyl}phenyl]-1-methyl-1,6-dihydro-7H-pyrrolo[2,3-c]pyridin-7-one;

3-[5-{[(2-cyclopentylethyl)amino]methyl}-2-(2,4-difluorophenoxy)phenyl]-1-methyl-1,6-dihydro-7H-pyrrolo[2,3-c]pyridin-7-one;

3-[2-(2,4-difluorophenoxy)-5-{[4-(trifluoromethyl)piperidin-1-yl]methyl}phenyl]-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)benzyl]-2-methoxybenzenesulfonamide;

1-(4-chlorophenyl)-N-[4-(2,4-difluorophenoxy)-3-(1-methyl-7-oxo-6,7-dihydro-1H-pyrrolo[2,3-c]pyridin-3-yl)benzyl]methanesulfonamide;

N-[4-(2,4-difluorophenoxy)-3-(1-methyl-7-oxo-6,7-dihydro-1H-pyrrolo[2,3-c]pyridin-3-yl)benzyl]-1-(4-methylphenyl)methanesulfonamide;

N-[4-(2,4-difluorophenoxy)-3-(1-methyl-7-oxo-6,7-dihydro-1H-pyrrolo[2,3-c]pyridin-3-yl)benzyl]-1-[4-(trifluoromethyl)phenyl]methanesulfonamide;

1-(4-cyanophenyl)-N-[4-(2,4-difluorophenoxy)-3-(1-methyl-7-oxo-6,7-dihydro-1H-pyrrolo[2,3-c]pyridin-3-yl)benzyl]methanesulfonamide;

N-[4-(2,4-difluorophenoxy)-3-(1-methyl-7-oxo-6,7-dihydro-1H-pyrrolo[2,3-c]pyridin-3-yl)benzyl]-2,2,2-trifluoroethanesulfonamide;

3-[(5-(aminomethyl)-2-(2,4-difluorophenoxy)phenyl]-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)benzyl]cyclopentanesulfonamide;

2,5-dichloro-N-[4-(2,4-difluorophenoxy)-3-(1-methyl-7-oxo-6,7-dihydro-1H-pyrrolo[2,3-c]pyridin-3-yl)benzyl]thiophene-3-sulfonamide;

N-[4-(2,4-difluorophenoxy)-3-(1-methyl-7-oxo-6,7-dihydro-1H-pyrrolo[2,3-c]pyridin-3-yl)benzyl]-5-methyl-1,2-oxazole-4-sulfonamide;

N-[4-(2,4-difluorophenoxy)-3-(1-methyl-7-oxo-6,7-dihydro-1H-pyrrolo[2,3-c]pyridin-3-yl)benzyl]-3,5-dimethyl-1,2-oxazole-4-sulfonamide; and N-[4-(2,4-difluorophenoxy)-3-(1-methyl-7-oxo-6,7-dihydro-1H-pyrrolo[2,3-c]pyridin-3-yl)benzyl]benzenesulfonamide.

In certain embodiments, a compound of formula (I) is selected from the group consisting of:

3-{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]pyridin-3-yl}-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)phenyl]ethanesulfonamide;

3-[2-(2,4-difluorophenoxy)-5-(methylsulfonyl)phenyl]-1-methyl-1,6-dihydro-7H-pyrrolo[2,3-c]pyridin-7-one;

5-chloro-3-{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one;

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]methanesulfonamide;

1-[4-(2,4-difluorophenoxy)-3-(1-methyl-7-oxo-6,7-dihydro-1H-pyrrolo[2,3-c]pyridin-3-yl)phenyl]-N-methylmethanesulfonamide;

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide;
N-{4-[(trans-4-methoxycyclohexyl)oxy]-3-(1-methyl-7-oxo-6,7-dihydro-1H-pyrrolo[2,3-c]pyridin-3-yl)phenyl}ethanesulfonamide;
N-{4-[(4,4-difluorocyclohexyl)oxy]-3-(1-methyl-7-oxo-6,7-dihydro-1H-pyrrolo[2,3-c]pyridin-3-yl)phenyl}ethanesulfonamide;
N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide;
N-[4-(4-fluorophenoxy)-3-(1-methyl-7-oxo-6,7-dihydro-1H-pyrrolo[2,3-c]pyridin-3-yl)phenyl]ethanesulfonamide;
N-[4-(2,4-difluorophenoxy)-3-(1-methyl-7-oxo-6,7-dihydro-1H-pyrrolo[2,3-c]pyridin-3-yl)phenyl]methanesulfonamide;
3-{2-(2,4-difluorophenoxy)-5-[(ethylsulfonyl)methyl]phenyl}-1-methyl-1,6-dihydro-7H-pyrrolo[2,3-c]pyridin-7-one;
3-{2-[(4-fluorophenyl)amino]-5-[(methylsulfonyl)methyl]phenyl}-1-methyl-1,6-dihydro-7H-pyrrolo[2,3-c]pyridin-7-one;
3-{2-[(2,4-difluorophenyl)amino]-5-[(methylsulfonyl)methyl]phenyl}-1-methyl-1,6-dihydro-7H-pyrrolo[2,3-c]pyridin-7-one;
N-[4-(4-cyanophenoxy)-3-(1-methyl-7-oxo-6,7-dihydro-1H-pyrrolo[2,3-c]pyridin-3-yl)phenyl]methanesulfonamide;
3-{2-[(4,4-difluorocyclohexyl)oxy]-5-(methylsulfonyl)phenyl}-1-methyl-1,6-dihydro-7H-pyrrolo[2,3-c]pyridin-7-one;
3-{2-[(trans-4-hydroxycyclohexyl)oxy]-5-(methylsulfonyl)phenyl}-1-methyl-1,6-dihydro-7H-pyrrolo[2,3-c]pyridin-7-one;
3-{2-[(cyclopropylmethyl)amino]-5-[(methylsulfonyl)methyl]phenyl}-1-methyl-1,6-dihydro-7H-pyrrolo[2,3-c]pyridin-7-one;
1-(4-cyanophenyl)-N-[4-(2,4-difluorophenoxy)-3-(1-methyl-7-oxo-6,7-dihydro-1H-pyrrolo[2,3-c]pyridin-3-yl)benzyl]methanesulfonamide;
3-{2-[(cyclopropylmethyl)amino]phenyl}-1-methyl-1,6-dihydro-7H-pyrrolo[2,3-c]pyridin-7-one;
3-{2-chloro-5-[(methylsulfonyl)methyl]pyridin-3-yl}-1-methyl-1,6-dihydro-7H-pyrrolo[2,3-c]pyridin-7-one;
3-[2-{[trans-4-(dimethylamino)cyclohexyl]oxy}-5-(pyrrolidin-1-ylsulfonyl)phenyl]-1-methyl-1,6-dihydro-7H-pyrrolo[2,3-c]pyridin-7-one;
3-{5-fluoro-2-[(4-fluorophenyl)amino]pyridin-3-yl}-1-methyl-1,6-dihydro-7H-pyrrolo[2,3-c]pyridin-7-one;
3-[5-amino-2-(2,4-difluorophenoxy)phenyl]-1-methyl-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)phenyl]-4-methylpentanamide;
2,5-dichloro-N-[4-(2,4-difluorophenoxy)-3-(1-methyl-7-oxo-6,7-dihydro-1H-pyrrolo[2,3-c]pyridin-3-yl)phenyl]benzamide;
N-[4-(2,4-difluorophenoxy)-3-(1-methyl-7-oxo-6,7-dihydro-1H-pyrrolo[2,3-c]pyridin-3-yl)phenyl]-2-(2-methoxyphenyl)acetamide;
N-[4-(2,4-difluorophenoxy)-3-(1-methyl-7-oxo-6,7-dihydro-1H-pyrrolo[2,3-c]pyridin-3-yl)phenyl]pyridine-2-carboxamide;
N-[4-(2,4-difluorophenoxy)-3-(1-methyl-7-oxo-6,7-dihydro-1H-pyrrolo[2,3-c]pyridin-3-yl)phenyl]-5-methylpyrazine-2-carboxamide;
N-[4-(2,4-difluorophenoxy)-3-(1-methyl-7-oxo-6,7-dihydro-1H-pyrrolo[2,3-c]pyridin-3-yl)phenyl]-3-phenylpropanamide;
N-[4-(2,4-difluorophenoxy)-3-(1-methyl-7-oxo-6,7-dihydro-1H-pyrrolo[2,3-c]pyridin-3-yl)phenyl]-4-phenoxybutanamide;
N-[4-(2,4-difluorophenoxy)-3-(1-methyl-7-oxo-6,7-dihydro-1H-pyrrolo[2,3-c]pyridin-3-yl)phenyl]-2-(3-phenoxyphenyl)acetamide;
4-(acetylamino)-N-[4-(2,4-difluorophenoxy)-3-(1-methyl-7-oxo-6,7-dihydro-1H-pyrrolo[2,3-c]pyridin-3-yl)phenyl]benzamide;
N-[4-(2,4-difluorophenoxy)-3-(1-methyl-7-oxo-6,7-dihydro-1H-pyrrolo[2,3-c]pyridin-3-yl)phenyl]-4-(phenoxymethyl)benzamide;
N-[4-(2,4-difluorophenoxy)-3-(1-methyl-7-oxo-6,7-dihydro-1H-pyrrolo[2,3-c]pyridin-3-yl)phenyl]-2-oxo-1-phenylpyrrolidine-3-carboxamide;
2-(1,2-benzoxazol-3-yl)-N-[4-(2,4-difluorophenoxy)-3-(1-methyl-7-oxo-6,7-dihydro-1H-pyrrolo[2,3-c]pyridin-3-yl)phenyl]acetamide;
2-(5-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide;
2-(4-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide;
N-[4-(2,4-difluorophenoxy)-3-(1-methyl-7-oxo-6,7-dihydro-1H-pyrrolo[2,3-c]pyridin-3-yl)phenyl]-2-(6-methylpyridin-3-yl)acetamide;
N-[4-(2,4-difluorophenoxy)-3-(1-methyl-7-oxo-6,7-dihydro-1H-pyrrolo[2,3-c]pyridin-3-yl)phenyl]-2-(3,4-dihydro-2H-chromen-6-yl)acetamide;
N-[4-(2,4-difluorophenoxy)-3-(1-methyl-7-oxo-6,7-dihydro-1H-pyrrolo[2,3-c]pyridin-3-yl)phenyl]-2-(2-methyl-1,3-thiazol-5-yl)acetamide;
N-[4-(2,4-difluorophenoxy)-3-(1-methyl-7-oxo-6,7-dihydro-1H-pyrrolo[2,3-c]pyridin-3-yl)phenyl]-2-(1,5-dimethyl-1H-pyrazol-3-yl)acetamide;
N-[4-(2,4-difluorophenoxy)-3-(1-methyl-7-oxo-6,7-dihydro-1H-pyrrolo[2,3-c]pyridin-3-yl)phenyl]-2-[4-(2-fluorophenyl)-1H-pyrazol-1-yl]acetamide;
methyl (2E)-3-[(4-fluorophenyl){2-(1-methyl-7-oxo-6,7-dihydro-1H-pyrrolo[2,3-c]pyridin-3-yl)-4-[(methylsulfonyl)methyl]phenyl}amino]prop-2-enoate;
4-({[4-(2,4-difluorophenoxy)-3-(1-methyl-7-oxo-6,7-dihydro-1H-pyrrolo[2,3-c]pyridin-3-yl)phenyl]amino}methyl)benzonitrile;
3-[2-(2,4-difluorophenoxy)-5-{[3-(4-methoxyphenoxy)benzyl]amino}phenyl]-1-methyl-1,6-dihydro-7H-pyrrolo[2,3-c]pyridin-7-one;
3-[2-(2,4-difluorophenoxy)-5-{[(3-methylpyridin-2-yl)methyl]amino}phenyl]-1-methyl-1,6-dihydro-7H-pyrrolo[2,3-c]pyridin-7-one;
3-[5-{[4-(benzyloxy)benzyl]amino}-2-(2,4-difluorophenoxy)phenyl]-1-methyl-1,6-dihydro-7H-pyrrolo[2,3-c]pyridin-7-one;
3-[5-{[(5-chloro-3-methyl-1-phenyl-1H-pyrazol-4-yl)methyl]amino}-2-(2,4-difluorophenoxy)phenyl]-1-methyl-1,6-dihydro-7H-pyrrolo[2,3-c]pyridin-7-one;
3-({[4-(2,4-difluorophenoxy)-3-(1-methyl-7-oxo-6,7-dihydro-1H-pyrrolo[2,3-c]pyridin-3-yl)phenyl]amino}methyl)benzonitrile;

3-{2-(2,4-difluorophenoxy)-5-[(4-phenoxybenzyl)amino]
  phenyl}-1-methyl-1,6-dihydro-7H-pyrrolo[2,3-c]pyridin-
  7-one;
3-{2-(2,4-difluorophenoxy)-5-[(3,3-dimethylbutyl)amino]
  phenyl}-1-methyl-1,6-dihydro-7H-pyrrolo[2,3-c]pyridin-
  7-one;
3-{5-[(2,6-difluorobenzyl)amino]-2-(2,4-difluorophenoxy)
  phenyl}-1-methyl-1,6-dihydro-7H-pyrrolo[2,3-c]pyridin-
  7-one;
3-{2-(2,4-difluorophenoxy)-5-[(6,7-dihydro-5H-pyrrolo[1,
  2-a]imidazol-2-ylmethyl)amino]phenyl}-1-methyl-1,6-
  dihydro-7H-pyrrolo[2,3-c]pyridin-7-one;
3-{5-{[2-(benzyloxy)-3-methoxybenzyl]amino}-2-(2,4-difluorophenoxy)phenyl]-1-methyl-1,6-dihydro-7H-pyrrolo
  [2,3-c]pyridin-7-one;
2-({[4-(2,4-difluorophenoxy)-3-(1-methyl-7-oxo-6,7-dihydro-1H-pyrrolo[2,3-c]pyridin-3-yl)phenyl]
  amino}methyl)benzonitrile;
3-{2-(2,4-difluorophenoxy)-5-[(quinolin-4-ylmethyl)
  amino]phenyl}-1-methyl-1,6-dihydro-7H-pyrrolo[2,3-c]
  pyridin-7-one;
N-[4-(2,4-difluorophenoxy)-3-(1-methyl-7-oxo-6,7-dihydro-1H-pyrrolo[2,3-c]pyridin-3-yl)phenyl]-1-phenyl-
  methanesulfonamide;
1-(2-chloro-5-fluorophenyl)-N-[4-(2,4-difluorophenoxy)-3-
  (1-methyl-7-oxo-6,7-dihydro-1H-pyrrolo[2,3-c]pyridin-
  3-yl)phenyl]methanesulfonamide;
N-{4-(2,4-difluorophenoxy)-3-[1-methyl-5-(morpholin-4-
  ylmethyl)-7-oxo-6,7-dihydro-1H-pyrrolo[2,3-c]pyridin-
  3-yl]phenyl}ethanesulfonamide;
N-{4-(2,4-difluorophenoxy)-3-[1-methyl-7-oxo-5-(piperidin-4-yl)-6,7-dihydro-1H-pyrrolo[2,3-c]pyridin-3-yl]
  phenyl}ethanesulfonamide;
N-[6-(2,4-difluorophenoxy)-5-(1-methyl-7-oxo-6,7-dihydro-1H-pyrrolo[2,3-c]pyridin-3-yl)pyridin-3-yl]ethanesulfonamide;
N-[3-{5-[1-(cyclopropylcarbonyl)piperidin-4-yl]-1-methyl-
  7-oxo-6,7-dihydro-1H-pyrrolo[2,3-c]pyridin-3-yl}-4-(2,
  4-difluorophenoxy)phenyl]ethanesulfonamide;
N-[4-(2,4-difluorophenoxy)-3-{5-[1-(ethylsulfonyl)piperidin-4-yl]-1-methyl-7-oxo-6,7-dihydro-1H-pyrrolo[2,3-c]
  pyridin-3-yl}phenyl]ethanesulfonamide;
3-{2-(2,4-difluorophenoxy)-5-[(ethylsulfonyl)amino]phenyl}-N-[3-(1H-imidazol-1-yl)propyl]-1-methyl-7-oxo-6,
  7-dihydro-1H-pyrrolo[2,3-c]pyridine-5-carboxamide;
3-{2-(2,4-difluorophenoxy)-5-[(ethylsulfonyl)amino]phenyl}-N-[2-(dimethylamino)ethyl]-1-methyl-7-oxo-6,7-dihydro-1H-pyrrolo[2,3-c]pyridine-5-carboxamide;
N-(cyanomethyl)-3-{2-(2,4-difluorophenoxy)-5-[(ethylsulfonyl)amino]phenyl}-1-methyl-7-oxo-6,7-dihydro-1H-
  pyrrolo[2,3-c]pyridine-5-carboxamide;
3-{2-(2,4-difluorophenoxy)-5-[(ethylsulfonyl)amino]phenyl}-N-(3-hydroxypropyl)-1-methyl-7-oxo-6,7-dihydro-
  1H-pyrrolo[2,3-c]pyridine-5-carboxamide;
N-{4-(2,4-difluorophenoxy)-3-[1-methyl-5-(morpholin-4-
  ylcarbonyl)-7-oxo-6,7-dihydro-1H-pyrrolo[2,3-c]pyridin-3-yl]phenyl}ethanesulfonamide;
3-{2-(2,4-difluorophenoxy)-5-[(ethylsulfonyl)amino]phenyl}-1-methyl-7-oxo-N-(pyridin-3-ylmethyl)-6,7-dihydro-1H-pyrrolo[2,3-c]pyridine-5-carboxamide;
N-{4-(2,4-difluorophenoxy)-3-[1-methyl-7-oxo-5-(pyrrolidin-1-ylcarbonyl)-6,7-dihydro-1H-pyrrolo[2,3-c]pyridin-3-yl]phenyl}ethanesulfonamide;
N-[4-(2,4-difluorophenoxy)-3-{5-[(4-hydroxypiperidin-1-
  yl)carbonyl]-1-methyl-7-oxo-6,7-dihydro-1H-pyrrolo[2,
  3-c]pyridin-3-yl}phenyl]ethanesulfonamide;
N-(cyclopentylmethyl)-3-{2-(2,4-difluorophenoxy)-5-[(ethylsulfonyl)amino]phenyl}-1-methyl-7-oxo-6,7-dihydro-
  1H-pyrrolo[2,3-c]pyridine-5-carboxamide;
3-{2-(2,4-difluorophenoxy)-5-[(ethylsulfonyl)amino]phenyl}-1-methyl-N-[2-(morpholin-4-yl)ethyl]-7-oxo-6,7-
  dihydro-1H-pyrrolo[2,3-c]pyridine-5-carboxamide;
3-{2-(2,4-difluorophenoxy)-5-[(ethylsulfonyl)amino]phenyl}-1-methyl-N-[2-(4-methylpiperazin-1-yl)ethyl]-7-
  oxo-6,7-dihydro-1H-pyrrolo[2,3-c]pyridine-5-carboxamide;
3-{2-(2,4-difluorophenoxy)-5-[(ethylsulfonyl)amino]phenyl}-1-methyl-7-oxo-N-[2-(piperidin-1-yl)ethyl]-6,7-dihydro-1H-pyrrolo[2,3-c]pyridine-5-carboxamide;
3-{2-(2,4-difluorophenoxy)-5-[(ethylsulfonyl)amino]phenyl}-1-methyl-7-oxo-N-(tetrahydrofuran-3-ylmethyl)-6,
  7-dihydro-1H-pyrrolo[2,3-c]pyridine-5-carboxamide;
3-{2-(2,4-difluorophenoxy)-5-[(ethylsulfonyl)amino]phenyl}-N,1-dimethyl-7-oxo-6,7-dihydro-1H-pyrrolo[2,3-c]
  pyridine-5-carboxamide;
3-{2-(2,4-difluorophenoxy)-5-[(ethylsulfonyl)amino]phenyl}-N-(furan-3-ylmethyl)-1-methyl-7-oxo-6,7-dihydro-
  1H-pyrrolo[2,3-c]pyridine-5-carboxamide;
3-{3-cyclopropyl-2-[(2,4-difluorophenyl)amino]-5-[(methylsulfonyl)methyl]phenyl}-1-methyl-1,6-dihydro-7H-
  pyrrolo[2,3-c]pyridin-7-one; and
1-methyl-3-{5-[(methylsulfonyl)methyl]-2-(pyridin-2-
  ylamino)phenyl}-1,6-dihydro-7H-pyrrolo[2,3-c]pyridin-
  7-one.

Exemplary compounds are named using the software ACD/NAME 2012.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; aralkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, can be prepared by methodologies known in the art, for example, through the reaction schemes depicted in schemes 1-6. The variables $A^1$, $A^2$, $A^3$, $A^4$, $R^1$, $R^2$, $R^3$, $R^4$, $R^5$, $R^6$, $R^a$, $R^b$, $R^c$, and $R^d$, used in the following schemes have the meanings as set forth in the summary and detailed description sections, unless otherwise noted.

Abbreviations used in the descriptions of the schemes and the specific examples have the following meanings: DMSO for dimethyl sulfoxide, dppf for 1,1'-bis(diphenylphosphino) ferrocene; EDAC or EDCI or EDC for 1-ethyl-3-[3-(dimethylamino)propyl]-carbodiimide hydrochloride; HOBT for 1-hydroxybenzotriazole hydrate; MeOH for methanol; mCPBA for 3-chloroperbenzoic acid; $Pd(PPh_3)_4$ for tetrakis(triphenylphosphine)palladium(0); $PdCl_2(PPh_3)_2$ for bis(triphenylphosphine)palladium(II) dichloride; $PdCl_2(dppf)$ for [1,1'-bis(diphenylphosphino)ferrocene]dichloropalladium(II); THF for tetrahydrofuran, TFA for trifluoroacetic acid, and HPLC for High Performance Liquid chromatography.

Compounds of general formula (I) may be prepared using the general procedure as outlined in Scheme 1. Conversion of (1), wherein Z is Cl, Br, or I, to compounds of general formula (3) may be achieved by reaction of (1) with a boronic acid of formula (2) or derivative thereof (e.g. pinacol ester) under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydrofuran, toluene, and water, or a mixture thereof. Compounds of general formula (I) wherein $R^2$ is H may be synthesized by the treatment of compounds (3) with an acid such as, for example, hydrochloric acid, acetic acid, or p-toluene sulfonic acid in a solvent such as, for example, water, dioxane, or dimethylformamide, at a temperature such as, for example, about 25° C. to about 120° C. Alternatively, compounds of general formula (I) wherein $R^2$ is H may be obtained from the reaction of compounds (3) with trimethylsilyl iodide in a solvent such as, for example, dichloromethane or chloroform, and at a temperature such as, for example, about 25° C. to about 75° C. Alkylation of compounds of general formula (I) wherein $R^2$ is H with $C_1$-$C_3$ alkyl halides in the presence of a base such as, for example, sodium hydride, provide compounds of general formula (I) wherein $R^2$ is $C_1$-$C_3$ alkyl Compounds of general formula (3) may also be prepared from the reaction of (4) or the corresponding boronic acids with halides (5) wherein X is Cl, Br, or I under Suzuki coupling conditions as described in the preceding paragraph.

Pinacol esters of formula (4), may be synthesized, for example, by treatment of compounds of formula (1), wherein Z is Br, Cl, or I, with a reagent such as, but not limited to, butyllithium followed by 2-isopropoxy-4,4,5,5-tetramethyl-1,3,2-dioxaborolane, in a solvent such as, for example, tetrahydrofuran, at a temperature such as, for example, about −78° C. The corresponding boronic acids of (4) may be prepared by reaction of compounds of general formula (1), wherein Z is Br, Cl, or I, with a reagent such as, but not limited to, bis(pinacolato)diboron or 4,4,5,5-tetramethyl-1,3,2-dioxaborolane in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydrofuran, and water, or a mixture thereof Scheme 1

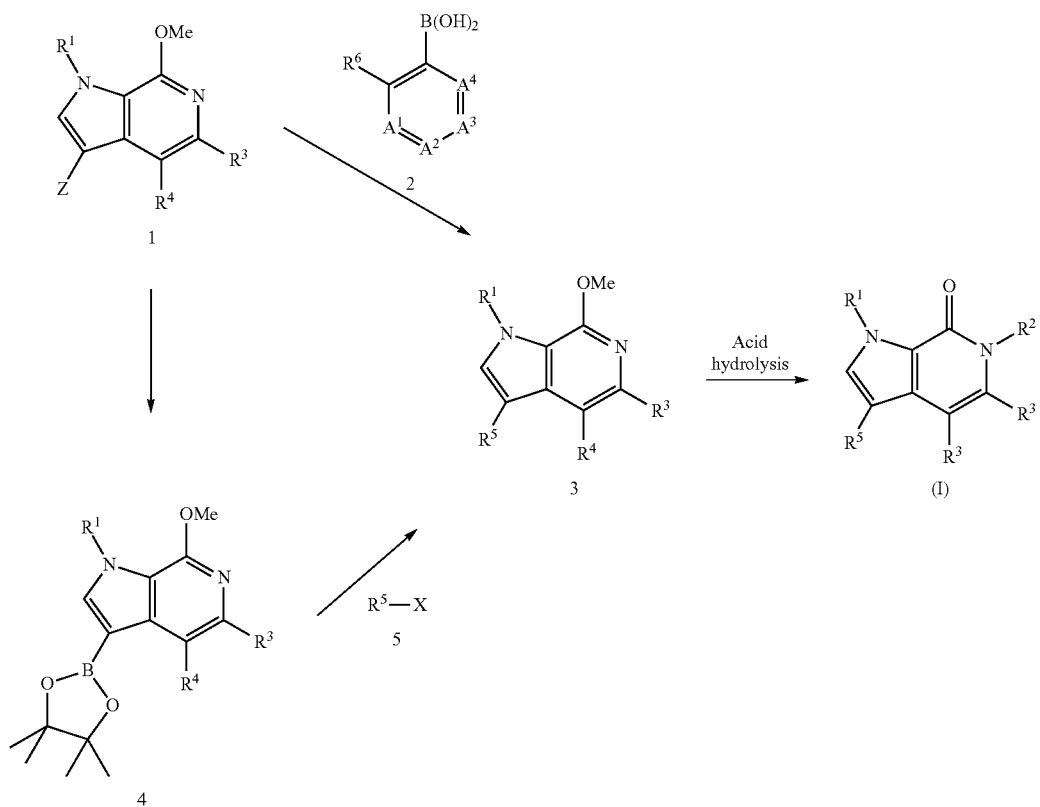

Compounds of formula (1) wherein $R^1$ is $C_1$-$C_3$ alkyl may be prepared using synthetic routes such as, for example, those illustrated in Scheme 2. Reaction of compounds of formula (6) wherein Z is Br, Cl, I, with a $C_1$-$C_3$ alkyl halide, in the presence of a base such as carbonate of cesium, sodium, or potassium and in a solvent such as, for example, dimethylformamide, tetrahydrofuran, or dimethylsulfoxide, provides intermediates of formula (1) wherein $R^1$ is $C_1$-$C_3$ alkyl. The reaction may be conducted at temperature such as, for example, about 25° C. to about 60° C.

Scheme 2

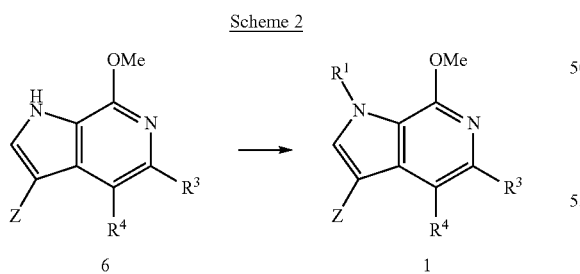

An alternative route for the preparation of compounds (1) wherein $R^1$ is $C_1$-$C_3$ alkyl is outlined in Scheme 3. For example, compounds of formula (8), prepared from compounds (7) using general procedure as outlined in Scheme 2, may be converted to (9) by treatment with a reagent such as, for example, sodium methoxide, in a solvent such as, for example, methanol, and at a temperature of about 80° C. to about 150° C. Treatment of compounds (9) with a reagent such as, for example, N-iodosuccinimide or N-bromosuccinimide, in a solvent such as, for example, dimethylformamide, at temperatures at about 0° C. to about 50° C., provides compounds (1).

Scheme 3

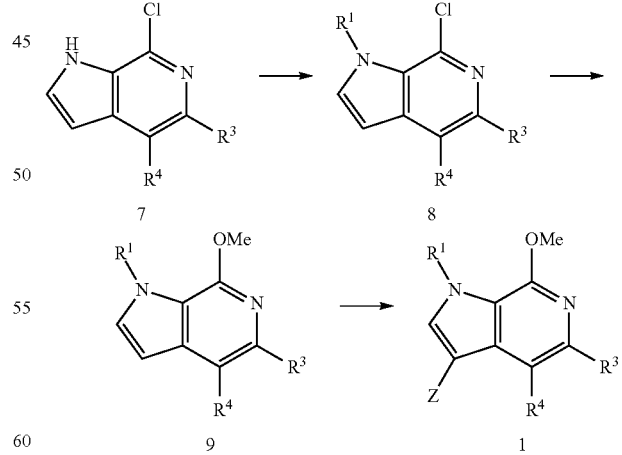

Compounds of formula (3) wherein $R^5$ is phenyl or pyridine, and each of which is substituted with at least one substituent selected from the group consisting of $OR^a$ and $NR^cR^d$, may be prepared as described in Scheme 4. Compounds of formula (11) wherein $R^{101}$ is fluorine or $NH_2$ may be obtained from compounds of formula (1) or (4) (or the corresponding boronic acid) via Suzuki coupling condition as described in Scheme 1. Displacement of the fluorine atom of (10) with alcohols of formula $R^aOH$ provides compounds (13) wherein $R^6$ is $OR^a$. Displacement of the fluorine atom may be accomplished in a solvent such as, for example, dimethylsulfoxide, dimethylformamide, dioxane, or tetrahydrofuran and in the presence of a base such as, for example, carbonate of cesium, potassium, or sodium, or sodium hydride, and at a temperature from about 40° C. to about 120° C.

Reductive amination of amines (11) wherein $R^{101}$ is $NH_2$ with a suitable aldehyde or ketone in the presence of a reducing agent such as, for example, sodium triacetoxyhydroborate, sodium borohydride, or sodium cyanoborohydride, and an acid (e.g. acetic acid), provide compounds (13) wherein $R^6$ is $NR^cR^d$. The reaction is generally conducted in a solvent such as, for example, dichloromethane, methanol, or ethanol, at a temperature of about 0° C. to about 100° C., provide compounds (13) wherein $R^6$ is $NR^bR^c$.

Conversion of (11) wherein $R^{101}$ is $NH_2$ to compounds (13) wherein $R^6$ is $NR^cR^d$ may also be achieved using Buchwald reaction conditions wherein (11) is treated with a suitable aryl halide or heteroaryl halide in the presence of a catalyst, a ligand, a base, and in a solvent. Examples of catalysts that may be employed include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include toluene, tert-butanol, methanol, ethanol, dimethoxyethane, N,N-dimethylformamide, dimethylsulfoxide, dioxane, tetrahydrofuran, and water, or a mixture thereof.

Scheme 4

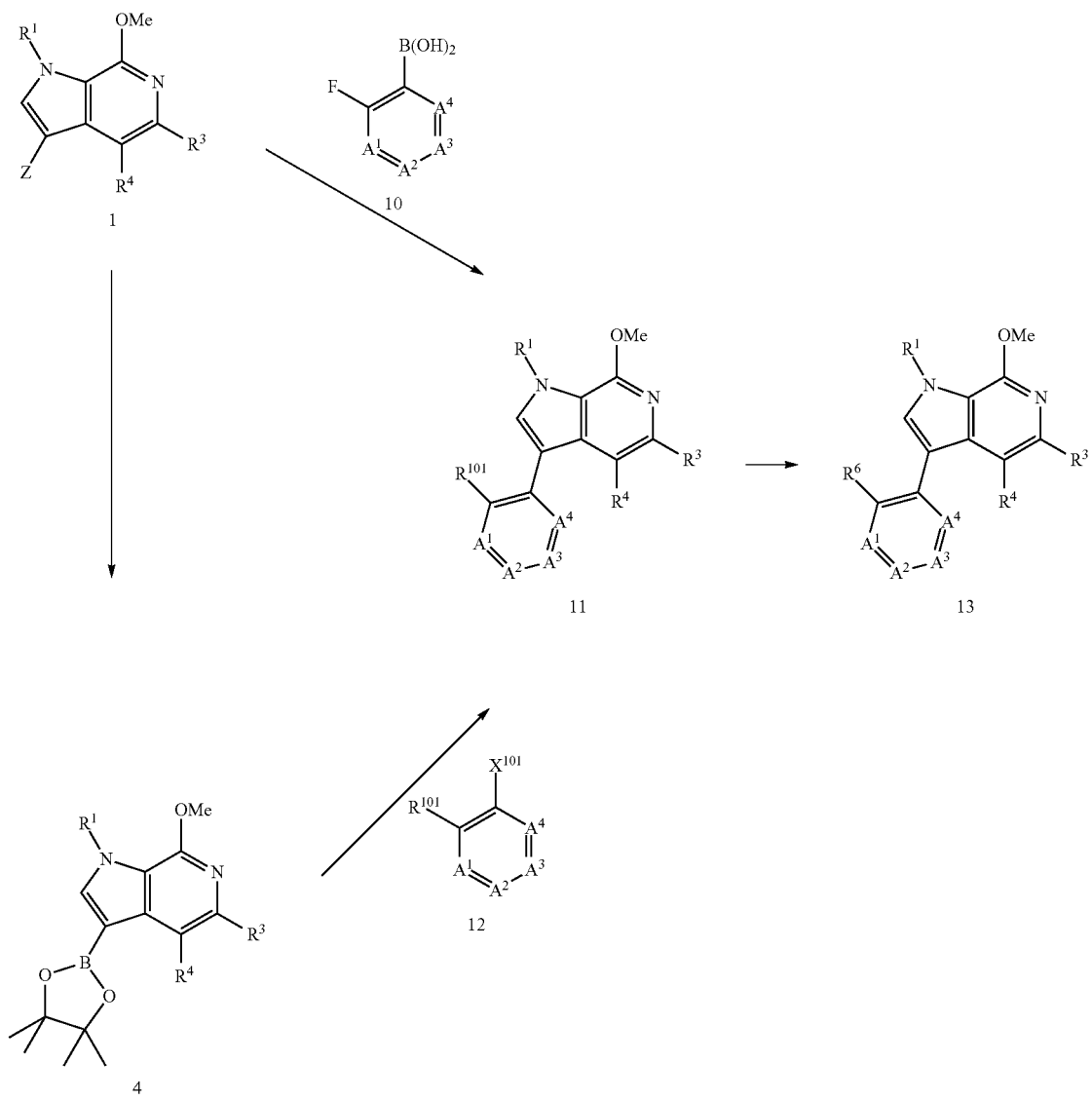

Compounds of formula (13) wherein $A^3$ is $C(R^9)$ and $R^9$ is $N(H)SO_2R^b$ may be synthesized as shown in Scheme 5. Reduction of the nitro compounds of formula (14) to the amines (15) may be achieved using iron powder in the presence of ammonium chloride in a solvent such as, for example, tetrahydrofuran, ethanol, or water, or a mixture thereof, and at a temperature of about 80° C. to about 120° C. The reduction may also be achieved by treatment of (14) with tin chloride in hydrochloric acid at a temperature of about 80° C. to about 120° C. Transformation of (14) to (15) may also be conducted in the presence of a catalyst such as platinum oxide or palladium on charcoal, in a solvent such as ethanol or methanol and under hydrogen pressure. Treatment of amines (15) with sulfonyl chlorides of formula $R^bSO_2Cl$, in the presence of a base such as triethylamine or diisopropylethylamine in a solvent such as dichloromethane or tetrahydrofuran and at a temperature of about 0° C. to about 40° C. provides sulfonamides (16).

Scheme 5

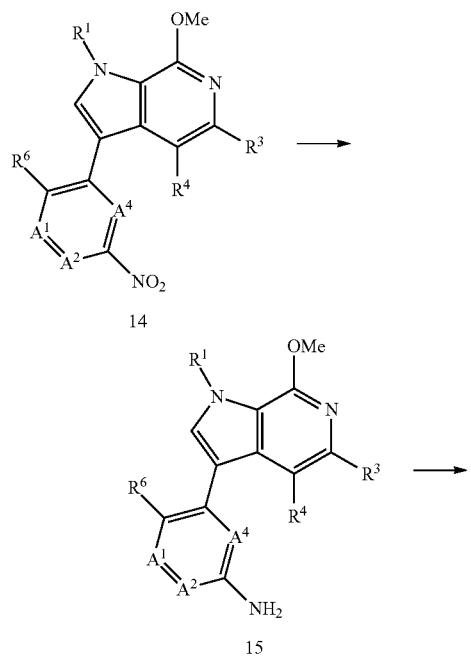

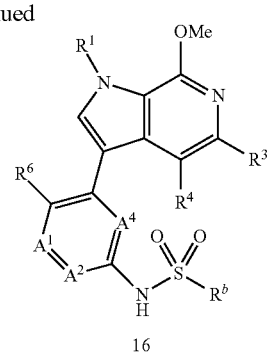

16

Compounds of formula (13) wherein $A^3$ is $C(R^9)$ and $R^9$ is $CH_2SO_2R^a$ or is $-CH_2SO_2NR^cR^d$ may be synthesized as shown in Scheme 6. Reduction of aldehydes (17) to alcohols of (18) may be achieved by reaction with a reducing agent such as, for example, sodium borohydride or lithium aluminum hydride, in a solvent such as, for example, ethanol, methanol, tetrahydrofuran, dioxane, or mixtures thereof, and at temperatures of about 0° C. to about 50° C. Reaction of alcohols (18) with a brominating agent such as, for example, phosphorus tribromide in a solvent such as, for example, dichloromethane, at temperatures of about 0° C. to about 50° C. provides compounds of formula (19). Reaction of compounds (19) with appropriate sodium thiooxides in a solvent such as, for example, dimethylformamide at a temperature of about 0° C. to about 50° C., provides compounds (20). Oxidation of compounds (20) with an oxidizing agent such as, for example, oxone, m-chloroperoxy benzoic acid, or hydrogen peroxide in a solvent such as, for example, methanol, acetonitrile, hexane, dichloromethane, or water, at temperatures of about 0° C. to about 70° C. yields compounds (21).

Reaction of compounds (19) with a reagent such as, for example, sodium sulfite, in the presence of a reagent such as, for example, tetrabutylammonium iodide in a solvent, such as, for example, ethanol, methanol, or water, or mixtures thereof, at a temperature of about 25° C. to about 100° C., may generate compounds (22). Treatment of compounds (22) with a reagent such as, for example, oxalyl chloride or thionyl chloride, in a solvent such as, for example, dichloromethane, at temperatures of about 0° C. to about 50° C. followed by reaction of the thus generated intermediate sulfonyl chloride with an appropriate amine in a solvent such as, for example, dichloromethane, provides (23).

Scheme 6

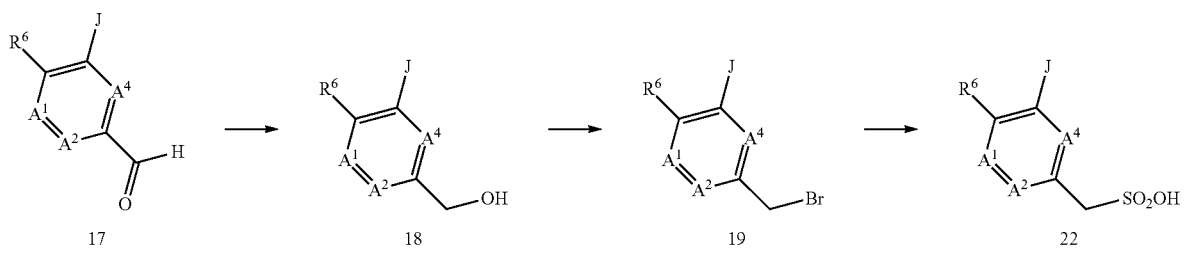

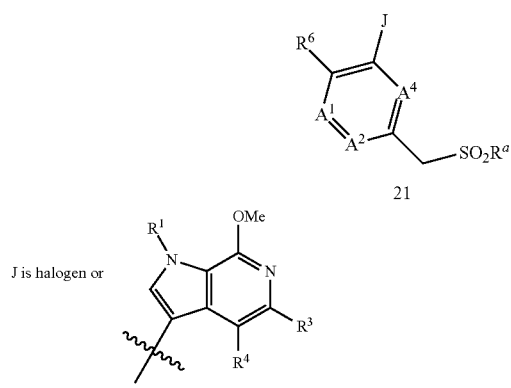

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-44(1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-veMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-10 converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrosewater; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1

1-methyl-3-(2-phenoxyphenyl)-1,6-dihydro-7H-pyrrolo[2,3-c]pyridin-7-one

Example 1A 7-methoxy-3-(2-phenoxyphenyl)-1H-pyrrolo[2,3-c]pyridine

A mixture of 3-iodo-7-methoxy-1H-pyrrolo[2,3-c]pyridine (0.274 g, 1.0 mmol), 2-phenoxyphenylboronic acid (0.278 g, 1.3 mmol, 1.3 equivalents), Pd(PPh$_3$)$_4$ (0.058 g, 0.05 mmol), and cesium fluoride (0.456 g, 3 mmol) in dimethoxyethane (3 mL) and methanol (1.5 mL) was heated under microwave conditions (120° C., 30 minutes). The reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The residue was purified by flash column chromatography (silica gel, 30% ethyl acetate/hexanes) to give the title compound (0.122 g, 38.6% yield).

Example 1B 7-methoxy-1-methyl-3-(2-phenoxyphenyl)-1H-pyrrolo[2,3-c]pyridine

Example 1A (0.058 g, 0.183 mmol) in dimethylformamide (2 mL) was treated with 60% sodium hydride in mineral oil (0.015 g, 0.367 mmol) at room temperature for 10 minutes. To this solution was added methyl iodide (0.052 g, 0.367 mmol). The reaction mixture was stirred for 3 hours at room temperature. The reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The residue was purified by flash column chromatography (silica gel, 10% ethyl acetate/hexanes) to give the title compound (0.051 g 84%).

Example 1C 1-methyl-3-(2-phenoxyphenyl)-1,6-dihydro-7H-pyrrolo[2,3-c]pyridin-7-one Example 1B (0.045 g, 0.136 mmol) in dioxane (2 mL) was treated with 4.0 N HCl in dioxane (1 mL). The reaction mixture was heated at 90° C. overnight. The solvent was removed, and the residue was purified by reverse phase HPLC (C18, CH₃CN/water (0.1% TFA), 10-100%) to afford the title compound (0.035 g, 81%). $^1$H NMR (500 MHz, DMSO-$d_6$) δ ppm 10.90 (d, J=4.88 Hz, 1H), 7.54 (dd, J=7.63, 1.83 Hz, 1H), 7.47 (s, 1H), 7.22-7.32 (m, 4H), 6.98-7.05 (m, 2H), 6.85-6.90 (m, 3H), 6.53 (d, J=6.1 Hz, 1H), 4.05 (s, 3H). MS (ESI+) m/z 317.2 (M+H)$^+$.

Example 2

N-[4-(2,4-difluorophenoxy)-3-(1-methyl-7-oxo-6,7-dihydro-1H-pyrrolo[2,3-c]pyridin-3-yl)phenyl]methanesulfonamide

Example 2A 3-iodo-7-methoxy-1-methyl-1H-pyrrolo[2,3-c]pyridine

3-Iodo-7-methoxy-1H-pyrrolo[2,3-c]pyridine (0.75 g, 2.74 mmol) in dimethylformamide (10 mL) was treated with 60% sodium hydride in mineral oil (0.219 g, 5.47 mmol) at room temperature for 20 minutes. To this solution was added methyl iodide (0.505 g, 3.56 mmol). The reaction mixture was stirred for 3 hours at room temperature. The reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The residue was purified by flash column chromatography (silica gel, 10% ethyl acetate/hexanes to give 0.75 g (95%) of the title compound.

Example 2B 3-(2-fluoro-5-nitrophenyl)-7-methoxy-1-methyl-1H-pyrrolo[2,3-c]pyridine Example 2A (0.56 g, 1.944 mmol), 2-fluoro-5-nitrophenylboronic acid (0.467 g, 2.53 mmol), Pd(PPh₃)₄ (0.112 g, 0.097 mmol) and sodium carbonate (0.412 g, 3.89 mmol) were combined in toluene (8 mL), ethanol (2 mL) and water (2 mL) and the mixture was degassed and purged with nitrogen. The reaction mixture was heated at 90° C. overnight, and then cooled to room temperature. The mixture was partitioned between ethyl acetate and water. The organic layer was washed with saturated aqueous sodium chloride, dried over anhydrous magnesium sulfate, filtered, and concentrated. The crude product was purified by flash chromatography (silica gel, 20-50% ethyl acetate in hexanes) to provide 0.398 g (20.5%) of the title compound.

Example 2C 3-(2-(2,4-difluorophenoxy)-5-nitrophenyl)-7-methoxy-1-methyl-1H-pyrrolo[2,3-c]pyridine A mixture of Example 2B (0.123 g, 0.408 mmol), 2,4-difluorophenol (0.069 g, 0.531 mmol) and cesium carbonate (0.173 g, 0.531 mmol) in dimethylsulfoxide (5 mL) was heated at 110° C. for 1 hour. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The crude product was purified by flash chromatography (silica gel, 20-50% ethyl acetate in hexanes) to provide 0.16 g (95%) of the title compound.

Example 2D 4-(2,4-difluorophenoxy)-3-(7-methoxy-1-methyl-1H-pyrrolo[2,3-c]pyridin-3-yl)aniline A mixture of Example 2C (0.165 g, 0.401 mmol) and 10% palladium on carbon (0.043 g, 0.040 mmol) in ethyl acetate (10 mL) was treated with a balloon of hydrogen gas. The reaction mixture was stirred for 10 hours at ambient temperature. The solid was removed by filtration, and the filtrate was concentrated to give the title compound (0.152 g, 0.399 mmol, 99% yield).

Example 2E

N-(4-(2,4-difluorophenoxy)-3-(7-methoxy-1-methyl-1H-pyrrolo[2,3-c]pyridin-3-yl)phenyl)methanesulfonamide A mixture of Example 2D (0.05 g, 0.131 mmol), methanesulfonyl chloride (0.031 mL, 0.393 mmol), and triethylamine (0.080 g, 0.787 mmol) in dichloromethane (3 mL) was stirred at room temperature for 2 hours. The solvent was removed, and the residue was treated with sodium hydroxide (0.656 mL, 1.31 mmol) and dioxane (3 mL). The reaction mixture was heated at 80° C. for 3 hours. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated to the title compound.

Example 2F

N-[4-(2,4-difluorophenoxy)-3-(1-methyl-7-oxo-6,7-dihydro-1H-pyrrolo[2,3-c]pyridin-3-yl)phenyl]methanesulfonamide Example 2E (0.055 g, 0.120 mmol) in dioxane (3 ml) was treated with hydrogen chloride (2.99 ml, 11.97 mmol). The reaction mixture was heated at 75° C. overnight. The solvent was removed, and the residue was purified by reverse phase HPLC (C18, CH₃CN/water (0.1% TFA), 0-100%) to give title compound (0.042 g, 0.094 mmol, 79% yield). $^1$H NMR (500 MHz, DMSO-$d_6$) δ ppm 10.97 (d, J=5.19 Hz, 1H), 9.68 (s, 1H), 7.54 (s, 1H), 7.40-7.45 (m, 2H), 7.02-7.13 (m, 3H), 6.93 (dd, J=7.02, 5.8 Hz, 1H), 6.86 (d, J=8.85 Hz, 1H), 6.56 (d, J=6.41 Hz, 1H), 4.08 (s, 3H), 3.00 (s, 3H). MS (ESI+) m/z 446.1 (M+H)$^+$.

Example 3

N-[4-(2,4-difluorophenoxy)-3-(1-methyl-7-oxo-6,7-dihydro-1H-pyrrolo[2,3-c]pyridin-3-yl)phenyl]propane-2-sulfonamide

Example 3A

N-(4-(2,4-difluorophenoxy)-3-(7-methoxy-1-methyl-1H-pyrrolo[2,3-c]pyridin-3-yl)phenyl)propane-2-sulfonamide Example 3A was prepared according to the procedure used for the preparation of Example 2E, substituting propane-2-sulfonyl chloride for methanesulfonyl chloride.

Example 3B

N-[4-(2,4-difluorophenoxy)-3-(1-methyl-7-oxo-6,7-dihydro-1H-pyrrolo[2,3-c]pyridin-3-yl)phenyl]propane-2-sulfonamide Example 3B was prepared according to the procedure used for the preparation of Example 1C, substituting Example 3A for Example 1B. $^1$H NMR (500 MHz, DMSO-d$_6$) δ ppm 10.97 (d, J=5.49 Hz, 1H), 9.75 (s, 1H), 7.52 (s, 1H), 7.45 (d, J=2.75 Hz, 1H), 7.39-7.43 (m, 1H), 7.03-7.13 (m, 3H), 6.90-6.93 (m, 1H), 6.84 (d, J=8.85 Hz, 1H), 6.55 (d, J=6.41 Hz, 1H), 4.08 (s, 3H), 3.00 (s, 3H), 3.21-3.26 (m, 1H), 1.26 (d, J=7.02 Hz, 6H). MS (ESI+) m/z 474.1 (M+H)$^+$.

Example 4

N-[4-(2,4-difluorophenoxy)-3-(1-methyl-7-oxo-6,7-dihydro-1H-pyrrolo[2,3-c]pyridin-3-yl)phenyl]ethanesulfonamide

Example 4A

N-(4-(2,4-difluorophenoxy)-3-(7-methoxy-1-methyl-1H-pyrrolo[2,3-c]pyridin-3-yl)phenyl)ethanesulfonamide A mixture of Example 2D (0.05 g, 0.131 mmol), ethanesulfonyl chloride (0.051 g, 0.393 mmol), and triethylamine (0.080 g, 0.787 mmol) in dichloromethane (3 mL) was stirred at ambient temperature for 2 hours. The solvent was removed, and the residue was treated with sodium hydroxide (0.656 mL, 1.31 mmol) and dioxane (3 mL). The reaction mixture was heated at 80° C. for 3 hours. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated to give the title compound.

Example 4B

N-[4-(2,4-difluorophenoxy)-3-(1-methyl-7-oxo-6,7-dihydro-1H-pyrrolo[2,3-c]pyridin-3-yl)phenyl]ethanesulfonamide Example 4A (0.038 g, 0.080 mmol) in dioxane (2 mL) was treated with hydrogen chloride (2.006 mL, 8.03 mmol). The reaction mixture was stirred at 75° C. overnight. The solvent was removed, and the residue was purified by reverse phase HPLC (C18, CH$_3$CN/water (0.1% TFA), 0-100%) to provide the title compound (0.031 g, 0.067 mmol, 84% yield). $^1$H NMR (500 MHz, DMSO-d$_6$) δ ppm 10.97 (d, J=5.19 Hz, 1H), 9.76 (s, 1H), 7.53 (s, 1H), 7.40-7.45 (m, 1H), 7.01-7.11 (m, 3H), 6.89-6.92 (m, 1H), 6.84 (d, J=8.85 Hz, 1H), 6.55 (d, J=6.41 Hz, 1H), 4.08 (s, 3H), 3.09 (q, J=7.32 Hz, 2H), 1.22 (t, J=7.48 Hz, 3H). MS (ESI+) m/z 460.1 (M+H)$^+$.

Example 5

N-[4-(4-chlorophenoxy)-3-(1-methyl-7-oxo-6,7-dihydro-1H-pyrrolo[2,3-c]pyridin-3-yl)phenyl]ethanesulfonamide

Example 5A 3-(2-(4-chlorophenoxy)-5-nitophenyl)-7-methoxy-1-methyl-1H-pyrrolo[2,3-c]pyridine Example 5A was prepared according to the procedure used for the preparation of Example 2C, substituting 4-chlorophenol for 2,4-difluorophenol, with the exception that the reaction mixture was heated at 100° C. for 18 hours, and the residue was purified by flash column chromatography (silica gel, 0-1% methanol in dichloromethane) to provide the title compound.

Example 5B 4-(4-chlorophenoxy)-3-(7-methoxy-1-methyl-1H-pyrrolo[2,3-c]pyridin-3-yl)aniline A mixture of Example 5A (0.162 g, 0.395 mmol) in tetrahydrofuran (20 mL) was added to platinum oxide (0.034 g, 0.150 mmol) in a 50 mL pressure bottle and stirred at ambient temperature under hydrogen at 30 psi for 1 hour. The solid was removed by filtration, and the filtrate was concentrated to provide the title compound (0.140 g, 93% yield).

Example 5C

N-4-(4-chlorophenoxy)-3-(7-methoxy-1-methyl-1H-pyrrolo[2,3-c]pyridin-3-yl)phenyl)ethanesulfonamide A mixture of Example 5B (0.137 g, 0.361 mmol) and triethylamine (0.201 mL, 1.44 mmol) in dichloromethane (9 mL) was treated with ethanesulfonyl chloride (0.103 mL, 1.08 mmol). The mixture was stirred for 18 hours at ambient temperature under nitrogen. The reaction mixture was concentrated and the residue was dissolved in a mixture of dioxane (14 mL) and 1M aqueous sodium hydroxide, (8.66 mL, 8.66 mmol). The mixture was stirred at 50° C. for 1 hour. Upon cooling, the mixture was diluted with saturated ammonium chloride (100 mL) and extracted with ethyl acetate (100 mL, 50 mL). The combined organics were dried over anhydrous sodium sulfate, filtered, and concentrated. The residue was purified by flash column chromatography (silica gel, 0-5% methanol in dichloromethane) to provide the title compound (0.139 g, 82%).

Example 5D

N-[4-(4-chlorophenoxy)-3-(1-methyl-7-oxo-6,7-dihydro-1H-pyrrolo[2,3-c]pyridin-3-yl)phenyl]ethanesulfonamide Example 5D was prepared according to the procedure used for the preparation of Example 1C, substituting Example 5C for Example 1B, with the exception that the reaction mixture was heated at 70° C., and the material was purified by flash chromatography (silica gel, 1-7.5% methanol in dichloromethane) to provide the title compound. $^1$H NMR (400 MHz, DMSO-d$_6$) δ ppm 10.96 (d, J=5.19 Hz, 1H), 9.83 (s, 1H), 7.44-7.50 (m, 2H), 7.27-7.34 (m, 2H), 7.12-7.19 (m, 1H), 7.03-7.10 (m, 1H), 6.83-6.94 (m, 3H), 6.55 (d, J=7.02 Hz, 1H), 4.03 (s, 3H), 3.12 (q, J=7.32 Hz, 2H), 1.24 (t, J=7.32 Hz, 3H). MS (ESI+) m/z 458.0 (M+H)$^+$.

Example 6

N-{4-[(trans-4-methoxycyclohexyl)oxy]-3-(1-methyl-7-oxo-6,7-dihydro-1H-pyrrolo[2,3-c]pyridin-3-yl)phenyl}ethanesulfonamide

Example 6A 4-methoxycyclohexanol

A mixture of 4-methoxyphenol (0.10 g, 0.806 mmol) in acetic acid (10 mL) was added to platinum oxide (0.020 g, 0.088 mmol) in a 50 mL pressure bottle and heated at 50° C. under hydrogen at 30 psi for 1 hour. The solid was removed by filtration, and the filtrate was concentrated to provide the title compound.

Example 6B 7-methoxy-3-(2-((trans)-4-methoxycyclohexyloxy)-5-nitrophenyl)-1-methyl-1H-pyrrolo[2,3-c]pyridine A solution of Example 6A (0.130 g, 0.996 mmol) in tetrahydrofuran (4 mL) was treated with sodium hydride (0.080 g, 2.0 mmol). The resulting white suspension was stirred for 30 minutes at ambient temperature and Example 2B (0.150 g, 0.498 mmol) was added. The mixture was heated at 60° C. for 18 hours. Separately a solution of Example 6A (130 mg, 0.996 mmol) in tetrahydrofuran (4 mL) was treated with sodium hydride (0.080 g, 1.99 mmol). The resulting white suspension was stirred for 30 minutes at ambient temperature and then added to the reaction mixture which was heated at 60° C. for 18 hours. Upon cooling, the reaction mixture was quenched with saturated aqueous ammonium chloride solution (5 mL), diluted with 50% aqueous sodium chloride solution (75 mL) and extracted with ethyl acetate (75 mL, 50 mL). The combined organics were dried over anhydrous sodium sulfate, filtered, and concentrated. The residue was purified by flash chromatography (silica gel, 10-100% ethyl acetate in hexane). Pure fractions of the trans isomer, which was first to elute, were concentrated to provide the title compound (27.2 mg, 13%).

Example 6C 3-(7-methoxy-1-methyl-1H-pyrrolo[2,3-c]pyridin-3-yl)-4-((trans)-4-methoxycyclohexyloxy)aniline A mixture of Example 6B (0.025 g, 0.061 mmol) in tetrahydrofuran (10 mL) was added to 10% palladium on carbon (0.005 g, 0.047 mmol) in a 50 mL pressure bottle and stirred at ambient temperature under hydrogen at 30 psi for 2 hours. The solid was removed by filtration, and the filtrate was concentrated to provide the title compound (0.023 g, 100% yield).

Example 6D

N-(3-(7-methoxy-1-methyl-1H-pyrrolo[2,3-c]pyridin-3-yl)-4-((trans)-4-methoxycyclohexyloxy)phenyl)ethanesulfonamide Example 6D was prepared according to the procedure used for the preparation of Example 5C, substituting Example 6C for Example 5B.

Example 6E

N-{4-[(trans-4-methoxycyclohexyl)oxy]-3-(1-methyl-7-oxo-6,7-dihydro-1H-pyrrolo[2,3-c]pyridin-3-yl)phenyl}ethanesulfonamide Example 6E was prepared according to the procedure used for the preparation of Example 1C, substituting Example 6D for Example 1B, with the exception that the reaction mixture was heated at 70° C., and the material was purified by flash chromatography (silica gel, 1-7.5% methanol in dichloromethane) to provide the title compound. $^1$H NMR (400 MHz, DMSO-$d_6$) δ ppm 10.91 (d, J=5.19 Hz, 1H), 9.49 (s, 1H), 7.45-7.52 (m, 1H), 7.31 (d, J=1.83 Hz, 1H), 7.02-7.13 (m, 2H), 6.83-6.93 (m, 1H), 6.51 (d, J=7.02 Hz, 1H), 4.26-4.38 (m, 1H), 4.10 (s, 3H), 3.14-3.24 (m, 4H), 3.02 (q, J=7.32 Hz, 2H), 1.92 (d, J=8.24 Hz, 2H), 1.78-1.88 (m, 2H), 1.26-1.48 (m, 4H), 1.21 (t, J=7.32 Hz, 3H). MS (ESI+) m/z 460.0 (M+H)$^+$.

Example 7

N-[3-(1-methyl-7-oxo-6,7-dihydro-1H-pyrrolo[2,3-c]pyridin-3-yl)-4-(tetrahydro-2H-pyran-4-yloxy)phenyl]ethanesulfonamide

Example 7A 7-methoxy-1-methyl-3-(5-nitro-2-(tetrahydro-2H-pyran-4-yloxy)phenyl)-1H-pyrrolo[2,3-c]pyridine A solution of tetrahydro-2H-pyran-4-ol (102 mg, 0.996 mmol) in tetrahydrofuran (4 mL) was treated with sodium hydride (80 mg, 1.992 mmol) at ambient temperature. The resulting white suspension was stirred for 30 minutes at ambient temperature and Example 2B (150 mg, 0.498 mmol) was added. The mixture was heated at 60° C. for 18 hours. Upon cooling, the reaction mixture was quenched with saturated ammonium chloride solution (5 mL), diluted with 50% saturated aqueous sodium chloride (75 mL) and extracted with ethyl acetate (75 mL, 50 mL). The combined organics were dried over anhydrous sodium sulfate, filtered, and concentrated. The residue was purified by flash chromatography (silica gel, 0-5% methanol in dichloromethane) to provide the title compound (0.074 g, 39%).

Example 7B 3-(7-methoxy-1-methyl-1H-pyrrolo[2,3-c]pyridin-3-yl)-4-(tetrahydro-2H-pyran-4-yloxy)aniline Example 7B was prepared according to the procedure used for the preparation of Example 6C, substituting Example 7A for Example 6B.

Example 7C

N-(3-(7-methoxy-1-methyl-1H-pyrrolo[2,3-c]pyridin-3-yl)-4-(tetrahydro-2H-pyran-4-yloxy)phenyl)ethanesulfonamide Example 7C was prepared according to the procedure used for the preparation of Example 5C, substituting Example 7B for Example 5B.

Example 7D

N-[3-(1-methyl-7-oxo-6,7-dihydro-1H-pyrrolo[2,3-c]pyridin-3-yl)-4-(tetrahydro-2H-pyran-4-yloxy)phenyl]ethanesulfonamide Example 7D was prepared according to the procedure used for the preparation of Example 1C, substituting Example 7C for Example 1B, with the exception that the reaction mixture was heated at 70° C., and the material was purified by flash-chromatography (silica gel, 1-7.5% methanol in dichloromethane) to provide the title compound. $^1$H NMR (300 MHz, DMSO-$d_6$) ppm 10.91 (d, J=5.43 Hz, 1H), 9.50 (s, 1H), 7.50-7.54 (m, 1H), 7.32 (d, J=2.37 Hz, 1H), 7.04-7.15 (m, 2H), 6.85-6.92 (m, 1H), 6.51 (d, J=6.10 Hz, 1H), 4.44-4.55 (m, 1H), 4.12 (s, 3H), 3.66-3.77 (m, 2H), 3.36-3.47 (m, 2H), 3.02 (q, J=7.12 Hz, 2H), 1.84-1.96 (m, 2H), 1.49-1.64 (m, 2H), 1.21 (t, J=7.29 Hz, 3H). MS (ESI+) m/z 432.0 (M+H)$^+$.

Example 8

N-{4[(4,4-difluorocyclohexyl)oxy]-3-(1-methyl-7-oxo-6,7-dihydro-1H-pyrrolo[2,3-c]pyridin-3-yl)phenyl}ethanesulfonamide Example 8A 3-(2-(4,4-difluorocyclohexyloxy)-5-nitrophenyl)-7-methoxy-1-methyl-1H-pyrrolo[2,3-c]pyridine Example 8A was prepared according to the procedure used for the preparation of Example 7A, substituting 4,4-difluorocyclohexanol for tetrahydro-2H-pyran-4-ol.

Example 8B 4-(4,4-difluorocyclohexyloxy)-3-(7-methoxy-1-methyl-1H-pyrrolo[2,3-c]pyridin-3-yl)aniline Example 8B was prepared according to the procedure used for the preparation of Example 6C, substituting Example 8A for Example 6B.

Example 8C

N-(4-(4,4-difluorocyclohexyloxy)-3-(7-methoxy-1-methyl-1H-pyrrolo[2,3-c]pyridin-3-yl)phenyl)ethanesulfonamide Example 8C was prepared according to the procedure used for the preparation of Example 5C, substituting Example 8B for Example 5B.

Example 8D

N-{4-[(4,4-difluorocyclohexyl)oxy]-3-(1-methyl-7-oxo-6,7-dihydro-1H-pyrrolo[2,3-c]pyridin-3-yl)phenyl}ethanesulfonamide Example 8D was prepared according to the procedure used for the preparation of Example 1C, substituting Example 8C for Example 1B, with the exception that the reaction mixture was heated at 70° C., and the material was purified by flash chromatography (silica gel, 1-7.5% methanol in dichloromethane) to provide the title compound. $^1$H NMR (300 MHz, DMSO-$d_6$) δ ppm 10.91 (d, J=5.43 Hz, 1H), 9.52 (s, 1H), 7.49 (s, 1H), 7.30 (d, J=2.71 Hz, 1H), 7.05-7.20 (m, 2H), 6.87 (dd, J=7.12, 5.76 Hz, 1H), 6.48 (d, J=6.10 Hz, 1H), 4.52 (d, J=3.39 Hz, 1H), 4.10 (s, 3H), 3.03 (q, J=7.35 Hz, 2H), 1.70-1.94 (m, 8H), 1.21 (t, J=7.29 Hz, 3H). MS (ESI+) m/z 466.1 (M+H)$^+$.

Example 9

N-{4-[(cis-4-methoxycyclohexyl)oxy]-3-(1-methyl-7-oxo-6,7-dihydro-1H-pyrrolo[2,3-c]pyridin-3-yl)phenyl}ethanesulfonamide Example 9A 7-methoxy-3-(2-((cis)-4-methoxycyclohexyloxy)-5-nitrophenyl)-1-methyl-1H-pyrrolo[2,3-c]pyridine The title compound (98.5 mg, 48.1%) was obtained as the second eluting isomer from the flash chromatography purification described in Example 6B.

Example 9B 3-(7-methoxy-1-methyl-1H-pyrrolo[2,3-c]pyridin-3-yl)-4-((cis)-4-methoxycyclohexyloxy)aniline Example 9B was prepared according to the procedure used for the preparation of Example 6C, substituting Example 9A for Example 6B.

Example 9C

N-(3-(7-methoxy-1-methyl-1H-pyrrolo[2,3-c]pyridin-3-yl)-4-((cis)-4-methoxycyclohexyloxy)phenyl)ethanesulfonamide Example 9C was prepared according to the procedure used for the preparation of Example 5C, substituting Example 9B for Example 5B.

Example 9D

N-{4-[(cis-4-methoxycyclohexyl)oxy]-3-(1-methyl-7-oxo-6,7-dihydro-1H-pyrrolo[2,3-c]pyridin-3-yl)phenyl}ethanesulfonamide Example 9D was prepared according to the procedure used for the preparation of Example 1C, substituting Example 9C for Example 1B, with the exception that the reaction mixture was heated at 70° C., and the material was purified by flash chromatography (silica gel, 1-7.5% methanol in dichloromethane) to provide the title compound. $^1$H NMR (300 MHz, DMSO-$d_6$) δ ppm 10.91 (d, J=5.43 Hz, 1H), 9.47 (s, 1H), 7.49 (s, 1H), 7.32 (s, 1H), 7.07 (s, 2H), 6.87 (dd, J=7.12, 5.76 Hz, 1H), 6.52 (d, J=5.76 Hz, 1H), 4.31-4.42 (m, 1H), 4.06-4.14 (m, 3H), 3.18-3.26 (m, 1H), 3.15-3.18 (m, 3H), 3.02 (q, J=7.46 Hz, 2H), 1.67-1.79 (m, 2H), 1.46-1.66 (m, 6H), 1.16-1.27 (m, 3H). MS (ESI+) m/z 460.0 (M+H)$^+$.

Example 10

N-[3-(1-methyl-7-oxo-6,7-dihydro-1H-pyrrolo[2,3-c]pyridin-3-yl)-4-(oxetan-3-yloxy)phenyl]ethanesulfonamide Example 10A 7-methoxy-1-methyl-3-(5-nitro-2-(oxetan-3-yloxy)phenyl)-1H-pyrrolo[2,3-c]pyridine Example 10A was prepared according to the procedure used for the preparation of Example 7A, substituting oxetan-3-ol for tetrahydro-2H-pyran-4-ol.

Example 10B 3-(7-methoxy-1-methyl-1H-pyrrolo[2,3-c]pyridin-3-yl)-4-(oxetan-3-yloxy)aniline Example 10B was prepared according to the procedure used for the preparation of Example 6C, substituting Example 10A for Example 6B.

Example 10C

N-(3-(7-methoxy-1-methyl-1H-pyrrolo[2,3-c]pyridin-3-yl)-4-(oxetan-3-yloxy)phenyl)ethanesulfonamide Example 10C was prepared according to the procedure used for the preparation of Example 5C, substituting Example 10B for Example 5B.

Example 10D

N-(4-(1-chloro-3-hydroxypropan-2-yloxy)-3-(1-methyl-7-oxo-6,7-dihydro-1H-pyrrolo[2,3-c]pyridin-3-yl)phenyl)ethanesulfonamide Example 10D was prepared according to the procedure used for the preparation of Example 1C, substituting Example 10C for Example 1B, and with the exception that the reaction mixture was heated at 70° C.

Example 10E

N-[3-(1-methyl-7-oxo-6,7-dihydro-1H-pyrrolo[2,3-c]pyridin-3-yl)-4-(oxetan-3-yloxy)phenyl]ethanesulfonamide A solution of Example 10D (82 mg, 0.188 mmol) in a mixture of tetrahydrofuran (7.5 mL) and N,N-dimethylformamide (0.5 mL) was treated with sodium hydride (66 mg, 1.6 mmol) at ambient temperature. The reaction mixture was heated at 62° C. for 72 hours. The reaction mixture was concentrated and the residue was quenched with water. The mixture was treated with ammonium chloride to neutral pH, diluted with saturated aqueous sodium chloride and extracted with dichloromethane. The organics were dried over anhydrous sodium sulfate, filtered, and concentrated. The residue was purified by flash chromatography (silica gel, 1-7.5% methanol in dichloromethane) to provide the title compound (25.4 mg, 34% yield). $^1$H NMR (400 MHz, DMSO-$d_6$) δ ppm 10.94 (d, J=5.19 Hz, 1H), 9.55 (s, 1H), 7.60 (s, 1H), 7.36 (d, J=2.75 Hz, 1H), 7.05 (dd, J=8.70, 2.59 Hz, 1H), 6.86-6.94 (m, 1H), 6.65 (d, J=8.54 Hz, 1H), 6.52 (d, J=7.02 Hz, 1H), 5.17-5.30 (m, 1H), 4.90 (t, J=6.71 Hz, 2H), 4.56 (dd, J=7.02, 5.19 Hz, 2H), 4.13 (s, 3H), 3.02 (q, J=7.32 Hz, 2H), 1.20 (t, J=7.48 Hz, 3H). MS (ESI+) m/z 404.0 (M+H)$^+$.

Example 11

N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide

Example 11A 1-bromo-2-(2,4-difluorophenoxy)-4-fluoro-5-nitrobenzene

A mixture of 1-bromo-2,4-difluoro-5-nitrobenzene (0.5 g, 2.10 mmol) and cesium carbonate (0.685 g, 2.10 mmol) in DMSO (10.50 mL) was treated dropwise with 2,4-difluorophenol (0.273 g, 2.10 mmol), stirred for 60 minutes at ambient temperature and partitioned between ethyl acetate and water, adjusting the pH to 6 with 1 M HCl. The organic layer was washed with water, saturated aqueous sodium chloride, dried (MgSO$_4$), filtered, and concentrated. Purification by chromatography (silica gel, 0-30% ethyl acetate in heptanes) afforded the title compound and 1-bromo-4-(2,4-difluorophenoxy)-2-fluoro-5-nitrobenzene as an inseparable mixture (0.59 g, 81%).

Example 11B 5-bromo-4-(2,4-difluorophenoxy)-2-fluoroaniline

The product from Example 11A (0.59 g, 1.69 mmol), iron (0.47 g, 8.48 mmol) and ammonium chloride (0.136 g, 2.54 mmol) were combined in a solvent mixture of ethanol (9 mL), tetrahydrofuran (9 mL) and water (3 mL) and heated at 90° C. for 2 hours. The mixture was cooled, filtered through Celite and the Celite pad was washed repeatedly with methanol. The filtrate was concentrated and the residue was partitioned between ethyl acetate and water. The organic layer was washed with saturated aqueous sodium chloride, dried (anhydrous Na$_2$SO$_4$), filtered, and concentrated. Purification by chromatography (silica gel, 0-60% ethyl acetate in heptanes) afforded the title compound and 5-bromo-2-(2,4-difluorophenoxy)-4-fluoroaniline as an inseparable mixture (0.43 g, 80%).

Example 11C

N-(5-bromo-4-(2,4-difluorophenoxy)-2-fluorophenyl)methanesulfonamide

A mixture of the product from Example 11B (0.428 g, 1.35 mmol) and triethylamine (0.469 mL, 3.36 mmol) in dichloromethane (13.5 mL) was treated dropwise with methanesulfonyl chloride (0.23 mL, 2.96 mmol), stirred for 2 hours and concentrated. The residue was dissolved in a mixture of dioxane (4 mL) and 1M sodium hydroxide (1 mL), heated for 1 hour at 90° C., cooled and diluted with ethyl acetate. The mixture was brought to pH 7 with 1 M HCl and the organic layer was separated, dried (anhydrous Na$_2$SO$_4$), filtered, and concentrated. Purification by chromatography (silica gel, 0-60% ethyl acetate in heptanes) afforded the title compound as the second eluting regioisomer (0.346 g, 65%).

Example 11D

N-(5-bromo-2-(2,4-difluorophenoxy)-4-fluorophenyl)methanesulfonamide

A mixture of the product from Example 11B (0.428 g, 1.35 mmol) and triethylamine (0.469 mL, 3.36 mmol) in dichloromethane (13.5 mL) was treated dropwise with methanesulfonyl chloride (0.23 mL, 2.96 mmol), stirred for 2 hours at ambient temperature and concentrated. The residue was dissolved in a mixture of dioxane (4 mL) and 1M sodium hydroxide (1 mL), heated for 1 hour at 90° C., cooled and diluted with ethyl acetate. The mixture was brought to pH 7 with 1 M HCl and the organic layer was separated, dried (anhydrous Na$_2$SO$_4$), filtered, and concentrated. Purification by chromatography (silica gel, 0-60% ethyl acetate in heptanes) afforded the title compound as the first eluting regioisomer (0.057 g, 11%).

Example 11E

N-(4-(2,4-difluorophenoxy)-2-fluoro-5-(7-methoxy-1-methyl-1H-pyrrolo[2,3-c]pyridin-3-yl)phenyl)methanesulfonamide The product from Example 59A (0.073 g, 0.252 mmol), the product from Example 11C (0.1 g, 0.252 mmol), tris(dibenzylideneacetone)dipalladium(0) (6.93 mg, 7.57 μmol), 1,3,5,7-tetramethyl-6-phenyl-2,4,8-trioxa-6-phosphaadamante (7.38 mg, 0.025 mmol) and sodium carbonate (0.094 g, 0.883 mmol) were combined and sparged with argon for 15 minutes. Meanwhile a solution of 4:1 dioxane/water (2 mL) was sparged with nitrogen for 15 minutes and transferred by syringe into the reaction vessel under argon. The mixture was stirred at 60° C. for 4 hours under argon and partitioned between ethyl acetate and water. The organic layer was washed with saturated aqueous sodium chloride, dried (anhydrous $Na_2SO_4$), treated with 3-mercaptopropyl functionalized silica gel, filtered, and concentrated to afford the title compound (0.12 g, 99%).

Example 11F

N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide The product from Example 11E (0.120 g, 0.252 mmol) and 4 M hydrogen chloride in dioxane (10 mL, 40.0 mmol) were combined and heated at 70° C. for 24 hours, cooled and concentrated. The residue was purified by reverse phase HPLC (C18, $CH_3CN$/water (0.1% TFA), 10-100%) to afford the title compound (0.080 g, 68%). $^1$H NMR (300 MHz, DMSO-$d_6$) δ ppm 10.95 (d, J=5.43 Hz, 1H) 9.57 (s, 1H) 7.41-7.55 (m, 3H) 7.23-7.34 (m, 1H) 7.05-7.15 (m, 1H) 6.86-6.93 (m, 1H) 6.79 (d, J=11.19 Hz, 1H) 6.51 (d, J=5.76 Hz, 1H) 4.09 (s, 3H) 3.03 (s, 3H). MS (ESI+) m/z 464 (M+H)$^+$.

Example 12

N-[2-(2,4-difluorophenoxy)-4-fluoro-5-(1-methyl-7-oxo-6,7-dihydro-1H-pyrrolo[2,3-c]pyridin-3-yl)phenyl]methanesulfonamide

Example 12A

N-(2-(2,4-difluorophenoxy)-4-fluoro-5-(7-methoxy-1-methyl-1H-pyrrolo[2,3-c]pyridin-3-yl)phenyl)methanesulfonamide Example 59A (0.040 g, 0.139 mmol), Example 11D (0.055 g, 0.139 mmol), tris(dibenzylideneacetone)dipalladium(0) (3.81 mg, 4.16 μmol), 1,3,5,7-tetramethyl-6-phenyl-2,4,8-trioxa-6-phosphaadamante (4.06 mg, 0.014 mmol) and sodium carbonate (0.051 g, 0.486 mmol) were combined and sparged with argon for 15 minutes. Meanwhile a solution of 4:1 dioxane/water (2 mL) was sparged with nitrogen gas for 15 minutes and transferred by syringe into the reaction vessel under argon. The mixture was stirred at 60° C. for 4 hours and partitioned between ethyl acetate and water. The organic layer was washed with brine, dried (anhydrous $Na_2SO_4$), treated with mercaptopropyl silica gel, filtered, and concentrated to afford the title compound (0.066 g, 99%).

Example 12B

N-[2-(2,4-difluorophenoxy)-4-fluoro-5-(1-methyl-7-oxo-6,7-dihydro-1H-pyrrolo[2,3-c]pyridin-3-yl)phenyl]methanesulfonamide The product from Example 12A (0.066 g, 0.138 mmol) and 4 M hydrogen chloride in dioxane (10 mL, 40.0 mmol) were combined and heated at 70° C. for 24 hours, cooled and concentrated. The residue was purified by reverse phase HPLC (C18, $CH_3CN$/water (0.1% TFA), 10-100%) to afford the title compound (0.022 g, 34%). $^1$H NMR (300 MHz, DMSO-$d_6$) δ ppm 11.00 (d, J=5.09 Hz, 1H) 9.53 (s, 1H) 7.47-7.59 (m, 3H) 7.30-7.41 (m, 1H) 7.11-7.20 (m, 1H) 6.90-6.96 (m, 1H) 6.78 (d, J=10.85 Hz, 1H) 6.49 (d, J=7.12 Hz, 1H) 4.11 (s, 3H) 3.05 (s, 3H). MS (ESI+) m/z 464 (M+H)$^+$.

Example 13

N-[2,4-bis(2,4-difluorophenoxy)-5-(1-methyl-7-oxo-6,7-dihydro-1H-pyrrolo[2,3-c]pyridin-3-yl)phenyl]methanesulfonamide

Example 13A 4,4'-(4-bromo-6-nitro-1,3-phenylene)bis(oxy)bis(1,3-difluorobenzene)

To a solution of 1-bromo-2,4-difluoro-5-nitrobenzene (0.3 g, 1.26 mmol) and cesium carbonate (0.86 g, 2.65 mmol) in DMSO (6.3 mL) was added dropwise 2,4-difluorophenol (0.27 g, 2.10 mmol). The mix was stirred for 60 minutes at ambient temperature and partitioned between ethyl acetate and water, adjusting the pH to 6 with HCl. The organic layer was washed with water, saturated aqueous sodium chloride, dried ($MgSO_4$), filtered, and concentrated to afford the title compound (0.578 g, 100%).

Example 13B 5-bromo-2,4-bis(2,4-difluorophenoxy)aniline

The product from Example 13A (0.578 g, 1.26 mmol), iron (0.352 g, 6.31 mmol), and ammonium chloride (0.101 g, 1.89 mmol) were combined in a mixture of tetrahydrofuran (9 mL), ethanol (9 mL), water (3 mL) and heated at 90° C. for 2 hours. The mixture was cooled, filtered through Celite and the Celite pad was washed repeatedly with methanol. The filtrate was concentrated and the residue was partitioned between ethyl acetate and water. The organic layer was washed with saturated aqueous sodium chloride, dried (anhydrous $Na_2SO_4$), filtered, and concentrated to afford the title compound (0.52 g, 96%).

Example 13C

N-(5-bromo-2,4-bis(2,4-difluorophenoxy)phenyl)methanesulfonamide

To the product from Example 13B (0.52 g, 1.214 mmol) and triethylamine (0.423 mL, 3.04 mmol) in dichloromethane (12.14 mL) was added dropwise methanesulfonyl chloride (0.207 mL, 2.67 mmol). The mixture was stirred for 2 hours at ambient temperature, and concentrated. The residue was dissolved in a mixture of dioxane (4 mL) and 1 M sodium hydroxide (1 mL) and heated for 1 hour at 90° C. The mixture was cooled and diluted with ethyl acetate, brought to pH 7 with 1 M HCl and the organic layer was separated, dried (anhydrous $Na_2SO_4$), filtered, and concentrated. Purification by chromatography (silica gel, 20-60% ethyl acetate in heptanes) afforded the title compound (0.5 g, 81%).

Example 13D

N-(2,4-bis(2,4-difluorophenoxy)-5-(7-methoxy-1-methyl-1H-pyrrolo[2,3-c]pyridin-3-yl)phenyl)methanesulfonamide Example 13D (0.122 g, 99%) was prepared according to the procedure for the preparation of Example 11E substituting Example 13C for Example 11C.

Example 13E

N-[2,4-bis(2,4-difluorophenoxy)-5-(1-methyl-7-oxo-6,7-dihydro-1H-pyrrolo[2,3-c]pyridin-3-yl)phenyl]methanesulfonamide Example 13D (0.122 g, 0.208 mmol) and 4 M hydrogen chloride in dioxane (5 mL, 20.0 mmol) were combined and heated at 70° C. for 24 hours, cooled and concentrated. The residue was purified by reverse phase HPLC (C18, $CH_3CN$/water (0.1% TFA), 10-100%) to afford the title compound (0.055 g, 46%). $^1H$ NMR (300 MHz, DMSO-$d_6$) δ ppm 10.94 (d, J=5.43 Hz, 1H) 9.48 (s, 1H) 7.53 (d, J=12.21 Hz, 2H) 7.32-7.48 (m, 2H) 6.94-7.28 (m, 4H) 6.90 (dd, J=7.12, 5.76 Hz, 1H) 6.55 (d, J=6.10 Hz, 1H) 6.22 (s, 1H) 4.08 (s, 3H) 3.04 (s, 3H). MS (ESI+) m/z 574 $(M+H)^+$.

Example 14

N-[4-(cyclopropylmethoxy)-2-methyl-3-(1-methyl-7-oxo-6,7-dihydro-1H-pyrrolo[2,3-c]pyridin-3-yl)phenyl]ethanesulfonamide Example 14A 2-bromo-1-(cyclopropylmethoxy)-3-methyl-4-nitrobenzene A flask with stirbar was charged with 2-bromo-3-methyl-4-nitrophenol (Parkway Scientific, 1.15 g, 4.96 mmol), (bromomethyl)cyclopropane (0.60 mL, 6.19 mmol) and cesium carbonate (2.65 g, 8.13 mmol) in dimethylformamide (16 mL). The mixture was stirred overnight at ambient temperature. The mixture was then heated to 50° C. in an oil bath. After 3 hours, the mixture was cooled and shaken in a separatory funnel with 100 mL each of ethyl acetate and saturated aqueous sodium chloride. The organics were washed twice with saturated aqueous sodium chloride, dried over sodium sulfate, filtered, and concentrated. The crude product was purified by flash chromatography (silica gel, 0-30% ethyl acetate in hexanes) to provide 1.24 g (87%) of the title compound Example 14B 3-bromo-4-(cyclopropylmethoxy)-2-methylaniline Example 14A (0.656 g, 2.293 mmol) in ethanol (18.00 mL) and tetrahydrofuran (18.00 mL) at 65° C. was treated sequentially with iron powder, <10 micron (1.32 g, 23.64 mmol) and a solution of ammonium chloride (0.310 g, 5.80 mmol) in water (9 mL). The resulting mixture was stirred vigorously at 65° C. for 20 hours. The reaction mixture was cooled and filtered through a fritted funnel containing a pad of Celite 503 filter aid, rinsing with ethyl acetate. The filtrate was washed with aqueous sodium bicarbonate and saturated aqueous sodium chloride, dried over sodium sulfate, filtered, and concentrated. The crude product was purified by flash chromatography (silica gel, 0-30% ethyl acetate in hexanes) to provide 0.38 g (65%) of the title compound.

Example 14C 4-(cyclopropylmethoxy)-3-(7-methoxy-1-methyl-1H-pyrrolo[2,3-c]pyridin-3-yl)-2-methylaniline Example 59A (0.0743 g, 0.258 mmol), tris(dibenzylidineacetone)dipalladium(0) (0.0070 g, 7.64 µmol), 1,3,5,7-tetramethyl-6-phenyl-2,4,8-trioxa-6-phosphaadamantane (0.0080 g, 0.027 mmol) and tris-potassium phosphate (0.175 g, 0.824 mmol) were combined in a sealed 2 mL microwave tube with stir bar and sparged with nitrogen for 15 minutes. A solution of Example 14B (0.0750 g, 0.293 mmol) in degassed mixture of 4:1 dioxane/water (1.25 mL) was added by syringe into the reaction vessel which was then heated at 65° C. for 2 hours in an oil bath, then cooled to ambient temperature. The reaction mixture was shaken in a separatory funnel with 30 mL ethyl acetate and 20 mL saturated aqueous sodium chloride. The organics were dried over sodium sulfate filtered, and concentrated. The crude product was purified by flash chromatography (silica gel, 0-100% ethyl acetate in hexanes) to provide 0.070 g (80%) of the title compound.

Example 14D

N-(4-(cyclopropylmethoxy)-3-(7-methoxy-1-methyl-1H-pyrrolo[2,3-c]pyridin-3-yl)-2-methylphenyl)ethanesulfonamide Example 14D was prepared according to the procedure used for the preparation of Example 2E, substituting Example 14C for Example 2D and substituting ethanesulfonyl chloride for methanesulfonyl chloride, respectively.

Example 14E

N-(4-(cyclopropylmethoxy)-2-methyl-3-(1-methyl-7-oxo-6,7-dihydro-1H-pyrrolo[2,3-c]pyridin-3-yl)phenyl)ethanesulfonamide Example 14E was prepared according to the procedure used for the preparation of Example 1C, substituting Example 14D for Example 1B. $^1H$ NMR (500 MHz, DMSO-$d_6$) δ ppm 10.69 (d, J=4.9 Hz, 1H), 8.76 (bds, 1H), 7.08 (s, 1H), 7.04 (d, J=8.9 Hz, 1H), 6.75 (d, J=8.9 Hz, 1H), 6.66 (m, 1H), 5.81 (d, J=6.7 Hz, 1H), 3.60 (d, J=6.4 Hz, 2H), 2.93 (q, J=7.6 Hz, 2H), 2.37 (s, 3H), 1.96 (s, 3H), 1.15 (t, =7.3 Hz, 3H), 0.87 (m, 1H), 0.26 (dt, J=7.6, 3.8 Hz, 2H), 0.01 (m, 2H). MS (ESI+) m/z 416.1 $(M+H)^+$.

Example 15

N-[4-(4-fluorophenoxy)-3-(1-methyl-7-oxo-6,7-dihydro-1H-pyrrolo[2,3-c]pyridin-3-yl)phenyl]ethanesulfonamide Example 15A 3-(2-(4-fluorophenoxy)-5-nitrophenyl)-7-methoxy-1-methyl-1H-pyrrolo[2,3-c]pyridine A 5 mL microwave vial was charged with Example 2B (150 mg, 0.498 mmol), 4-fluorophenol (84 mg, 0.747 mmol), cesium carbonate (243 mg, 0.747 mmol), and dimethylsulfoxide (5 mL). The reaction mixture was heated at 110° C. overnight under a nitrogen bubbler. Upon cooling, the reaction was partitioned between 50% brine (75 mL) and ethyl acetate (75 mL). The layers were separated and the aqueous layer was extracted with ethyl acetate (40 ml). The combined organics were dried over sodium sulfate, filtered and concentrated. The residue was purified by flash chromatography (silica gel, 0-1% methanol in dichloromethane) to give the title compound (171 mg, 87%).

Example 15B 4-(4-fluorophenoxy)-3-(7-methoxy-1-methyl-1H-pyrrolo[2,3-c]pyridin-3-yl)aniline A solution of Example 15A (167 mg, 0.425 mmol) in tetrahydrofuran (20 mL) was added to 10% palladium on carbon (34 mg, 0.319 mmol) in a 50 mL pressure bottle and stirred at ambient temperature under hydrogen at 30 psi for 1 hour. The solution was filtered through a syringe filter and concentrated to give the title compound (152 mg, 99%).

Example 15C

N-(4-(4-fluorophenoxy)-3-(7-methoxy-1-methyl-1H-pyrrolo[2,3-c]pyridin-3-yl)phenyl)ethanesulfonamide A 50 mL flask was charged with Example 15B (149 mg, 0.410 mmol) and dichloromethane (10 mL). Triethylamine (0.229 mL, 1.640 mmol) was added, followed by ethanesulfonyl chloride (0.117 mL, 1.230 mmol). The reaction mixture was stirred overnight at ambient temperature and then concentrated. The residue was diluted with dioxane (16 mL) and 1M aqueous sodium hydroxide (9.84 mL, 9.84 mmol). The mixture was stirred at 50° C. for 1 hour. Upon cooling to ambient temperature, the mixture was diluted with saturated ammonium chloride (100 mL) and extracted with ethyl acetate (80 mL). The organic layer was dried over sodium sulfate, filtered, and concentrated. The residue was purified by flash chromatography (silica gel, 0-10% methanol in methylene chloride) to provide the title compound (166 mg, 89%).

Example 15D

N-[4-(4-fluorophenoxy)-3-(1-methyl-7-oxo-6,7-dihydro-1H-pyrrolo[2,3-c]pyridin-3-yl)phenyl]ethanesulfonamide A 100 mL flask was charged with Example 15C (163 mg, 0.358 mmol) and dioxane (4 mL). Hydrogen chloride in dioxane (4N, 4.61 mL, 18.43 mmol) was added and the reaction mixture was heated at 70° C. for 18 hours. The reaction mixture was concentrated and purified by flash chromatography (silica gel, 1-7.5% methanol in dichloromethane) to provide the title compound (96.6 mg, 61%). $^1$H NMR (400 MHz, DMSO-$d_6$) δ ppm 10.96 (d, J=5.49 Hz, 1H), 9.79 (s, 1H), 7.50 (s, 1H), 7.45 (d, J=2.75 Hz, 1H), 7.07-7.18 (m, 3H), 6.98 (d, J=8.54 Hz, 1H), 6.86-6.95 (m, 3H), 6.56 (d, J=6.71 Hz, 1H), 4.05 (s, 3H), 3.11 (q, J=7.32 Hz, 2H), 1.23 (t, J=7.32 Hz, 3H). MS (ESI+) m/z 442.1 (M+H)$^+$.

Example 16

N-[4-(4-cyanophenoxy)-3-(1-methyl-7-oxo-6,7-dihydro-1H-pyrrolo[2,3-c]pyridin-3-yl)phenyl]methanesulfonamide Example 16A 4-(2-bromo-4-nitrophenoxy)benzonitrile A mixture of 2-bromo-1-fluoro-4-nitrobenzene (2.20 g, 10 mmol), 4-hydroxybenzonitrile (1.31 g, 11 mmol), and cesium carbonate (3.58 g, 11 mmol) in DMSO (20 mL) was heated at 90° C. for 2 hours. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated to give 3.19 g (110%) of the title compound.

Example 16B 4-(4-amino-2-bromophenoxy)benzonitrile

Example 16A (3.21 g, 10.06 mmol) in tetrahydrofuran (70 mL) was added to platinum(IV) oxide (0.642 g, 2.83 mmol) in a 250 mL stainless steel pressure bottle. The mixture was stirred for 45 minutes at 30 psi and room temperature. The solid was fitered off, and the filtrate was concentrated. The residue was purified by flash chromatography on silica gel, eluting with 30% ethyl acetate in hexanes to provide 1.75 g (60%) of the title compound.

Example 16C 4-(4-amino-2-(4,4,5,5-tetramethyl-1,3,2-dioxaborolan-2-yl)phenoxy)benzonitrile A mixture of Example 16B (1.75 g, 6.05 mmol), 4,4,4',4', 5,5,5',5'-octamethyl-2,2'-bi(1,3,2-dioxaborolane) (3.07 g, 12.11 mmol), 1,3,5,7-tetramethyl-6-phenyl-2,4,8-trioxa-6-phosphaadamantane (0.159 g, 0.545 mmol), tris(dibenzylideneacetone)dipalladium(0) (0.166 g, 0.182 mmol), and potassium acetate (1.307 g, 13.32 mmol) in dioxane (30 mL) was degassed and back-filled with nitrogen several times. The reaction mixture was heated at 80° C. for 20 hours. The solvent was removed, and the residue was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The crude product was purified by flash chromatography (silica gel, 40-70% ethyl acetate in hexanes) to provide 2.0 g (98%) of the title compound.

Example 16D 4-(4-amino-2-(7-methoxy-1-methyl-1H-pyrrolo[2,3-c]pyridin-3-yl)phenoxy)benzonitrile A mixture of Example 2A (0.086 g, 0.3 mmol), Example 16C (0.121 g, 0.360 mmol, 1.3 equivalents), tetrakis(triphenylphosphine)palladium(0) (0.017 g, 0.015 mmol), and cesium fluoride (0.137 g, 0.9 mmol) in dimethoxyethane (2 mL) and methanol (1.0 mL) was heated under microwave conditions (120° C., 30 minutes). The reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The residue was purified by flash column chromatography (silica gel, 40% ethyl acetate/hexanes) to give the title compound (0.03 g, 27% yield).

Example 16E

N-(4-(4-cyanophenoxy)-3-(7-methoxy-1-methyl-1H-pyrrolo[2,3-c]pyridin-3-yl)phenyl)methanesulfonamide A mixture of Example 16D (0.03 g, 0.081 mmol), methanesulfonyl chloride (0.028 g, 0.243 mmol), and triethylamine (0.049 g, 0.486 mmol) in dichloromethane (3 mL) was stirred at ambient temperature for 2 hours. The solvent was removed, and the residue was treated with sodium hydroxide (0.656 mL, 1.31 mmol) and dioxane (3 mL). The reaction mixture was heated at 80° C. for 3 hours. After cooling, the reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated to give the title compound.

Example 16F

N-[4-(4-cyanophenoxy)-3-(1-methyl-7-oxo-6,7-dihydro-1H-pyrrolo[2,3-c]pyridin-3-yl)phenyl]methanesulfonamide Example 16E (0.032 g, 0.071 mmol) in dioxane (2 ml) was treated with hydrogen chloride (0.9 ml, 3.6 mmol). The reaction mixture was heated at 75° C. overnight. The solvent was removed, and the residue was purified by reverse phase HPLC (C18, $CH_3CN$/water (0.1% TFA), 0-100%) to provide the title compound (0.024 g, 0.055 mmol, 77% yield). $^1$H NMR (500 MHz, DMSO-$d_6$) δ ppm 10.97 (d, J=5.19 Hz, 1H), 9.86 (s, 1H), 7.69-7.73 (m, 2H), 7.47-7.48 (m, 1H), 7.46 (s, 1H), 7.18-7.23 (m, 2H), 6.93-6.97 (m, 1H), 6.88-6.92 (m, 1H), 6.55 (d, J=6.71 Hz, 1H), 4.01 (s, 3H), 3.06 (s, 3H). MS (ESI+) m/z 435.2 (M+H)$^+$.

Example 17

3-[2-(2,4-difluorophenoxy)-5-(methylsulfonyl)phenyl]-1-methyl-1,6-dihydro-7H-pyrrolo[2,3-c]pyridin-7-one Example 17A 2-bromo-1-fluoro-4-(methylsulfonyl)benzene 1-Fluoro-4-(methylsulfonyl)benzene (5.0 g, 28.7 mmol) in conc. sulfuric acid (30 mL) was cooled to 0° C. To this solution was added N-bromosuccinimide (5.62 g, 31.6 mmol). The reaction mixture was stirred at room temperature for 6 hours and then poured into ice-water. The resulting solid was collected by filtration, washed with cold water three times, and dried in a vacuum oven overnight to give the title compound (6.95 g, 27.5 mmol, 96% yield).

Example 17B 2-(2-fluoro-5-(methylsulfonyl)phenyl)-4,4,5,5-tetramethyl-1,3,2-dioxaborolane A mixture of Example 17A (1.6 g, 5.33 mmol), bis(pinacolato)diboron (1.625 g, 6.40 mmol), $PdCl_2$(dppf)-$CH_2Cl_2$ adduct (0.218 g, 0.267 mmol), and potassium acetate (0.785 g, 8.00 mmol) in dimethylsulfoxide (20 mL) was degassed and back-filled with nitrogen several times. The reaction mixture was heated at 80° C. overnight. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography (silica gel, 10% ethyl acetate/hexanes) to afford the title compound (0.67 g, 42% yield).

Example 17C 3-(2-fluoro-5-(methylsulfonyl)phenyl)-7-methoxy-1-methyl-1H-pyrrolo[2,3-c]pyridine A mixture of Example 2A (0.086 g, 0.3 mmol), Example 17B (0.108 g, 0.360 mmol), tetrakis(triphenylphosphine)palladium(0) (0.017 g, 0.015 mmol), and sodium carbonate (0.064 g, 0.600 mmol) in toluene (2 mL), ethanol (0.5 mL), and water (0.5 mL) was degassed and back-filled with nitrogen gas several times. The reaction mixture was heated at 95° C. for 3 hours. The reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash column chromatography on silica gel eluting with 30% ethyl acetate in hexanes to afford the title compound (0.045 g, 0.135 mmol, 44.9% yield).

Example 17D 3-(2-(2,4-difluorophenoxy)-5-(methylsulfonyl)phenyl)-7-methoxy-1-methyl-1H-pyrrolo[2,3-c]pyridine A mixture of Example 17C (0.02 g, 0.060 mmol), 2,4-difluorophenol (2) (0.012 g, 0.090 mmol), and cesium carbonate (0.029 g, 0.090 mmol) in DMSO was heated at 110° C. overnight. The reaction mixture was partitioned between water and ethyl acetate. The aqueous layer was extracted with additional ethyl acetate twice. The combined organic layers were washed with brine, dried over $MgSO_4$, filtered, and concentrated to give the title compound (0.025 g, 0.056 mmol, 94% yield).

Example 17E

3-[2-(2,4-difluorophenoxy)-5-(methylsulfonyl)phenyl]-1-methyl-1,6-dihydro-7H-pyrrolo[2,3-c]pyridin-7-one Example 17D (0.025 g, 0.056 mmol) in dioxane (1 mL) was treated with hydrogen chloride (1.406 mL, 5.62 mmol). The reaction mixture was heated at 70° C. overnight. The solvent was removed, and the residue was purified by reverse phase HPLC (C18, CH₃CN/water (0.1% TFA), 0-100%) to give the title compound (0.021 g, 0.049 mmol, 87% yield). $^1$H NMR (500 MHz, DMSO-$d_6$) δ ppm 11.00 (d, J=5.19 Hz, 1H), 7.99 (d, J=2.14 Hz, 1H), 7.77 (dd, J=8.54, 2.44 Hz, 1H), 7.70 (s, 1H), 7.52-7.58 (m, 1H), 7.42-7.48 (m, 1H), 7.17-7.22 (m, 1H), 6.92-6.95 (m, 2H), 6.54 (d, J=6.71 Hz, 1H), 4.13 (s, 3H), 3.25 (s, 3H). MS (DCI+) m/z 430.0 (M+H)⁺.

Example 18

1-methyl-3-[5-(methylsulfonyl)-2-phenoxyphenyl]-1,6-dihydro-7H-pyrrolo[2,3-c]pyridin-7-one Example 18A 7-methoxy-1-methyl-3-(5-(methylsulfonyl)-2-phenoxyphenyl)-1H-pyrrolo[2,3-c]pyridine Example 18A was prepared according to the procedure used for the preparation of Example 2C, substituting Example 17C for Example 2B, and substituting phenol for 2,4-difluorophenol, respectively.

Example 18B 1-methyl-3-[5-(methylsulfonyl)-2-phenoxyphenyl]-1,6-dihydro-7H-pyrrolo[2,3-c]pyridin-7-one Example 18B was prepared according to the procedure used for the preparation of Example 1C, substituting Example 18A for Example 1B. $^1$H NMR (500 MHz, DMSO-$d_6$) δ ppm 10.99 (d, J=5.19 Hz, 1H), 8.01 (d, J=2.14 Hz, 1H), 7.79 (dd, J=8.85, 2.44 Hz, 1H), 7.68 (s, 1H), 7.42-7.46 (m, 2H), 7.20-7.24 (m, 1H), 7.13 (d, J=7.63 Hz, 2H), 7.02 (d, J=8.54 Hz, 1H), 6.91-6.94 (m 1H), 6.71 (d, J=6.71 Hz, 1H), 4.11 (s, 3H), 3.25 (s, 3H). MS (DCI+) m/z 395.1 (M+H)⁺.

Example 19

3-[2-(3,4-difluorophenoxy)-5-(methylsulfonyl)phenyl]-1-methyl-1,6-dihydro-7H-pyrrolo[2,3-c]pyridin-7-one A mixture of Example 17C (0.1 g, 0.299 mmol), 3,4-difluorophenol (0.058 g, 0.449 mmol) and Cs₂CO₃ (0.146 g, 0.449 mmol) in DMSO (5 mL) was stirred at 110° C. for 12 hours, cooled and partitioned between ethyl acetate and water. The organic layer was washed with saturated aqueous sodium chloride, dried (anhydrous Na₂SO₄), filtered, and concentrated. The resulting residue (0.13 g, 0.405 mmol) and 4M HCl in dioxane (4 M, 13 mL) was heated at 70° C. for 12 hours, cooled and concentrated. The residue was purified by reverse phase HPLC (C18, CH₃CN/water (0.1% TFA), 10-100%) to afford the title compound (0.05 g, 0.116 mmol, 38.7%). $^1$H NMR (400 MHz, DMSO-$d_6$) δ ppm 11.00 (d, J=5.3 Hz, 1H), 8.01 (d, J=2.4 Hz, 1H), 7.80 (dd, J=8.7, 2.4 Hz, 1H), 7.68 (s, 1H), 7.50 (d, J=19.6, 9.2 Hz, 1H), 7.40 (ddd, J=11.5, 6.8, 2.9 Hz, 1H), 7.11 (d, J=8.6 Hz, 1H), 7.00 (d, J=7.7 Hz, 1H), 6.95-6.88 (m, 1H), 6.54 (d, J=6.3 Hz, 1H), 4.11 (s, 3H), 3.26 (s, 3H). MS (ESI+) m/z 431.0 (M+H)⁺.

Example 20

3-[2-(cyclopropylmethoxy)-5-(methylsulfonyl)phenyl]-1-methyl-1,6-dihydro-7H-pyrrolo[2,3-c]pyridin-7-one Example 20A 3-(2-(cyclopropylmethoxy)-5-(methylsulfonyl)phenyl)-7-methoxy-1-methyl-1H-pyrrolo[2,3-c]pyridine Cyclopropylmethanol (0.086 g, 1.196 mmol) in tetrahydrofuran (5 mL) was treated with sodium hydride (0.029 g, 1.20 mmol) at ambient temperature. The reaction mixture was stirred at room temperature for 5 minutes. To this solution was added Example 17C (0.10 g, 0.30 mmol). The reaction mixture was heated at 60° C. for 12 hours. The solvent was removed under reduced pressure to provide the title compound.

Example 20B

3-[2-(cyclopropylmethoxy)-5-(methylsulfonyl)phenyl]-1-methyl-1,6-dihydro-7H-pyrrolo[2,3-c]pyridin-7-one Example 20B was prepared according to the procedure used for the preparation of Example 1C, substituting Example 20A for Example 1B. $^1$H NMR (400 MHz, CDCl₃) δ ppm 9.90-9.72 (m, 1H), 7.98 (d, J=2.2 Hz, 1H), 7.79 (dd, J=8.6, 2.3 Hz, 1H), 7.44 (s, 1H), 7.04 (d, J=8.7 Hz, 1H), 6.90 (s, 1H), 6.66 (d, J=6.9 Hz, 1H), 4.24 (s, 3H), 3.96 (d, J=6.9 Hz, 2H), 3.06 (s, 3H), 1.29 (s, 1H), 0.67 (d, J=7.4 Hz, 2H), 0.38 (d, J=5.3 Hz, 2H). MS (ESI+) m/z 373.1 (M+H).

Example 21

3-[2-methoxy-5-(methylsulfonyl)phenyl]-1-methyl-1,6-dihydro-7H-pyrrolo[2,3-c]pyridin-7-one Example 21A 7-methoxy-3-(2-methoxy-5-(methylsulfonyl)phenyl)-1-methyl-1H-pyrrolo[2,3-c]pyridine Sodium methanolate (0.048 g, 0.90 mmol) in tetrahydrofuran (6 mL) was treated with Example 17C (0.20 g, 0.60 mmol). The reaction mixture was heated at 60° C. for 12 hours. The solvent was removed to provide the title compound (0.17 g, 54% yield).

Example 21B

3-[2-methoxy-5-(methylsulfonyl)phenyl]-1-methyl-1,6-dihydro-7H-pyrrolo[2,3-c]pyridin-7-one Example 21B was prepared according to the procedure used for the preparation of Example 1C, substituting Example 21A for Example 1B. $^1$H NMR (400 MHz, DMSO-$d_6$) δ ppm 9.86 (s, 1H), 8.00 (d, J=2.4 Hz, 1H), 7.87 (dd, J=8.7, 2.4 Hz, 1H), 7.34 (s, 1H), 7.11 (d, J=8.7 Hz, 1H), 6.93 (d, J=6.7 Hz, 1H), 6.57 (d, J=6.9 Hz, 1H), 4.26 (s, 3H), 3.96 (s, 3H), 3.08 (s, 3H). MS (ESI) m/z 335.1 (M+H).

Example 22

1-methyl-3-[5-(methylsulfonyl)-2-(tetrahydrofuran-3-yloxy)phenyl]-1,6-dihydro-7H-pyrrolo[2,3-c]pyridin-7-one Example 22A Example 22A was prepared according to the procedure used for the preparation of Example 20A, substituting tetrahydrofuran-3-ol for cyclopropylmethanol.

Example 22B 1-methyl-3-[5-(methylsulfonyl)-2-(tetrahydrofuran-3-yloxy)phenyl]-1,6-dihydro-7H-pyrrolo[2,3-c]pyridin-7-one Example 22B was prepared according to the procedure used for the preparation of Example 1C, substituting Example 22A for Example 1B. $^1$H NMR (400 MHz, CDCl$_3$) δ ppm 10.98 (d, J=5.3 Hz, 1H), 7.86 (d, J=2.4 Hz, 1H), 7.83-7.74 (m, 1H), 7.57 (s, 1H), 7.30 (d, J=8.8 Hz, 1H), 6.94-6.86 (m, 1H), 6.43 (d, J=6.8 Hz, 1H), 5.22 (s, 1H), 4.12 (s, 3H), 3.93 (dd, J=10.2, 4.5 Hz, 1H), 3.77 (ddd, J=16.6, 16.1, 9.7 Hz, 3H), 3.21 (s, 3H), 2.35-2.22 (m, 1H), 2.04-1.93 (m, 1H). MS (ESI) m/z 389.1 (M+H).

Example 23

1-methyl-3-[5-(methylsulfonyl)-2-(tetrahydrofuran-3-ylmethoxy)phenyl]-1,6-dihydro-7H-pyrrolo[2,3-c]pyridin-7-one Example 23A 7-methoxy-1-methyl-3-(5-(methylsulfonyl)-2-((tetrahydrofuran-3-yl)methoxy)phenyl)-1H-pyrrolo[2,3-c]pyridine Example 23A was prepared according to the procedure used for the preparation of Example 20A, substituting (tetrahydrofuran-3-yl)methanol for cyclopropylmethanol.

Example 23B 1-methyl-3-[5-(methylsulfonyl)-2-(tetrahydrofuran-3-ylmethoxy)phenyl]-1,6-dihydro-7H-pyrrolo[2,3-c]pyridin-7-one Example 23B was prepared according to the procedure used for the preparation of Example 1C, substituting Example 23A for Example 1B. $^1$H NMR (400 MHz, DMSO-d$_6$) δ ppm 11.00 (s, 1H), 7.86 (d, J=2.3 Hz, 1H), 7.79 (dd, J=8.7, 2.3 Hz, 1H), 7.58 (s, 1H), 7.34 (d, J=8.7 Hz, 1H), 6.92 (d, J=7.0 Hz, 1H), 6.44 (d, J=7.0 Hz, 1H), 4.12 (s, 3H), 4.09-4.02 (m, 1H), 3.72 (dd, J=14.8, 7.8 Hz, 2H), 3.62 (dd, J=15.2, 7.6 Hz, 1H), 3.50 (dd, J=8.6, 5.8 Hz, 1H), 3.21 (s, 3H), 2.67 (s, 1H), 1.98 (d, J=8.1 Hz, 1H), 1.64 (dd, J=12.4, 6.7 Hz, 1H). MS (ESI) m/z 403.1 (M+H).

Example 24

1-methyl-3-[5-(methylsulfonyl)-2-(tetrahydro-2H-pyran-4-yloxy)phenyl]-1,6-dihydro-7H-pyrrolo[2,3-c]pyridin-7-one Example 24A 7-methoxy-1-methyl-3-(5-(methylsulfonyl)-2-(tetrahydro-2H-pyran-4-yloxy)phenyl)-1H-pyrrolo[2,3-c]pyridine Example 24A was prepared according to the procedure used for the preparation of Example 20A, substituting tetrahydro-2H-pyran-4-ol for cyclopropylmethanol.

Example 24B 1-methyl-3-[5-(methylsulfonyl)-2-(tetrahydro-2H-pyran-4-yloxy)phenyl]-1,6-dihydro-7H-pyrrolo[2,3-c]pyridin-7-one Example 24B was prepared according to the procedure used for the preparation of Example 1C, substituting Example 24A for Example 1B. $^1$H NMR (400 MHz, CDCl$_3$) δ ppm 9.74 (s, 1H), 8.00 (d, J=2.4 Hz, 1H), 7.82 (dd, J=8.7, 2.4 Hz, 1H), 7.34 (s, 1H), 7.10 (d, J=8.8 Hz, 1H), 6.92 (s, 1H), 6.61 (d, J=7.0 Hz, 1H), 4.68 (d, J=3.8 Hz, 1H), 4.25 (s, 3H), 3.83 (dd, J=12.3, 5.5 Hz, 2H), 3.57 (ddd, J=11.5, 8.0, 3.2 Hz, 2H), 3.08 (s, 3H), 2.02 (d, J=7.4 Hz, 2H), 1.79 (dd, J=13.2, 3.9 Hz, 2H). MS (ESI) m/z 403.1 (M+H).

Example 25

3-{2-[(4,4-difluorocyclohexyl)oxy]-5-(methylsulfonyl)phenyl}-1-methyl-1,6-dihydro-7H-pyrrolo[2,3-c]pyridin-7-one Example 25A 3-(2-(4,4-difluorocyclohexyloxy)-5-(methylsulfonyl)phenyl)-7-methoxy-1-methyl-1H-pyrrolo[2,3-c]pyridine Example 25A was prepared according to the procedure used for the preparation of Example 20A, substituting 4,4-difluorocyclohexanol for cyclopropylmethanol.

Example 25B

3-{2-[(4,4-difluorocyclohexyl)oxy]-5-(methylsulfonyl)phenyl}-1-methyl-1,6-dihydro-7H-pyrrolo[2,3-c]pyridin-7-one Example 25B was prepared according to the procedure used for the preparation of Example 1C, substituting Example 25A for Example 1B. $^1$H NMR (400 MHz, DMSO-d$_6$) δ ppm 10.98 (d, J=5.2 Hz, 1H), 7.86 (d, J=2.4 Hz, 1H), 7.80 (dd, J=8.7, 2.4 Hz, 1H), 7.58 (s, 1H), 7.43 (d, J=8.9 Hz, 1H), 6.93-6.87 (m, 1H), 6.43 (d, J=6.9 Hz, 1H), 4.83 (s, 1H), 4.12 (s, 3H), 3.22 (s, 3H), 1.99-1.77 (m, 8H). MS (ESI+) m/z 437.2 (M+H).

Example 26

1-methyl-3-[5-(methylsulfonyl)-2-(tetrahydro-2H-pyran-3-yloxy)phenyl]-1,6-dihydro-7H-pyrrolo[2,3-c]pyridin-7-one

Example 26A 7-methoxy-1-methyl-3-(5-(methylsulfonyl)-2-(tetrahydro-2H-pyran-3-yloxy)phenyl)-1H-pyrrolo[2,3-c]pyridine Example 26A was prepared according to the procedure used for the preparation of Example 20A, substituting tetrahydro-2H-pyran-3-ol for cyclopropylmethanol.

Example 26B 1-methyl-3-[5-(methylsulfonyl)-2-(tetrahydro-2H-pyran-3-yloxy)phenyl]-1,6-dihydro-7H-pyrrolo[2,3-c]pyridin-7-one Example 26B was prepared according to the procedure used for the preparation of Example 1C, substituting Example 26A for Example 1B. $^1$H NMR (400 MHz, DMSO-$d_6$) δ ppm 10.98 (s, 1H), 7.87 (d, J=2.4 Hz, 1H), 7.76 (dd, J=8.7, 2.4 Hz, 1H), 7.64 (s, 1H), 7.38 (d, J=8.9 Hz, 1H), 6.92 (d, J=6.9 Hz, 1H), 6.50 (d, J=7.0 Hz, 1H), 4.64 (s, 1H), 4.12 (s, 3H), 3.81 (d, J=9.3 Hz, 1H), 3.57 (dd, J=11.7, 5.8 Hz, 3H), 3.21 (s, 3H), 2.04 (s, 1H), 1.73 (s, 2H), 1.51 (s, 1H). MS (ESI) m/z 403.1 (M+H).

Example 27

3-[2-(2,2-dimethylpropoxy)-5-(methylsulfonyl)phenyl]-1-methyl-1,6-dihydro-7H-pyrrolo[2,3-c]pyridin-7-one

Example 27A 7-methoxy-1-methyl-3-(5-(methylsulfonyl)-2-(neopentyloxy)phenyl)-1H-pyrrolo[2,3-c]pyridine Example 27A was prepared according to the procedure used for the preparation of Example 20A, substituting 2,2-dimethylpropan-1-ol for cyclopropylmethanol.

Example 27B

3-[2-(2,2-dimethylpropoxy)-5-(methylsulfonyl)phenyl]-1-methyl-1,6-dihydro-7H-pyrrolo[2,3-c]pyridin-7-one Example 27B was prepared according to the procedure used for the preparation of Example 1C, substituting Example 27A for Example 1B. $^1$H NMR (400 MHz, DMSO-$d_6$) δ ppm 10.99 (d, J=5.5 Hz, 1H), 7.84 (d, J=2.4 Hz, 1H), 7.79 (dd, J=8.7, 2.4 Hz, 1H), 7.55 (s, 1H), 7.33 (d, J=8.8 Hz, 1H), 6.93-6.89 (m, 1H), 6.42 (d, J=6.9 Hz, 1H), 4.12 (s, 3H), 3.80 (s, 2H), 3.20 (s, 3H), 0.93 (s, 9H). MS (ESI) m/z 389.1 (M+H).

Example 28

3-[2-(cyclobutylmethoxy)-5-(methylsulfonyl)phenyl]-1-methyl-1,6-dihydro-7H-pyrrolo[2,3-c]pyridin-7-one

Example 28A 3-(2-(cyclobutylmethoxy)-5-(methylsulfonyl)phenyl)-7-methoxy-1-methyl-1H-pyrrolo[2,3-c]pyridine Example 28A was prepared according to the procedure used for the preparation of Example 20A, substituting cyclobutylmethanol for cyclopropylmethanol.

Example 28B

3-[2-(cyclobutylmethoxy)-5-(methylsulfonyl)phenyl]-1-methyl-1,6-dihydro-7H-pyrrolo[2,3-c]pyridin-7-one Example 28B was prepared according to the procedure used for the preparation of Example 1C, substituting Example 28A for Example 1B. $^1$H NMR (400 MHz, DMSO-$d_6$) δ ppm 10.97 (d, J=4.1 Hz, 1H), 7.86 (d, J=2.4 Hz, 1H), 7.78 (dd, J=8.7, 2.3 Hz, 1H), 7.55 (s, 1H), 7.32 (d, J=8.7 Hz, 1H), 6.93-6.88 (m, 1H), 6.43 (d, J=7.0 Hz, 1H), 4.11 (d, J=8.7 Hz, 5H), 3.20 (s, 3H), 2.73 (qd, J=11.0, 5.1 Hz, 1H), 2.08-1.98 (m, 2H), 1.94-1.79 (m, 4H). MS (ESI) m/z 387.1 (M+H).

Example 29

1-methyl-3-{2-[(1-methylcyclopropyl)methoxy]-5-(methylsulfonyl)phenyl}-1,6-dihydro-7H-pyrrolo[2,3-c]pyridin-7-one

Example 29A 7-methoxy-1-methyl-3-(2-((1-methylcyclopropyl)methoxy)-5-(methylsulfonyl)phenyl)-1H-pyrrolo[2,3-c]pyridine Example 29A was prepared according to the procedure used for the preparation of Example 20A, substituting (1-methylcyclopropyl)methanol for cyclopropylmethanol.

Example 29B 1-methyl-3-{2-[(1-methylcyclopropyl)methoxy]-5-(methylsulfonyl)phenyl}-1,6-dihydro-7H-pyrrolo[2,3-c]pyridin-7-one Example 29B was prepared according to the procedure used for the preparation of Example 1C, substituting Example 29A for Example 1B. $^1$H NMR (400 MHz, DMSO-$d_6$) δ ppm 10.98 (d, J=5.1 Hz, 1H), 7.86 (d, J=2.4 Hz, 1H), 7.77 (dd, J=8.7, 2.4 Hz, 1H), 7.60 (s, 1H), 7.26 (d, J=8.8 Hz, 1H), 6.95-6.89 (m, 1H), 6.48 (d, J=6.8 Hz, 1H), 4.13 (s, 3H), 3.93 (s, 2H), 3.19 (s, 3H), 1.09 (s, 3H), 0.53 (t, J=4.7 Hz, 2H), 0.37 (t, J=5.0 Hz, 2H). MS (ESI) m/z 387.1 (M+H).

Example 30

1-methyl-3-[5-(methylsulfonyl)-2-(oxetan-3-yl-methoxy)phenyl]-1,6-dihydro-7H-pyrrolo[2,3-c]pyridin-7-one

Example 30A

7-methoxy-1-methyl-3-(5-(methylsulfonyl)-2-(oxetan-3-ylmethoxy)phenyl)-1H-pyrrolo[2,3-c]pyridine Example 30A was prepared according to the procedure used for the preparation of Example 20A, substituting oxetan-3-ylmethanol for cyclopropylmethanol.

Example 30B

3-chloro-2-((2-(7-methoxy-1-methyl-1H-pyrrolo[2,3-c]pyridin-3-yl)-4-(methylsulfonyl)phenoxy)methyl)propan-1-ol Example 30A (0.15 g, 0.373 mmol) in dioxane 12.2 mL) was treated with HCl (1.132 mL, 37.3 mmol). The reaction mixture was heated at 70° C. for 12 hours. The reaction mixture was cooled to room temperature and combined with ethyl acetate. The solution was washed with saturated aqueous sodium chloride solution, and the organic layer separated, dried over anhydrous magnesium sulfate, filtered, and concentrated under reduced pressure to provide the title compound.

Example 30C

1-methyl-3-[5-(methylsulfonyl)-2-(oxetan-3-yl-methoxy)phenyl]-1,6-dihydro-7H-pyrrolo[2,3-c]pyridin-7-one Example 30B (0.15 g, 0.353 mmol) in ethanol (6 mL) was treated with $K_2CO_3$ (0.098 g, 0.706 mmol). The reaction mixture was heated at 80° C. for 4 hours. The solvent was evaporated under reduced pressure, and the residue was purified by reverse phase HPLC (C18, water (10 mM ammonium carbonate)/acetonitrile) to provide the title compound (0.13 g, 0.269 mmol, 72% yield) $^1$H NMR (400 MHz, $CDCl_3$) δ ppm 9.50 (s, 1H), 7.98 (d, J=5.6, 2.4 Hz, 1H), 7.84 (dd, J=8.7, 2.3 Hz, 1H), 7.33 (d, J=7.6 Hz, 1H), 7.13 (dd, J=8.7, 4.2 Hz, 1H), 6.92 (dd, J=23.4, 7.0 Hz, 1H), 6.55 (dd, J=9.6, 7.1 Hz, 1H), 5.25 (d, J=27.4 Hz, 2H), 4.73 (d, J=5.2 Hz, 2H), 4.22 (d, J=5.2 Hz, 3H), 4.16 (d, J=11.9 Hz, 2H), 3.97 (s, 1H), 3.07 (d, J=1.5 Hz, 3H). MS (ESI) m/z 389.1 (M+H).

Example 31

1-methyl-3-[5-(methylsulfonyl)-2-(tetrahydro-2H-pyran-4-ylmethoxy)phenyl]-1,6-dihydro-7H-pyrrolo[2,3-c]pyridin-7-one

Example 31A

7-methoxy-1-methyl-3-(5-(methylsulfonyl)-2-((tetrahydro-2H-pyran-4-yl)methoxy)phenyl)-1H-pyrrolo[2,3-c]pyridine Example 31A was prepared according to the procedure used for the preparation of Example 20A, substituting (tetrahydro-2H-pyran-4-yl)methanol for cyclopropylmethanol.

Example 31B

1-methyl-3-[5-(methylsulfonyl)-2-(tetrahydro-2H-pyran-4-ylmethoxy)phenyl]-1,6-dihydro-7H-pyrrolo[2,3-c]pyridin-7-one Example 31B was prepared according to the procedure used for the preparation of Example 1C, substituting Example 31A for Example 1B. $^1$H NMR (400 MHz, DMSO-$d_6$) δ ppm 10.98 (s, 1H), 7.85 (d, J=2.4 Hz, 1H), 7.79 (dd, J=8.7, 2.4 Hz, 1H), 7.56 (s, 1H), 7.34 (d, J=8.8 Hz, 1H), 6.95-6.87 (m, 1H), 6.42 (d, J=6.9 Hz, 1H), 4.12 (s, 3H), 4.00 (d, J=6.5 Hz, 2H), 3.83 (d, J=8.4 Hz, 2H), 3.27 (dd, J=11.6, 1.4 Hz, 2H), 3.20 (s, 3H), 2.04 (s, 1H), 1.59 (dd, J=12.6, 1.1 Hz, 2H), 1.29 (ddd, J=24.9, 12.3, 4.4 Hz, 2H). MS (ESI) m/z 417.1 (M+H).

Example 32

3-[2-(2-cyclopropylethoxy)-5-(methylsulfonyl)phenyl]-1-methyl-1,6-dihydro-7H-pyrrolo[2,3-c]pyridin-7-one

Example 32A

3-(2-(2-cyclopropylethoxy)-5-(methylsulfonyl)phenyl)-7-methoxy-1-methyl-1H-pyrrolo[2,3-c]pyridine Example 32A was prepared according to the procedure used for the preparation of Example 20A, substituting 2-cyclopropylethanol for cyclopropylmethanol.

Example 32B

3-[2-(2-cyclopropylethoxy)-5-(methylsulfonyl)phenyl]-1-methyl-1,6-dihydro-7H-pyrrolo[2,3-c]pyridin-7-one Example 32B was prepared according to the procedure used for the preparation of Example 1C, substituting Example 32A for Example 1B. $^1$H NMR (400 MHz, DMSO-$d_6$) δ ppm 10.96 (d, J=3.8 Hz, 1H), 7.85 (d, J=2.4 Hz, 1H), 7.79 (dd, J=8.7, 2.4 Hz, 1H), 7.59 (s, 1H), 7.34 (d, J=8.7 Hz, 1H), 6.94-6.87 (m, 1H), 6.43 (d, J=7.0 Hz, 1H), 4.18 (t, J=6.6 Hz, 2H), 4.12 (s, 3H), 3.20 (s, 3H), 1.65 (q, J=6.6 Hz, 2H), 0.80-0.70 (m, 1H), 0.46-0.33 (m, 2H), 0.14-0.02 (m, 2H). MS (ESI) m/z 387.1 (M+H).

Example 33

3-{2-[(cis-4-hydroxycyclohexyl)oxy]-5-(methylsulfonyl)phenyl}-1-methyl-1,6-dihydro-7H-pyrrolo[2,3-c]pyridin-7-one

Example 33A

4-(2-(7-methoxy-1-methyl-1H-pyrrolo[2,3-c]pyridin-3-yl)-4-(methylsulfonyl)phenoxy)cyclohexanol Example 33A was prepared according to the procedure used for the preparation of Example 20A, substituting cyclohexane-1,4-diol (cis/trans mixture) for cyclopropylmethanol.

Example 33B

3-{2-[(cis-4-hydroxycyclohexyl)oxy]-5-(methylsulfonyl)phenyl}-1-methyl-1,6-dihydro-7H-pyrrolo[2,3-c]pyridin-7-one Example 33B was prepared according to the procedure used for the preparation of Example 1C, substituting Example 33A for Example 1B. This material was separated from the trans isomer (Example 34) by preparative HPLC (C18, water (0.1% TFA): acetonitrile, 34-80% gradient). Example 33B was the second isomer to elute (retention time=1.509 minutes). $^1$H NMR (400 MHz, DMSO-d$_6$) δ ppm 10.98 (s, 1H), 7.86 (d, J=2.4 Hz, 1H), 7.76 (d, J=8.7 Hz, 1H), 7.59 (s, 1H), 7.34 (d, J=8.9 Hz, 1H), 6.96-6.87 (m, 1H), 6.48 (d, J=6.9 Hz, 1H), 4.65 (s, 1H), 4.13 (s, 4H), 3.58 (s, 1H), 3.20 (s, 3H), 1.85 (s, 2H), 1.67 (s, 2H), 1.55 (s, 2H), 1.45 (s, 2H). MS (ESI) m/z 417.1 (M+H).

Example 34

3-{2-[(trans-4-hydroxycyclohexyl)oxy]-5-(methylsulfonyl)phenyl}-1-methyl-1,6-dihydro-7H-pyrrolo[2,3-c]pyridin-7-one Example 34 was isolated as the first eluting isomer (retention time=1.493 minutes) from the preparative HPLC purification described in Example 33B. $^1$H NMR (400 MHz, DMSO-d$_6$) δ ppm 10.95 (d, J=5.2 Hz, 1H), 7.83 (d, J=2.4 Hz, 1H), 7.75 (dd, J=2.4, 6.4 Hz, 1H), 7.58 (s, 1H), 7.36 (d, J=9.2 Hz, 1H), 6.90 (t, J=6.4 Hz, 1H), 6.43 (d, J=6.8 Hz, 1H), 4.58-4.53 (m, 2H), 4.13 (s, 3H), 3.52-3.49 (m, 1H), 3.19 (s, 3H), 2.04-2.01 (m, 2H), 1.79-1.75 (m, 2H), 1.46-1.32 (m, 4H). MS (ESI) m/z 417.1 (M+H).

Example 35

3-[2-(2-cyclopentylethoxy)-5-(methylsulfonyl)phenyl]-1-methyl-1,6-dihydro-7H-pyrrolo[2,3-c]pyridin-7-one 2-cyclopentylethanol (0.137 g, 1.196 mmol) in tetrahydrofuran (5 mL) was treated with NaH (0.029 g, 1.196 mmol) at ambient temperature, stirred for 5 minutes and treated with the product from Example 17C (0.1 g, 0.299 mmol). The reaction mixture was heated at 60° C. for 12 hours and partitioned with ethyl acetate and water. The organic layer was washed with saturated aqueous sodium chloride, dried (anhydrous Na$_2$SO$_4$), filtered, and concentrated. The resulting residue (0.15 g) was treated with 4 M HCl in dioxane (15 mL), heated at 70° C. for 12 hours, cooled, concentrated and the residue was purified by reverse phase HPLC (C18, CH$_3$CN/water (0.1% TFA), 10-100%) to give the title compound (0.05 g, 0.121 mmol, 34.5%). $^1$H NMR (400 MHz, DMSO-d$_6$) δ ppm 10.96 (d, J=5.0 Hz, 1H), 7.84 (d, J=2.4 Hz, 1H), 7.79 (dd, J=8.7, 2.4 Hz, 1H), 7.57 (s, 1H), 7.33 (d, J=8.7 Hz, 1H), 6.94-6.86 (m, 1H), 6.42 (d, J=6.5 Hz, 1H), 4.31-3.99 (m, 5H), 3.20 (s, 3H), 1.85 (dd, J=14.6, 7.3 Hz, 1H), 1.79-1.63 (m, 4H), 1.62-1.39 (m, 4H), 1.11 (dd, J=12.0, 7.9 Hz, 2H). MS (ESI+) m/z 415.1 (M+H)$^+$.

Example 36

3-[2-(2-cyclohexylethoxy)-5-(methylsulfonyl)phenyl]-1-methyl-1,6-dihydro-7H-pyrrolo[2,3-c]pyridin-7-one The title compound was prepared according to the procedure in Example 35 substituting 2-cyclohexylethanol for 2-cyclopentylethanol. $^1$H NMR (400 MHz, DMSO-d$_6$) δ ppm 10.97 (d, J=5.1 Hz, 1H), 7.84 (d, J=2.3 Hz, 1H), 7.79 (dd, J=8.7, 2.3 Hz, 1H), 7.55 (s, 1H), 7.33 (d, J=8.7 Hz, 1H), 6.97-6.86 (m, 1H), 6.42 (d, J=6.8 Hz, 1H), 4.26-4.01 (m, 5H), 3.20 (s, 3H), 1.77-1.51 (m, 7H), 1.38 (s, 1H), 1.13 (t, J=9.5 Hz, 3H), 0.90 (d, J=11.3 Hz, 2H). MS (ESI+) m/z 429.1 (M+H)$^+$.

Example 37

1-methyl-3-[5-(methylsulfonyl)-2-(2-phenylethoxy)phenyl]-1,6-dihydro-7H-pyrrolo[2,3-c]pyridin-7-one The title compound was prepared according to the procedure in Example 35 substituting 2-phenylethanol for 2-cyclopentylethanol. $^1$H NMR (400 MHz, DMSO-d$_6$) δ ppm 10.98 (d, J=5.1 Hz, 1H), 7.84 (d, J=2.4 Hz, 1H), 7.78 (dd, J=8.7, 2.4 Hz, 1H), 7.36 (d, J=8.8 Hz, 1H), 7.33-7.14 (m, 6H), 6.93-6.86 (m, 1H), 6.43 (d, J=6.4 Hz, 1H), 4.41 (t, J=6.5 Hz, 2H), 4.06 (s, 3H), 3.19 (s, 3H), 3.08 (t, J=6.5 Hz, 2H). MS (ESI+) m/z 423.1 (M+H)$^+$.

Example 38

3-[2-(2,3-dihydro-1H-inden-2-yloxy)-5-(methylsulfonyl)phenyl]-1-methyl-1,6-dihydro-7H-pyrrolo[2,3-c]pyridin-7-one The title compound was prepared according to the procedure in Example 35 substituting 2,3-dihydro-1H-inden-2-ol for 2-cyclopentylethanol. $^1$H NMR (400 MHz, DMSO-d$_6$) δ ppm 10.88 (d, J=5.2 Hz, 1H), 7.88-7.79 (m, 2H), 7.45 (d, J=8.5 Hz, 1H), 7.27 (dd, J=5.2, 3.4 Hz, 2H), 7.23-7.11 (m, 3H), 6.74-6.64 (m, 1H), 6.25 (d, J=6.4 Hz, 1H), 5.47 (s, 1H), 3.95 (s, 3H), 3.42 (dd, J=16.9, 5.8 Hz, 2H), 3.22 (s, 3H), 3.06 (d, J=16.9 Hz, 2H). MS (ESI+) m/z 435.1 (M+H)$^+$.

Example 39

1-methyl-3-{5-(methylsulfonyl)-2-[2-(thiophen-2-yl)ethoxy]phenyl}-1,6-dihydro-7H-pyrrolo[2,3-c]pyridin-7-one The title compound was prepared according to the procedure in Example 35 substituting 2-(thiophen-2-yl)ethanol for 2-cyclopentylethanol. $^1$H NMR (400 MHz, DMSO-d$_6$) δ ppm 10.98 (d, J=5.2 Hz, 1H), 7.87 (d, J=2.4 Hz, 1H), 7.78 (dd, J=8.7, 2.4 Hz, 1H), 7.36 (dd, J=4.9, 3.6 Hz, 2H), 7.32 (s, 1H), 7.05-6.94 (m, 2H), 6.93-6.86 (m, 1H), 6.46 (d, J=6.3 Hz, 1H), 4.39 (t, J=6.3 Hz, 2H), 4.07 (s, 3H), 3.30 (s, 2H), 3.20 (s, 3H). MS (ESI+) m/z 429.1 (M+H)$^+$.

Example 40

3-[2-(3,3-dimethylbutoxy)-5-(methylsulfonyl)phenyl]-1-methyl-1,6-dihydro-7H-pyrrolo[2,3-c]pyridin-7-one The title compound was prepared according to the procedure in Example 35 substituting 3,3-dimethylbutan-1-ol for 2-cyclopentylethanol. $^1$H NMR (400 MHz, DMSO-d$_6$) δ ppm 10.96 (d, J=5.3 Hz, 1H), 7.84 (d, J=2.4 Hz, 1H), 7.79 (dd, J=8.7, 2.4 Hz, 1H), 7.58 (s, 1H), 7.37 (d, J=8.7 Hz, 1H), 6.94-6.87 (m, 1H), 6.42 (d, J=6.3 Hz, 1H), 4.18 (t, J=7.4 Hz, 2H), 4.11 (s, 3H), 3.20 (s, 3H), 1.69 (t, J=7.3 Hz, 2H), 0.92 (s, 9H). MS (ESI+) m/z 403.1 (M+H)$^+$.

Example 41

3-{2-[(4,4-difluorocyclohexyl)methoxy]-5-(methylsulfonyl)phenyl}-1-methyl-1,6-dihydro-7H-pyrrolo[2,3-c]pyridin-7-one

Example 41A 3-(2-((4,4-difluorocyclohexyl)methoxy)-5-(methylsulfonyl)phenyl)-7-methoxy-1-methyl-1H-pyrrolo[2,3-c]pyridine A solution of (4,4-difluorocyclohexyl)methanol (0.156 g, 1.04 mmol) in anhydrous tetrahydrofuran (4.33 mL) under nitrogen was treated with sodium hydride (0.042 g, 1.040 mmol) at ambient temperature, stirred for 10 minutes, treated with the product from Example 17C (0.087 g, 0.26 mmol) and heated under nitrogen at 60° C. for 18 hours. The mixture was cooled and partitioned into ethyl acetate/water. The organic layer was washed with saturated aqueous sodium chloride, dried (anhydrous $Na_2SO_4$), filtered, and concentrated. Purification by chromatography (silica gel, 0-60% ethyl acetate in heptanes) afforded the title compound (0.1 g, 83%).

Example 41B

3-{2-[(4,4-difluorocyclohexyl)methoxy]-5-(methylsulfonyl)phenyl}-1-methyl-1,6-dihydro-7H-pyrrolo[2,3-c]pyridin-7-one The product from Example 41A (0.1 g, 0.215 mmol) and 4 M hydrogen chloride in dioxane (5 mL, 20.00 mmol) were combined and heated at 70° C. for 24 hours, cooled and concentrated. Purification by chromatography (silica gel, 0-4% MeOH in dichloromethane) afforded the title compound (0.078 g, 80%). $^1$H NMR (300 MHz, DMSO-$d_6$) δ ppm 10.96 (d, J=5.43 Hz, 1H) 7.86 (d, J=2.37 Hz, 1H) 7.79 (dd, J=8.65, 2.54 Hz, 1H) 7.55 (s, 1H) 7.33 (d, J=8.48 Hz, 1H) 6.88-6.95 (m, 1H) 6.43 (d, J=6.10 Hz, 1H) 4.12 (s, 3H) 4.04 (d, J=6.10 Hz, 2H) 3.20 (s, 3H) 1.60-2.12 (m, 7H) 1.24-1.41 (m, 2H). MS (ESI+) m/z 451 (M+H)$^+$.

Example 42

3-{2-[(2,2-difluorocyclopropyl)methoxy]-5-(methylsulfonyl)phenyl}-1-methyl-1,6-dihydro-7H-pyrrolo[2,3-c]pyridin-7-one

Example 42A 3-(2-((2,2-difluorocyclopropyl)methoxy)-5-(methylsulfonyl)phenyl)-7-methoxy-1-methyl-1H-pyrrolo[2,3-c]pyridine Example 42A was prepared according to the procedure used for the preparation of Example 20A, substituting (2,2-difluorocyclopropyl)methanol for cyclopropylmethanol.

Example 42B

3-{2-[(2,2-difluorocyclopropyl)methoxy]-5-(methylsulfonyl)phenyl}-1-methyl-1,6-dihydro-7H-pyrrolo[2,3-c]pyridin-7-one Example 42B was prepared according to the procedure used for the preparation of Example 1C, substituting Example 42A for Example 1B. $^1$H NMR (400 MHz, DMSO-$d_6$)

Example 43

3-{2-[(2,2-difluorocyclopropyl)methoxy]-5-(methylsulfonyl)phenyl}-1,6-dimethyl-1,6-dihydro-7H-pyrrolo[2,3-c]pyridin-7-one A solution of the product from Example 42B (0.027 g, 0.066 mmol) in dimethylformamide (0.5 mL) was treated with sodium hydride (5.29 mg, 0.132 mmol) at ambient temperature, stirred until gas evolution had subsided (10 minutes) and treated with iodomethane (0.019 g, 0.132 mmol). The mixture was stirred for 20 minutes at ambient temperature and partitioned between ethyl acetate and water adjusting the pH to 7 with HCl. The organic layer was washed with water, saturated aqueous sodium chloride, dried (anhydrous $Na_2SO_4$), filtered, and concentrated. Purification by chromatography (silica gel, 0-3% MeOH in dichloromethane) afforded the title compound (0.013 g, 46%). $^1$H NMR (300 MHz, DMSO-$d_6$) δ ppm 7.87 (d, J=2.71 Hz, 1H) 7.80 (dd, J=8.65, 2.54 Hz, 1H) 7.60 (s, 1H) 7.34 (d, J=8.82 Hz, 1H) 7.21 (d, J=7.12 Hz, 1H) 6.49 (d, J=7.12 Hz, 1H) 4.15-4.36 (m, 2H) 4.13 (s, 3H) 3.48 (s, 3H) 3.21 (s, 3H) 2.16-2.34 (m, 1H) 1.65-1.80 (m, 1H) 1.45-1.60 (m, 1H). MS (ESI+) m/z 423 (M+H)$^+$.

Example 44

3-{2-[(cyclopropylmethyl)amino]-5-(methylsulfonyl)phenyl}-1-methyl-1,6-dihydro-7H-pyrrolo[2,3-c]pyridin-7-one

Example 44A 2-(7-methoxy-1-methyl-1H-pyrrolo[2,3-c]pyridin-3-yl)-4-(methylsulfonyl)aniline The product from Example 59A (1.0 g, 3.47 mmol), 2-bromo-4-methanesulfonylaniline (Oakwood, 0.868 g, 3.47 mmol), tris(dibenzylideneacetone)dipalladium(0) (0.095 g, 0.104 mmol), 1,3,5,7-tetramethyl-6-phenyl-2,4,8-trioxa-6-phosphaadamante (0.101 g, 0.347 mmol) and sodium carbonate (1.287 g, 12.15 mmol) were combined and sparged with argon for 15 minutes. Meanwhile a solution of 4:1 dioxane/water (35 mL) was sparged with nitrogen for 15 minutes and transferred by syringe into the reaction vessel under argon. The mixture was stirred at 60° C. for 4 hours, diluted with water and filtered to collect a solid. The solid was dissolved in 100 mL of hot 1:1 ethyl acetate/methanol, filtered to remove the solid palladium and the filtrate was concentrated to afford the title compound (0.98 g, 85%).

Example 44B

N-(cyclopropylmethyl)-2-(7-methoxy-1-methyl-1H-pyrrolo[2,3-c]pyridin-3-yl)-4-(methylsulfonyl)aniline The product from Example 44A (0.1 g, 0.302 mmol), cyclopropanecarboxaldehyde (0.063 g, 0.905 mmol) and sodium triacetoxyhydroborate (0.192 g, 0.905 mmol) were combined in dichloromethane (1.0 mL) and acetic acid (1.0 mL) under nitrogen, stirred for 6 hours and partitioned into water/ethyl acetate. The organic layer was washed with 5% aqueous sodium bicarbonate, saturated aqueous sodium chloride, dried (anhydrous $Na_2SO_4$), filtered, and concentrated to afford the title compound (0.116 g, 100%).

Example 44C

3-{2-[(cyclopropylmethyl)amino]-5-(methylsulfonyl)phenyl}-1-methyl-1,6-dihydro-7H-pyrrolo[2,3-c]pyridin-7-one The product from Example 44B (0.035 g, 0.091 mmol) and 4 M hydrogen chloride in dioxane (0.023 mL, 0.091 mmol) were combined and heated at 70° C. for 24 hours, cooled and concentrated. Purification by reverse phase chromatography (C18, CH$_3$CN/water (0.1% TFA), 10-100%) afforded the title compound (0.024 g, 53%) as the TFA salt. $^1$H NMR (300 MHz, DMSO-d$_6$) δ ppm 10.95 (d, J=5.43 Hz, 1H) 7.62 (dd, J=8.82, 2.37 Hz, 1H) 7.45-7.48 (m, 2H) 6.86-6.91 (m, 1H) 6.84 (d, J=8.82 Hz, 1H) 6.21 (dd, J=6.78, 1.02 Hz, 1H) 5.50 (s, 1H) 4.12 (s, 3H) 3.09 (s, 3H) 3.05 (d, J=6.44 Hz, 2H) 0.95-1.14 (m, 1H) 0.38-0.45 (m, 2H) 0.17-0.24 (m, 2H). MS (ESI+) m/z 372 (M+H)$^+$.

Example 45

3-{2-[(cyclopropylmethyl)(methyl)amino]-5-(methylsulfonyl)phenyl}-1-methyl-1,6-dihydro-7H-pyrrolo[2,3-c]pyridin-7-one

Example 45A

N-(cyclopropylmethyl)-2-(7-methoxy-1-methyl-1H-pyrrolo[2,3-c]pyridin-3-yl)-N-methyl-4-(methylsulfonyl)aniline A solution of the product from Example 44B (0.116 g, 0.301 mmol) in dimethylformamide (2 mL) under nitrogen was treated with sodium hydride (0.018 g, 0.451 mmol) at ambient temperature, stirred for 30 minutes, treated with iodomethane (0.038 mL, 0.602 mmol), stirred for 30 minutes at ambient temperature and quenched into cold water. The mixture was extracted into ethyl acetate and the organic layer was washed with saturated aqueous sodium chloride, dried (anhydrous Na$_2$SO$_4$), filtered, and concentrated to afford the title compound (0.12 g, 100%).

Example 45B

3-{2-[(cyclopropylmethyl)(methyl)amino]-5-(methylsulfonyl)phenyl}-1-methyl-1,6-dihydro-7H-pyrrolo[2,3-c]pyridin-7-one The product from Example 45A (0.12 g, 0.30 mmol) and 4 M hydrogen chloride in dioxane (5 mL, 20.00 mmol) were combined and heated at 70° C. for 24 hours, cooled and concentrated. Purification by reverse phase chromatography (C18, CH$_3$CN/water (0.1% TFA), 10-100%) afforded the title compound (0.068 g, 45%) as the TFA salt. $^1$H NMR (300 MHz, DMSO-d$_6$) δ ppm 10.91 (d, J=5.09 Hz, 1H) 7.70 (dd, J=8.48, 2.37 Hz, 1H) 7.61 (d, J=2.37 Hz, 1H) 7.54-7.56 (m, 1H) 7.21 (d, J=8.48 Hz, 1H) 6.84 (dd, J=7.12, 5.76 Hz, 1H) 6.31 (d, J=5.76 Hz, 1H) 4.11 (s, 3H) 3.15 (s, 3H) 2.77 (s, 3H) 2.74 (d, J=6.78 Hz, 2H) 0.64-0.78 (m, 1H) 0.28-0.37 (m, 2H) −0.11--0.05 (m, 2H). MS (ESI+) m/z 386 (M+H)$^+$.

Example 46

4-({[2-(1-methyl-7-oxo-6,7-dihydro-1H-pyrrolo[2,3-c]pyridin-3-yl)-4-(methylsulfonyl)phenyl]amino}methyl)benzonitrile

Example 46A

4-((2-(7-methoxy-1-methyl-1H-pyrrolo[2,3-c]pyridin-3-yl)-4-(methylsulfonyl)phenylamino)methyl)benzonitrile The title compound was prepared according to the procedure in Example 44B substituting 4-cyanobenzaldehyde for cyclopropanecarboxaldehyde (0.067 g, 100%).

Example 46B

4-({[2-(1-methyl-7-oxo-6,7-dihydro-1H-pyrrolo[2,3-c]pyridin-3-yl)-4-(methylsulfonyl)phenyl]amino}methyl)benzonitrile The product from Example 46A (0.067 g, 0.15 mmol) and 4 M hydrogen chloride in dioxane (5 mL, 20.00 mmol) were combined and heated at 70° C. for 24 hours, cooled and concentrated Purification by reverse phase chromatography (C18, CH$_3$CN/water (0.1% TFA), 10-100%) afforded the title compound (0.01 g, 15%). $^1$H NMR (400 MHz, DMSO-d$_6$) δ ppm 10.97 (d, J=5.19 Hz, 1H) 7.80 (d, J=8.54 Hz, 2H) 7.45-7.61 (m, 5H) 6.87-6.95 (m, 1H) 6.54 (d, J=8.85 Hz, 1H) 6.48-6.53 (m, 1H) 6.23 (d, J=6.71 Hz, 1H) 4.48 (d, J=6.10 Hz, 2H) 4.14 (s, 3H) 3.07 (s, 3H). MS (ESI+) m/z 433 (M+H)$^+$.

Example 47

3-{2-[(cyclohexylmethyl)amino]-5-(methylsulfonyl)phenyl}-1-methyl-1,6-dihydro-7H-pyrrolo[2,3-c]pyridin-7-one

Example 47A

N-(cyclohexylmethyl)-2-(7-methoxy-1-methyl-1H-pyrrolo[2,3-c]pyridin-3-yl)-4-(methylsulfonyl)aniline The title compound was prepared according to the procedure in Example 44B substituting cyclohexylcarboxaldehyde for cyclopropanecarboxaldehyde (0.050 g, 63%).

Example 47B

3-{2-[(cyclohexylmethyl)amino]-5-(methylsulfonyl)phenyl}-1-methyl-1,6-dihydro-7H-pyrrolo[2,3-c]pyridin-7-one The title compound was prepared according to the procedure in Example 44C substituting the product from Example 47A for the product from Example 44C (0.027 g, 53%). $^1$H NMR (500 MHz, DMSO-d$_6$/D$_2$O) δ ppm 7.64 (dd, J=8.70, 2.29 Hz, 1H) 7.44-7.46 (m, 2H) 6.93 (d, J=7.02 Hz, 1H) 6.83 (d, J=8.85 Hz, 1H) 6.24 (d, J=6.71 Hz, 1H) 4.12 (s, 3H) 3.09 (s, 3H) 3.06 (d, J=7.32 Hz, 2H) 2.10-2.17 (m, 1H) 1.61-1.69

(m, 2H) 1.51-1.58 (m, 2H) 1.44-1.50 (m, 4H) 1.15-1.24 (m, 2H). MS (ESI+) m/z 414 (M+H)+.

Example 48

3-[2-(4-chlorophenoxy)-5-(ethylsulfonyl)phenyl]-1-methyl-1,6-dihydro-7H-pyrrolo[2,3-c]pyridin-7-one Example 48A ethyl(4-fluorophenyl)sulfane A solution of 4-fluorobenzenethiol (10 g, 78 mmol) and iodoethane (7.57 mL, 94 mmol) in tetrahydrofuran (100 mL) was treated with triethylamine (13.05 mL, 94 mmol) at room temperature for 2 hours. The reaction mixture was filtered and the filtrate was concentrated, washed with hexane and dried under vacuum to provide the title compound (10.5 g, 81%).

Example 48B 1-(ethylsulfonyl)-4-fluorobenzene

Example 48A (10 g, 64.0 mmol) was treated with 3-chloroperoxybenzoic acid (28.6 g, 141 mmol) at room temperature for 4 hours. The reaction mixture was filtered, and the solids were washed with dichloromethane. The filtrate was washed twice with 10% sodium hydroxide, and saturated sodium bicarbonate. The organic solvent was removed under reduced pressure to provide the title compound (11.5 g (95%).

Example 48C 2-bromo-4-(ethylsulfonyl)-1-fluorobenzene

Example 48C was prepared according to the procedure of Example 17A, substituting Example 48B for 1-fluoro-4-(methylsulfonyl)benzene to provide the title compound.

Example 48D 2-(5-(ethylsulfonyl)-2-fluorophenyl)-4,4,5,5-tetramethyl-1,3,2-dioxaborolane Example 48D was prepared according to the procedure of Example 17B, substituting Example 48C for Example 17A to provide the title compound.

Example 48E 3-(5-(ethylsulfonyl)-2-fluorophenyl)-7-methoxy-1-methyl-1H-pyrrolo[2,3-c]pyridine Example 48E was prepared according to the procedure of Example 2B, substituting Example 48D for 2-fluoro-5-nitrophenylboronic acid to provide the title compound.

Example 48F 3-(2-(4-chlorophenoxy)-5-(ethylsulfonyl)phenyl)-7-methoxy-1-methyl-1H-pyrrolo[2,3-c]pyridine Example 48F was prepared according to the procedure used for the preparation of Example 2C, substituting Example 48E for Example 2B and 4-chlorophenol for 2,4-difluorophenol, with the exception that the reaction mixture was heated at 100° C. for 18 hours, and the residue was purified by flash column chromatography (silica gel, 0-2.5% methanol in dichloromethane) to provide the title compound.

Example 48G

3-[2-(4-chlorophenoxy)-5-(ethylsulfonyl)phenyl]-1-methyl-1,6-dihydro-7H-pyrrolo[2,3-c]pyridin-7-one Example 48G was prepared according to the procedure used for the preparation of Example 1C, substituting Example 48F for Example 1B, with the exception that the reaction mixture was heated at 70° C. to provide the title compound. $^1$H NMR (400 MHz, CDCl$_3$) δ ppm 9.80 (s, 1H), 8.10 (d, J=2.44 Hz, 1H), 7.72 (dd, J=8.54, 2.44 Hz, 1H), 7.29-7.40 (m, 3H), 7.02 (d, J=8.54 Hz, 1H), 6.91-6.99 (m, 3H), 6.66 (d, J=7.02 Hz, 1H), 4.22 (s, 3H), 3.16 (q, J=7.53 Hz, 2H), 1.33 (t, J=7.48 Hz, 3H). MS (ESI+) m/z 443.2 (M+H)+.

Example 49

3-[2-(2,4-difluorophenoxy)-5-(ethylsulfonyl)phenyl]-1-methyl-1,6-dihydro-7H-pyrrolo[2,3-c]pyridin-7-one Example 49A 3-(2-(2,4-difluorophenoxy)-5-(ethylsulfonyl)phenyl)-7-methoxy-1-methyl-1H-pyrrolo[2,3-c]pyridine Example 49A was prepared according to the procedure used for the preparation of Example 2C, substituting Example 48E for Example 2B with the exception that the reaction mixture was heated at 100° C. for 18 hours, and the residue was purified by flash column chromatography (silica gel, 0-2.5% methanol in dichloromethane) to provide the title compound.

Example 49B

3-[2-(2,4-difluorophenoxy)-5-(ethylsulfonyl)phenyl]-1-methyl-1,6-dihydro-7H-pyrrolo[2,3-c]pyridin-7-one Example 49B was prepared according to the procedure used for the preparation of Example 1C, substituting Example 49A for Example 1B, with the exception that the reaction mixture was heated at 70° C. to provide the title compound. $^1$H NMR (500 MHz, CDCl$_3$) δ ppm 9.95 (s, 1H), 8.07 (d, J=2.44 Hz, 1H), 7.71 (dd, J=8.70, 2.29 Hz, 1H), 7.43 (s, 1H), 7.06-7.15 (m, 1H), 6.98-7.05 (m, 1H), 6.89-6.98 (m, 2H), 6.85 (d, J=8.54 Hz, 1H), 6.71 (d, J=7.02 Hz, 1H), 4.25 (s, 3H), 3.15 (q, J=7.53 Hz, 2H), 1.32 (t, J=7.48 Hz, 3H). MS (ESI+) m/z 445.1 (M+H)+.

Example 50

3-[2-(cyclopropylmethoxy)-6-methylphenyl]-1-methyl-1,6-dihydro-7H-pyrrolo[2,3-c]pyridin-7-one Example 50A 2-bromo-1-(cyclopropylmethoxy)-3-methylbenzene Example 50A was prepared according to the procedure used for the preparation of Example 14A, substituting 2-bromo-3-methyl-phenol for 2-bromo-3-methyl-4-nitrophenol.

Example 50B 3-(2-(cyclopropylmethoxy)-6-methylphenyl)-7-methoxy-1-methyl-1H-pyrrolo[2,3-c]pyridine Example 50B was prepared according to the procedure used for the preparation of Example 14C, substituting Example 50A for Example 14B.

Example 50C 3-(2-(cyclopropylmethoxy)-6-methylphenyl)-1-methyl-1H-pyrrolo[2,3-c]pyridin-7(6H)-one Example 50C was prepared according to the procedure used for the preparation of Example 1C, substituting Example 50B for Example 1B. $^1$H NMR (500 MHz, DMSO-d$_6$) δ ppm 10.79 (d, J=4.9 Hz, 1H), 7.22 (s, 1H), 7.16 (t, J=7.9 Hz, 1H), 6.87 (dd, J=7.8, 3.2 Hz, 1H), 6.79-6.75 (m, 2H), 5.97 (d, J=6.7 Hz, 1H), 3.72 (d, J=6.4 Hz, 2H), 2.50 (s, 3H), 2.09 (s, 3H), 0.99 (m, 1H), 0.38 (m, 2H), 0.15 (m, 2H). MS (DCI+) m/z 309.0 (M+H)$^+$.

Example 51

4-(2,4-difluorophenoxy)-3-(1-methyl-7-oxo-6,7-dihydro-1H-pyrrolo[2,3-c]pyridin-3-yl)benzenesulfonamide

Example 51A 4-(2,4-difluorophenoxy)-3-nitrobenzenesulfonamide

A solution of 2,4-difluorophenol (5.39 g, 41.4 mmol) in dimethylformamide (34.5 mL) at 10° C. under nitrogen was treated portionwise with sodium hydride (1.657 g, 41.4 mmol), stirred for 15 minutes and treated portionwise with 4-fluoro-3-nitrobenzenesulfonamide (2.28 g, 10.36 mmol). The solution was stirred at ambient temperature for 1.5 hours, diluted into ethyl acetate and carefully quenched with 0.5 M HCl to a constant pH of 6. The organic layer was washed with saturated aqueous sodium chloride, dried (MgSO$_4$), filtered, and concentrated. The residue was triturated in 3:1 hexane/ethyl acetate to afford the title compound (3.24 g, 95%).

Example 51B 3-amino-4-(2,4-difluorophenoxy)benzenesulfonamide

The product from Example 51A (3.24 g, 9.81 mmol), iron (2.74 g, 49.1 mmol), and ammonium chloride (0.787 g, 14.72 mmol) were combined in the solvent mixture of tetrahydrofuran (21.0 mL), ethanol (21.0 mL) and water (7.0 mL) and heated at 95° C. with vigorous stirring for 3 hours. The mixture was cooled and filtered through a plug of Celite to remove solids. The plug was rinsed repeatedly with methanol and tetrahydrofuran. The filtrate was concentrated and the residue partitioned between ethyl acetate and water. The organic layer was washed with saturated aqueous sodium chloride, dried (anhydrous Na$_2$SO$_4$), filtered, and concentrated to afford the title compound (2.81 g, 95%).

Example 51C 4-(2,4-difluorophenoxy)-3-iodobenzenesulfonamide

A solution of the product from Example 51B (2.8 g, 9.32 mmol) in dioxane (20.0 mL) at 0° C. was treated with concentrated hydrogen chloride (40 mL, 9.32 mmol), stirred for 15 minutes and treated with a solution of sodium nitrite (0.772 g, 11.19 mmol) in water (10 mL). The mixture was stirred for 1 hour at 0° C., treated with a solution of potassium iodide (3.10 g, 18.65 mmol) in water (10 mL) and stirred for 1 hour at ambient temperature. The mixture was partitioned between ethyl acetate and water. The organic layer was washed with saturated sodium thiosulfate, water, saturated aqueous sodium chloride, dried (MgSO$_4$), filtered, and concentrated. Purification by chromatography (silica gel, 0-60% ethyl acetate in hexane) afforded the title compound (2.24 g, 58%).

Example 51D 4-(2,4-difluorophenoxy)-3-(7-methoxy-1-methyl-1H-pyrrolo[2,3-c]pyridin-3-yl)benzenesulfonamide The product from Example 59A (0.075 g, 0.260 mmol), the product from Example 51C (0.107 g, 0.260 mmol), tris(dibenzylideneacetone)dipalladium(0) (7.15 mg, 7.81 µmol), 1,3,5,7-tetramethyl-6-phenyl-2,4,8-trioxa-6-phosphaadamante (7.61 mg, 0.026 mmol) and sodium carbonate (0.097 g, 0.911 mmol) were combined and sparged with argon for 15 minutes. Meanwhile a solution of 4:1 dioxane/water (2 mL) was sparged with nitrogen for 15 minutes and transferred by syringe into the reaction vessel under argon. The mixture was stirred at 60° C. for 4 hours and partitioned between ethyl acetate and water. The organic layer was washed with saturated aqueous sodium chloride, dried (anhydrous Na$_2$SO$_4$), treated with 3-mercaptopropyl functionalized silica gel, filtered, and concentrated to afford the title compound (0.116 g, 100%).

Example 51E 4-(2,4-difluorophenoxy)-3-(1-methyl-7-oxo-6,7-dihydro-1H-pyrrolo[2,3-c]pyridin-3-yl)benzenesulfonamide The product from Example 51D (0.116 g, 0.26 mmol) and 4 M hydrogen chloride (5 mL, 20.0 mmol) in dioxane were combined and heated at 70° C. for 24 hours, cooled and concentrated. Purification by reverse phase chromatography (C18, CH$_3$CN/water (0.1% TFA), 10-100%) afforded the title compound (0.051 g, 45%). $^1$H NMR (300 MHz, DMSO-d$_6$) δ ppm 10.99 (d, J=5.09 Hz, 1H) 7.96 (d, J=2.37 Hz, 1H) 7.66 (dd, J=8.82, 2.37 Hz, 1H) 7.64 (s, 1H) 7.46-7.57 (m, 1H) 7.35-7.43 (m, 1H) 7.33 (s, 2H) 7.12-7.21 (m, 1H) 6.94 (d, J=6.78 Hz, 1H) 6.90 (d, J=8.48 Hz, 1H) 6.55 (d, J=6.10 Hz, 1H) 4.12 (s, 3H). MS (ESI+) m/z 432 (M+H)$^+$.

Example 52

3-{2-(2,4-difluorophenoxy)-5-[(methylsulfonyl)methyl]phenyl}-1-methyl-1,6-dihydro-7H-pyrrolo[2,3-c]pyridin-7-one

Example 52A 3-bromo-4-(2,4-difluorophenoxy)benzaldehyde

A mixture of 3-bromo-4-fluorobenzaldehyde (4.06 g, 20 mmol), 2,4-difluorophenol (2.60 g, 20 mmol) and cesium carbonate (7.17 g, 22 mmol) in dimethyl sulfoxide (20 mL) was heated at 100° C. for 1 hour. The reaction mixture was partitioned with ethyl acetate and water. The organic layer was washed with saturated aqueous sodium chloride twice, dried with anhydrous sodium sulfate, filtered, and concentrated. The residue was purified by flash chromatography (silica gel, 20% ethyl acetate in heptanes) to provide the title compound (5.94 g, 95%).

Example 52B (3-bromo-4-(2,4-difluorophenoxy)phenyl)methanol

Example 52A (3.76 g, 12 mmol) in the mixture of ethanol (10 mL) and tetrahydrofuran (10 mL) was added sodium borohydride (0.136 g, 3.60 mmol). The reaction mixture was stirred at room temperature for 1 hour. The solvent was evaporated and the residue was partitioned with ethyl acetate and water. The organic layer was washed with saturated aqueous sodium chloride, dried with anhydrous sodium sulfate, filtered, and concentrated to provide the title compound (3.72 g, 98%).

Example 52C 2-bromo-4-(bromomethyl)-1-(2,4-difluorophenoxy)benzene

Example 52B (3.70 g, 11.74 mmol) in dichloromethane (20 mL) was added phosphorus tribromide (1.107 mL, 11.74 mmol) dropwise. The reaction mixture was stirred at room temperature for 3 hours, poured into ice water, adjusted the pH to basic by saturated aqueous sodium bicarbonate slowly and extracted by dichloromethane. The organic layer was washed with saturated aqueous sodium chloride, dried with anhydrous sodium sulfate, filtered, and concentrated to provide the title compound (4.15 g, 93%).

Example 52D (3-bromo-4-(2,4-difluorophenoxy)benzyl)(methyl)sulfane

A mixture of Example 52C (1.512 g, 4.00 mmol) and sodium thiomethoxide (0.280 g, 4.00 mmol) in dimethylformamide (8 mL) was stirred at room temperature for 6 hours. The reaction mixture was partitioned with ethyl acetate and water. The organic layer was washed with saturated aqueous sodium chloride twice, dried with anhydrous sodium sulfate, filtered, and concentrated to provide the title compound (1.38 g, 100%).

Example 52E 2-bromo-1-(2,4-difluorophenoxy)-4-(methylsulfonylmethyl)benzene

Example 52D (1.38 g, 4.00 mmol) in methanol (15 mL) was added oxone (5.16 g, 8.40 mmol) in water (15 mL) at 0° C. The reaction mixture was stirred at room temperature for 1 hour. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (1.485 g, 98%).

Example 52F 3-(2-(2,4-difluorophenoxy)-5-(methylsulfonylmethyl)phenyl)-7-methoxy-1-methyl-1H-pyrrolo[2,3-c]pyridine Example 52E (0.453 g, 1.20 mmol), Example 59A (0.415 g, 1.44 mmol), potassium phosphate (0.892 g, 4.20 mmol), tris(dibenzylideneacetone)dipalladium (0.033 g, 0.036 mmol) and 1,3,5,7-tetramethyl-6-phenyl-2,4,8-trioxa-6-phosphaadamantane (0.032 g, 0.108 mmol) were combined in a microwave tube and purged with nitrogen for 15 minutes. The mixture of dioxane (8 mL) and water (2 mL) was purged with nitrogen for 15 minutes and transferred to the microwave tube. The reaction mixture was heated at 60° C. for 4 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20 to 60% ethyl acetate in heptanes) to provide the title compound (0.492 g, 89%).

Example 52G

3-{2-(2,4-difluorophenoxy)-5-[(methylsulfonyl)methyl]phenyl}-1-methyl-1,6-dihydro-7H-pyrrolo[2,3-c]pyridin-7-one Example 52F (0.490 g, 1.069 mmol) in a solution of 4 M HCl in dioxane (20 mL, 80 mmol) was heated at 70° C. for 16 hours, cooled and concentrated. The residue was added water, adjusted to pH 7 by saturated aqueous sodium bicarbonate and added ethyl acetate. The resulting solid was filtered and dissolved in warm ethyl acetate. The filtrate was separated and the organic layer was washed with saturated aqueous sodium chloride. Both of the ethyl acetate solutions were combined, dried with anhydrous sodium sulfate, filtered, and concentrated. The residue was triturated with ethyl acetate to provide the title compound (0.413 g, 87%). $^1$H NMR (300 MHz, DMSO-$d_6$) δ ppm 10.94 (d, J=5.43 Hz, 1H) 7.59 (d, J=2.03 Hz, 1H) 7.55 (s, 1H) 7.40-7.51 (m, 1H) 7.18-7.29 (m, 2H) 7.04-7.14 (m, 1H) 6.86-6.93 (m, 1H) 6.82 (d, J=8.14 Hz, 1H) 6.60 (d, J=6.44 Hz, 1H) 4.51 (s, 2H) 4.10 (s, 3H) 2.93 (s, 3H). MS (ESI+) m/z 445 (M+H)$^+$.

Example 53

3-{2-(2,4-difluorophenoxy)-5-[(ethylsulfonyl)methyl]phenyl}-1-methyl-1,6-dihydro-7H-pyrrolo[2,3-c]pyridin-7-one

Example 53A (3-bromo-4-(2,4-difluorophenoxy)benzyl)(ethyl)sulfane

A mixture of Example 52C (1.10 g, 2.91 mmol) and sodium ethanethiolate (0.245 g, 2.91 mmol) in dimethylformamide (10 mL) was stirred at ambient temperature for 4 hours. The reaction mixture was partitioned with ethyl acetate and water. The organic layer was washed with saturated aqueous sodium chloride twice, dried with anhydrous sodium sulfate, filtered, and concentrated to provide the title compound (1.04 g, 99%).

Example 53B 2-bromo-1-(2,4-difluorophenoxy)-4-(ethylsulfonylmethyl)benzene

To Example 53A (1.04 g, 2.90 mmol) in methanol (15 mL) was added oxone (3.74 g, 6.08 mmol) in water (15 mL) at 0° C. The reaction mixture was stirred at ambient temperature for 1 hour. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (1.01 g, 89%).

Example 53C 3-(2-(2,4-difluorophenoxy)-5-(ethylsulfonylmethyl)phenyl)-7-methoxy-1-methyl-1H-pyrrolo[2,3-c]pyridine Example 53B (98 mg, 0.25 mmol), Example 59A (86 mg, 0.30 mmol), potassium phosphate (186 mg, 0.875 mmol), tris(dibenzylideneacetone)dipalladium (6.9 mg, 7.5 μmol), and 1,3,5,7-tetramethyl-6-phenyl-2,4,8-trioxa-6-phosphaadamantane (6.6 mg, 0.023 mmol) were combined in a microwave tube and purged with nitrogen for 15 minutes. The mixture of dioxane (2 mL) and water (0.5 mL) was purged with nitrogen for 15 minutes and transferred to the microwave tube. The reaction mixture was heated at 60° C. for 4 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 0 to 50% ethyl acetate in heptanes) to provide the title compound (113 g, 96%).

Example 53D

3-{2-(2,4-difluorophenoxy)-5-[(ethylsulfonyl)methyl]phenyl}-1-methyl-1,6-dihydro-7H-pyrrolo[2,3-c]pyridin-7-one Example 53C (111 mg, 0.235 mmol) in a solution of 4 M HCl in dioxane (8 mL, 32.0 mmol) was heated at 70° C. for 24 hours, cooled and concentrated. The residue was purified by flash chromatography (silica gel, 0 to 4% methanol in dichloromethane) to provide the title compound (88 mg, 82%). $^1$H NMR (400 MHz, DMSO-$d_6$) δ ppm 10.95 (d, J=5.49 Hz, 1H) 7.59 (d, J=2.14 Hz, 1H) 7.55 (s, 1H) 7.42-7.50 (m, 1H) 7.20-7.29 (m, 2H) 7.05-7.14 (m, 1H) 6.86-6.93 (m, 1H) 6.81 (d, J=8.24 Hz, 1H) 6.61 (d, J=6.41 Hz, 1H) 4.50 (s, 2H) 4.10 (s, 3H) 3.06 (q, J=7.32 Hz, 2H) 1.24 (t, J=7.48 Hz, 3H). MS (ESI+) m/z 459 (M+H)$^+$.

Example 54

3-{2-(2,4-difluorophenoxy)-5-[2-(ethylsulfonyl)propan-2-yl]phenyl}-1-methyl-1,6-dihydro-7H-pyrrolo[2,3-c]pyridin-7-one

Example 54A 2-bromo-1-(2,4-difluorophenoxy)-4-(2-(ethylsulfonyl)propan-2-yl)benzene Example 53B (469 mg, 1.2 mmol) in tetrahydrofuran (10 mL) was added 60% sodium hydride in mineral oil (240 mg, 6.00 mmol) at 0° C. The reaction mixture was stirred at room temperature under nitrogen for 10 minutes. The iodomethane (0.750 mL, 12.00 mmol) was added. The reaction mixture was stirred at room temperature for 20 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (442 mg, 88%).

Example 54B 3-(2-(2,4-difluorophenoxy)-5-(2-(ethylsulfonyl)propan-2-yl)phenyl)-7-methoxy-1-methyl-1H-pyrrolo[2,3-c]pyridine Example 54B was prepared according to the procedure used for the preparation of Example 52F, substituting Example 54A for Example 52E. Purification by flash chromatography (silica gel, 0 to 50% ethyl acetate in heptanes) afforded the title compound (85 mg, 85%).

Example 54C

3-{2-(2,4-difluorophenoxy)-5-[2-(ethylsulfonyl)propan-2-yl]phenyl}-1-methyl-1,6-dihydro-7H-pyrrolo[2,3-c]pyridin-7-one Example 54C was prepared according to the procedure used for the preparation of Example 53D, substituting Example 54B for Example 53C. The reaction time was 16 hours instead of 24 hours. Purification by flash chromatography (silica gel, 0.5 to 3.5% methanol in dichloromethane) and trituration (10% ethyl acetate in heptanes) afforded the title compound (70 mg, 87%). $^1$H NMR (300 MHz, DMSO-$d_6$) δ ppm 10.93 (d, J=5.43 Hz, 1H) 7.72 (d, J=2.37 Hz, 1H) 7.56 (s, 1H) 7.40-7.52 (m, 2H) 7.19-7.31 (m, 1H) 7.06-7.16 (m, 1H) 6.85-6.94 (m, 1H) 6.79 (d, J=8.48 Hz, 1H) 6.57 (d, J=6.10 Hz, 1H) 4.10 (s, 3H) 2.88 (q, J=7.46 Hz, 2H) 1.77 (s, 6H) 1.05 (t, J=7.29 Hz, 3H). MS (ESI+) m/z 487 (M+H)$^+$.

Example 55

3-{2-(2,4-difluorophenoxy)-5-[1-(ethylsulfonyl)ethyl]phenyl}-1-methyl-1,6-dihydro-7H-pyrrolo[2,3-c]pyridin-7-one

Example 55A 2-bromo-1-(2,4-difluorophenoxy)-4-(1-(ethylsulfonyl)ethyl)benzene To Example 53B (196 mg, 0.50 mmol) in tetrahydrofuran (10 mL) was added 60% sodium hydride in mineral oil (100 mg, 2.50 mmol) at 0° C. The reaction mixture was stirred at room temperature under nitrogen for 10 minutes. Iodomethane (0.313 mL, 5.00 mmol) was added. The reaction mixture was stirred at room temperature for 2 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (174 mg, 86%).

Example 55B 3-(2-(2,4-difluorophenoxy)-5-(1-(ethylsulfonyl)
ethyl)phenyl)-7-methoxy-1-methyl-1H-pyrrolo[2,3-
c]pyridine Example 55B was prepared according to the procedure used for the preparation of Example 52F, substituting Example 55A for Example 52E. Purification by flash chromatography (silica gel, 0 to 50% ethyl acetate in heptanes) afforded the title compound (200 mg, 98%).

Example 55C

3-{2-(2,4-difluorophenoxy)-5-[1-(ethylsulfonyl)
ethyl]phenyl}-1-methyl-1,6-dihydro-7H-pyrrolo[2,3-
c]pyridin-7-one Example 55C was prepared according to the procedure used for the preparation of Example 53D, substituting Example 55B for Example 53C. The reaction time was 16 hours instead of 24 hours. Purification by flash chromatography (silica gel, 2 to 4% methanol in dichloromethane afforded the title compound (180 mg, 95%). $^1$H NMR (300 MHz, DMSO-$d_6$) δ ppm 10.94 (d, J=5.09 Hz, 1H) 7.61 (d, J=2.03 Hz, 1H) 7.55 (s, 1H) 7.41-7.51 (m, 1H) 7.18-7.34 (m, 2H) 7.05-7.15 (m, 1H) 6.90 (dd, J=7.12, 5.76 Hz, 1H) 6.80 (d, J=8.48 Hz, 1H) 6.54-6.60 (m, 1H) 4.54-4.69 (m, 1H) 4.10 (s, 3H) 2.84-3.09 (m, 2H) 1.64 (d, J=7.12 Hz, 3H) 1.16 (t, J=7.29 Hz, 3H). MS (ESI+) m/z 473 (M+H)$^+$.

Example 56

3-{2-(2,4-difluorophenoxy)-5-[(1R)-1-(ethylsulfo-
nyl)ethyl]phenyl}-1-methyl-1,6-dihydro-7H-pyrrolo
[2,3-c]pyridin-7-one The product from Example 55C was purified by chiral chromatography on a Chiralpak IA column eluting with a 3:7 mixture of 0.1% diethylamine in methanol/carbondioxide. The title compound was randomly assigned to the first of the 2 diastereomers eluted. $^1$H NMR (300 MHz, DMSO-$d_6$) δ ppm 10.94 (d, J=5.43 Hz, 1H) 7.61 (d, J=2.37 Hz, 1H) 7.55 (s, 1H) 7.40-7.52 (m, 1H) 7.31 (dd, J=8.65, 2.20 Hz, 1H) 7.19-7.28 (m, 1H) 7.04-7.15 (m, 1H) 6.86-6.94 (m, 1H) 6.80 (d, J=8.48 Hz, 1H) 6.57 (d, J=6.44 Hz, 1H) 4.58 (q, J=7.11 Hz, 1H) 4.10 (s, 3H) 2.92-3.03 (m, 2H) 1.64 (d, J=7.12 Hz, 3H) 1.16 (t, J=7.46 Hz, 3H). MS (ESI+) m/z 473 (M+H)$^+$.

Example 57

3-{2-(2,4-difluorophenoxy)-5-[(1S)-1-(ethylsulfo-
nyl)ethyl]phenyl}-1-methyl-1,6-dihydro-7H-pyrrolo
[2,3-c]pyridin-7-one The product from Example 55C was purified by chiral chromatography on a Chiralpak IA column eluting with a 3:7 mixture of 0.1% diethylamine in methanol/carbondioxide. The title compound was randomly assigned to the second of the 2 diastereomers eluted. $^1$H NMR (300 MHz, DMSO-$d_6$) δ ppm 10.94 (d, J=5.43 Hz, 1H) 7.61 (d, J=2.37 Hz, 1H) 7.55 (s, 1H) 7.41-7.51 (m, 1H) 7.31 (dd, J=8.48, 2.37 Hz, 1H) 7.19-7.29 (m, 1H) 7.04-7.15 (m, 1H) 6.84-6.95 (m, 1H) 6.80 (d, J=8.14 Hz, 1H) 6.57 (d, J=6.44 Hz, 1H) 4.61 (q, J=7.11 Hz, 1H) 4.10 (s, 3H) 2.89-3.04 (m, 2H) 1.64 (d, J=7.12 Hz, 3H) 1.16 (t, J=7.46 Hz, 3H). MS (ESI+) m/z 473 (M+H)$^+$.

Example 58

3-{2-(2,4-difluorophenoxy)-5-[(phenylsulfonyl)me-
thyl]phenyl}-1-methyl-1,6-dihydro-7H-pyrrolo[2,3-
c]pyridin-7-one

Example 58A (3-bromo-4-(2,4-difluorophenoxy)benzyl)(phenyl)
sulfane

Example 58A (815 mg, 100%) was prepared according to the procedure used for the preparation of Example 52D, substituting sodium thiophenoxide for sodium thiomethoxide.

Example 58B 2-bromo-1-(2,4-difluorophenoxy)-4-(phenylsulfonyl-
methyl)benzene Example 58B (867 g, 99%) was prepared according to the procedure used for the preparation of Example 52E, substituting Example 58A for Example 52D.

Example 58C 3-(2-(2,4-difluorophenoxy)-5-(phenylsulfonylm-
ethyl)phenyl)-7-methoxy-1-methyl-1H-pyrrolo[2,3-
c]pyridine Example 58C was prepared according to the procedure used for the preparation of Example 52F, substituting Example 58B for Example 52E. Purification by flash chromatography (silica gel, 0 to 50% ethyl acetate in heptanes) afforded the title compound (91 mg, 87%).

Example 58D

3-{2-(2,4-difluorophenoxy)-5-[(phenylsulfonyl)me-
thyl]phenyl}-1-methyl-1,6-dihydro-7H-pyrrolo[2,3-
c]pyridin-7-one Example 58D was prepared according to the procedure used for the preparation of Example 53D, substituting Example 58C for Example 53C. The reaction time was 16 hours instead of 24 hours. Purification by flash chromatography (silica gel, 2 to 4% methanol in dichloromethane) afforded the title compound (68 mg, 79%). $^1$H NMR (300 MHz, DMSO-$d_6$) δ ppm 10.95 (d, J=5.43 Hz, 1H) 7.69-7.80 (m, 3H) 7.58-7.67 (m, 2H) 7.39-7.51 (m, 2H) 7.32 (d, J=2.03 Hz, 1H) 7.00-7.21 (m, 3H) 6.85 (dd, J=7.12, 5.76 Hz, 1H) 6.74 (d, J=8.14 Hz, 1H) 6.25 (d, J=6.10 Hz, 1H) 4.72 (s, 2H) 4.08 (s, 3H). MS (ESI+) m/z 507 (M+H)$^+$.

Example 59

3-[2-(2,4-difluorophenoxy)-5-(ethylsulfonyl)pyridin-
3-yl]-1-methyl-1,6-dihydro-7H-pyrrolo[2,3-c]pyri-
din-7-one

Example 59A 7-methoxy-1-methyl-3-(4,4,5,5-tetramethyl-1,3,2-
dioxaborolan-2-yl)-1H-pyrrolo[2,3-c]pyridine 3-Iodo-7-methoxy-1-methyl-1H-pyrrolo[2,3-c]pyridine (3.89 g, 13.50 mmol) was flow purged with nitrogen for 30 minutes, then treated with tetrahydrofuran (135 mL). The reaction mixture was cooled to −78° C. Butyllithium (5.40 mL, 13.50 mmol) was added dropwise. The reaction mixture was stirred at −78° C. for 30 minutes. 2-isopropoxy-4,4,5,5-tetramethyl-1,3,2-dioxaborolane (2.75 mL, 13.50 mmol) was added dropwise. The reaction mixture was stirred at −78° C. for 2.5 hours. The reaction mixture was poured onto water and extracted twice with ethyl acetate. The organic layer was washed with saturated aqueous sodium chloride, dried over anhydrous magnesium sulfate, filtered, and concentrated. The residue was purified by flash chromatography (silica gel, 100% heptane to 30% ethyl acetate/heptane) to provide the title compound (2.75 g, 70% yield).

Example 59B 3-bromo-2-chloro-5-(ethylsulfonyl)pyridine

Sodium sulfite (4.94 g, 39.2 mmol) and sodium bicarbonate (3.46 g, 41.2 mmol) in water (100 mL) were heated to 75° C. 3-bromo-2-chloropyridine-5-sulfonyl chloride (6.00 g, 20.6 mmol) was added portionwise over 1 hour. The reaction mixture was stirred at 75° C. for 1 hour after complete addition. The mixture was concentrated under vacuum. N,N-Dimethylformamide (37.5 mL), sodium bicarbonate (3.46 g, 41.2 mmol) and iodoethane (1.658 mL, 20.62 mmol) were added. The resulting mixture was heated to 75° C. for 2 hours then cooled to room temperature. The mixture was partitioned between ethyl acetate and water. The organic layer was washed with saturated aqueous sodium chloride, dried over anhydrous magnesium sulfate, filtered, and concentrated. The reaction mixture was purified by flash chromatography (silica gel, 100% heptane to 100% ethyl acetate) to provide the title compound (3.15 g, 53% yield).

Example 59C 3-(2-chloro-5-(ethylsulfonyl)pyridin-3-yl)-7-methoxy-1-methyl-1H-pyrrolo[2,3-c]pyridine Example 59A (0.0643 g, 0.223 mmol), Example 59B (0.063 g, 0.223 mmol), cesium fluoride (0.102 g, 0.669 mmol), and dichloropalladiumbis(triphenylphosphine) (7.83 mg, 0.011 mmol) in 1,2-dimethoxyethane (1.352 mL) and methanol (0.676 mL) were heated in a Biotage Creator microwave at 120° C. for 30 minutes for 30 minutes. The reaction mixture was partitioned between ethyl acetate and water. The organic layer was washed with saturated aqueous sodium chloride, dried over anhydrous magnesium sulfate, filtered, and concentrated. The residue purified by flash chromatography using an (silica gel, 20% ethyl acetate/heptane to 80% ethyl acetate/heptane) to provide the title compound (78.5 mg, 96% yield).

Example 59D

Example 59C (0.0548 g, 0.150 mmol), 2,4-difluorophenol (0.021 mL, 0.225 mmol), and cesium carbonate (0.073 g, 0.225 mmol) in dimethylsulfoxide (1.498 mL) were stirred at room temperature over 4 nights. The reaction mixture was diluted with water and extracted twice with ethyl acetate. The combined organic layers were washed with saturated aqueous sodium chloride, dried over anhydrous magnesium sulfate, filtered and. The reaction mixture was purified by flash chromatography (silica gel, 20% ethyl acetate/heptane to 80% ethyl acetate/heptane) to provide the title compound (58.3 mg, 85% yield).

Example 59E

Example 59D (0.0583 g, 0.127 mmol) in dioxane (1.269 mL) was treated with 4N hydrogen chloride in dioxane (1.586 mL, 6.34 mmol) at 70° C. overnight. The solvent was removed, and the residue was purified by reverse-phase HPLC to provide the title compound (16.9 mg, 30% yield). $^1$H NMR (300 MHz, DMSO-$d_6$) δ ppm 11.07 (s, J=5.76 Hz, 1H) 8.45 (d, J=2.37 Hz, 1H) 8.28 (d, J=2.37 Hz, 1H) 7.86 (s, 1H) 7.52 (m, 2H) 7.19 (m, 1H) 6.98 (dd, J=6.95, 5.93 Hz, 1H) 6.57 (dd, J=7.12, 1.02 Hz, 1H) 4.15 (s, 3H) 3.43 (q, J=7.35 Hz, 2H) 1.17 (t, J=7.29 Hz, 3H). MS (ESI+) m/z 446.2 (M+H)$^+$ Example 60

3-{2-(2,4-difluorophenoxy)-5-[(methylsulfonyl)methyl]pyridin-3-yl}-1-methyl-1,6-dihydro-7H-pyrrolo[2,3-c]pyridin-7-one Example 60A 5-bromo-6-(2,4-difluorophenoxy)nicotinic acid 5-Bromo-6-chloronicotinic acid (3.00 g, 12.7 mmol), 2,4-difluorophenol (3.30 g, 25.4 mmol) and cesium carbonate (16.5 g, 50.8 mmol) were combined in DMSO (25.4 mL), heated at 100° C. for 6 hours, cooled, diluted with 150 mL of iced water and the pH was adjusted to pH 3 with 12M HCl. The resulting solid was collected by filtration, washed with cold water and dried to constant mass to afford the title compound (2.84 g, 64%).

Example 60B (5-bromo-6-(2,4-difluorophenoxy)pyridin-3-yl)methanol

The product from Example 60A (1.0 g, 3.03 mmol) and borane tetrahydrofuran complex (6.06 mL, 6.06 mmol) were combined in tetrahydrofuran (15.15 mL) and heated at 50° C. for 2 hours, cooled, treated with 10 mL of methanol, heated at 50° C. for 1 hour, cooled and concentrated. The residue was partitioned between ethyl acetate and water. The organic layer was washed with saturated aqueous sodium chloride, dried (anhydrous Na$_2$SO$_4$), filtered, and concentrated. Purification by chromatography (silica gel, 0-50% ethyl acetate in heptanes) afforded the title compound (0.73 g, 76%).

Example 60C 3-bromo-5-(bromomethyl)-2-(2,4-difluorophenoxy)pyridine

A solution of the product from Example 60B (0.73 g, 2.309 mmol) in dichloromethane (11.55 mL) under nitrogen was treated dropwise with tribromophosphine (0.218 mL, 2.309 mmol), stirred for one hour and poured into ice water and the pH was adjusted to pH 9 by addition of solid sodium bicarbonate added portionwise. An emulsion formed that was partially removed by filtration. The aqueous layer was extracted with dichloromethane and the organics were combined, washed with saturated aqueous sodium chloride, dried (anhydrous Na$_2$SO$_4$) filtered, and concentrated to afford the title compound (0.75 g, 86%).

Example 60D 3-bromo-2-(2,4-difluorophenoxy)-5-(methylthiomethyl)pyridine

The product from Example 60C (0.75 g, 1.979 mmol) and sodium thiomethoxide (0.139 g, 1.979 mmol) were combined in dimethylformamide (3.96 mL), stirred for 4 hours and partitioned into ethyl acetate and cold water. The organic layer was washed with saturated aqueous sodium chloride, dried (anhydrous $Na_2SO_4$), filtered, and concentrated to afford the title compound (0.66 g, 96%).

Example 60E 3-bromo-2-(2,4-difluorophenoxy)-5-(methylsulfonylmethyl)pyridine A solution of the product from Example 60D (0.66 g, 1.906 mmol) at 0° C. in methanol (7.33 mL) was treated with a solution of Oxone (2.461 g, 4.00 mmol) in water (7.33 mL), stirred at ambient temperature for two hours and partitioned between ethyl acetate and water. The organic layer was washed with saturated aqueous sodium chloride, dried (anhydrous $Na_2SO_4$), filtered, and concentrated. Purification by chromatography (silica gel, 0-5% methanol in dichloromethane) afforded the title compound (0.433 g, 60%).

Example 60F 3-(2-(2,4-difluorophenoxy)-5-(methylsulfonylmethyl)pyridin-3-yl)-7-methoxy-1-methyl-1H-pyrrolo[2,3-c]pyridine The product from Example 59A (0.061 g, 0.212 mmol), the product from Example 60E (0.08 g, 0.212 mmol), tris(dibenzylideneacetone)dipalladium(0) (5.8 mg, 6.35 µmol), 1,3,5,7-tetramethyl-6-phenyl-2,4,8-trioxa-6-phosphaadamante (6.2 mg, 0.021 mmol) and potassium phosphate (0.157 g, 0.74 mmol) were combined and sparged with argon for 15 minutes. Meanwhile a solution of 4:1 dioxane/water (2 mL) was sparged with nitrogen for 15 minutes and transferred by syringe into the reaction vessel under argon. The mixture was stirred at 60° C. for 2 hours and partitioned between ethyl acetate and water. The organic layer was washed with saturated aqueous sodium chloride, dried (anhydrous $Na_2SO_4$), treated with 3-mercaptopropyl functionalized silica gel, filtered, and concentrated to afford the title compound (0.1 g, 100%).

Example 60G

3-{2-(2,4-difluorophenoxy)-5-[(methylsulfonyl)methyl]pyridin-3-yl}-1-methyl-1,6-dihydro-7H-pyrrolo[2,3-c]pyridin-7-one The product from Example 60F (0.097 g, 0.211 mmol) and 4 M hydrogen chloride in dioxane (5 mL, 20.00 mmol) were combined and heated at 70° C. for 18 hours, cooled and concentrated. The residue was partitioned between ethyl acetate and water adjusting the pH to 7. The organic layer was washed with saturated aqueous sodium chloride, dried (anhydrous $Na_2SO_4$), treated with 3-mercaptopropyl functionalized silica gel, filtered, and concentrated. Purification by trituration (1:1 dichloromethane/heptane) afforded the title compound (0.077 g, 82%). $^1$H NMR (300 MHz, DMSO-$d_6$) δ ppm 11.03 (d, J=5.43 Hz, 1H) 8.02 (d, J=2.37 Hz, 1H) 7.95 (d, J=2.37 Hz, 1H) 7.75 (s, 1H) 7.39-7.50 (m, 2H) 7.10-7.19 (m, 1H) 6.93-6.97 (m, 1H) 6.66 (d, J=6.44 Hz, 1H) 4.57 (s, 2H) 4.14 (s, 3H) 2.98 (s, 3H). MS (ESI+) m/z 446 (M+H)$^+$.

Example 61

3-[2-(4-fluorophenoxy)-5-(methylsulfonyl)phenyl]-1-methyl-1,6-dihydro-7H-pyrrolo[2,3-c]pyridin-7-one The title compound was prepared according to the procedure used for the preparation of Example 19 substituting 4-fluorophenol for 3,4-difluorophenol. $^1$H NMR (400 MHz, DMSO-$d_6$) δ ppm 11.00 (d, J=5.5 Hz, 1H), 7.99 (d, J=2.3 Hz, 1H), 7.78 (dd, J=8.7, 2.4 Hz, 1H), 7.69 (s, 1H), 7.28 (t, J=8.7 Hz, 2H), 7.20 (dd, J=9.1, 4.6 Hz, 1H), 6.99 (d, J=8.7 Hz, 1H), 6.96-6.89 (m, 1H), 6.54 (d, J=6.4 Hz, 1H), 4.11 (s, 3H), 3.24 (s, 3H).). MS (ESI+) m/z 413 (M+H)$^+$.

Example 62

3-[2-(4-tert-butylphenoxy)-5-(methylsulfonyl)phenyl]-1-methyl-1,6-dihydro-7H-pyrrolo[2,3-c]pyridin-7-one The title compound was prepared according to the procedure used for the preparation of Example 19 substituting 4-tert-butylphenol for 3,4-difluorophenol. $^1$H NMR (400 MHz, DMSO-$d_6$) δ ppm 10.99 (d, J=5.1 Hz, 1H), 7.99 (d, J=2.4 Hz, 1H), 7.77 (dd, J=8.7, 2.4 Hz, 1H), 7.69 (s, 1H), 7.45 (d, J=8.7 Hz, 2H), 7.07 (d, J=8.7 Hz, 2H), 6.99 (d, J=8.7 Hz, 1H), 6.96-6.90 (m, 1H), 6.55 (d, J=6.9 Hz, 1H), 4.11 (s, 3H), 3.24 (s, 3H), 1.29 (s, 9H). MS (ESI+) m/z 451 (M+H)$^+$.

Example 63

1-methyl-3-[5-(methylsulfonyl)-2-(naphthalen-2-yloxy)phenyl]-1,6-dihydro-7H-pyrrolo[2,3-c]pyridin-7-one The title compound was prepared according to the procedure used for the preparation of Example 19 substituting 2-naphthol for 3,4-difluorophenol. $^1$H NMR (400 MHz, DMSO-$d_6$) δ ppm 11.00 (d, J=5.0 Hz, 1H), 8.05 (d, J=2.2 Hz, 1H), 8.01 (d, J=9.0 Hz, 1H), 7.95 (d, J=7.8 Hz, 1H), 7.87 (d, J=7.9 Hz, 1H), 7.79 (dd, J=8.6, 2.2 Hz, 1H), 7.73 (s, 1H), 7.59 (s, 1H), 7.52 (dd, J=15.9, 7.5 Hz, 2H), 7.37 (dd, J=8.9, 2.2 Hz, 1H), 7.12 (d, J=8.6 Hz, 1H), 6.97-6.90 (m, 1H), 6.60 (d, J=7.0 Hz, 1H), 4.10 (s, 3H), 3.27 (s, 3H). MS (ESI+) m/z 445 (M+H)$^+$.

Example 64

1-methyl-3-[5-(methylsulfonyl)-2-(2,2,3,3,3-pentafluoropropoxy)phenyl]-1,6-dihydro-7H-pyrrolo[2,3-c]pyridin-7-one The title compound was prepared according to the procedure used for the preparation of Example 35 substituting 2,2,3,3,3-pentafluoropropanol for 2-cyclopentylethanol. $^1$H NMR (400 MHz, DMSO-$d_6$) δ ppm 11.01 (d, J=5.3 Hz, 1H), 7.91 (d, J=2.3 Hz, 1H), 7.86 (dd, J=8.7, 2.3 Hz, 1H), 7.54-7.45 (m, 2H), 6.95-6.89 (m, 1H), 6.44 (d, J=6.8 Hz, 1H), 5.03 (t, J=13.6 Hz, 2H), 4.11 (s, 3H), 3.24 (s, 3H). MS (ESI+) m/z 451 (M+H)$^+$.

Example 65

1-methyl-3-[(5-(methylsulfonyl)-2-{2-[tricyclo [3.3.1.1$^{3,7}$]dec-1-yl]ethoxy}phenyl]-1,6-dihydro-7H-pyrrolo[2,3-c]pyridin-7-one The title compound was prepared according to the procedure used for the preparation of Example 35 substituting 2-adamantanylethanol for 2-cyclopentylethanol. $^1$H NMR (400 MHz, DMSO-d$_6$) δ ppm 10.95 (d, J=5.0 Hz, 1H), 7.83 (d, J=2.4 Hz, 1H), 7.79 (dd, J=8.6, 2.4 Hz, 1H), 7.56 (s, 1H), 7.35 (d, J=8.7 Hz, 1H), 6.94-6.86 (m, 1H), 6.40 (d, J=6.9 Hz, 1H), 4.17 (t, J=7.3 Hz, 2H), 4.11 (s, 3H), 3.20 (s, 3H), 1.88 (s, 3H), 1.70-1.44 (m, 14H). MS (ESI+) m/z 481 (M+H)$^+$.

Example 66

3-[2-(3-cyclopentylpropoxy)-5-(methylsulfonyl) phenyl]-1-methyl-1,6-dihydro-7H-pyrrolo[2,3-c] pyridin-7-one The title compound was prepared according to the procedure used for the preparation of Example 35 substituting 3-cyclopentylpropanol for 2-cyclopentylethanol. $^1$H NMR (400 MHz, DMSO-d$_6$) δ ppm 10.97 (d, J=5.0 Hz, 1H), 7.84 (d, J=2.4 Hz, 1H), 7.79 (dd, J=8.7, 2.4 Hz, 1H), 7.56 (s, 1H), 7.30 (d, J=8.7 Hz, 1H), 6.94-6.86 (m, 1H), 6.42 (d, J=6.9 Hz, 1H), 4.10 (d, J=9.0 Hz, 5H), 3.20 (s, 3H), 1.85-1.62 (m, 5H), 1.49 (ddd, J=15.1, 9.3, 5.4 Hz, 4H), 1.35 (dd, J=15.1, 7.1 Hz, 2H), 1.07-0.95 (m, 2H). MS (ESI+) m/z 429 (M+H)$^+$.

Example 67

3-{2-[(1-acetylpiperidin-4-yl)oxy]-5-(methylsulfonyl)phenyl}-1-methyl-1,6-dihydro-7H-pyrrolo[2,3-c] pyridin-7-one The title compound was prepared according to the procedure used for the preparation of Example 35 substituting 1-(4-hydroxypiperidin-1-yl)ethanone for 2-cyclopentylethanol. $^1$H NMR (400 MHz, DMSO-d$_6$) δ ppm 10.96 (d, J=5.6 Hz, 1H), 7.86 (d, J=2.4 Hz, 1H), 7.78 (d, J=8.7 Hz, 1H), 7.60 (s, 1H), 7.42 (d, J=8.9 Hz, 1H), 6.96-6.88 (m, 1H), 6.44 (d, J=6.7 Hz, 1H), 4.85 (s, 1H), 4.12 (s, 3H), 3.58 (d, J=58.6 Hz, 3H), 3.21 (s, 3H), 1.94 (d, J=34.4 Hz, 5H), 1.62 (d, J=43.9 Hz, 3H). MS (ESI+) m/z 444 (M+H)$^+$.

Example 68

3-{2-[(cyclopentylmethyl)amino]-5-(methylsulfonyl) phenyl}-1-methyl-1,6-dihydro-7H-pyrrolo[2,3-c] pyridin-7-one

Example 68A

N-(cyclopentylmethyl)-2-(7-methoxy-1-methyl-1H-pyrrolo[2,3-c]pyridin-3-yl)-4-(methylsulfonyl) aniline The product from Example 44A (55 mg, 0.166 mmol) and cyclopentanecarbaldehyde (58.64 mg, 0.597 mmol) in dichloroethane/acetic acid (1:1, 1 mL) was heated in a sealed tube at 60° C. for 24 hours, cooled, and concentrated. Purification by reverse phase HPLC (C18, CH$_3$CN/water (0.1% TFA), 10-100%) afforded the title compound (0.021 g, 31%).

Example 68B

3-{2-[(cyclopentylmethyl)amino]-5-(methylsulfonyl) phenyl}-1-methyl-1,6-dihydro-7H-pyrrolo[2,3-c] pyridin-7-one The product from Example 68A, (0.021 g) in dioxane (0.5 mL) and 4N HCl in dioxane (0.5 mL) was heated at 70° C. for 24 hours, cooled, and concentrated. Purification by reverse phase HPLC (C18, CH$_3$CN/water (0.1% TFA), 10-100%) afforded the title compound (0.007 g, 27%) as the TFA salt. $^1$H NMR (500 MHz, DMSO-d$_6$/D$_2$O) δ ppm 7.64 (dd, J=8.70, 2.29 Hz, 1H) 7.44-7.46 (m, 2H) 6.93 (d, J=7.02 Hz, 1H) 6.83 (d, J=8.85 Hz, 1H) 6.24 (d, J=6.71 Hz, 1H) 4.12 (s, 3H) 3.09 (s, 3H) 3.06 (d, J=7.32 Hz, 2H) 2.10-2.17 (m, 1H) 1.61-1.69 (m, 2H) 1.51-1.58 (m, 2H) 1.44-1.50 (m, 2H) 1.15-1.24 (m, 2H). MS (ESI+) m/z 400 (M+H)$^+$.

Example 69

1-methyl-3-{5-(methylsulfonyl)-2-[(2,2,2-trifluoroethyl)amino]phenyl}-1,6-dihydro-7H-pyrrolo[2,3-c] pyridin-7-one

Example 69A 2-(7-methoxy-1-methyl-1H-pyrrolo[2,3-c]pyridin-3-yl)-4-(methylsulfonyl)-N-(2,2,2-trifluoroethyl) aniline The title compound was prepared according to the procedure used in Example 68A substituting trifluoroacetaldehyde for cyclopentanecarbaldehyde (0.025 g, 36%).

Example 69B 1-methyl-3-{5-(methylsulfonyl)-2-[(2,2,2-trifluoroethyl)amino]phenyl}-1,6-dihydro-7H-pyrrolo[2,3-c] pyridin-7-one The TFA salt of the title compound was prepared according to the procedure used in Example 68B, substituting the product from Example 69A for the product from Example 68A (0.004 g, 18%). $^1$H NMR (500 MHz, DMSO-d$_6$/D$_2$O) δ ppm 7.69 (dd, J=8.70, 2.29 Hz, 1H) 7.51 (d, J=2.14 Hz, 1H) 7.45 (s, 1H) 7.08 (d, J=8.85 Hz, 1H) 6.93 (d, J=7.02 Hz, 1H) 6.20 (d, J=7.02 Hz, 1H) 4.12 (s, 3H) 3.12 (s, 3H). MS (ESI+) m/z 400 (M+H)$^+$.

Example 70

3-{2-[(2,2,3,3,4,4,4-heptafluorobutyl)amino]-5-(methylsulfonyl)phenyl}-1-methyl-1,6-dihydro-7H-pyrrolo[2,3-c]pyridin-7-one

Example 70A

N-(2,2,3,3,4,4,4-heptafluorobutyl)-2-(7-methoxy-1-methyl-1H-pyrrolo[2,3-c]pyridin-3-yl)-4-(methylsulfonyl)aniline The title compound was prepared according to the procedure used in Example 68A substituting 2,2,3,3,4,4,4-heptafluorobutanal for cyclopentanecarbaldehyde (0.010 g, 12%).

Example 70B

3-{2-[(2,2,3,3,4,4,4-heptafluorobutyl)amino]-5-(methylsulfonyl)phenyl}-1-methyl-1,6-dihydro-7H-pyrrolo[2,3-c]pyridin-7-one The TFA salt of the title compound was prepared according to the procedure used in Example 68B, substituting the product from Example 70A for the product from Example 68A (0.003 g, 11%). $^1$H NMR (500 MHz, DMSO-$d_6$/$D_2$O). δ ppm 7.71 (dd, J=8.70, 2.29 Hz, 1H) 7.51 (d, J=2.44 Hz, 1H) 7.44 (s, 1H) 7.02 (d, J=8.85 Hz, 1H) 6.93 (d, J=6.71 Hz, 1H) 6.21 (d, J=7.02 Hz, 1H) 4.06-4.17 (m, 5H) 3.13 (s, 3H). MS (ESI+) m/z 398 (M+H)$^+$.

Example 71

3-[2-{[(1S,4R)-bicyclo[2.2.1]hept-2-ylmethyl]amino}-5-(methylsulfonyl)phenyl]-1-methyl-1,6-dihydro-7H-pyrrolo[2,3-c]pyridin-7-one

Example 71A

N-((1S,4R)-bicyclo[2.2.1]heptan-2-ylmethyl)-2-(7-methoxy-1-methyl-1H-pyrrolo[2,3-c]pyridin-3-yl)-4-(methylsulfonyl)aniline The title compound was prepared according to the procedure used in Example 68A substituting (1S,4R)-bicyclo[2.2.1]heptane-2-carbaldehyde for cyclopentanecarbaldehyde (0.013 g, 18%).

Example 71B

3-[2-{[(1S,4R)-bicyclo[2.2.1]hept-2-ylmethyl]amino}-5-(methylsulfonyl)phenyl]-1-methyl-1,6-dihydro-7H-pyrrolo[2,3-c]pyridin-7-one The TFA salt of the title compound was prepared according to the procedure used in Example 68B, substituting the product from Example 71A for the product from Example 68A (0.004 g, 15%). $^1$H NMR (500 MHz, DMSO-$d_6$/$D_2$O) δ ppm 7.61-7.67 (m, 1H) 7.43-7.46 (m, 1H) 6.90-6.94 (m, 1H) 6.79-6.85 (m, 1H) 6.20-6.24 (m, 1H) 4.10-4.12 (m, 3H) 2.98-3.16 (m, 4H) 2.85 (dd, J=13.28, 6.87 Hz, 1H) 2.13-2.19 (m, 1H) 2.00-2.11 (m, 1H) 1.62-1.74 (m, J=6.10 Hz, 1H) 1.41-1.50 (m, J=3.05 Hz, 2H) 1.22-1.34 (m, 2H) 1.01-1.14 (m, 3H). MS (ESI+) m/z 426 (M+H)$^+$.

Example 72

3-{2-[(2-cyclopentylethyl)amino]-5-(methylsulfonyl)phenyl}-1-methyl-1,6-dihydro-7H-pyrrolo[2,3-c]pyridin-7-one

Example 72A

N-(2-cyclopentylethyl)-2-(7-methoxy-1-methyl-1H-pyrrolo[2,3-c]pyridin-3-yl)-4-(methylsulfonyl)aniline The title compound was prepared according to the procedure used in Example 68A substituting 2-cyclopentylacetaldehyde for cyclopentanecarbaldehyde (0.005 g, 8%).

Example 72B

3-{2-[(2-cyclopentylethyl)amino]-5-(methylsulfonyl)phenyl}-1-methyl-1,6-dihydro-7H-pyrrolo[2,3-c]pyridin-7-one The TFA salt of the title compound was prepared according to the procedure used in Example 68B, substituting the product from Example 72A for the product from Example 68A (0.0017 g, 6%). $^1$H NMR (500 MHz, DMSO-$d_6$/$D_2$O) δ ppm 7.65 (dd, J=8.70, 2.29 Hz, 1H) 7.43-7.46 (m, 1H) 6.92 (d, J=7.02 Hz, 1H) 6.80 (d, J=8.85 Hz, 1H) 6.23 (d, J=7.02 Hz, 1H) 4.11 (s, 3H) 3.13-3.17 (m, 2H) 3.09 (s, 3H) 1.69-1.80 (m, J=17.09, 3.97 Hz, 3H) 1.43-1.60 (m, 6H) 1.01-1.12 (m, 2H). ESI$^+$ m/z=414.0 (M+H)$^+$. MS (ESI+) m/z 414 (M+H)$^+$.

Example 73

3-[2-(2-chloro-4-methylphenoxy)-5-(ethylsulfonyl)phenyl]-1-methyl-1,6-dihydro-7H-pyrrolo[2,3-c]pyridin-7-one Example 48E (33 mg, 0.09 mmol) in dimethylsulfoxide (0.5 mL) was treated with a solution of 2-chloro-4-methylphenol (28 mg, 0.2 mmol) dissolved in dimethylsulfoxide (0.4 mL), followed by cesium carbonate (77 mg, 0.2 mmol). The reaction mixture was placed in an Anton Paar microwave and heated for 40 minutes at 150° C. The reaction mixture was dried and 0.500 mL of dioxane was added followed by 0.500 mL of 4M hydrochloric acid in dioxane. The reaction mixture was heated at 70° C. overnight. The reaction mixture was concentrated to dryness and purified by reverse phase HPLC (C18, CH$_3$CN/water (0.1% TFA), 10-100%) to provide the title compound. $^1$H NMR (500 MHz, DMSO-$d_6$/$D_2$O) δ ppm 7.94 (d, J=2.44 Hz, 1H) 7.69-7.75 (m, 2H) 7.46-7.48 (m, 1H) 7.17-7.29 (m, 2H) 6.99 (d, J=7.32 Hz, 1H) 6.82 (d, J=8.85 Hz, 1H) 6.60-6.65 (m, 1H) 4.12 (s, 3H) 3.31 (q, J=7.32 Hz, 2H) 2.34 (s, 3H) 1.16 (t, J=7.32 Hz, 3H); MS (ESI+) m/z 457 (M+H)$^+$.

Example 74

3-[5-(ethylsulfonyl)-2-(pyridin-4-yloxy)phenyl]-1-methyl-1,6-dihydro-7H-pyrrolo[2,3-c]pyridin-7-one The TFA salt of Example 74 was prepared according to the procedure used for the preparation of Example 73, substituting pyridin-4-ol for 2-chloro-4-methylphenol. $^1$H NMR (500 MHz, DMSO-$d_6$/$D_2$O) δ ppm 8.28 (d, 2H) 8.07-8.11 (m, 1H) 8.03 (d, J=2.14 Hz, 1H) 7.97 (d, J=8.24 Hz, 1H) 7.32 (s, 1H) 6.78-6.88 (m, 3H) 6.11 (d, J=7.02 Hz, 1H) 4.04 (s, 3H) 3.40-3.49 (m, 2H) 1.21 (t, J=7.32 Hz, 3H); MS (ESI+) m/z 410 (M+H)$^+$.

Example 75

3-{2[(4,6-dimethylpyridin-3-yl)oxy]-5-(ethylsulfonyl)phenyl}-1-methyl-1,6-dihydro-7H-pyrrolo[2,3-c]pyridin-7-one The TFA salt of Example 75 was prepared according to the procedure used for the preparation of Example 73, substituting 4,6-dimethylpyridin-3-ol for 2-chloro-4-methylphenol. $^1$H NMR (500 MHz, DMSO-$d_6$/$D_2$O) δ ppm 8.47 (s, 1H) 8.00 (d, J=2.14 Hz, 1H) 7.72-7.81 (m, 3H) 7.16 (d, J=8.85 Hz, 1H) 7.01 (d, J=7.02 Hz, 1H) 6.58 (d, J=7.02 Hz, 1H) 4.11 (s, 3H)

3.35 (q, J=7.32 Hz, 2H) 2.61 (s, 3H) 2.52-2.55 (m, 3H) 2.33 (s, 3H); MS (ESI+) m/z 438 (M+H)$^+$.

Example 76

3-[2-(3,4-dichlorophenoxy)-5-(ethylsulfonyl)phenyl]-1-methyl-1,6-dihydro-7H-pyrrolo[2,3-c]pyridin-7-one Example 76 was prepared according to the procedure used for the preparation of Example 73, substituting 3,4-dichlorophenol for 2-chloro-4-methylphenol. $^1$H NMR (500 MHz, DMSO-d$_6$/D$_2$O) δ ppm 7.95 (d, J=2.14 Hz, 1H) 7.80 (dd, J=8.70, 2.29 Hz, 1H) 7.68 (s, 1H) 7.62-7.66 (m, 1H) 7.44 (d, J=2.75 Hz, 1H) 7.21-7.26 (m, 1H) 7.10 (dd, J=8.85, 2.75 Hz, 1H) 6.98 (d, J=7.02 Hz, 1H) 6.53-6.57 (m, 1H) 4.09 (s, 3H) 3.34 (q, J=7.02 Hz, 2H) 1.17 (t, J=7.32 Hz, 3H); MS (ESI+) m/z 477 (M+H)$^+$.

Example 77

3-{5-(ethylsulfonyl)-2-[4-(trifluoromethyl)phenoxy]phenyl}-1-methyl-1,6-dihydro-7H-pyrrolo[2,3-c]pyridin-7-one Example 77 was prepared according to the procedure used for the preparation of Example 73, substituting 4-(trifluoromethyl)phenol for 2-chloro-4-methylphenol. $^1$H NMR (500 MHz, DMSO-d$_6$/D$_2$O) δ ppm 7.99 (d, J=2.44 Hz, 1H) 7.82 (dd, J=8.54, 2.44 Hz, 1H) 7.74 (d, J=8.85 Hz, 2H) 7.66 (s, 1H) 7.21-7.31 (m, 3H) 6.97 (d, J=7.02 Hz, 1H) 6.55 (d, J=7.02 Hz, 1H) 4.07 (s, 3H) 3.35 (q, J=7.32 Hz, 2H) 1.18 (t, J=7.32 Hz, 3H); MS (ESI+) m/z 477 (M+H)$^+$.

Example 78

4-[4-(ethylsulfonyl)-2-(1-methyl-7-oxo-6,7-dihydro-1H-pyrrolo[2,3-c]pyridin-3-yl)phenoxy]benzonitrile Example 78 was prepared according to the procedure used for the preparation of Example 73, substituting 4-hydroxybenzonitrile for 2-chloro-4-methylphenol. $^1$H NMR (500 MHz, DMSO-d$_6$/D$_2$O) δ ppm 7.99 (d, J=2.14 Hz, 1H) 7.78-7.87 (m, 3H) 7.63 (s, 1H) 7.33-7.38 (m, 1H) 7.16 (d, J=8.85 Hz, 2H) 6.97 (d, J=7.02 Hz, 1H) 6.53 (d, J=7.02 Hz, 1H) 4.06 (s, 3H) 3.36 (q, J=7.32 Hz, 2H) 1.18 (t, J=7.32 Hz, 3H); MS (ESI+) m/z 434 (M+H)$^+$.

Example 79

3-[2-(4-chloro-3-ethylphenoxy)-5-(ethylsulfonyl)phenyl]-1-methyl-1,6-dihydro-7H-pyrrolo[2,3-c]pyridin-7-one Example 79 was prepared according to the procedure used for the preparation of Example 73, substituting 4-chloro-3-ethylphenol for 2-chloro-4-methylphenol. $^1$H NMR (500 MHz, DMSO-d$_6$/D$_2$O) δ ppm 7.93 (d, J=2.14 Hz, 1H) 7.77 (dd, J=8.70, 2.29 Hz, 1H) 7.67 (s, 1H) 7.41-7.47 (m, 1H) 7.08-7.12 (m, 2H) 6.94-7.00 (m, 2H) 6.55 (d, J=7.02 Hz, 1H) 4.10 (s, 3H) 3.32 (q, J=7.32 Hz, 2H) 2.67 (q, J=7.63 Hz, 2H) 1.11-1.20 (m, 6H); MS (ESI+) m/z 471 (M+H)$^+$.

Example 80

4-[4-(ethylsulfonyl)-2-(1-methyl-7-oxo-6,7-dihydro-1H-pyrrolo[2,3-c]pyridin-3-yl)phenoxy]-3-methoxybenzonitrile Example 80 was prepared according to the procedure used for the preparation of Example 73, substituting 4-hydroxy-3-methoxybenzonitrile for 2-chloro-4-methylphenol. $^1$H NMR (500 MHz, DMSO-d$_6$/D$_2$O) δ ppm 7.92 (d, J=2.44 Hz, 1H) 7.72 (dd, J=8.70, 2.29 Hz, 1H) 7.66-7.68 (m, 2H) 7.48 (dd, J=8.24, 1.83 Hz, 1H) 7.29 (d, J=8.24 Hz, 1H) 6.92-6.99 (m, 2H) 6.60 (d, J=7.02 Hz, 1H) 4.10 (s, 3H) 3.82 (s, 3H) 3.32 (q, J=7.32 Hz, 2H) 1.16 (t, J=7.32 Hz, 3H); MS (ESI+) m/z 464 (M+H)$^+$.

Example 81

3-[5-(ethylsulfonyl)-2-(pyridin-3-yloxy)phenyl]-1-methyl-1,6-dihydro-7H-pyrrolo[2,3-c]pyridin-7-one The TFA salt of Example 81 was prepared according to the procedure used for the preparation of Example 73, substituting pyridin-3-ol for 2-chloro-4-methylphenol. $^1$H NMR (500 MHz, DMSO-d$_6$/D$_2$O) δ ppm 8.55 (d, J=2.44 Hz, 1H) 8.48 (d, J=4.27 Hz, 1H) 7.93-8.00 (m, 1H) 7.69-7.89 (m, 3H) 7.58-7.67 (m, 1H) 7.25-7.36 (m, 1H) 6.99 (d, J=7.02 Hz, 1H) 6.56 (d, J=7.02 Hz, 1H) 4.08 (d, J=5.19 Hz, 3H) 3.30-3.41 (m, 2H) 1.15-1.23 (m, 3H); MS (ESI+) m/z 424 (M+H)$^+$.

Example 82

3-[2-(2,4-dichlorophenoxy)-5-(ethylsulfonyl)phenyl]-1-methyl-1,6-dihydro-7H-pyrrolo[2,3-c]pyridin-7-one Example 82 was prepared according to the procedure used for the preparation of Example 73, substituting 2,4-dichlorophenol for 2-chloro-4-methylphenol. $^1$H NMR (500 MHz, DMSO-d$_6$/D$_2$O) δ ppm 7.95 (d, J=2.14 Hz, 1H) 7.80 (d, J=2.44 Hz, 1H) 7.75 (dd, J=8.54, 2.44 Hz, 1H) 7.70 (s, 1H) 7.49 (dd, J=8.70, 2.59 Hz, 1H) 7.30 (d, J=8.85 Hz, 1H) 6.98 (t, J=7.48 Hz, 2H) 6.60 (d, J=7.32 Hz, 1H) 4.11 (s, 3H) 3.32 (q, J=7.32 Hz, 2H) 1.16 (t, J=7.32 Hz, 3H); MS (ESI+) m/z 477 (M+H)$^1$.

Example 83

2-[4-(ethylsulfonyl)-2-(1-methyl-7-oxo-6,7-dihydro-1H-pyrrolo[2,3-c]pyridin-3-yl)phenoxy]benzonitrile Example 83 was prepared according to the procedure used for the preparation of Example 73, substituting 2-hydroxybenzonitrile for 2-chloro-4-methylphenol. $^1$H NMR (500 MHz, DMSO-d$_6$/D$_2$O) δ ppm 8.00 (d, J=2.14 Hz, 1H) 7.82-7.90 (m, 2H) 7.63-7.71 (m, 2H) 7.34 (t, J=7.63 Hz, 1H) 7.28 (d, J=8.54 Hz, 1H) 7.10 (d, J=8.54 Hz, 1H) 6.96 (d, J=7.02 Hz, 1H) 6.57 (d, J=7.02 Hz, 1H) 4.09 (s, 3H) 3.36 (q, J=7.32 Hz, 2H) 1.18 (t, J=7.32 Hz, 3H); MS (ESI+) m/z 434 (M+H)$^+$.

Example 84

3-[2-(2,3-dichlorophenoxy)-5-(ethylsulfonyl)phenyl]-1-methyl-1,6-dihydro-7H-pyrrolo[2,3-c]pyridin-7-one Example 84 was prepared according to the procedure used for the preparation of Example 73, substituting 2,3-dichlorophenol for 2-chloro-4-methylphenol. $^1$H NMR (500 MHz, DMSO-d$_6$/D$_2$O) δ ppm 7.97 (d, J=2.14 Hz, 1H) 7.77 (dd, J=8.70, 2.29 Hz, 1H) 7.70 (s, 1H) 7.55 (dd, J=8.24, 1.22 Hz, 1H) 7.43 (t, J=8.09 Hz, 1H) 7.23 (dd, J=8.24, 1.22 Hz, 1H) 6.99 (dd, J=7.78, 3.20 Hz, 2H) 6.61 (d, J=7.02 Hz, 1H) 4.08-4.13 (s, 3H) 3.33 (q, J=7.32 Hz, 2H) 1.17 (t, J=7.32 Hz, 3H); MS (ESI+) m/z 477 (M+H)$^+$.

Example 85

3-[2-(2-chloro-4-methoxyphenoxy)-5-(ethylsulfonyl) phenyl]-1-methyl-1,6-dihydro-7H-pyrrolo[2,3-c] pyridin-7-one Example 85 was prepared according to the procedure used for the preparation of Example 73, substituting 2-chloro-4-methoxyphenol for 2-chloro-4-methylphenol. $^1$H NMR (500 MHz, DMSO-d$_6$/D$_2$O) δ ppm 7.93 (d, J=2.44 Hz, 1H) 7.69-7.74 (m, 2H) 7.28-7.32 (m, 1H) 7.24 (d, J=2.75 Hz, 1H) 7.03 (dd, J=8.85, 3.05 Hz, 1H) 6.99 (d, J=7.02 Hz, 1H) 6.78 (d, J=8.54 Hz, 1H) 6.63 (d, J=7.02 Hz, 1H) 4.13 (s, 3H) 3.81 (s, 3H) 3.30 (q, J=7.32 Hz, 2H) 1.15 (t, J=7.32 Hz, 3H); MS (ESI+) m/z 473 (M+H)$^+$.

Example 86

3-{5-(ethylsulfonyl)-2-[(6-methylpyrazin-2-yl)oxy] phenyl}-1-methyl-1,6-dihydro-7H-pyrrolo[2,3-c] pyridin-7-one Example 86 was prepared according to the procedure used for the preparation of Example 73, substituting 6-methylpyrazin-2-ol for 2-chloro-4-methylphenol. $^1$H NMR (500 MHz, DMSO-d$_6$/D$_2$O) δ ppm 8.26 (s, 1H) 8.22 (s, 1H) 7.96 (d, J=2.14 Hz, 1H) 7.86 (dd, J=8.54, 2.44 Hz, 1H) 7.58 (s, 1H) 7.52 (d, J=8.54 Hz, 1H) 6.95 (d, J=6.71 Hz, 1H) 6.48 (d, J=7.02 Hz, 1H) 4.03 (s, 3H) 3.38 (q, J=7.53 Hz, 2H) 2.27 (s, 3H) 1.19 (t, J=7.32 Hz, 3H); MS (ESI+) m/z 425 (M+H)$^+$.

Example 87

3-[5-(ethylsulfonyl)-2-(pyridazin-4-yloxy)phenyl]-1-methyl-1,6-dihydro-7H-pyrrolo[2,3-c]pyridin-7-one Example 87 was prepared according to the procedure used for the preparation of Example 73, substituting pyridazin-4-ol for 2-chloro-4-methylphenol. $^1$H NMR (500 MHz, DMSO-d$_6$/D$_2$O) δ ppm 8.19 (d, J=7.93 Hz, 1H) 7.98-8.07 (m, 2H) 7.89-7.95 (m, 2H) 7.43 (s, 1H) 6.85 (d, J=7.02 Hz, 1H) 6.31 (dd, J=7.93, 3.05 Hz, 1H) 5.98 (d, J=7.02 Hz, 1H) 4.08 (s, 3H) 3.43 (q, J=7.32 Hz, 2H) 1.20 (t, J=7.32 Hz, 3H); MS (ESI+) m/z 411 (M+H)$^+$.

Example 88

3-[5-(ethylsulfonyl)-2-(pyrimidin-5-yloxy)phenyl]-1-methyl-1,6-dihydro-7H-pyrrolo[2,3-c]pyridin-7-one Example 88 was prepared according to the procedure used for the preparation of Example 73, substituting pyrimidin-5-ol for 2-chloro-4-methylphenol. $^1$H NMR (500 MHz, DMSO-d$_6$/D$_2$O) δ ppm 8.99 (s, 1H) 8.66 (s, 2H) 7.98 (d, J=2.14 Hz, 1H) 7.83 (dd, J=8.70, 2.29 Hz, 1H) 7.71 (s, 1H) 7.34 (d, J=8.54 Hz, 1H) 6.99 (d, J=7.02 Hz, 1H) 6.56 (d, J=7.02 Hz, 1H) 4.08 (s, 3H) 3.35 (q, J=7.32 Hz, 2H) 1.18 (t, J=7.32 Hz, 3H); MS (ESI+) m/z 411 (M+H)$^+$.

Example 89

3-{5-(ethylsulfonyl)-2-[(3-methylpyrazin-2-yl)oxy] phenyl}-1-methyl-1,6-dihydro-7H-pyrrolo[2,3-c] pyridin-7-one Example 89 was prepared according to the procedure used for the preparation of Example 73, substituting 3-methylpyrazin-2-ol for 2-chloro-4-methylphenol. $^1$H NMR (500 MHz, DMSO-d$_6$/D$_2$O) δ ppm 7.99-8.02 (m, 1H) 7.99 (s, 1H) 7.83 (d, J=8.24 Hz, 1H) 7.25 (s, 1H) 7.20 (d, J=4.58 Hz, 1H) 7.06 (d, J=4.58 Hz, 1H) 6.86 (d, J=7.02 Hz, 1H) 6.16 (d, J=7.02 Hz, 1H) 4.02 (s, 3H) 3.43 (q, J=7.32 Hz, 2H) 2.26-2.32 (m, 3H) 1.21 (t, J=7.32 Hz, 3H); MS (ESI+) m/z 425 (M+H)$^+$.

Example 90

3-{5-(ethylsulfonyl)-2-[(1,3,5-trimethyl-1H-pyrazol-4-yl)oxy]phenyl}-1-methyl-1,6-dihydro-7H-pyrrolo [2,3-c]pyridin-7-one Example 90 was prepared according to the procedure used for the preparation of Example 73, substituting 1,3,5-trimethyl-1H-pyrazol-4-ol for 2-chloro-4-methylphenol. $^1$H NMR (500 MHz, DMSO-d$_6$/D$_2$O) δ ppm 7.90 (d, J=2.14 Hz, 1H) 7.68-7.75 (m, 2H) 7.01 (d, J=7.02 Hz, 1H) 6.93 (d, J=8.54 Hz, 1H) 6.55 (d, J=7.02 Hz, 1H) 4.14 (s, 3H) 3.68 (s, 3H) 3.29 (q, J=7.32 Hz, 2H) 2.05 (s, 3H) 1.94 (s, 3H) 1.16 (t, J=7.32 Hz, 3H); MS (ESI+) m/z 441 (M+H)$^+$.

Example 91

5-chloro-3-{2-(2,4-difluorophenoxy)-5-[(methylsulfonyl)methyl]phenyl}-1-methyl-1,6-dihydro-7H-pyrrolo[2,3-c]pyridin-7-one

Example 91A 5-bromo-7-chloro-1-methyl-1H-pyrrolo[2,3-c]pyridine

A solution of 5-bromo-7-chloro-1H-pyrrolo[2,3-c]pyridine (Aldrich, 0.86 g, 3.72 mmol) in tetrahydrofuran (37.2 mL) was treated with sodium hydride (0.297 g, 7.43 mmol) at ambient temperature, stirred for 15 minutes, treated with iodomethane (0.348 mL, 5.57 mmol), stirred for 1 hour at ambient temperature and quenched with saturated aqueous ammonium chloride. The mixture was partitioned with ethyl acetate and the organic layer was washed with saturated aqueous sodium chloride, dried (anhydrous Na$_2$SO$_4$), filtered, and concentrated. Purification by chromatography (silica gel, 0-40% ethyl acetate in heptanes) afforded the title compound (0.75 g, 82%).

Example 91B 5-bromo-7-methoxy-1-methyl-1H-pyrrolo[2,3-c] pyridine

The product from Example 91A (0.43 g, 1.752 mmol) and 0.5 M sodium methoxide in methanol (15 mL, 7.50 mmol) were combined in a sealed microwave tube, heated by microwave at 130° C. for 45 minutes, cooled and concentrated. The residue was partitioned between ethyl acetate and water adjusting the pH to 7 with 1 M HCl. The organic layer was washed with saturated aqueous sodium chloride, dried (anhydrous Na$_2$SO$_4$), filtered, and concentrated to afford the title compound (0.41 g, 97%).

Example 91C 5-bromo-3-iodo-7-methoxy-1-methyl-1H-pyrrolo[2,3-c]pyridine

The product from Example 91B (0.82 g, 3.40 mmol) and N-iodosuccinimide (0.918 g, 4.08 mmol) were combined in dimethylformamide (17.01 mL), stirred for two hours at ambient temperature, and quenched with 100 mL of 10% aqueous sodium thiosulfate. The mixture was stirred for 15 minutes and the resulting solid was collected by filtration, washed repeatedly with water and dried to constant mass to afford the title compound (1.17 g, 94%).

Example 91D 2-(2-(2,4-difluorophenoxy)-5-(methylsulfonylmethyl)phenyl)-4,4,5,5-tetramethyl-1,3,2-dioxaborolane The product from Example 52E (1.0 g, 2.65 mmol), 4,4,4',4',5,5,5',5'-octamethyl-2,2'-bi(1,3,2-dioxaborolane) (1.346 g, 5.30 mmol), potassium acetate (1.041 g, 10.60 mmol) and Pd(PPh$_3$)$_2$Cl$_2$ (0.112 g, 0.159 mmol) were combined and sparged with argon for 30 minutes. To the solids was added argon sparged dioxane (13.26 mL). The reaction mixture was heated for 18 hours under argon at 90° C., cooled and partitioned between ethyl acetate and water. The organic layer was washed with saturated aqueous sodium chloride, dried with sodium sulfate, treated with 3-mercaptopropyl functionalized silica gel, filtered, and concentrated. Purification by chromatography (silica gel, 0-70% ethyl acetate in heptanes) afforded the title compound (1.0 g, 89%).

Example 91E 5-bromo-3-(2-(2,4-difluorophenoxy)-5-(methylsulfonylmethyl)phenyl)-7-methoxy-1-methyl-1H-pyrrolo[2,3-c]pyridine The product from Example 91D (0.058 g, 0.136 mmol), the product from Example 91C (0.05 g, 0.136 mmol), tris(dibenzylideneacetone)dipalladium(0) (3.74 mg, 4.09 µmol), 1,3,5,7-tetramethyl-6-phenyl-2,4,8-trioxa-6-phosphaadamante (3.98 mg, 0.014 mmol) and potassium phosphate (0.087 g, 0.409 mmol) were combined and sparged with argon for 15 minutes. Meanwhile a solution of 4:1 dioxane/water (2 mL) was sparged with nitrogen for 15 minutes and transferred by syringe into the reaction vessel under argon. The mixture was stirred for 2 hours at ambient temperature and partitioned between ethyl acetate and water. The organic layer was washed with saturated aqueous sodium chloride, dried (anhydrous Na$_2$SO$_4$), treated with 3-mercaptopropyl functionalized silica gel, filtered, and concentrated. Purification by chromatography (silica gel, 10-50% ethyl acetate in heptanes) afforded the title compound (0.064 g, 87%).

Example 91F 5-chloro-3-{2-(2,4-difluorophenoxy)-5-[(methylsulfonyl)methyl]phenyl}-1-methyl-1,6-dihydro-7H-pyrrolo[2,3-c]pyridin-7-one The product from Example 91E (0.064 g, 0.119 mmol) and 4 M hydrogen chloride in dioxane (2 mL, 8.00 mmol) were combined and heated at 70° C. for 2 hours, cooled and concentrated. Purification by trituration (1:1 dichloromethane/heptane) afforded the title compound (0.042 g, 74%). $^1$H NMR (400 MHz, DMSO-d$_6$) δ ppm 11.91 (s, 1H) 7.60 (s, 1H) 7.57 (d, J=2.03 Hz, 1H) 7.43-7.52 (m, 1H) 7.19-7.30 (m, 2H) 7.05-7.15 (m, 1H) 6.82 (d, J=8.14 Hz, 1H) 6.68 (s, 1H) 4.53 (s, 2H) 4.07 (s, 3H) 2.94 (s, 3H). MS (ESI+) m/z 479 (M+H)$^+$.

Example 92

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one

Example 92A 3-(2-(2,4-difluorophenoxy)-5-(methylsulfonylmethyl)phenyl)-7-methoxy-1-methyl-5-vinyl-1H-pyrrolo[2,3-c]pyridine Tributyl(vinyl)tin (0.053 g, 0.167 mmol), the product from Example 91E (0.075 g, 0.140 mmol) and Pd(PPh$_3$)$_2$Cl$_2$ (9.80 mg, 0.014 mmol) were combined in dioxane (1.163 mL) and sparged with argon for 15 minutes. The mixture was stirred for 2 hours at 100° C., cooled and partitioned between ethyl acetate and water. The organic layer was washed with saturated aqueous sodium chloride, dried (anhydrous Na$_2$SO$_4$), treated with 3-mercaptopropyl functionalized silica gel, filtered, and concentrated. Purification by chromatography (silica gel, 0-40% ethyl acetate in heptanes) afforded the title compound (0.041 g, 61%).

Example 92B 3-(2-(2,4-difluorophenoxy)-5-(methylsulfonylmethyl)phenyl)-5-ethyl-7-methoxy-1-methyl-1H-pyrrolo[2,3-c]pyridine The product from Example 92A (0.04 g, 0.083 mmol) and 10% Pd/C (0.022 g, 0.021 mmol) were combined in ethyl acetate (3 mL)/ethanol (3 mL), degassed under vacuum, placed under a balloon of hydrogen and stirred for 2 hours. The mixture was filtered through Celite and the Celite pad was washed repeatedly with ethyl acetate. The filtrate was concentrated to afford the title compound (0.042 g, 105%).

Example 92C

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one The product from Example 92B (0.04 g, 0.082 mmol) and 4M hydrogen chloride in dioxane (5 mL, 20.00 mmol) were combined, heated at 70° C. for 3 hours, cooled and concentrated. Purification by chromatography (silica gel, 0-4% methanol in dichloromethane) afforded the title compound (0.035 g, 90%). $^1$H NMR (300 MHz, DMSO-d$_6$) δ ppm 10.87 (s, 1H) 7.58 (d, J=2.03 Hz, 1H) 7.49 (s, 1H) 7.41-7.52 (m, 1H) 7.17-7.28 (m, 2H) 7.05-7.14 (m, 1H) 6.82 (d, J=8.14 Hz, 1H) 6.38 (s, 1H) 4.51 (s, 2H) 4.07 (s, 3H) 2.94 (s, 3H) 2.43 (q, J=7.63 Hz, 2H) 1.14 (t, J=7.46 Hz, 3H). MS (ESI+) m/z 473 (M+H)$^+$.

Example 93

3,5-bis{2-(2,4-difluorophenoxy)-5-[(methylsulfonyl) methyl]phenyl}-1-methyl-1,6-dihydro-7H-pyrrolo[2,3-c]pyridin-7-one

Example 93A 3,5-bis(2-(2,4-difluorophenoxy)-5-(methylsulfonylmethyl)phenyl)-7-methoxy-1-methyl-1H-pyrrolo[2,3-c]pyridine The product from Example 91D (1.233 g, 2.180 mmol), the product from Example 91C (0.8 g, 2.180 mmol), tris(dibenzylideneacetone)dipalladium(0) (0.060 g, 0.065 mmol), 1,3,5,7-tetramethyl-6-phenyl-2,4,8-trioxa-6-phosphaadamante (0.064 g, 0.218 mmol) and potassium phosphate (1.388 g, 6.54 mmol) were combined and sparged with argon for 15 minutes. Meanwhile a solution of 4:1 dioxane/water (18 mL) was sparged with nitrogen for 15 minutes and transferred by syringe into the reaction vessel under argon. The mixture was stirred for 2 hours at ambient temperature, and partitioned between ethyl acetate and water. The organic layer was washed with saturated aqueous sodium chloride, dried (anhydrous $Na_2SO_4$), treated with 3-mercaptopropyl functionalized silica gel, filtered, and concentrated. Purification by chromatography (silica gel, 10-50% ethyl acetate in heptanes) afforded the title compound (0.104 g, 6%).

Example 93B 3,5-bis{2-(2,4-difluorophenoxy)-5-[(methylsulfonyl) methyl]phenyl}-1-methyl-1,6-dihydro-7H-pyrrolo[2,3-c]pyridin-7-one The product from Example 93A (0.1 g, 0.132 mmol) and 4 M hydrogen chloride in dioxane (5 mL, 20.00 mmol) were combined and heated at 70° C. for 4 hours, cooled and concentrated. The residue was partitioned between ethyl acetate and water adjusting the pH to 7. The organic layer was washed with saturated aqueous sodium chloride, dried (anhydrous $Na_2SO_4$), filtered, and concentrated. Purification by chromatography (0-4% methanol in dichloromethane) afforded the title compound (0.07 g, 71%). %). $^1$H NMR (300 MHz, DMSO-$d_6$) δ ppm 11.12 (s, 1H) 7.59 (s, 2H) 7.54 (d, J=2.37 Hz, 1H) 7.36-7.50 (m, 4H) 7.17-7.30 (m, 2H) 7.02-7.15 (m, 2H) 6.80 (dd, J=8.31, 1.53 Hz, 2H) 6.74 (s, 1H) 4.48 (s, 2H) 4.46 (s, 2H) 4.12 (s, 3H) 2.93 (s, 3H) 2.91 (s, 3H). MS (ESI+) m/z 741 (M+H)$^+$.

Example 94

3-{2-(2,4-difluorophenoxy)-5-[(methylsulfonyl)methyl]phenyl}-5-(3,5-dimethyl-1,2-oxazol-4-yl)-1-methyl-1,6-dihydro-7H-pyrrolo[2,3-c]pyridin-7-one

Example 94A 4-(3-(2-(2,4-difluorophenoxy)-5-(methylsulfonylmethyl)phenyl)-7-methoxy-1-methyl-1H-pyrrolo[2,3-c]pyridin-5-yl)-3,5-dimethylisoxazole 3,5-dimethylisoxazole-4-boronic acid (0.016 g, 0.112 mmol), the product from Example 91E (0.05 g, 0.093 mmol), tris(dibenzylideneacetone)dipalladium(0) (2.56 mg, 2.79 μmol), 1,3,5,7-tetramethyl-6-phenyl-2,4,8-trioxa-6-phosphaadamante (2.72 mg, 9.30 μmol) and potassium phosphate (0.059 g, 0.279 mmol) were combined and sparged with argon for 15 minutes. Meanwhile a solution of 4:1 dioxane/water (0.8 mL) was sparged with $N_2$ for 15 minutes and transferred by syringe into the reaction vessel under argon. The mixture was heated at 60° C. for 2 hours and partitioned between ethyl acetate and water. The organic layer was washed with saturated aqueous sodium chloride, dried (anhydrous $Na_2SO_4$), treated with 3-mercaptopropyl functionalized silica gel, filtered, and concentrated to afford the title compound (0.052 g, 100%).

Example 94B

3-{2-(2,4-difluorophenoxy)-5-[(methylsulfonyl)methyl]phenyl}-5-(3,5-dimethyl-1,2-oxazol-4-yl)-1-methyl-1,6-dihydro-7H-pyrrolo[2,3-c]pyridin-7-one The product from Example 94A (0.052 g, 0.094 mmol) and 4 M hydrogen chloride in dioxane (5 mL, 20.00 mmol) were combined and heated at 70° C. for 4 hours, cooled and concentrated. Purification by chromatography (silica gel, 0-4% methanol in dichloromethane) afforded the title compound (0.042 g, 83%). $^1$H NMR (300 MHz, DMSO-$d_6$) δ ppm 11.09 (s, 1H) 7.60-7.64 (m, 2H) 7.41-7.53 (m, 1H) 7.21-7.32 (m, 2H) 7.06-7.16 (m, 1H) 6.81 (d, J=8.48 Hz, 1H) 6.57 (s, 1H) 4.51 (s, 2H) 4.13 (s, 3H) 2.92 (s, 3H) 2.35 (s, 3H) 2.18 (s, 3H). MS (ESI+) m/z 540 (M+H)$^+$.

Example 95

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one

Example 95A 4-fluoro-3-(7-methoxy-1-methyl-1H-pyrrolo[2,3-c]pyridin-3-yl)benzaldehyde Example 2A (4.61 g, 16.0 mmol), 2-fluoro-5-formylphenylboronic acid (2.69 g, 16.0 mmol), potassium phosphate (10.19 g, 48.0 mmol), tris(dibenzylideneacetone)dipalladium (0.440 g, 0.480 mmol) and 1,3,5,7-tetramethyl-6-phenyl-2,4,8-trioxa-6-phosphaadamantane (0.421 g, 1.44 mmol) were combined and purged with nitrogen for 15 minutes. The mixture of dioxane (80 mL) and water (20 mL) was purged with nitrogen for 15 minutes and transferred to the reaction flask. The reaction mixture was heated at 60° C. for 4 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20 to 40% ethyl acetate in heptanes) to provide the title compound (3.27 g, 72%).

Example 95B 4-(2,4-difluorophenoxy)-3-(7-methoxy-1-methyl-1H-pyrrolo[2,3-c]pyridin-3-yl)benzaldehyde A mixture of Example 95A (3.26 g, 11.47 mmol), 2,4-difluorophenol (1.492 g, 11.47 mmol) and cesium carbonate (4.11 g, 12.61 mmol) in dimethyl sulfoxide (40 mL) was heated at 100° C. for 3 hours. The reaction mixture was partitioned with ethyl acetate and water. The organic layer was washed with saturated aqueous sodium chloride twice, dried with anhydrous sodium sulfate, filtered, and concentrated. The residue was purified by flash chromatography (silica gel, 20 to 40% ethyl acetate in heptanes) to provide the title compound (3.98 g, 88%).

Example 95C (4-(2,4-difluorophenoxy)-3-(7-methoxy-1-methyl-1H-pyrrolo[2,3-c]pyridin-3-yl)phenyl)methanol Example 95B (3.73 g, 9.46 mmol) in the mixture of ethanol (20 mL) and tetrahydrofuran (20 mL) was added sodium borohydride (0.107 g, 2.84 mmol). The reaction mixture was stirred at room temperature for 1 hour. The solvent was concentrated and the residue was partitioned with ethyl acetate and water. The organic layer was washed with saturated aqueous sodium chloride, dried with anhydrous sodium sulfate, filtered, and concentrated to provide the title compound (3.43 g, 91%).

Example 95D 3-(5-(bromomethyl)-2-(2,4-difluorophenoxy)phenyl)-7-methoxy-1-methyl-1H-pyrrolo[2,3-c]pyridine Example 95C (3.33 g, 8.40 mmol) in dichloromethane (40 mL) was added phosphorus tribromide (0.792 mL, 8.40 mmol) dropwise. The reaction mixture was stirred at room temperature for 3 hours and concentrated. The residue was added water and the pH was adjusted to basic with saturated aqueous sodium bicarbonate slowly, and extracted with ethyl acetate. The organic layer was washed with saturated aqueous sodium chloride, dried with anhydrous sodium sulfate, filtered, and concentrated to provide the title compound (3.83 g, 99%).

Example 95E

Sodium (4-(2,4-difluorophenoxy)-3-(7-methoxy-1-methyl-1H-pyrrolo[2,3-c]pyridin-3-yl)phenyl)methanesulfonate Example 95D (2.296 g, 5.00 mmol), sodium sulfite (0.693 g, 5.50 mmol) and tetrabutylammonium iodide (0.923 g, 2.50 mmol) were combined in the mixture of ethanol (125 mL) and water (125 mL). The reaction mixture was heated at 70° C. for 2 hours. The solvent was evaporated and the residue was partitioned with ethyl ether and water. The organic layer was washed with water. The aqueous layers were combined and concentrated. The residue was triturated with ethyl acetate and filtered. The filtrate was concentrated to provide the title compound (1.76 g, 73%).

Example 95F 4-(4-(2,4-difluorophenoxy)-3-(7-methoxy-1-methyl-1H-pyrrolo[2,3-c]pyridin-3-yl)benzylsulfonyl)morpholine Example 95E (96 mg, 0.20 mmol) in dichloromethane (2 mL) was added a drop of dimethylformamide and oxalyl chloride (0.021 mL, 0.24 mmol). The reaction mixture was stirred at room temperature for 30 minutes and concentrated. The residue was dissolved in dichloromethane (2 mL), added morpholine (0.087 mL, 1.0 mmol) and stirred at room temperature for 30 minutes. The solvent was evaporated and the residue was triturated with water to provide the title compound (92 mg, 87%).

Example 95G

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one Example 95F (90 mg, 0.17 mmol) in a solution of 4 M HCl in dioxane (5 mL, 20 mmol) was heated at 70° C. for 16 hours, cooled and concentrated. The residue was purified by flash chromatography (silica gel, 2 to 4% methanol in dichloromethane) to provide the title compound (81 mg, 92%). $^1$H NMR (300 MHz, DMSO-$d_6$) δ ppm 10.94 (d, J=5.09 Hz, 1H) 7.60 (d, J=2.37 Hz, 1H) 7.54 (s, 1H) 7.40-7.51 (m, 1H) 7.28 (dd, J=8.48, 2.37 Hz, 1H) 7.16-7.24 (m, 1H) 7.03-7.14 (m, 1H) 6.90 (dd, J=7.12, 5.76 Hz, 1H) 6.82 (d, J=8.14 Hz, 1H) 6.61 (dd, J=7.12, 1.02 Hz, 1H) 4.48 (s, 2H) 4.10 (s, 3H) 3.53-3.65 (m, 4H) 3.09-3.17 (m, 4H). MS (ESI+) m/z 516 (M+H)$^+$.

Example 96

1-[4-(2,4-difluorophenoxy)-3-(1-methyl-7-oxo-6,7-dihydro-1H-pyrrolo[2,3-c]pyridin-3-yl)phenyl]methanesulfonamide

Example 96A (4-(2,4-difluorophenoxy)-3-(7-methoxy-1-methyl-1H-pyrrolo[2,3-c]pyridin-3-yl)phenyl)methanesulfonamide Example 95E (96 mg, 0.20 mmol) in dichloromethane (2 mL) was added a drop of dimethylformamide and oxalyl chloride (0.021 mL, 0.24 mmol). The reaction mixture was stirred at ambient temperature for 30 minutes and concentrated. The residue was dissolved in dichloromethane (2 mL), added 0.5 M ammonia in dioxane (2.0 mL, 1.0 mmol) and stirred at ambient temperature for 30 minutes. The solvent was evaporated and the residue was triturated with water to provide the title compound (82 mg, 89%).

Example 96B

1-[4-(2,4-difluorophenoxy)-3-(1-methyl-7-oxo-6,7-dihydro-1H-pyrrolo[2,3-c]pyridin-3-yl)phenyl]methanesulfonamide Example 96A (80.0 mg, 0.174 mmol) in a solution of 4 M HCl in dioxane (5 mL, 20 mmol) was heated at 70° C. for 16 hours, cooled and concentrated. The residue was purified by flash chromatography (silica gel, 2 to 4% methanol in dichloromethane) to provide the title compound (61 mg, 79%). $^1$H NMR (300 MHz, DMSO-$d_6$) δ ppm 10.93 (d, J=5.09 Hz, 1H) 7.55 (d, J=2.03 Hz, 1H) 7.53 (s, 1H) 7.39-7.50 (m, 1H) 7.14-7.26 (m, 2H) 7.01-7.14 (m, 1H) 6.75-6.91 (m, 4H) 6.61 (d, J=6.78 Hz, 1H) 4.29 (s, 2H) 4.10 (s, 3H). MS (ESI+) m/z 446 (M+H)$^+$.

Example 97

3-[2-(cyclopropylmethoxy)-5-(2,3-dihydro-1H-indol-1-ylsulfonyl)phenyl]-1-methyl-1,6-dihydro-7H-pyrrolo[2,3-c]pyridin-7-one

Example 97A 1-(3-bromo-4-fluorophenylsulfonyl)indoline

A mixture of 3-bromo-4-fluorobenzene-1-sulfonyl chloride (2.53 g, 8.33 mmol), indoline (0.933 mL, 8.33 mmol), and N,N-diisopropylethyl-amine (1.60 mL, 9.16 mmol) in tetrahydrofuran (20 mL) was stirred at room temperature for 20 hours. The reaction mixture was partitioned between water and ether. The organic layer was washed with saturated aqueous sodium chloride, dried over anhydrous magnesium sulfate, filtered, and concentrated to a solid residue. Recrystallization from ether and heptane provided the title compound (1.99 g, 67%).

Example 97B 1-(3-bromo-4-(cyclopropylmethoxy)phenylsulfonyl)indoline

A solution of cyclopropylmethanol (118 mg, 1.63 mmol) in dioxane (10 mL) was treated with sodium hydride (60% oil dispersion, 87 mg, 2.2 mmol). The mixture was stirred at ambient temperature for 15 minutes and Example 97A (388 mg, 1.089 mmol) was added to the reaction mixture in one portion as a solid. The reaction mixture was heated at 65° C. for 18 hours. After cooling to ambient temperature, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The crude product was purified by flash chromatography (silica gel, 10% ethyl acetate in heptanes) to provide 0.40 g (90%) of the title compound.

Example 97C 3-(2-(cyclopropylmethoxy)-5-(indolin-1-ylsulfonyl)phenyl)-7-methoxy-1-methyl-1H-pyrrolo[2,3-c]pyridine Example 97C was prepared according to the procedure used for the preparation of Example 11E, substituting Example 97B for Example 11C.

Example 97D

3-[2-(cyclopropylmethoxy)-5-(2,3-dihydro-1H-indol-1-ylsulfonyl)phenyl]-1-methyl-1,6-dihydro-7H-pyrrolo[2,3-c]pyridin-7-one Example 97D was prepared according to the procedure used for the preparation of Example 11F, substituting Example 97C for Example 11E. $^1$H NMR (300 MHz, DMSO-$d_6$) δ ppm 10.97 (d, J=5.5 Hz, 1H), 7.70 (dd, J=8.7, 2.4 Hz, 1H), 7.65 (d, J=2.4 Hz, 1H), 7.47-7.56 (m, 2H), 7.23-7.31 (m, 1H), 7.14-7.22 (m, 2H), 7.03 (td, J=7.4, 0.9 Hz, 1H), 6.84 (dd, J=7.0, 5.8 Hz, 1H), 6.04 (dd, J=7.0, 1.0 Hz, 1H), 4.10 (s, 3H), 3.95 (d, J=7.0 Hz, 2H), 3.89 (t, J=8.4 Hz, 2H), 2.90 (t, J=8.4 Hz, 2H), 1.13-1.30 (m, 1H), 0.56-0.60 (m, 2H), 0.26-0.36 (m, 2H). MS (ESI+) m/z 476.2 (M+H)$^+$.

Example 98

3-[6-(cyclopropylmethoxy)-1H-indol-7-yl]-1-methyl-1,6-dihydro-7H-pyrrolo[2,3-c]pyridin-7-one

Example 98A 2-bromo-1-(cyclopropylmethoxy)-3-nitrobenzene

Example 98A was prepared according to the procedure used for the preparation of Example 14A, substituting 2-bromo-3-nitrophenol for 2-bromo-3-methyl-4-nitrophenol. Example 98B 7-bromo-6-(cyclopropylmethoxy)-1H-indole A 250 mL roundbottom flask with stirbar was charged with a solution of Example 98A (6.18 g, 22.7 mmol) in tetrahydrofuran (80 mL) and cooled to −45° C. under nitrogen. A solution of 0.7 M vinylmagnesium bromide in tetrahydrofuran (100 mL, 70.0 mmol) was added over 20 minutes and the mixture stirred at −45° C. for 30 minutes. The mixture was then poured into aqueous ammonium chloride and extracted with 3×150 mL of ether. The combined organics were dried over anhydrous magnesium sulfate. After filtration and solvent removal the residues were adsorbed on silica gel and chromatographed on a 150 g silica cartridge eluting with 0-10-100% ethyl acetate/heptane to provide 3.087 g, (51%) of the title compound.

Example 98C 3-(6-(cyclopropylmethoxy)-1H-indol-7-yl)-7-methoxy-1-methyl-1H-pyrrolo[2,3-c]pyridine A mixture of Example 59A (0.087 g, 0.3 mmol), Example 98B (0.088 g, 0.33 mmol), tris(dibenzylideneacetone)dipalladium(0) (0.0083 g, 0.009 mmol), 1,3,5,7-tetramethyl-6-phenyl-2,4,8-trioxa-6-phosphaadamantane (0.0088 g, 0.03 mmol), and sodium carbonate (0.137 g, 1.3 mmol) was sparged with nitrogen for 30 minutes. To this was added a nitrogen-sparged solution of dioxane/H$_2$O (4:1, 1.875 mL). The reaction mixture was heated at 60° C. for 5 hours. The reaction mixture was partitioned between ethyl acetate and water. The organic layer was washed with saturated aqueous sodium chloride, dried over anhydrous magnesium sulfate, treated with mercapto-functionalized silica gel, filtered, and concentrated. The residue was purified by flash chromatography (silica gel, 0 to 40% ethyl acetate in heptanes) to give the title compound (0.09 g, 86%).

Example 98D

3-[6-(cyclopropylmethoxy)-1H-indol-7-yl]-1-methyl-1,6-dihydro-7H-pyrrolo[2,3-c]pyridin-7-one A mixture of Example 98C (0.09 g, 0.26 mmol) in dioxane (5.2 mL) was treated with hydrogen chloride (4M in dioxane) (6.5 mL, 26 mmol) and heated at 75° C. for 30 minutes. The reaction mixture was neutralized with saturated sodium bicarbonate solution. The resulting mixture was partitioned between ethyl acetate and water. The organic layer was washed with saturated aqueous sodium chloride, dried over anhydrous magnesium sulfate, filtered, and concentrated. The residue was purified by flash chromatography (silica gel, 0 to 20% methanol in dichloromethane). The material was further purified by reverse phase HPLC (C18, CH$_3$CN/water (0.1% TFA), 10-80%) to provide the title compound (0.0066 g, 7.6%). $^1$H NMR (400 MHz, DMSO-$d_6$) δ ppm 10.81 (d, J=4.88 Hz, 1H), 10.38 (s, 1H), 7.41 (m, 2H), 7.12 (t, J=2.75

Hz, 1H), 6.86 (d, J=8.54 Hz, 1H), 6.80 (dd, J=6.71, 5.80 Hz, 1H), 6.37 (dd, J=3.05, 1.83 Hz, 1H), 6.14 (m, 1H), 4.15 (s, 3H), 3.74 (d, J=6.71 Hz, 2H), 1.03 (m, 1H), 0.40 (ddd, J=8.09, 5.95, 4.27 Hz, 2H), 0.15 (ddd, J=5.95, 4.58, 4.43 Hz, 2H). MS (ESI+) m/z 334.1 (M+H)$^+$.

Example 99 ethyl 5-(cyclopropylmethoxy)-4-(1-methyl-7-oxo-6, 7-dihydro-1H-pyrrolo[2,3-c]pyridin-3-yl)-1H-indole-2-carboxylate Example 99A 2-bromo-1-(cyclopropylmethoxy)-3-nitrobenzene Example 98A was prepared according to the procedure used for the preparation of Example 14A, substituting 2-bromo-3-hydroxybenzaldehyde for 2-bromo-3-methyl-4-nitrophenol.

Example 99B (Z)-ethyl 2-azido-3-(2-bromo-3-(cyclopropyl-methoxy)phenyl)acrylate

A 50 mL roundbottom flask with stirbar was charged with sodium ethanolate, 21 wt % in ethanol (14 mL, 37.6 mmol), sealed and cooled to −20° C. under nitrogen. A mixture of Example 99A (6.38 g, 25.01 mmol) and ethyl 2-azidoacetate (10 g, 77 mmol) were added dropwise over 15 minutes. The solution was stirred for 3.5 hours, then poured into a separatory funnel and extracted from 100 mL water with 3×100 mL ether. The combined organics were washed with saturated aqueous sodium chloride, dried over magnesium sulfate. After filtration and solvent removal the residues were chromatographed on a 60 g silica cartridge eluting with 0-10-100% ethyl acetate/heptane to provide 2.56 g (28%) of the title compound.

Example 99C ethyl 4-bromo-5-(cyclopropylmethoxy)-1H-indole-2-carboxylate

A 50 mL recovery flask with stirbar was charged with Example 99B (2.586 g, 7.06 mmol) and rhodium(II) heptafluorobutyrate dimer (0.215 g, 0.203 mmol) in toluene (7 mL). The mixture was heated at 60° C. for 46 hours, adsorbed on silica gel and chromatographed on a 150 g silica gel cartridge eluting with 0-10-100% ethyl acetate/heptane to provide 0.88 g (37%) of the title compound.

Example 99D ethyl 5-(cyclopropylmethoxy)-4-(7-methoxy-1-methyl-1H-pyrrolo[2,3-c]pyridin-3-yl)-1H-indole-2-carboxylate Example 99D (0.0345 g, 27%) was prepared according to the procedure used for the preparation of Example 98C, substituting Example 99C for Example 98B.

Example 99E ethyl 5-(cyclopropylmethoxy)-4-(1-methyl-7-oxo-6, 7-dihydro-1H-pyrrolo[2,3-c]pyridin-3-yl)-1H-indole-2-carboxylate Example 99E (0.023 g, 79%) was prepared according to the procedure used for the preparation of Example 1C, substituting Example 99D for Example 1B. $^1$H NMR (400 MHz, DMSO-d$_6$) δ ppm 11.77 (d, J=1.53 Hz, 1H), 10.84 (d, J=5.19 Hz, 1H), 7.47 (s, 1H), 7.35 (d, J=8.85 Hz, 1H), 7.17 (d, J=8.85 Hz, 1H), 6.87 (d, J=1.53 Hz, 1H), 6.81 (m, 1H), 6.18 (d, J=7.02 Hz, 1H), 4.30 (q, J=7.02 Hz, 2H), 4.17 (s, 3H), 3.71 (d, J=6.71 Hz, 2H), 1.30 (t, J=7.02 Hz, 3H), 1.03 (m, 1H), 0.41 (m, 2H), 0.14 (m, 2H). MS (ESI+) m/z 406.2 (M+H)$^+$.

Example 100

1-[4-(2,4-difluorophenoxy)-3-(1-methyl-7-oxo-6,7-dihydro-1H-pyrrolo[2,3-c]pyridin-3-yl)phenyl]-N-methylmethanesulfonamide Example 100A 1-(4-(2,4-difluorophenoxy)-3-(7-methoxy-1-methyl-1H-pyrrolo[2,3-c]pyridin-3-yl)phenyl)-N-methylmethanesulfonamide Example 95E (96 mg, 0.20 mmol) in dichloromethane (2 mL) was added a drop of dimethylformamide and oxalyl chloride (0.021 mL, 0.24 mmol). The reaction mixture was stirred at ambient temperature for 30 minutes and concentrated. The residue was dissolved in dichloromethane (2 mL), treated with 2M methanamine in tetrahydrofuran (0.50 mL, 1.0 mmol) and stirred at ambient temperature for 30 minutes. The solvent was evaporated and the residue was triturated with water to provide the title compound (86 mg, 91%).

Example 100B

1-[4-(2,4-difluorophenoxy)-3-(1-methyl-7-oxo-6,7-dihydro-1H-pyrrolo[2,3-c]pyridin-3-yl)phenyl]-N-methylmethanesulfonamide Example 100A (84.0 mg, 0.177 mmol) in a solution of 4 M HCl in dioxane (5 mL, 20 mmol) was heated at 70° C. for 16 hours, cooled and concentrated. The residue was purified by flash chromatography (silica gel, 2 to 4% methanol in dichloromethane) to provide the title compound (61 mg, 75%). $^1$H NMR (300 MHz, DMSO-d$_6$) δ ppm 10.93 (d, J=5.09 Hz, 1H) 7.55 (d, J=2.37 Hz, 1H) 7.53 (s, 1H) 7.39-7.51 (m, 1H) 7.14-7.26 (m, 2H) 7.04-7.13 (m, 1H) 6.85-6.97 (m, 2H) 6.80 (d, J=8.48 Hz, 1H) 6.61 (d, J=7.12 Hz, 1H) 4.36 (s, 2H) 4.10 (s, 3H) 2.59 (s, 3H). MS (ESI+) m/z 460 (M+H)$^+$.

Example 101

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide Example 101A 1-(4-(2,4-difluorophenoxy)-3-(7-methoxy-1-methyl-1H-pyrrolo[2,3-c]pyridin-3-yl)phenyl)-N,N-dimethylmethanesulfonamide Example 101A (88 mg, 90%) was prepared according to the procedure used for the preparation of Example 95F, substituting dimethylamine for morpholine.

Example 101B

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide Example 101B was prepared according to the procedure used for the preparation of Example 95G, substituting Example 101A for Example 95F (64 mg, 77%). $^1$H NMR (300 MHz, DMSO-$d_6$) δ ppm 10.94 (d, J=5.43 Hz, 1H) 7.59 (d, J=2.37 Hz, 1H) 7.54 (s, 1H) 7.38-7.50 (m, 1H) 7.27 (dd, J=8.48, 2.37 Hz, 1H) 7.15-7.24 (m, 1H) 7.04-7.14 (m, 1H) 6.90 (dd, J=7.12, 5.76 Hz, 1H) 6.81 (d, J=7.80 Hz, 1H) 6.59 (d, J=6.10 Hz, 1H) 4.44 (s, 2H) 4.10 (s, 3H) 2.75 (s, 6H). MS (ESI+) m/z 474 (M+H)$^+$.

Example 102

N-cyclohexyl-1-[4-(2,4-difluorophenoxy)-3-(1-methyl-7-oxo-6,7-dihydro-1H-pyrrolo[2,3-c]pyridin-3-yl)phenyl]methanesulfonamide

Example 102A

N-cyclohexyl-1-(4-(2,4-difluorophenoxy)-3-(7-methoxy-1-methyl-1H-pyrrolo[2,3-c]pyridin-3-yl)phenyl)methanesulfonamide Example 102A (72 mg, 89%) was prepared according to the procedure used for the preparation of Example 95F, substituting cyclohexanamine for morpholine.

Example 102B

N-cyclohexyl-1-[4-(2,4-difluorophenoxy)-3-(1-methyl-7-oxo-6,7-dihydro-1H-pyrrolo[2,3-c]pyridin-3-yl)phenyl]methanesulfonamide Example 102B (50 mg, 73%) was prepared according to the procedure used for the preparation of Example 95G, substituting Example 102A for Example 95F. $^1$H NMR (300 MHz, DMSO-$d_6$) δ ppm 10.93 (d, J=5.43 Hz, 1H) 7.56 (d, J=2.37 Hz, 1H) 7.52 (s, 1H) 7.39-7.50 (m, 1H) 7.01-7.27 (m, 4H) 6.81-6.93 (m, 1H) 6.79 (d, J=8.48 Hz, 1H) 6.62 (d, J=6.44 Hz, 1H) 4.32 (s, 2H) 4.10 (s, 3H) 2.95-3.08 (m, 1H) 1.72-1.87 (m, 2H) 1.57-1.69 (m, 2H) 1.41-1.55 (m, 1H) 0.97-1.27 (m, 5H). MS (ESI+) m/z 528 (M+H)$^+$.

Example 103

3-{2-(2,4-difluorophenoxy)-5-[(piperidin-1-ylsulfonyl)methyl]phenyl}-1-methyl-1,6-dihydro-7H-pyrrolo[2,3-c]pyridin-7-one

Example 103A 3-(2-(2,4-difluorophenoxy)-5-((piperidin-1-ylsulfonyl)methyl)phenyl)-7-methoxy-1-methyl-1H-pyrrolo[2,3-c]pyridine Example 103A (71 mg, 90%) was prepared according to the procedure used for the preparation of Example 95F, substituting piperidine for morpholine.

Example 103B

3-{2-(2,4-difluorophenoxy)-5-[(piperidin-1-ylsulfonyl)methyl]phenyl}-1-methyl-1,6-dihydro-7H-pyrrolo[2,3-c]pyridin-7-one Example 103B (45 mg, 67%) was prepared according to the procedure used for the preparation of Example 95G, substituting Example 103A for Example 95F. $^1$H NMR (300 MHz, DMSO-$d_6$) δ ppm 10.94 (d, J=5.43 Hz, 1H) 7.58 (d, J=2.03 Hz, 1H) 7.53 (s, 1H) 7.37-7.50 (m, 1H) 7.26 (dd, J=8.48, 2.37 Hz, 1H) 7.14-7.23 (m, 1H) 7.04-7.14 (m, 1H) 6.86-6.94 (m, 1H) 6.80 (d, J=8.48 Hz, 1H) 6.60 (d, J=6.78 Hz, 1H) 4.39 (s, 2H) 4.10 (s, 3H) 3.08-3.15 (m, 4H) 1.41-1.57 (m, 6H).). MS (ESI+) m/z 514 (M+H)$^+$.

Example 104

1-[4-(2,4-difluorophenoxy)-3-(1-methyl-7-oxo-6,7-dihydro-1H-pyrrolo[2,3-c]pyridin-3-yl)phenyl]-N-(1,3-thiazol-2-yl)methanesulfonamide

Example 104A 1-(4-(2,4-difluorophenoxy)-3-(7-methoxy-1-methyl-1H-pyrrolo[2,3-c]pyridin-3-yl)phenyl)-N-(thiazol-2-yl)methanesulfonamide Example 104A was prepared according to the procedure used for the preparation of Example 95F, substituting thiazol-2-amine for morpholine. Purification by flash chromatography (silica gel, 2 to 4% methanol in dichloromethane) afforded the title compound (8 mg, 10%).

Example 104B

1-[4-(2,4-difluorophenoxy)-3-(1-methyl-7-oxo-6,7-dihydro-1H-pyrrolo[2,3-c]pyridin-3-yl)phenyl]-N-(1,3-thiazol-2-yl)methanesulfonamide Example 104B (4 mg, 51%) was prepared according to the procedure used for the preparation of Example 95G, substituting Example 104A for Example 95F. $^1$H NMR (300 MHz, DMSO-$d_6$) δ ppm 12.54 (s, 1H), 10.92 (d, J=5.7 Hz, 1H), 7.51 (d, J=2.2 Hz, 1H), 7.33-7.49 (m, 2H), 7.20 (dd, J=8.4, 2.1 Hz, 1H), 7.15 (d, J=4.6 Hz, 1H), 6.93-7.12 (m, 2H), 6.88 (dd, J=7.0, 5.8 Hz, 1H), 6.76 (d, J=8.3 Hz, 1H), 6.72 (d, J=4.6 Hz, 1H), 6.55 (dd, J=7.0, 0.9 Hz, 1H), 4.32 (s, 2H), 4.08 (s, 3H). MS (ESI+) m/z 529 (M+H)$^+$.

Example 105

3-[2-(2,4-difluorophenoxy)-5-(piperazin-1-ylmethyl)phenyl]-1-methyl-1,6-dihydro-7H-pyrrolo[2,3-c]pyridin-7-one

Example 105A 3-bromo-4-(2,4-difluorophenoxy)benzaldehyde

A suspension of 3-bromo-4-fluorobenzaldehyde (500 mg, 2.46 mmol), 2,4-difluorophenol (0.353 mL, 3.69 mmol) and cesium carbonate (1204 mg, 3.69 mmol) in dimethylsulfoxide (24 mL) was heated at 105° C. overnight. The reaction mixture was partitioned between ethyl acetate (200 mL) and 50% saturated aqueous sodium chloride (200 mL). The layers were separated and the aqueous layer was extracted with ethyl acetate (2×75 mL). The combined organics were dried over anhydrous sodium sulfate, filtered, and concentrated. The residue was purified by flash column chromatography (silica gel, 2.5-100% ethyl acetate in heptanes) to afford the title compound (524 mg, 68% yield).

Example 105B 4-(2,4-difluorophenoxy)-3-(7-methoxy-1-methyl-1H-pyrrolo[2,3-c]pyridin-3-yl)benzaldehyde Example 105B was prepared according to the procedure used for the preparation of Example 11E, substituting Example 105A for Example 11C and potassium phosphate for sodium carbonate. The crude product was purified by flash column chromatography (silica gel, 0-30% ethyl acetate in heptane) to provide the title compound.

Example 105C tert-butyl 4-(4-(2,4-difluorophenoxy)-3-(7-methoxy-1-methyl-1H-pyrrolo[2,3-c]pyridin-3-yl)benzyl)piperazine-1-carboxylate A suspension of Example 105B (100 mg, 0.254 mmol), sodium cyanoborohydride (47.8 mg, 0.761 mmol) and tert-butyl piperazine-1-carboxylate (94 mg, 0.51 mmol) in a mixture of methanol (3 mL), acetic acid (0.073 mL, 1.3 mmol), and dichloromethane (1 mL) was heated at 75° C. 2 hours. Upon cooling, the reaction mixture was partitioned between 50% saturated sodium bicarbonate solution (50 mL) and ethyl acetate (50 mL). The organic layer was dried over anhydrous sodium sulfate, filtered, and concentrated. The residue was purified by flash column chromatography (silica gel, 0-3% methanol in dichloromethane) to provide the title compound (66.7 mg, 47% yield).

Example 105D

3-[2-(2,4-difluorophenoxy)-5-(piperazin-1-ylmethyl)phenyl]-1-methyl-1,6-dihydro-7H-pyrrolo[2,3-c]pyridin-7-one The TFA salt of Example 105D was prepared according to the procedure used for the preparation of Example 1C, substituting Example 105C for Example 1B, and with the exception that the reaction mixture was heated at 70° C. $^1$H NMR (400 MHz, DMSO-$d_6$) δ ppm 10.98 (d, J=5.49 Hz, 1H), 8.89 (s, 1H), 7.59 (s, 1H), 7.55 (s, 1H), 7.44-7.52 (m, 1H), 7.30 (dd, J=8.39, 1.68 Hz, 1H), 7.18-7.26 (m, 1H), 7.08-7.15 (m, 1H), 6.86-6.93 (m, 1H), 6.83 (d, J=8.24 Hz, 1H), 6.55 (d, J=6.41 Hz, 1H), 4.11 (s, 3H), 4.06 (s, 2H), 3.26 (s, 4H), 3.03 (s, 4H). MS (ESI+) m/z 451.0 (M+H)$^+$.

Example 106

N-[4-(2,4-difluorophenoxy)-3-(1-methyl-7-oxo-6,7-dihydro-1H-pyrrolo[2,3-c]pyridin-3-yl)benzyl]ethanesulfonamide Example 106A N-benzyl-1-(4-(2,4-difluorophenoxy)-3-(7-methoxy-1-methyl-1H-pyrrolo[2,3-c]pyridin-3-yl)phenyl)methanamine Example 106A was prepared according to the procedure used for the preparation of Example 105C, substituting benzyl amine for tert-butyl piperazine-1-carboxylate.

Example 106B (4-(2,4-difluorophenoxy)-3-(7-methoxy-1-methyl-1H-pyrrolo[2,3-c]pyridin-3-yl)phenyl)methanamine A solution of Example 106A (78 mg, 0.161 mmol) in tetrahydrofuran (10 mL) was added to 20% palladium hydroxide on carbon (16 mg, 0.012 mmol) in a 50 mL pressure bottle and the mixture was stirred for 16 hours under a hydrogen atmosphere (30 psi). The mixture was filtered through a nylon membrane and concentrated. The residue was purified by flash column chromatography (silica gel, 0-5% 7N methanolic ammonia in dichloromethane) to afford the title compound (57 mg, 90% yield).

Example 106C

N-(4-(2,4-difluorophenoxy)-3-(7-methoxy-1-methyl-1H-pyrrolo[2,3-c]pyridin-3-yl)benzyl)ethanesulfonamide Example 106C was prepared according to the procedure used for the preparation of Example 5C, substituting Example 106B for Example 5B.

Example 106D

N-[4-(2,4-difluorophenoxy)-3-(1-methyl-7-oxo-6,7-dihydro-1H-pyrrolo[2,3-c]pyridin-3-yl)benzyl]ethanesulfonamide Example 106D was prepared according to the procedure used for the preparation of Example 1C, substituting Example 106C for Example 1B, with the exception that the reaction mixture was heated at 70° C. The material was purified by flash chromatography (silica gel, 0-5% methanol in dichloromethane) to provide the title compound. $^1$H NMR (500 MHz, DMSO-$d_6$) δ ppm 10.94 (d, J=4.58 Hz, 1H), 7.61 (s, 1H), 7.49-7.53 (m, 2H), 7.40-7.46 (m, 1H), 7.22 (dd, J=8.39, 1.98 Hz, 1H), 7.10-7.16 (m, 1H), 7.03-7.09 (m, 1H), 6.87-6.92 (m, 1H), 6.81 (d, J=8.24 Hz, 1H), 6.58 (d, J=7.02 Hz, 1H), 4.16 (s, 2H), 4.09 (s, 3H), 2.97 (q, J=7.32 Hz, 2H), 1.17 (t, J=7.32 Hz, 3H). MS (ESI+) m/z 474.2 (M+H)$^+$.

Example 107

5-(cyclopropylmethoxy)-N-methyl-4-(1-methyl-7-oxo-6,7-dihydro-1H-pyrrolo[2,3-c]pyridin-3-yl)-1H-indole-2-carboxamide Example 107A 5-(cyclopropylmethoxy)-4-(1-methyl-7-oxo-6,7-dihydro-1H-pyrrolo[2,3-c]pyridin-3-yl)-1H-indole-2-carboxylic acid A 2 mL reaction vessel equipped with stirbar was charged with Example 99E (17.9 mg, 0.044 mmol) and a solution of lithium hydroxide monohydrate (42.0 mg, 1 mmol) in tetrahydrofuran (1 mL)/water (0.5 mL), then sealed. The mixture was heated at 100° C. for 22 hours, cooled, then partitioned between saturated aqueous sodium chloride acidified with 1 M HCl (25 mL) and dichloromethane (3×25 mL). The combined organics were dried over sodium sulfate. Filtration and solvent removal provided the title compound (12 mg, 72%).

Example 107B 5-(cyclopropylmethoxy)-N-methyl-4-(1-methyl-7-oxo-6,7-dihydro-1H-pyrrolo[2,3-c]pyridin-3-yl)-1H-indole-2-carboxamide A 25 mL roundbottom flask with stirbar was charged with Example 107A (11 mg, 0.029 mmol), EDC (10.4 mg, 0.054 mmol) and HOBT (7.7 mg, 0.050 mmol) in dichloromethane (1 mL). N-methylmorpholine (10 µL, 0.091 mmol) was added, and the mixture was stirred at ambient temperature. After 2 minutes, the solution was treated with 2.0 M methylamine in tetrahydrofuran (125 µL, 0.250 mmol), then stirred an additional 18 hours at ambient temperature. The mixture was concentrated and the residue was purified by reverse phase HPLC (C18, CH$_3$CN/water (0.1% TFA), 10-100%) to afford the title compound (0.0035 g, 31%). $^1$H NMR (300 MHz, DMSO-d$_6$) δ ppm 11.41 (bds, 1H), 10.82 (d, J=5.4 Hz, 1H), 8.28 (bds, 1H), 7.42 (s, 1H), 7.32 (d, J=8.8 Hz, 1H), 7.05 (d, J=8.8 Hz, 1H), 6.88 (m, 1H), 6.81 (m, 1H), 6.18 (d, J=6.1 Hz, 1H), 4.17 (s, 3H), 3.68 (m, 2H), 2.74 (s, 3H) 1.02 (m, 1H), 0.40 (m, 2H), 0.15 (m, 2H). MS (ESI+) m/z 391.2.

Example 108

4-chloro-3-[2-(2,4-difluorophenoxy)-5-(methylsulfonyl)phenyl]-1-methyl-1,6-dihydro-7H-pyrrolo[2,3-c]pyridin-7-one

Example 108A 5-chloro-4-methyl-3-nitropyridin-2-amine 5-chloro-4-methylpyridin-2-amine (30 g, 210 mmol) was dissolved in concentrated sulfuric acid (150 mL), and the solution was cooled to −10° C. Nitric acid (36 mL, 806 mmol) was added dropwise. The reaction mixture was stirred at 55° C. for 3 hours. The reaction mixture was poured into an ice/water mixture, and the pH was adjusted to 8 by addition of concentrated aqueous ammonium hydroxide (22%). The resulting suspension was filtered, and the solids were washed with water and dried under vacuum to provide the title compound (23 g, 123 mmol, 58.3% yield).

Example 108B 5-chloro-2-methoxy-4-methyl-3-nitropyridine

To a solution of methanol (600 mL) and acetyl chloride (7.61 mL, 107 mmol) was added Example 108A (67 g, 357 mmol), then tert-butyl nitrite (225 mL, 1893 mmol) was added at a rate such that the temperature did not exceed 5° C. After complete addition, cooling bath was removed and the reaction mixture was allowed to warm to room temperature and stirred for 5 hours. The reaction mixture was concentrated in vacuo to about half volume. Then saturated aqueous sodium bicarbonate solution was added and the precipitates were collected by filtration. The solid was dried under vacuum to provide the title compound (62 g, 282 mmol, 79% yield)

Example 108C 2-(5-chloro-2-methoxy-3-nitropyridin-4-yl)-N,N-dimethylethenamine Example 108B (20 g, 99 mmol) was dissolved in dimethylformamide (160 mL), and lithium methoxide (9.87 mL, 9.87 mmol, 1 M in MeOH) was added. The reaction mixture was heated to 80° C. To this mixture was added dimethylformamide dimethyl acetal (106 mL, 790 mmol) over 10 minutes. The reaction mixture was stirred at 95° C. for 12 hours. The reaction mixture was cooled to room temperature and water was added carefully. The resulting precipitate was collected by vacuum filtration, washed with water, and dried to provide the title compound (21 g, 81 mmol, 83% yield).

Example 108D 4-chloro-7-methoxy-1H-pyrrolo[2,3-c]pyridine

To a solution of Example 108C (12 g, 46.6 mmol) in ethyl acetate (150 mL) was added Raney-Ni (20.0 g, 4.66 mmol), and the reaction mixture was stirred for 20 hours at room temperature under 30 atm. hydrogen. The reaction mixture was filtered and rinsed with ethyl acetate. The filtrate was concentrated to a small volume, and the precipitates were collected by filtration and dried to provide the title compound (10 g, 93% yield).

Example 108E

To a solution of Example 108D (19 g, 104 mmol) in acetonitrile (100 mL) was added N-iodosuccinimide (28.1 g, 125 mmol). The mixture was stirred at 20° C. for 12 hours, and then partitioned between ethyl acetate and water. The organic layer was extracted twice with additional ethyl acetate. The combined organic layers were washed with saturated aqueous sodium chloride, dried over anhydrous magnesium sulfate, filtered, and concentrated to provide the title compound (25 g, 78% yield)

Example 108F 4-chloro-3-iodo-7-methoxy-1-methyl-1H-pyrrolo[2,3-c]pyridine

Example 108E (5 g, 16.21 mmol) in dimethylformamide (60 mL) was treated with sodium hydride (0.778 g, 32.4 mmol) at room temperature for 20 minutes. To this solution was added iodomethane (1.317 mL, 21.07 mmol). The reaction mixture was stirred at 20° C. for 3 hours. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel 10% ethyl acetate in hexanes) to provide the title compound (3 g, 57.4% yield).

Example 108G 4-chloro-3-(2-fluoro-5-(methylsulfonyl)phenyl)-7-methoxy-1-methyl-1H-pyrrolo[2,3-c]pyridine Example 108G was prepared according to the procedure used for the preparation of Example 11E, substituting Example 17B for Example 59A, and substituting Example 108F for Example 11C.

Example 108H 4-chloro-3-(2-(2,4-difluorophenoxy)-5-(methylsulfonyl)phenyl)-7-methoxy-1-methyl-1H-pyrrolo[2,3-c]pyridine Example 108H was prepared according to the procedure used for the preparation of Example 2C, substituting Example 108G for Example 2B, and heating for 12 hours instead of heating for 1 hour.

Example 108I 4-chloro-3-(2-(2,4-difluorophenoxy)-5-(methylsulfonyl)phenyl)-1-methyl-1H-pyrrolo[2,3-c]pyridin-7(6H)-one Example 108I was prepared according to the procedure used for the preparation of Example 1C, substituting Example 108H for Example 1B. $^1$H NMR (400 MHz, DMSO-$d_6$) δ ppm 11.25 (m, 1H), 7.79-7.91 (m, 2H), 7.54 (s, 1H), 7.48 (ddd, J=11.1, 8.6, 2.7 Hz, 1H), 7.32 (td, J=9.1, 5.5 Hz, 1H), 7.10-7.22 (m, 1H), 6.99-7.04 (m, 1H), 6.91 (d, J=8.5 Hz, 1H), 4.10 (s, 3H), 3.21 (s, 3H). MS (ESI+) m/z 464.8 (M+H)$^+$.

Example 109

4-chloro-3-[2-(2-cyclopropylethoxy)-5-(methylsulfonyl)phenyl]-1-methyl-1,6-dihydro-7H-pyrrolo[2,3-c]pyridin-7-one

Example 109A 4-chloro-3-(2-(2-cyclopropylethoxy)-5-(methylsulfonyl)phenyl)-7-methoxy-1-methyl-1H-pyrrolo[2,3-c]pyridine Example 109A was prepared according to the procedure used for the preparation of Example 2C, substituting Example 108G for Example 2B, substituting 2-cyclopropylethanol for 2,4-difluorophenol, and heating for 12 hours instead of heating for 1 hour.

Example 109B 4-chloro-3-(2-(2-cyclopropylethoxy)-5-(methylsulfonyl)phenyl)-1-methyl-1H-pyrrolo[2,3-c]pyridin-7(6H)-one Example 109B was prepared according to the procedure used for the preparation of Example 1C, substituting Example 109A for Example 1B. $^1$H NMR (400 MHz, DMSO-$d_6$) δ ppm 11.18 (bs, 1H), 7.84 (dd, J=8.6, 2.5 Hz, 1H), 7.70 (d, J=2.4 Hz, 1H), 7.41 (s, 1H), 7.23 (d, J=8.7 Hz, 1H), 6.95 (s, 1H), 3.97-4.14 (m, 5H), 3.17 (s, 3H), 1.48 (q, J=6.5 Hz, 2H), 0.54-0.68 (m, 1H), 0.21-0.38 (m, 2H), −0.02−−0.10 (m, 2H). MS (ESI+) m/z 421.0 (M+H)$^+$.

Example 110

3-{2-[(cyclopropylmethyl)amino]-5-[(methylsulfonyl)methyl]phenyl}-1-methyl-1,6-dihydro-7H-pyrrolo[2,3-c]pyridin-7-one

Example 110A 1-(methylsulfonylmethyl)-4-nitrobenzene

To a solution of 4-nitrobenzyl bromide (10.02 g, 46.4 mmol) in dimethylformamide (25 mL) was added sodium methanesulfinate (7.10 g, 69.6 mmol). The reaction mixture was stirred at 65° C. for 1 hour. The reaction mixture was cooled to room temperature, diluted with water, stirred for 10 minutes and filtered to give the title compound (9.27 g, 93%).

Example 110B 4-((methylsulfonyl)methyl)aniline

Example 110A (8.2 g, 38.1 mmol) and tetrahydrofuran (200 mL) were added to wet 5% Pd/C (1.6 g, 0.376 mmol) in a pressure bottle. The reaction mixture was stirred at 50° C. for 2 hours under 30 psi hydrogen. The reaction mixture was filtered through a nylon membrane, washed with the mixture of tetrahydrofuran and methanol, and concentrated to give the title compound (6.21 g, 88%).

Example 110C 2-iodo-4-((methylsulfonyl)methyl)aniline

To a solution of Example 110B (1.117 g, 6.03 mmol) in dimethylformamide (60.3 mL) was added N-iodosuccinimide (1.492 g, 6.63 mmol). The reaction mixture was stirred at room temperature for 90 minutes. The reaction mixture was quenched with 10% sodium thiosulfate and saturated aqueous sodium bicarbonate and extracted with ethyl acetate three times. The combined organic layers were washed with saturated aqueous sodium chloride, dried with anhydrous magnesium sulfate, filtered, and concentrated. Water was added to the residue, and the mixture was stirred at room temperature for 10 minutes and filtered to give the title compound (1.55 g, 83%).

Example 110D

N-(cyclopropylmethyl)-2-iodo-4-((methylsulfonyl)methyl)aniline

Example 110C (311 mg, 1.0 mmol), cyclopropanecarbaldehyde (0.187 mL, 2.50 mmol) and acetic acid (0.572 mL, 10.00 mmol) were combined in a mixture of dichloromethane (5 mL) and methanol (5 mL). The reaction mixture was heated at 50° C. for 30 minutes, and then cooled to room temperature. MP-cyanoborohydride (1271 mg, 2.36 mmol/g, 3.00 mmol) was added and the reaction mixture was stirred at room temperature for 3 hours. The reaction mixture was filtered, washed with dichloromethane and concentrated. The residue was purified by flash chromatography (silica gel, 20 to 60% ethyl acetate in heptanes) to provide the title compound (296 mg, 81%).

Example 110E

N-(cyclopropylmethyl)-2-(7-methoxy-1-methyl-1H-pyrrolo[2,3-c]pyridin-3-yl)-4-((methylsulfonyl)methyl)aniline Example 110D (183 mg, 0.50 mmol), Example 59A (173 mg, 0.600 mmol), sodium carbonate (185 mg, 1.75 mmol), tris(dibenzylideneacetone)dipalladium (13.7 mg, 0.015 mmol) and 1,3,5,7-tetramethyl-6-phenyl-2,4,8-trioxa-6-phosphaadamantane (13.1 mg, 0.045 mmol) were combined in a microwave tube and purged with nitrogen for 15 minutes. The mixture of dioxane (2 mL) and water (0.5 mL) was purged with nitrogen for 15 minutes and transferred to the microwave tube. The reaction mixture was heated at 60° C.

for 4 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20 to 50% ethyl acetate in heptanes) to provide the title compound (140 mg, 70%).

Example 110F

3-{2-[(cyclopropylmethyl)amino]-5-[(methylsulfonyl)methyl]phenyl}-1-methyl-1,6-dihydro-7H-pyrrolo[2,3-c]pyridin-7-one Example 110E (136 mg, 0.340 mmol) in a solution of 4M HCl in dioxane (5 mL, 20.0 mmol) was heated at 70° C. for 2 hours. The reaction mixture was cooled and concentrated. The residue was purified by flash chromatography (silica gel, 2 to 6% methanol in dichloromethane) to provide the title compound (130 mg, 91%) as the HCl salt. $^1$H NMR (300 MHz, DMSO-$d_6$) δ ppm 10.93 (d, J=5.43 Hz, 1H) 7.41 (s, 1H) 7.18 (dd, J=8.31, 2.20 Hz, 1H) 7.11 (d, J=2.03 Hz, 1H) 6.86 (dd, J=7.12, 5.76 Hz, 1H) 6.76 (d, J=8.14 Hz, 1H) 6.26 (dd, J=7.12, 1.02 Hz, 1H) 4.31 (s, 2H) 4.12 (s, 3H) 2.97 (d, J=6.78 Hz, 2H) 2.86 (s, 3H) 0.89-1.10 (m, 1H) 0.36-0.46 (m, 2H) 0.12-0.26 (m, 2H). MS (ESI+) m/z 386 (M+H)$^+$.

Example 111

3-{5-[(4-aminopiperidin-1-yl)methyl]-2-(2,4-difluorophenoxy)phenyl}-1-methyl-1,6-dihydro-7H-pyrrolo[2,3-c]pyridin-7-one

Example 111A tert-butyl 1-(4-(2,4-difluorophenoxy)-3-(7-methoxy-1-methyl-1H-pyrrolo[2,3-c]pyridin-3-yl)benzyl)piperidin-4-ylcarbamate A solution of Example 105B (125 mg, 0.317 mmol), tert-butyl piperidin-4-ylcarbamate (190 mg, 0.951 mmol) and acetic acid (0.181 mL, 3.17 mmol) in dichloromethane (3 mL) was heated at 50° C. for 1 hour. The reaction mixture was cooled in an ice bath and the sodium triacetoxyborohydride (134 mg, 0.634 mmol) was added portionwise over a few minutes. The reaction mixture was stirred 2 hours while warming to ambient temperature. The reaction mixture was quenched with 1 M sodium hydroxide (2 mL) and partitioned between saturated aqueous sodium bicarbonate solution (50 mL) and ethyl acetate (50 mL). The layers were separated and the organic layer was dried over anhydrous sodium sulfate, filtered, and concentrated to provide the title compound (783 mg, 100% yield).

Example 111B

3-{5-[(4-aminopiperidin-1-yl)methyl]-2-(2,4-difluorophenoxy)phenyl}-1-methyl-1,6-dihydro-7H-pyrrolo[2,3-c]pyridin-7-one The TFA salt of Example 111B was prepared according to the procedure used for the preparation of Example 1C, substituting Example 111A for Example 1B, and with the exception that the reaction mixture was heated at 70° C. $^1$H NMR (400 MHz, DMSO-$d_6$) δ ppm 11.00 (d, J=5.49 Hz, 1H), 8.18 (d, J=3.66 Hz, 2H), 7.65 (d, J=1.83 Hz, 1H), 7.58 (s, 1H), 7.46-7.53 (m, 1H), 7.34 (dd, J=8.39, 2.29 Hz, 1H), 7.23-7.31 (m, 1H), 7.10-7.17 (m, 1H), 6.87-6.92 (m, 1H), 6.85 (d, J=8.24 Hz, 1H), 6.60 (d, J=6.71 Hz, 1H), 4.31 (s, 2H), 4.11 (s, 3H), 3.48 (d, J=11.60 Hz, 2H), 3.27 (s, 1H), 3.03 (s, 2H), 2.12 (d, J=12.21 Hz, 2H), 1.75 (s, 2H). MS (ESI+) m/z 465.0 (M+H)$^+$.

Example 112

3-{2-(2,4-difluorophenoxy)-5-[(piperidin-4-ylamino)methyl]phenyl}-1-methyl-1,6-dihydro-7H-pyrrolo[2,3-c]pyridin-7-one

Example 112A tert-butyl 4-(4-(2,4-difluorophenoxy)-3-(7-methoxy-1-methyl-1H-pyrrolo[2,3-c]pyridin-3-yl)benzylamino)piperidine-1-carboxylate Example 112A was prepared according to the procedure used for the preparation of Example 111A, substituting tert-butyl 4-aminopiperidine-1-carboxylate for tert-butyl piperidin-4-ylcarbamate.

Example 112B

3-{2-(2,4-difluorophenoxy)-5-[(piperidin-4-ylamino)methyl]phenyl}-1-methyl-1,6-dihydro-7H-pyrrolo[2,3-c]pyridin-7-one The TFA salt of Example 112B was prepared according to the procedure used for the preparation of Example 1C, substituting Example 112A for Example 1B, and with the exception that the reaction mixture was heated at 70° C. $^1$H NMR (400 MHz, DMSO-$d_6$) δ ppm 11.00 (d, J=5.19 Hz, 1H), 9.19 (s, 1H), 8.71 (s, 1H), 7.70 (d, J=2.14 Hz, 1H), 7.55 (s, 1H), 7.45-7.52 (m, 1H), 7.37 (dd, J=8.54, 2.14 Hz, 1H), 7.19-7.28 (m, 1H), 7.08-7.16 (m, 1H), 6.90 (dd, J=7.02, 5.80 Hz, 1H), 6.85 (d, J=8.24 Hz, 1H), 6.60-6.65 (m, 1H), 4.23 (s, 2H), 4.13-4.13 (m, 3H), 3.41 (d, J=12.82 Hz, 3H), 2.91-3.03 (m, 2H), 2.26 (d, J=12.51 Hz, 2H), 1.69-1.83 (m, 2H). MS (ESI+) m/z 464.9 (M+H)$^+$.

Example 113

3-[2-(2,4-difluorophenoxy)-5-{[4-(dimethylamino)piperidin-1-yl]methyl}phenyl]-1-methyl-1,6-dihydro-7H-pyrrolo[2,3-c]pyridin-7-one

Example 113A 1-(4-(2,4-difluorophenoxy)-3-(7-methoxy-1-methyl-1H-pyrrolo[2,3-c]pyridin-3-yl)benzyl)-N,N-dimethylpiperidin-4-amine Example 113A was prepared according to the procedure used for the preparation of Example 111A, substituting N,N-dimethylpiperidin-4-amine for tert-butyl piperidin-4-ylcarbamate.

Example 113B

3-[2-(2,4-difluorophenoxy)-5-{[4-(dimethylamino)piperidin-1-yl]methyl}phenyl]-1-methyl-1,6-dihydro-7H-pyrrolo[2,3-c]pyridin-7-one The TFA salt of Example 113B was prepared according to the procedure used for the preparation of Example 1C, substituting Example 113A for Example 1B, and with the exception that the reaction mixture was heated at 70° C. $^1$H NMR (400 MHz, DMSO-d$_6$) δ ppm 10.71 (d, J=5.49 Hz, 1H), 7.39 (d, J=1.83 Hz, 1H), 7.29 (s, 1H), 7.17-7.25 (m, 1H), 7.09 (dd, J=8.39, 1.98 Hz, 1H), 6.95-7.03 (m, 1), 6.82-6.88 (m, 1H), 6.60-6.65 (m, 1H), 6.58 (d, J=8.54 Hz, 1H), 6.32 (d, J=7.02 Hz, 1H), 4.07 (s, 2H), 3.83 (s, 3H), 3.07-3.17 (m, 3H), 2.72 (s, 2H), 2.49 (s, 6H), 1.94 (s, 2H), 1.53-1.66 (m, 2H). MS (ESI+) m/z 493.0 (M+H)$^+$.

Example 114

3-[2-(2,4-difluorophenoxy)-5-{[(3,3-dimethylbutyl)amino]methyl}phenyl]-1-methyl-1,6-dihydro-7H-pyrrolo[2,3-c]pyridin-7-one Example 114A N-(4-(2,4-difluorophenoxy)-3-(7-methoxy-1-methyl-1H-pyrrolo[2,3-c]pyridin-3-yl)benzyl)-3,3-dimethylbutan-1-amine Example 114A was prepared according to the procedure used for the preparation of Example 111A, substituting 3,3-dimethylbutan-1-amine for tert-butyl piperidin-4-ylcarbamate.

Example 114B

3-[2-(2,4-difluorophenoxy)-5-{[(3,3-dimethylbutyl)amino]methyl}phenyl]-1-methyl-1,6-dihydro-7H-pyrrolo[2,3-c]pyridin-7-one The TFA salt of Example 114B was prepared according to the procedure used for the preparation of Example 1C, substituting Example 114A for Example 1B, and with the exception that the reaction mixture was heated at 70° C. $^1$H NMR (400 MHz, DMSO-d$_6$) δ ppm 11.00 (d, J=5.49 Hz, 1H), 8.75 (s, 1H), 7.68 (d, J=2.14 Hz, 1H), 7.56 (s, 1H), 7.44-7.52 (m, 1H), 7.35 (dd, J=8.54, 2.14 Hz, 1H), 7.20-7.27 (m, 1H), 7.10-7.16 (m, 1H), 6.90 (dd, J=7.02, 5.80 Hz, 1H), 6.85 (d, J=8.24 Hz, 1H), 6.63 (d, J=6.10 Hz, 1H), 4.16-4.23 (m, 2H), 4.11 (s, 3H), 2.94-3.04 (m, 2H), 1.49-1.57 (m, 2H), 0.87-0.94 (m, 9H). MS (ESI+) m/z 465.9 (M+H)$^+$.

Example 115

3-{2-(2,4-difluorophenoxy)-5-[(4-methoxypiperidin-1-yl)methyl]phenyl}-1-methyl-1,6-dihydro-7H-pyrrolo[2,3-c]pyridin-7-one Example 115A 3-(2-(2,4-difluorophenoxy)-5-((4-methoxypiperidin-1-yl)methyl)phenyl)-7-methoxy-1-methyl-1H-pyrrolo[2,3-c]pyridine Example 115A was prepared according to the procedure used for the preparation of Example 111A, substituting 4-methoxypiperidine for tert-butyl piperidin-4-ylcarbamate.

Example 115B

3-{2-(2,4-difluorophenoxy)-5-[(4-methoxypiperidin-1-yl)methyl]phenyl}-1-methyl-1,6-dihydro-7H-pyrrolo[2,3-c]pyridin-7-one The TFA salt of Example 115B was prepared according to the procedure used for the preparation of Example 1C, substituting Example 115A for Example 1B, and with the exception that the reaction mixture was heated at 70° C. $^1$H NMR (400 MHz, DMSO-d$_6$) δ ppm 10.99 (d, J=5.19 Hz, 1H), 7.68 (dd, J=10.53, 1.98 Hz, 1H), 7.58 (s, 1H), 7.44-7.53 (m, 1H), 7.32-7.40 (m, 1H), 7.23-7.31 (m, 1H), 7.08-7.17 (m, 1H), 6.88-6.94 (m, 1H), 6.86 (dd, J=8.39, 2.29 Hz, 1H), 6.59 (d, J=7.02 Hz, 1H), 4.29-4.40 (m, 2H), 4.11 (s, 3H), 3.55 (s, 1H), 3.32-3.47 (m, 1H), 3.25 (d, J=2.44 Hz, 3H), 3.20 (s, 1H), 2.92-3.12 (m, 2H), 2.17 (d, J=11.60 Hz, 1H), 2.01 (d, J=14.65 Hz, 1H), 1.72-1.86 (m, 1H), 1.45-1.59 (m, 1H). MS (ESI+) m/z 479.9 (M+H)$^+$.

Example 116

3-{2-(2,4-difluorophenoxy)-5-[(4-methylpiperazin-1-yl)methyl]phenyl}-1-methyl-1,6-dihydro-7H-pyrrolo[2,3-c]pyridin-7-one Example 116A 3-(2-(2,4-difluorophenoxy)-5-((4-methylpiperazin-1-yl)methyl)phenyl)-7-methoxy-1-methyl-1H-pyrrolo[2,3-c]pyridine Example 116A was prepared according to the procedure used for the preparation of Example 111A, substituting 1-methylpiperazine for tert-butyl piperidin-4-ylcarbamate.

Example 116B

3-{2-(2,4-difluorophenoxy)-5-[(4-methylpiperazin-1-yl)methyl]phenyl}-1-methyl-1,6-dihydro-7H-pyrrolo[2,3-c]pyridin-7-one The TFA salt of Example 116B was prepared according to the procedure used for the preparation of Example 1C, substituting Example 116A for Example 1B, and with the exception that the reaction mixture was heated at 70° C. $^1$H NMR (500 MHz, DMSO-d$_6$) δ ppm 10.98 (d, J=5.49 Hz, 1H), 7.57 (s, 1H), 7.54 (s, 1H), 7.44-7.50 (m, 1H), 7.28 (dd, J=8.54, 1.53 Hz, 1H), 7.18-7.25 (m, 1H), 7.07-7.14 (m, 1H), 6.87-6.92 (m, 1H), 6.82 (d, J=8.55 Hz, 1H), 6.55 (d, J=7.02 Hz, 1H), 4.11 (s, 3H), 3.96 (s, 2H), 3.47 (s, 4H), 3.25 (s, 4H), 2.81 (s, 3H). MS (ESI+) m/z 464.9 (M+H)$^+$.

Example 117

3-[2-(2,4-difluorophenoxy)-5-{[(3-methylbutyl)amino]methyl}phenyl]-1-methyl-1,6-dihydro-7H-pyrrolo[2,3-c]pyridin-7-one Example 117A N-(4-(2,4-difluorophenoxy)-3-(7-methoxy-1-methyl-1H-pyrrolo[2,3-c]pyridin-3-yl)benzyl)-3-methylbutan-1-amine Example 117A was prepared according to the procedure used for the preparation of Example 111A, substituting 3-methylbutan-1-amine for tert-butyl piperidin-4-ylcarbamate.

Example 117B

3-[2-(2,4-difluorophenoxy)-5-{[(3-methylbutyl)amino]methyl}phenyl]-1-methyl-1,6-dihydro-7H-pyrrolo[2,3-c]pyridin-7-one The TFA salt of Example 117B was prepared according to the procedure used for the preparation of Example 1C, substituting Example 117A for Example 1B, and with the exception that the reaction mixture was heated at 70° C. ¹H NMR (400 MHz, DMSO-d₆) δ ppm 11.00 (d, J=5.49 Hz, 1H), 8.77 (s, 1H), 7.68 (d, J=2.14 Hz, 1H), 7.56 (s, 1H), 7.45-7.52 (m, 1H), 7.35 (dd, J=8.54, 2.14 Hz, 1H), 7.19-7.28 (m, 1H), 7.09-7.16 (m, 1H), 6.90 (dd, J=6.87, 5.65 Hz, 1H), 6.85 (d, J=8.24 Hz, 1H), 6.63 (d, J=7.02 Hz, 1H), 4.18 (t, J=5.49 Hz, 2H), 4.11 (s, 3H), 2.92-3.02 (m, 2H), 1.57-1.69 (m, 1H), 1.53 (d, J=7.02 Hz, 2H), 0.88 (t, J=7.48 Hz, 6H). MS (ESI+) m/z 451.9 (M+H)⁺.

Example 118

3-[5-{[(cyclopropylmethyl)amino]methyl}-2-(2,4-difluorophenoxy)phenyl]-1-methyl-1,6-dihydro-7H-pyrrolo[2,3-c]pyridin-7-one Example 118A 1-cyclopropyl-N-(4-(2,4-difluorophenoxy)-3-(7-methoxy-1-methyl-1H-pyrrolo[2,3-c]pyridin-3-yl)benzyl)methanamine Example 118A was prepared according to the procedure used for the preparation of Example 111A, substituting cyclopropylmethanamine for tert-butyl piperidin-4-ylcarbamate.

Example 118B

3-[5-{[(cyclopropylmethyl)amino]methyl}-2-(2,4-difluorophenoxy)phenyl]-1-methyl-1,6-dihydro-7H-pyrrolo[2,3-c]pyridin-7-one The TFA salt of Example 118B was prepared according to the procedure used for the preparation of Example 1C, substituting Example 118A for Example 1B, and with the exception that the reaction mixture was heated at 70° C. ¹H NMR (400 MHz, DMSO-d₆) δ ppm 10.99 (d, J=5.19 Hz, 1H), 8.94 (s, 1H), 7.68 (d, J=2.14 Hz, 1H), 7.56 (s, 1H), 7.42-7.51 (m, 1H), 7.36 (dd, J=8.54, 2.14 Hz, 1H), 7.19-7.28 (m, 1H), 7.08-7.17 (m, 1H), 6.88-6.95 (m, 1H), 6.85 (d, J=8.24 Hz, 1H), 6.64 (d, J=7.02 Hz, 1H), 4.18 (t, J=5.65 Hz, 2H), 4.11 (s, 3H), 2.82-2.93 (m, 2H), 0.99-1.14 (m, 1H), 0.55-0.64 (m, 2H), 0.32-0.40 (m, 2H). MS (ESI+) m/z 465.9 (M+H)⁺.

Example 119

3-[2-(2,4-difluorophenoxy)-5-{[(1H-imidazol-4-ylmethyl)amino]methyl}phenyl]-1-methyl-1,6-dihydro-7H-pyrrolo[2,3-c]pyridin-7-one Example 119A N-((1H-imidazol-4-yl)methyl)-1-(4-(2,4-difluorophenoxy)-3-(7-methoxy-1-methyl-1H-pyrrolo[2,3-c]pyridin-3-yl)phenyl)methanamine To a suspension of 1H-imidazol-4-ylmethylamine dihydrochloride (269 mg, 1.59 mmol) in a mixture of dichloromethane (3 mL) and methanol (1 mL) was added triethylamine (0.442 mL, 3.17 mmol). After stirring the mixture for five minutes, Example 105B (125 mg, 0.317 mmol) and acetic acid (0.181 mL, 3.17 mmol) were added. The mixture was heated at 50° C. for 1 hour. The mixture was cooled in an ice bath and sodium triacetoxyborohydride (134 mg, 0.634 mmol) was added portionwise over several minutes. After 15 minutes, the ice bath was removed and the reaction mixture was stirred 2 hours while warming to ambient temperature. The reaction mixture was quenched with 1 M sodium hydroxide (2 mL) and partitioned between saturated aqueous sodium bicarbonate solution (50 mL) and ethyl acetate (50 mL). The organic layer was dried over anhydrous sodium sulfate, filtered, and concentrated. The residue was purified by flash column chromatography (silica gel, 0-10% 7N methanolic ammonia in methylene chloride) to provide the title compound (90.3 mg, 62% yield).

Example 119B

3-[2-(2,4-difluorophenoxy)-5-{[(1H-imidazol-4-ylmethyl)amino]methyl}phenyl]-1-methyl-1,6-dihydro-7H-pyrrolo[2,3-c]pyridin-7-one The TFA salt of Example 119B was prepared according to the procedure used for the preparation of Example 1C, substituting Example 119A for Example 1B, and with the exception that the reaction mixture was heated at 70° C. ¹H NMR (400 MHz, DMSO-d₆) δ ppm 10.97 (d, J=5.19 Hz, 1H), 9.43 (d, 1H), 8.77 (s, 1H), 7.66 (d, J=2.44 Hz, 1H), 7.62 (s, 1H), 7.53 (s, 1H), 7.42-7.49 (m, 1H), 7.33 (dd, J=8.54, 2.14 Hz, 1H), 7.18-7.27 (m, 1H), 7.06-7.15 (m, 1H), 6.86-6.91 (m, 1H), 6.82 (d, J=8.24 Hz, 1H), 6.66 (d, 1H), 4.29 (s, 2H), 4.22 (s, 2H), 4.09 (s, 3H), 3.54 (s, 1H). MS (ESI+) m/z 461.9 (M+H)⁺.

Example 120

3-[5-(chloromethyl)-2-(2,4-difluorophenoxy)phenyl]-1-methyl-1,6-dihydro-7H-pyrrolo[2,3-c]pyridin-7-one Example 120A A solution of Example 105B (100 mg, 0.254 mmol), sodium cyanoborohydride (47.8 mg, 0.761 mmol), phenylmethanamine (0.083 mL, 0.761 mmol), and acetic acid (0.833 mL, 14.6 mmol) in dichloromethane (2.5 mL) was heated at 50° C. for 1 hour. The reaction mixture was partitioned between saturated aqueous sodium bicarbonate solution (100 mL) and ethyl acetate (100 mL). The organic layer was dried over anhydrous sodium sulfate, filtered and concentrated. The residue was purified by flash column chromatography (silica gel, 0-4% methanol in methylene chloride) to provide the title compound (87 mg, 87% yield).

Example 120B

3-[(5-(chloromethyl)-2-(2,4-difluorophenoxy)phenyl]-1-methyl-1,6-dihydro-7H-pyrrolo[2,3-c]pyridin-7-one Example 120B was prepared according to the procedure used for the preparation of Example 1C, substituting Example 120A for Example 1B, and with the exception that the reaction mixture was heated at 70° C. ¹H NMR (400 MHz, DMSO-d₆) δ ppm 10.93 (d, J=4.88 Hz, 1H), 7.56 (d, J=2.44 Hz, 1H), 7.53 (s, 1H), 7.39-7.47 (m, 1H), 7.30 (dd, J=8.39, 2.29 Hz, 1H), 7.17-7.24 (m, 1H), 7.04-7.11 (m, 1H), 6.86-6.92 (m, 1H), 6.77 (d, J=8.54 Hz, 1H), 6.52 (d, J=7.02 Hz, 1H), 4.79 (s, 2H), 4.08 (s, 3H). MS (ESI+) m/z 401.1 (M+H)⁺.

Example 121

3-{2-[(4-fluorophenyl)amino]-5-[(methylsulfonyl)methyl]phenyl}-1-methyl-1,6-dihydro-7H-pyrrolo[2,3-c]pyridin-7-one

Example 121A 2-(7-methoxy-1-methyl-1H-pyrrolo[2,3-c]pyridin-3-yl)-4-((methylsulfonyl)methyl)aniline Example 110C (1.25 g, 4.00 mmol), Example 59A (1.15 g, 4.00 mmol), potassium phosphate (2.97 g, 14.0 mmol), tris(dibenzylideneacetone)dipalladium (0.110 g, 0.120 mmol) and 1,3,5,7-tetramethyl-6-phenyl-2,4,8-trioxa-6-phosphaadamantane (0.105 g, 0.360 mmol) were combined in a microwave tube and purged with nitrogen for 15 minutes. A mixture of dioxane (12 mL) and water (3 mL) was purged with nitrogen for 15 minutes and transferred via cannula to the microwave tube. The reaction mixture was heated at 60° C. for 4 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20 to 80% ethyl acetate in heptanes) to provide the title compound (0.985 g, 71%).

Example 121B

N-(4-fluorophenyl)-2-(7-methoxy-1-methyl-1H-pyrrolo[2,3-c]pyridin-3-yl)-4-((methylsulfonyl)methyl)aniline Example 121A (104 mg, 0.300 mmol), 1-bromo-4-fluorobenzene (105 mg, 0.600 mmol), diacetoxypalladium (2.7 mg, 0.012 mmol), dicyclohexyl(2',4',6'-triisopropyl-[1,1'-biphenyl]-2-yl)phosphine (11.4 mg, 0.0239 mmol) and cesium carbonate (195 mg, 0.600 mmol) were combined in a mixture of toluene (2.4 mL) and tert-butanol (0.6 mL). The reaction mixture was heated in a microwave reactor at 150° C. for 30 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2 to 4% methanol in dichloromethane) to provide the title compound (112 mg, 85%).

Example 121C

3-{2-[(4-fluorophenyl)amino]-5-[(methylsulfonyl)methyl]phenyl}-1-methyl-1,6-dihydro-7H-pyrrolo[2,3-c]pyridin-7-one Example 121B (110 mg, 0.250 mmol) in a solution of 4M HCl in dioxane (5.0 mL, 20 mmol) was heated at 70° C. for 2 hours. The reaction mixture was cooled to ambient temperature and concentrated. The residue was partitioned with ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2 to 4% methanol in dichloromethane) to provide the title compound (86 mg, 81%). $^1$H NMR (300 MHz, DMSO-$d_6$) δ ppm 10.91 (d, J=5.76 Hz, 1H) 7.45 (s, 1H) 7.30 (s, 1H) 7.14-7.25 (m, 3H) 6.98-7.09 (m, 4H) 6.82 (dd, J=6.78, 5.76 Hz, 1H) 6.32 (dd, J=7.12, 1.02 Hz, 1H) 4.40 (s, 2H) 4.08 (s, 3H) 2.91 (s, 3H). MS (ESI+) m/z 426 (M+H)$^+$.

Example 122

3-{2-[(2,4-difluorophenyl)amino]-5-[(methylsulfonyl)methyl]phenyl}-1-methyl-1,6-dihydro-7H-pyrrolo[2,3-c]pyridin-7-one

Example 122A

N-(2,4-difluorophenyl)-2-(7-methoxy-1-methyl-1H-pyrrolo[2,3-c]pyridin-3-yl)-4-((methylsulfonyl)methyl)aniline Example 121A (104 mg, 0.300 mmol), 1-bromo-2,4-difluorobenzene (116 mg, 0.600 mmol), diacetoxypalladium (2.7 mg, 0.012 mmol), dicyclohexyl(2',4',6'-triisopropyl-[1,1'-biphenyl]-2-yl)phosphine (11.4 mg, 0.0239 mmol) and cesium carbonate (195 mg, 0.600 mmol) were combined in a mixture of toluene (2.4 mL) and tert-butanol (0.6 mL). The reaction mixture was heated in a microwave reactor at 150° C. for 1 hour. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 1 to 2% methanol in dichloromethane) to provide the title compound (62 mg, 45%).

Example 122B

3-{2-[(2,4-difluorophenyl)amino]-5-[(methylsulfonyl)methyl]phenyl}-1-methyl-1,6-dihydro-7H-pyrrolo[2,3-c]pyridin-7-one Example 122A (60.0 mg, 0.131 mmol) in a solution of 4M HCl in dioxane (5.0 mL, 20 mmol) was heated at 70° C. for 2 hours. The reaction mixture was cooled to ambient temperature and concentrated. The residue was partitioned with ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2 to 4% methanol in dichloromethane) to provide the title compound (46 mg, 79%). $^1$H NMR (300 MHz, DMSO-$d_6$) δ ppm 10.92 (d, J=6.10 Hz, 1H) 7.48 (s, 1H) 7.07-7.31 (m, 4H) 6.91-7.04 (m, 2H) 6.81-6.88 (m, 1H) 6.74 (dd, J=8.48, 2.37 Hz, 1H) 6.38 (d, J=6.44 Hz, 1H) 4.39 (s, 2H) 4.09 (s, 3H) 2.91 (s, 3H). MS (ESI+) m/z 444 (M+H)$^+$.

Example 123

3-[2-(2,4-difluorophenoxy)-5-(methylsulfonyl)phenyl]-1,4-dimethyl-1,6-dihydro-7H-pyrrolo[2,3-c]pyridin-7-one

Example 123A 3-(2-fluoro-5-(methylsulfonyl)phenyl)-7-methoxy-1,4-dimethyl-1H-pyrrolo[2,3-c]pyridine A mixture of Example 108G (1.5 g, 4.1 mmol), methylboronic acid (1.217 g, 20.34 mmol), tris(dibenzylideneacetone)dipalladium (0.186 g, 0.203 mmol) and dicyclohexyl(2',4',6'-triisopropyl-[1',1'-biphenyl]-2-yl)phosphine (0.097 g, 0.203 mmol) indioxane (40 mL) and water (10 mL) was heated at 130° C. for 2 hours under microwave conditions. The mixture was diluted with ethyl acetate and washed with saturated aqueous sodium bicarbonate. The organics were dried over anhydrous magnesium sulfate, filtered, and concentrated. The residue was purified by flash chromatography (silica gel, 10-100% ethyl acetate in hexane) to provide the title compound (1.12 g, 52% yield)

Example 123B 3-(2-(2,4-difluorophenoxy)-5-(methylsulfonyl)phenyl)-7-methoxy-1,4-dimethyl-1H-pyrrolo[2,3-c]pyridine Example 123B was prepared according to the procedure used for the preparation of Example 2C, substituting Example 123A for Example 2B, and heating for 12 hours instead of heating for 1 hour.

Example 123C 3-(2-(2,4-difluorophenoxy)-5-(methylsulfonyl)phenyl)-1,4-dimethyl-1H-pyrrolo[2,3-c]pyridin-7(6H)-one Example 123C was prepared according to the procedure used for the preparation of Example 1C, substituting Example 123B for Example 1B. $^1$H NMR (400 MHz, MeOH-$d_4$) δ ppm 7.90-7.96 (m, 2H), 7.31 (s, 1H), 7.09-7.18 (m, 2H), 7.02 (d, J=8.4 Hz, 1H), 6.94-7.00 (m, 1H), 6.70 (s, 1H), 4.19 (s, 3H), 3.17 (s, 3H), 1.98 (d, J=1.0 Hz, 3H).

Example 124

3-[2-(2-cyclopropylethoxy)-5-(methylsulfonyl)phenyl]-1,4-dimethyl-1,6-dihydro-7H-pyrrolo[2,3-c]pyridin-7-one Example 124A 3-(2-(2-cyclopropylethoxy)-5-(methylsulfonyl)phenyl)-7-methoxy-1,4-dimethyl-1H-pyrrolo[2,3-c]pyridine Example 124A was prepared according to the procedure used for the preparation of Example 2C, substituting Example 123A for Example 2B, 2-cyclopropylethanol for 2,4-difluorophenol, and heating for 12 hours instead of heating for 1 hour.

Example 124B 3-(2-(2-cyclopropylethoxy)-5-(methylsulfonyl)phenyl)-1,4-dimethyl-1H-pyrrolo[2,3-c]pyridin-7(6H)-one Example 124B was prepared according to the procedure used for the preparation of Example 1C, substituting Example 124A for Example 1B. $^1$H NMR (400 MHz, MeOH-$d_4$) δ ppm 7.94 (dd, J=8.7, 2.5 Hz, 1H), 7.79 (d, J=2.5 Hz, 1H), 7.24 (d, J=8.8 Hz, 1H), 7.21 (s, 1H), 6.63 (d, J=1.0 Hz, 1H), 4.18 (s, 3H), 4.12 (t, J=6.1 Hz, 2H), 3.13 (s, 3H), 1.84 (d, J=1.0 Hz, 3H), 1.51 (dd, J=12.8, 6.3 Hz, 2H), 0.59 (d, J=7.6 Hz, 1H), 0.26-0.34 (m, 2H), −0.07 (q, J=4.9 Hz, 2H).

Example 125

3-{2-(cyclopropylmethoxy)-5-[(3,3-difluoroazetidin-1-yl)sulfonyl]phenyl}-1-methyl-1,6-dihydro-7H-pyrrolo[2,3-c]pyridin-7-one Example 125A 1-((3-bromo-4-fluorophenyl)sulfonyl)-3,3-difluoroazetidine Example 125A was prepared according to the procedure used for the preparation of Example 97A, substituting 3,3-difluoroazetidine for indoline.

Example 125B 1-((3-bromo-4-(cyclopropylmethoxy)phenyl)sulfonyl)-3,3-difluoroazetidine Example 125B was prepared according to the procedure used for the preparation of Example 97B, substituting Example 125A for Example 97A.

Example 125C 3-(2-(cyclopropylmethoxy)-5-((3,3-difluoroazetidin-1-yl)sulfonyl)phenyl)-7-methoxy-1-methyl-1H-pyrrolo[2,3-c]pyridine Example 125C was prepared according to the procedure used for the preparation of Example 11E, substituting Example 125B for Example 11C.

Example 125D

3-{2-(cyclopropylmethoxy)-5-[(3,3-difluoroazetidin-1-yl)sulfonyl]phenyl}-1-methyl-1,6-dihydro-7H-pyrrolo[2,3-c]pyridin-7-one Example 125D was prepared according to the procedure used for the preparation of Example 11F, substituting Example 125C for Example 11E. $^1$H NMR (300 MHz, DMSO-$d_6$) δ ppm 11.84 (s, 1H), 7.82-7.75 (m, 2H), 7.66 (s, 1H), 7.37-7.30 (m, 1H), 6.92 (dd, J=7.0, 5.7 Hz, 1H), 6.43 (dd, J=7.0, 1.1 Hz, 1H), 4.25 (t, J=12.7 Hz, 2H), 4.13 (s, 3H), 4.03 (d, J=6.9 Hz, 2H), 1.29-1.20 (m, 1H), 0.60-0.47 (m, 2H), 0.44-0.29 (m, 2H).

Example 126

5-[(1Z)-2-chloro-4-hydroxybut-1-en-1-yl]-3-[2-(2,4-difluorophenoxy)-5-(ethylsulfonyl)phenyl]-1-methyl-1,6-dihydro-7H-pyrrolo[2,3-c]pyridin-7-one Example 126A 5-bromo-3-(5-(ethylsulfonyl)-2-fluorophenyl)-7-methoxy-1-methyl-1H-pyrrolo[2,3-c]pyridine Example 126A was prepared according to the procedure used for the preparation of Example 91E, substituting Example 48D for Example 91D to provide the title compound.

Example 126B 4-(3-(5-(ethylsulfonyl)-2-fluorophenyl)-7-methoxy-1-methyl-1H-pyrrolo[2,3-c]pyridin-5-yl)but-3-yn-1-ol A mixture of Example 126A (300 mg, 0.702 mmol), but-3-yn-1-ol (63.8 μl, 0.843 mmol), Pd(dppf)CH$_2$Cl$_2$ (57.3 mg, 0.070 mmol), and copper(I) iodide (13.4 mg, 0.070 mmol) in tetrahydrofuran (9 mL) and triethylamine (3 mL) was purged with nitrogen and then stirred at 70° C. in a sealed tube for 2.5 hours. The mixture was partitioned between water and ethyl acetate. The aqueous phase was extracted with ethyl acetate (2×). The combined organic phases were washed with water and saturated aqueous sodium chloride, dried over anhydrous magnesium sulfate, filtered, and concentrated. The residue was purified on silica gel column (0-8% MeOH in dichloromethane) to give the title compound (200 mg, 68.4% yield)

Example 126C 4-(3-(2-(2,4-difluorophenoxy)-5-(ethylsulfonyl)phenyl)-7-methoxy-1-methyl-1H-pyrrolo[2,3-c]pyridin-5-yl)but-3-yn-1-ol A mixture of Example 126B (50 mg, 0.120 mmol), 2,4-difluorophenol (15.62 mg, 0.120 mmol) and cesium carbonate (58.7 mg, 0.180 mmol) in dimethylsulfoxide (0.5 mL) was heated at 120° C. in a microwave oven (Biotage Smith Synthesizer) for 45 minutes. The reaction mixture was partitioned between water and ethyl acetate. The aqueous phase was extracted with ethyl acetate (3×). The combined organic phases were washed with water (2×), saturated aqueous sodium chloride, dried over anhydrous magnesium sulfate, and filtered. The filtrate was concentrated and the residue was absorbed on silica gel and purified by flash chromatography (silica gel, 20-90% ethyl acetate/heptanes) to give the title compound (38 mg, 60% yield)

Example 126D

5-[(1Z)-2-chloro-4-hydroxybut-1-en-1-yl]-3-[2-(2,4-difluorophenoxy)-5-(ethylsulfonyl)phenyl]-1-methyl-1,6-dihydro-7H-pyrrolo[2,3-c]pyridin-7-one Example 126C (34 mg, 0.065 mmol) was treated with 4N HCl dioxane solution (2 mL). The mixture was stirred at 50° C. for 4 hours. The mixture was cooled to ambient temperature, and concentrated to 0.5 mL volume. Diethyl ether (4 mL) was added and the resulting precipitate was collected to give the title compound (12 mg, 34% yield). $^1$H NMR (300 MHz, DMSO-d$_6$) δ ppm 10.98 (s, 1H), 7.98 (d, J=2.3 Hz, 1H), 7.76 (s, 1H), 7.73 (dd, J=8.6, 2.4 Hz, 1H), 7.63-7.51 (m, 1H), 7.46 (td, J=9.2, 5.6 Hz, 1H), 7.26 (d, J=1.3 Hz, 1H), 7.25-7.16 (m, 1H), 6.97 (dd, J=8.6, 1.1 Hz, 1H), 6.49 (s, 1H), 4.13 (s, 1H), 3.63 (t, J=6.3 Hz, 2H), 3.33-3.25 (m, 1H), 2.57 (t, J=6.2 Hz, 2H), 1.13 (t, J=7.3 Hz, 3H).

Example 127

3-[2-(2,4-difluorophenoxy)-5-{[(furan-3-ylmethyl)amino]methyl}phenyl]-1-methyl-1,6-dihydro-7H-pyrrolo[2,3-c]pyridin-7-one

Example 127A

N-(4-(2,4-difluorophenoxy)-3-(7-methoxy-1-methyl-1H-pyrrolo[2,3-c]pyridin-3-yl)benzyl)-1-(furan-3-yl)methanamine Example 127A was prepared according to the procedure used for the preparation of Example 119A, substituting furan-3-ylmethanamine hydrochloride for 1H-imidazol-4-ylmethylamine dihydrochloride.

Example 127B

3-[2-(2,4-difluorophenoxy)-5-{[(furan-3-ylmethyl)amino]methyl}phenyl]-1-methyl-1,6-dihydro-7H-pyrrolo[2,3-c]pyridin-7-one The TFA salt of Example 127B was prepared according to the procedure used for the preparation of Example 1C, substituting Example 127A for Example 1B, and with the exception that the reaction mixture was heated at 70° C. $^1$H NMR (400 MHz, DMSO-d$_6$) δ ppm 10.98 (d, J=5.19 Hz, 1H), 9.22 (s, 1H), 7.82 (s, 1H), 7.74 (t, J=1.68 Hz, 1H), 7.67 (d, J=2.44 Hz, 1H), 7.56 (s, 1H), 7.44-7.52 (m, 1H), 7.34 (dd, J=8.54, 2.14 Hz, 1H), 7.19-7.27 (m, 1H), 7.08-7.17 (m, 1H), 6.87-6.93 (m, 1H), 6.84 (d, J=8.24 Hz, 1H), 6.60-6.67 (m, 2H), 4.15-4.22 (m, 2H), 4.06-4.13 (m, 5H). MS (ESI+) m/z 461.9 (M+H)$^+$.

Example 128

3-[5-{[(2-cyclopentylethyl)amino]methyl}-2-(2,4-difluorophenoxy)phenyl]-1-methyl-1,6-dihydro-7H-pyrrolo[2,3-c]pyridin-7-one

Example 128A 2-cyclopentyl-N-(4-(2,4-difluorophenoxy)-3-(7-methoxy-1-methyl-1H-pyrrolo[2,3-c]pyridin-3-yl)benzyl)ethanamine Example 128A was prepared according to the procedure used for the preparation of Example 119A, substituting 2-cyclopentylethanamine hydrochloride for 1H-imidazol-4-ylmethylamine dihydrochloride.

Example 128B

3-[5-{[(2-cyclopentylethyl)amino]methyl}-2-(2,4-difluorophenoxy)phenyl]-1-methyl-1,6-dihydro-7H-pyrrolo[2,3-c]pyridin-7-one The TFA salt of Example 128B was prepared according to the procedure used for the preparation of Example 1C, substituting Example 128A for Example 1B, and with the exception that the reaction mixture was heated at 70° C. $^1$H NMR (400 MHz, DMSO-d$_6$) δ ppm 10.99 (d, J=5.19 Hz, 1H), 8.77 (s, 1H), 7.68 (d, J=2.14 Hz, 1H), 7.54-7.57 (m, 1H), 7.44-7.52 (m, 1H), 7.35 (dd, J=8.54, 2.14 Hz, 1H), 7.19-7.27 (m, 1H), 7.08-7.16 (m, 1H), 6.88-6.93 (m, 1H), 6.85 (d, J=8.54 Hz, 1H), 6.63 (d, J=7.02 Hz, 1H), 4.18 (t, J=5.65 Hz, 2H), 4.11 (s, 3H), 2.91-3.01 (m, 2H), 1.69-1.83 (m, 3H), 1.43-1.67 (m, 6H), 1.02-1.14 (m, 2H). MS (ESI+) m/z 477.9 (M+H)+.

Example 129

3-[2-(2,4-difluorophenoxy)-5-{[4-(trifluoromethyl)piperidin-1-yl]methyl]phenyl}-1-methyl-1,6-dihydro-7H-pyrrolo[2,3-c]pyridin-7-one

Example 129A 3-(2-(2,4-difluorophenoxy)-5-((4-(trifluoromethyl)piperidin-1-yl)methyl)phenyl)-7-methoxy-1-methyl-1H-pyrrolo[2,3-c]pyridine Example 129A was prepared according to the procedure used for the preparation of Example 119A, substituting 4-(trifluoromethyl)piperidine hydrochloride for 1H-imidazol-4-ylmethylamine dihydrochloride.

Example 129B

3-[2-(2,4-difluorophenoxy)-5-{[4-(trifluoromethyl)piperidin-1-yl]methyl]phenyl}-1-methyl-1,6-dihydro-7H-pyrrolo[2,3-c]pyridin-7-one The TFA salt of Example 129B was prepared according to the procedure used for the preparation of Example 1C, substituting Example 129A for Example 1B, and with the exception that the reaction mixture was heated at 70° C. $^1$H NMR (400 MHz, DMSO-$d_6$) δ ppm 10.99 (d, J=5.49 Hz, 1H), 7.68 (d, J=1.83 Hz, 1H), 7.58 (s, 1H), 7.46-7.54 (m, 1H), 7.36 (dd, J=8.24, 2.14 Hz, 1H), 7.24-7.32 (m, 1H), 7.10-7.17 (m, 1H), 6.89-6.94 (m, 1H), 6.86 (d, J=8.54 Hz, 1H), 6.60 (d, J=6.71 Hz, 1H), 4.35 (s, 2H), 4.11 (s, 3H), 3.52 (d, J=12.51 Hz, 2H), 3.00 (s, 2H), 2.61-2.75 (m, 1H), 2.06 (d, J=13.12 Hz, 2H), 1.64-1.80 (m, 2H). MS (ESI+) m/z 517.9 (M+H)+.

Example 130

N-[4-(2,4-difluorophenoxy)-3-(1-methyl-7-oxo-6,7-dihydro-1H-pyrrolo[2,3-c]pyridin-3-yl)benzyl]-2-methoxybenzenesulfonamide

Example 130A

N-(4-(2,4-difluorophenoxy)-3-(7-methoxy-1-methyl-1H-pyrrolo[2,3-c]pyridin-3-yl)benzyl)-2-methoxy-benzenesulfonamide A solution of Example 106B (70 mg, 0.177 mmol) in dichloromethane (2.5 mL) was treated with 2-methoxybenzene-1-sulfonyl chloride (43.9 mg, 0.212 mmol) and triethylamine (0.049 mL, 0.354 mmol). The reaction mixture was stirred for 1 hour at ambient temperature and then partitioned between 50% aqueous saturated sodium chloride (50 mL) and ethyl acetate (50 mL). The organic layer was dried over anhydrous sodium sulfate, filtered, and concentrated to provide the title compound (104 mg, 100% yield).

Example 130B

N-[4-(2,4-difluorophenoxy)-3-(1-methyl-7-oxo-6,7-dihydro-1H-pyrrolo[2,3-c]pyridin-3-yl)benzyl]-2-methoxybenzenesulfonamide Example 130B was prepared according to the procedure used for the preparation of Example 1C, substituting Example 130A for Example 1B, and with the exception that the reaction mixture was heated at 70° C. $^1$H NMR (400 MHz, DMSO-$d_6$) δ ppm 10.92 (d, J=5.19 Hz, 1H), 7.81 (t, J=6.26 Hz, 1H), 7.68 (dd, J=7.78, 1.68 Hz, 1H), 7.48-7.55 (m, 1H), 7.38-7.45 (m, 2H), 7.32 (d, J=2.14 Hz, 1H), 6.94-7.11 (m, 5H), 6.85-6.90 (m, 1H), 6.65 (d, J=8.24 Hz, 1H), 6.50 (d, J=7.02 Hz, 1H), 4.09 (s, 3H), 4.06 (d, J=6.10 Hz, 2H), 3.76 (s, 3H). MS (ESI+) m/z 552.1 (M+H)+.

Example 131

1-(4-chlorophenyl)-N-[4-(2,4-difluorophenoxy)-3-(1-methyl-7-oxo-6,7-dihydro-1H-pyrrolo[2,3-c]pyridin-3-yl)benzyl]methanesulfonamide

Example 131A 1-(4-chlorophenyl)-N-(4-(2,4-difluorophenoxy)-3-(7-methoxy-1-methyl-1H-pyrrolo[2,3-c]pyridin-3-yl)benzyl)methanesulfonamide Example 131A was prepared according to the procedure used for the preparation of Example 130A, substituting (4-chlorophenyl)methanesulfonyl chloride for 2-methoxybenzene-1-sulfonyl chloride.

Example 131B 1-(4-chlorophenyl)-N-[4-(2,4-difluorophenoxy)-3-(1-methyl-7-oxo-6,7-dihydro-1H-pyrrolo[2,3-c]pyridin-3-yl)benzyl]methanesulfonamide Example 131B was prepared according to the procedure used for the preparation of Example 1C, substituting Example 131A for Example 1B, and with the exception that the reaction mixture was heated at 70° C. $^1$H NMR (400 MHz, DMSO-$d_6$) δ ppm 10.93 (d, J=5.19 Hz, 1H), 7.69 (s, 1H), 7.50 (s, 1H), 7.39-7.49 (m, 4H), 7.32-7.39 (m, 2H), 7.10-7.21 (m, 2H), 7.02-7.09 (m, 1H), 6.84-6.90 (m, 1H), 6.80 (d, J=8.24 Hz, 1H), 6.56 (d, J=7.02 Hz, 1H), 4.36 (s, 2H), 4.14 (s, 2H), 4.10 (s, 3H). MS (ESI+) m/z 570.3 (M+H)+.

Example 132

N-[4-(2,4-difluorophenoxy)-3-(1-methyl-7-oxo-6,7-dihydro-1H-pyrrolo[2,3-c]pyridin-3-yl)benzyl]-1-(4-methylphenyl)methanesulfonamide

Example 132A

N-(4-(2,4-difluorophenoxy)-3-(7-methoxy-1-methyl-1H-pyrrolo[2,3-c]pyridin-3-yl)benzyl)-1-(p-tolyl)methanesulfonamide Example 132A was prepared according to the procedure used for the preparation of Example 130A, substituting p-tolylmethanesulfonyl chloride for 2-methoxybenzene-1-sulfonyl chloride.

Example 132B

N-[4-(2,4-difluorophenoxy)-3-(1-methyl-7-oxo-6,7-dihydro-1H-pyrrolo[2,3-c]pyridin-3-yl)benzyl]-1-(4-methylphenyl)methanesulfonamide Example 132B was prepared according to the procedure used for the preparation of Example 1C, substituting Example 132A for Example 1B, with the exception that the reaction mixture was heated at 70° C. $^1$H NMR (400 MHz, DMSO-$d_6$) δ ppm 10.93 (d, J=5.49 Hz, 1H), 7.61 (t, J=6.26 Hz, 1H), 7.50 (s, 1H), 7.39-7.48 (m, 2H), 7.09-7.24 (m, 6H), 7.02-7.09 (m, 1H), 6.84-6.90 (m, 1H), 6.80 (d, J=8.24 Hz, 1H), 6.57 (d, J=6.71 Hz, 1H), 4.27 (s, 2H), 4.06-4.14 (m, 5H), 2.29 (s, 3H). MS (ESI+) m/z 550.2 (M+H)$^+$.

Example 133

N-[4-(2,4-difluorophenoxy)-3-(1-methyl-7-oxo-6,7-dihydro-1H-pyrrolo[2,3-c]pyridin-3-yl)benzyl]-1-[4-(trifluoromethyl)phenyl]methanesulfonamide Example 133A N-(4-(2,4-difluorophenoxy)-3-(7-methoxy-1-methyl-1H-pyrrolo[2,3-c]pyridin-3-yl)benzyl)-1-(4-(trifluoromethyl)phenyl)methanesulfonamide Example 133A was prepared according to the procedure used for the preparation of Example 130A, substituting (4-(trifluoromethyl)phenyl)methanesulfonyl chloride for 2-methoxybenzene-1-sulfonyl chloride.

Example 133B

N-[4-(2,4-difluorophenoxy)-3-(1-methyl-7-oxo-6,7-dihydro-1H-pyrrolo[2,3-c]pyridin-3-yl)benzyl]-1-[4-(trifluoromethyl)phenyl]methanesulfonamide Example 133B was prepared according to the procedure used for the preparation of Example 1C, substituting Example 133A for Example 1B, and with the exception that the reaction mixture was heated at 70° C. $^1$H NMR (400 MHz, DMSO-$d_6$) δ ppm 10.93 (d, J=5.49 Hz, 1H), 7.70-7.79 (m, 3H), 7.57 (d, J=8.24 Hz, 2H), 7.51 (s, 1H), 7.48 (d, J=2.14 Hz, 1H), 7.40-7.47 (m, 1H), 7.10-7.21 (m, 2H), 7.03-7.10 (m, 1H), 6.85-6.89 (m, 1H), 6.80 (d, J=8.24 Hz, 1H), 6.57 (d, J=7.02 Hz, 1H), 4.49 (s, 2H), 4.18 (d, J=6.10 Hz, 2H), 4.09 (s, 3H). MS (ESI+) m/z 604.2 (M+H)$^+$.

Example 134

1-(4-cyanophenyl)-N-[4-(2,4-difluorophenoxy)-3-(1-methyl-7-oxo-6,7-dihydro-1H-pyrrolo[2,3-c]pyridin-3-yl)benzyl]methanesulfonamide Example 134A 1-(4-cyanophenyl)-N-(4-(2,4-difluorophenoxy)-3-(7-methoxy-1-methyl-1H-pyrrolo[2,3-c]pyridin-3-yl)benzyl)methanesulfonamide Example 134A was prepared according to the procedure used for the preparation of Example 130A, substituting (4-cyanophenyl)methanesulfonyl chloride for 2-methoxybenzene-1-sulfonyl chloride.

Example 134B 1-(4-cyanophenyl)-N-[4-(2,4-difluorophenoxy)-3-(1-methyl-7-oxo-6,7-dihydro-1H-pyrrolo[2,3-c]pyridin-3-yl)benzyl]methanesulfonamide Example 134B was prepared according to the procedure used for the preparation of Example 1C, substituting Example 134A for Example 1B, and with the exception that the reaction mixture was heated at 70° C. $^1$H NMR (400 MHz, DMSO-$d_6$) δ ppm 10.94 (d, J=5.49 Hz, 1H), 7.83 (d, J=8.24 Hz, 2H), 7.78 (t, J=6.10 Hz, 1H), 7.55 (d, J=8.24 Hz, 2H), 7.51 (s, 1H), 7.39-7.49 (m, 2H), 7.10-7.22 (m, 2H), 7.02-7.10 (m, 1H), 6.84-6.91 (m, 1H), 6.80 (d, J=8.54 Hz, 1H), 6.56 (d, J=6.71 Hz, 1H), 4.50 (s, 2H), 4.16 (d, J=6.10 Hz, 2H), 4.10 (s, 3H). MS (ESI+) m/z 561.3 (M+H)$^+$.

Example 135

N-[4-(2,4-difluorophenoxy)-3-(1-methyl-7-oxo-6,7-dihydro-1H-pyrrolo[2,3-c]pyridin-3-yl)benzyl]-2,2,2-trifluoroethanesulfonamide Example 135A N-(4-(2,4-difluorophenoxy)-3-(7-methoxy-1-methyl-1H-pyrrolo[2,3-c]pyridin-3-yl)benzyl)-2,2,2-trifluoroethanesulfonamide Example 135A was prepared according to the procedure used for the preparation of Example 130A, substituting 2,2,2-trifluoroethanesulfonyl chloride for 2-methoxybenzene-1-sulfonyl chloride.

Example 135B

N-[4-(2,4-difluorophenoxy)-3-(1-methyl-7-oxo-6,7-dihydro-1H-pyrrolo[2,3-c]pyridin-3-yl)benzyl]-2,2,2-trifluoroethanesulfonamide Example 135B was prepared according to the procedure used for the preparation of Example 1C, substituting Example 135A for Example 1B, and with the exception that the reaction mixture was heated at 70° C. $^1$H NMR (400 MHz, DMSO-$d_6$) δ ppm 10.93 (d, J=5.19 Hz, 1H), 8.32 (s, 1H), 7.48-7.53 (m, 2H), 7.38-7.48 (m, 1H), 7.21 (dd, J=8.24, 2.14 Hz, 1H), 7.10-7.18 (m, 1H), 7.03-7.10 (m, 1H), 6.85-6.92 (m, 1H), 6.81 (d, J=8.24 Hz, 1H), 6.57 (d, J=6.71 Hz, 1H), 4.42 (q, J=9.87 Hz, 2H), 4.23 (s, 2H), 4.10 (s, 3H). MS (ESI+) m/z 528.1 (M+H)$^+$.

Example 136

3-[5-(aminomethyl)-2-(2,4-difluorophenoxy)phenyl]-1-methyl-1,6-dihydro-7H-pyrrolo[2,3-c]pyridin-7-one Example 136A N-(4-(2,4-difluorophenoxy)-3-(7-methoxy-1-methyl-1H-pyrrolo[2,3-c]pyridin-3-yl)benzyl)propane-2-sulfonamide Example 136A was prepared according to the procedure used for the preparation of Example 130A, substituting propane-2-sulfonyl chloride for 2-methoxybenzene-1-sulfonyl chloride to provide the title compound as a mixture with unreacted starting material.

Example 136B

3-[5-(aminomethyl)-2-(2,4-difluorophenoxy)phenyl]-1-methyl-1,6-dihydro-7H-pyrrolo[2,3-c]pyridin-7-one Example 136B was prepared according to the procedure used for the preparation of Example 1C, substituting Example 136A for Example 1B, with the exception that the reaction mixture was heated at 70° C. $^1$H NMR (400 MHz, DMSO-$d_6$) δ ppm 10.98 (d, J=5.19 Hz, 1H), 8.20 (s, 2H), 7.64 (d, J=2.14 Hz, 1H), 7.54 (s, 1H), 7.43-7.50 (m, 1H), 7.32 (dd, J=8.54, 2.14 Hz, 1H), 7.16-7.24 (m, 1H), 7.07-7.15 (m, 1H), 6.87-6.93 (m, 1H), 6.84 (d, J=8.54 Hz, 1H), 6.65 (d, J=6.71 Hz, 1H), 4.11 (s, 3H), 4.06 (d, J=5.49 Hz, 2H). MS (ESI+) m/z 382.1 (M+H)$^+$.

Example 137

N-[4-(2,4-difluorophenoxy)-3-(1-methyl-7-oxo-6,7-dihydro-1H-pyrrolo[2,3-c]pyridin-3-yl)benzyl]cyclopentanesulfonamide

Example 137A

N-(4-(2,4-difluorophenoxy)-3-(7-methoxy-1-methyl-1H-pyrrolo[2,3-c]pyridin-3-yl)benzyl)cyclopentanesulfonamide Example 137A was prepared according to the procedure used for the preparation of Example 130A, substituting cyclopentanesulfonyl chloride for 2-methoxybenzene-1-sulfonyl chloride.

Example 137B

N-[4-(2,4-difluorophenoxy)-3-(1-methyl-7-oxo-6,7-dihydro-1H-pyrrolo[2,3-c]pyridin-3-yl)benzyl]cyclopentanesulfonamide Example 137B was prepared according to the procedure used for the preparation of Example 1C, substituting Example 137A for Example 1B, and with the exception that the reaction mixture was heated at 70° C. $^1$H NMR (400 MHz, DMSO-$d_6$) δ ppm 10.93 (d, J=5.19 Hz, 1H), 7.58 (t, J=6.26 Hz, 1H), 7.48-7.53 (m, 2H), 7.39-7.47 (m, 1H), 7.21 (dd, J=8.54, 2.14 Hz, 1H), 7.01-7.16 (m, 2H), 6.85-6.91 (m, 1H), 6.81 (d, J=8.54 Hz, 1H), 6.57 (d, J=6.71 Hz, 1H), 4.19 (d, J=6.41 Hz, 2H), 4.09 (s, 3H), 3.39-3.50 (m, 1H), 1.81-1.89 (m, 4H), 1.59-1.71 (m, 2H), 1.48-1.58 (m, 2H). MS (ESI+) m/z 514.2 (M+H)$^+$.

Example 138

2,5-dichloro-N-[4-(2,4-difluorophenoxy)-3-(1-methyl-7-oxo-6,7-dihydro-1H-pyrrolo[2,3-c]pyridin-3-yl)benzyl]thiophene-3-sulfonamide

Example 138A 2,5-dichloro-N-(4-(2,4-difluorophenoxy)-3-(7-methoxy-1-methyl-1H-pyrrolo[2,3-c]pyridin-3-yl)benzyl)thiophene-3-sulfonamide Example 138A was prepared according to the procedure used for the preparation of Example 130A, substituting 2,5-dichlorothiophene-3-sulfonyl chloride for 2-methoxybenzene-1-sulfonyl chloride.

Example 138B 2,5-dichloro-N-[4-(2,4-difluorophenoxy)-3-(1-methyl-7-oxo-6,7-dihydro-1H-pyrrolo[2,3-c]pyridin-3-yl)benzyl]thiophene-3-sulfonamide Example 138B was prepared according to the procedure used for the preparation of Example 1C, substituting Example 138A for Example 1B, and with the exception that the reaction mixture was heated at 70° C. $^1$H NMR (400 MHz, DMSO-$d_6$) δ ppm 10.93 (d, J=5.19 Hz, 1H), 8.56-8.79 (m, 1H), 7.39-7.50 (m, 2H), 7.37 (d, J=2.14 Hz, 1H), 7.14-7.18 (m, 1H), 7.03-7.13 (m, 3H), 6.85-6.93 (m, 1H), 6.71 (d, J=8.55 Hz, 1H), 6.54 (d, J=7.02 Hz, 1H), 4.20 (s, 2H), 4.10 (s, 3H). MS (ESI+) m/z 596.2 (M+H)$^+$.

Example 139

N-[4-(2,4-difluorophenoxy)-3-(1-methyl-7-oxo-6,7-dihydro-1H-pyrrolo[2,3-c]pyridin-3-yl)benzyl]-5-methyl-1,2-oxazole-4-sulfonamide

Example 139A

N-(4-(2,4-difluorophenoxy)-3-(7-methoxy-1-methyl-1H-pyrrolo[2,3-c]pyridin-3-yl)benzyl)-5-methylisoxazole-4-sulfonamide Example 139A was prepared according to the procedure used for the preparation of Example 130A, substituting 5-methylisoxazole-4-sulfonyl chloride for 2-methoxybenzene-1-sulfonyl chloride.

Example 139B

N-[4-(2,4-difluorophenoxy)-3-(1-methyl-7-oxo-6,7-dihydro-1H-pyrrolo[2,3-c]pyridin-3-yl)benzyl]-5-methyl-1,2-oxazole-4-sulfonamide Example 139B was prepared according to the procedure used for the preparation of Example 1C, substituting Example 139A for Example 1B, and with the exception that the reaction mixture was heated at 70° C. $^1$H NMR (400 MHz, pyridine-$d_5$) δ ppm 7.95 (d, J=2.14 Hz, 1H), 7.59 (s, 2H), 7.48 (dd, 1H), 7.06-7.19 (m, 3H), 6.87-6.98 (m, 3H), 5.57 (s, 2H), 4.63 (s, 2H), 4.16-4.22 (m, 3H), 2.44-2.53 (m, 3H). MS (ESI+) m/z 526.9 (M+H)$^+$.

Example 140

N-[4-(2,4-difluorophenoxy)-3-(1-methyl-7-oxo-6,7-dihydro-1H-pyrrolo[2,3-c]pyridin-3-yl)benzyl]-3,5-dimethyl-1,2-oxazole-4-sulfonamide

Example 140A

N-(4-(2,4-difluorophenoxy)-3-(7-methoxy-1-methyl-1H-pyrrolo[2,3-c]pyridin-3-yl)benzyl)-3,5-dimethylisoxazole-4-sulfonamide Example 140A was prepared according to the procedure used for the preparation of Example 130A, substituting 3,5-dimethylisoxazole-4-sulfonyl chloride for 2-methoxybenzene-1-sulfonyl chloride.

Example 140B

N-[4-(2,4-difluorophenoxy)-3-(1-methyl-7-oxo-6,7-dihydro-1H-pyrrolo[2,3-c]pyridin-3-yl)benzyl]-3,5-dimethyl-1,2-oxazole-4-sulfonamide Example 140B was prepared according to the procedure used for the preparation of Example 1C, substituting Example 140A for Example 1B, and with the exception that the reaction mixture was heated at 70° C. $^1$H NMR (400 MHz, DMSO-d$_6$) δ ppm 10.93 (d, J=5.19 Hz, 1H), 8.47 (s, 1H), 7.37-7.49 (m, 3H), 7.12 (dd, J=8.24, 2.14 Hz, 1H), 7.01-7.09 (m, 2H), 6.85-6.92 (m, 1H), 6.75 (d, J=8.24 Hz, 1H), 6.52 (d, J=6.71 Hz, 1H), 4.05-4.14 (m, 5H), 2.51 (s, 3H), 2.28 (s, 3H). MS (ESI+) m/z 541.1 (M+H)$^+$.

Example 141

N-[4-(2,4-difluorophenoxy)-3-(1-methyl-7-oxo-6,7-dihydro-1H-pyrrolo[2,3-c]pyridin-3-yl)benzyl]benzenesulfonamide

Example 141A

N-(4-(2,4-difluorophenoxy)-3-(7-methoxy-1-methyl-1H-pyrrolo[2,3-c]pyridin-3-yl)benzyl)benzenesulfonamide Example 141A was prepared according to the procedure used for the preparation of Example 130A, substituting benzenesulfonyl chloride for 2-methoxybenzene-1-sulfonyl chloride.

Example 141B

N-[4-(2,4-difluorophenoxy)-3-(1-methyl-7-oxo-6,7-dihydro-1H-pyrrolo[2,3-c]pyridin-3-yl)benzyl]benzenesulfonamide Example 141B was prepared according to the procedure used for the preparation of Example 1C, substituting Example 141A for Example 1B, and with the exception that the reaction mixture was heated at 70° C. $^1$H NMR (400 MHz, DMSO-d$_6$) δ ppm 10.93 (d, J=5.19 Hz, 1H), 8.20 (s, 1H), 7.76-7.81 (m, 2H), 7.58-7.64 (m, 1H), 7.55 (t, J=7.32 Hz, 2H), 7.39-7.46 (m, 2H), 7.36 (d, J=2.14 Hz, 1H), 7.01-7.11 (m, 3H), 6.85-6.91 (m, 1H), 6.72 (d, J=8.24 Hz, 1H), 6.50 (d, J=7.02 Hz, 1H), 4.09 (s, 3H), 4.03 (s, 2H). MS (ESI+) m/z 522.2 (M+H)$^+$.

Example 142

3-{2-[(cyclopropylmethyl)amino]phenyl}-1-methyl-1,6-dihydro-7H-pyrrolo[2,3-c]pyridin-7-one

Example 142A 2-bromo-N-(cyclopropylmethyl)aniline

Example 142A was prepared as described in Example 111A substituting cyclopropanecarbaldehyde for Example 105B and 2-bromoaniline for tert-butyl piperidin-4-ylcarbamate. The isolated product was purified by flash chromatography (silica gel, 0-10% ethyl acetate in heptane) to give the title compound.

Example 142B

N-(cyclopropylmethyl)-2-(7-methoxy-1-methyl-1H-pyrrolo[2,3-c]pyridin-3-yl)aniline Example 142B was prepared as described in Example 11E substituting Example 142A for Example 11C, and with the exception that the reaction mixture was heated at 75° C. for 18 hours. The isolated product was purified by flash chromatography (silica gel, 0-5% methanol in methylene chloride) to give the title compound.

Example 142C

3-{2-[(cyclopropylmethyl)amino]phenyl}-1-methyl-1,6-dihydro-7H-pyrrolo[2,3-c]pyridin-7-one Example 142C was prepared according to the procedure used for the preparation of Example 1C, substituting Example 142B for Example 1B, and with the exception that the reaction mixture was heated at 70° C. The material was purified by flash chromatography (silica gel, 1-7.5% methanol in dichloromethane) to provide the title compound. $^1$H NMR (400 MHz, DMSO-d$_6$) δ ppm 10.99 (d, J=3.66 Hz, 1H) 7.56 (s, 1H) 7.34 (t, J=7.17 Hz, 1H) 7.23 (d, J=7.02 Hz, 2H) 7.11 (s, 1H) 6.85-6.92 (m, 1H) 6.17 (d, J=6.71 Hz, 1H) 4.12 (s, 3H) 3.69 (s, 1H) 2.99 (d, J=7.02 Hz, 2H) 0.89-1.00 (m, 1H) 0.37-0.45 (m, 2H) 0.11-0.18 (m, 2H). MS (ESI+) m/z 294.0 (M+H)$^+$.

Example 143

3-{2-chloro-5-[(methylsulfonyl)methyl]pyridin-3-yl}-1-methyl-1,6-dihydro-7H-pyrrolo[2,3-c]pyridin-7-one

Example 143A 3-bromo-5-(bromomethyl)-2-chloropyridine

3-Bromo-2-chloro-5-methylpyridine (4 g, 19.37 mmol), N-bromosuccinimide (3.79 g, 21.3 mmol) and benzoic peroxyanhydride (0.239 g, 0.969 mmol) were combined in carbon tetrachloride (40 mL), heated under reflux for 24 hours, cooled, and filtered to remove succinimide. The filtrate was concentrated. The resulting residue was purified by chromatography (silica gel, 0-30% ethyl acetate in heptanes) to afford the title compound (1.9 g, 34%).

Example 143B 3-bromo-2-chloro-5-((methylsulfonyl)methyl)pyridine

Sodium methanesulfinate (0.748 g, 7.32 mmol) and the product from Example 143A (1.9 g, 6.66 mmol) were combined in N,N-dimethylformamide (4.44 mL) and heated at 65° C. for 1 hour. The reaction mixture was cooled and diluted with 200 mL of cold water producing a precipitate that was collected by filtration and dried to constant mass affording the title compound (1.6 g, 84%).

Example 143C 3-(2-chloro-5-((methylsulfonyl)methyl)pyridin-3-yl)-7-methoxy-1-methyl-1H-pyrrolo[2,3-c]pyridine Example 143B (0.569 g, 2.0 mmol), Example 59A (0.576 g, 2.000 mmol), tris(dibenzylideneacetone)dipalladium (0) (0.055 g, 0.060 mmol), 1,3,5,7-tetramethyl-6-phenyl-2,4,8-trioxa-6-phosphaadamantane (0.058 g, 0.200 mmol) and potassium phosphate (1.486 g, 7.00 mmol) were combined and sparged with argon for 15 minutes. Meanwhile a solution of 4:1 dioxane/water (26 mL) was sparged with nitrogen for 15 minutes and transferred by syringe into the reaction vessel under argon. The mixture was stirred for 3 hours at 60° C., cooled, and partitioned between ethyl acetate and water. The organic layer was washed with saturated aqueous sodium chloride, dried over anhydrous sodium sulfate, treated with 3-mercaptopropyl functionalized silica for 30 minutes, filtered and concentrated. Purification by chromatography (silica gel, 1-4% methanol in dichloromethane) afforded the title compound (0.56 g, 77%).

Example 143D

3-{2-chloro-5-[(methylsulfonyl)methyl]pyridin-3-yl}-1-methyl-1,6-dihydro-7H-pyrrolo[2,3-c]pyridin-7-one Example 143C (0.055 g, 0.150 mmol) and 4 M hydrogen chloride in dioxane (5 mL, 20.00 mmol) were combined and heated at 85° C. for 20 hours. The mixture was cooled and concentrated. Purification by trituration in 9:1 heptanes/ethyl acetate afforded the title compound (0.05 g, 95%). $^1$H NMR (300 MHz, DMSO-$d_6$) δ 11.04 (d, J=5.43 Hz, 1H) 8.35 (d, J=2.03 Hz, 1H) 7.94 (d, J=2.37 Hz, 1H) 7.68 (s, 1H) 6.89-6.97 (m, 1H) 6.39 (d, J=6.44 Hz, 1H) 4.65 (s, 2H) 4.14 (s, 3H) 3.01 (s, 3H). MS (ESI+) m/z 352 (M+H)$^+$.

Example 144

3-[2-{[trans-4-(dimethylamino)cyclohexyl]oxy}-5-(pyrrolidin-1-ylsulfonyl)phenyl]-1-methyl-1,6-dihydro-7H-pyrrolo[2,3-c]pyridin-7-one

Example 144A

1((3-bromo-4-fluorophenyl)sulfonyl)pyrrolidine

To a solution of 3-bromo-4-fluorobenzene-1-sulfonyl chloride (0.83 g, 2.73 mmol) in tetrahydrofuran (10 mL) under argon was added diisopropylethylamine (0.525 mL, 3.00 mmol) followed by pyrrolidine (0.183 mL, 2.73 mmol). The reaction mixture was stirred at ambient temperature for 2 hours. The reaction mixture was partitioned between diethyl ether and aqueous ammonium chloride. The organic layer was separated, dried over anhydrous magnesium sulfate, filtered, and concentrated. The resulting residue was triturated with diethyl ether/heptane at −20° C. to provide the title compound (0.56 g, 67% yield).

Example 144B (trans)-4-(2-bromo-4-(pyrrolidin-1-ylsulfonyl)phenoxy)-N,N-dimethylcyclohexanamine To (trans)-4-(dimethylamino)cyclohexanol (0.290 g, 1.95 mmol) in dioxane (12 mL) stirring at ambient temperature under argon was added sodium hydride (0.161 g, 4.02 mmol, 60% oil dispersion). The mixture was stirred for 15 minutes and then Example 144A (0.40 g, 1.298 mmol) was added as a solid in one portion. The mixture was heated at 75° C. for 7 hours and then at 95° C. overnight. The mixture was cooled to ambient temperature and partitioned between saturated aqueous sodium chloride and ethyl acetate. The organic phase was dried over anhydrous magnesium sulfate, filtered, and concentrated. The residue was purified by flash chromatography (silica gel, dichloroethane/5-10% methanol gradient) to provide the title compound (0.12 g, 21% yield).

Example 144C (trans)-4-(2-(7-methoxy-1-methyl-1H-pyrrolo[2,3-c]pyridin-3-yl)-4-(pyrrolidin-1-ylsulfonyl)phenoxy)-N,N-dimethylcyclohexanamine A mixture of Example 144B (60 mg, 0.14 mmol) and Example 59A (40.1 mg, 0.14 mmol) was degassed under argon. To this mixture was added dioxane (8 mL) followed by degassing with argon. To this mixture was added potassium phosphate, dibasic (109 mg, 0.626 mmol) and water (2.000 mL) followed by degassing with argon. To this mixture was added 1,3,5,7-tetramethyl-6-phenyl-2,4,8-trioxa-6-phosphaadamantane (6.91 mg, 0.024 mmol) and then immediately tris(dibenzylideneacetone)dipalladium (0) (8.92 mg, 9.74 μmol) followed by degassing with argon. The reaction mixture was heated at 100° C. for 1 hour. The mixture was cooled to ambient temperature and partitioned between saturated aqueous sodium chloride and ethyl acetate. The organic phase was dried over anhydrous magnesium sulfate, filtered, and concentrated to provide the title compound (0.042 g, 59% yield)

Example 144D

3-[2-{[trans-4-(dimethylamino)cyclohexyl]oxy}-5-(pyrrolidin-1-ylsulfonyl)phenyl]-1-methyl-1,6-dihydro-7H-pyrrolo[2,3-c]pyridin-7-one To Example 144C (42 mg, 0.082 mmol) stirring under argon was added 4N hydrogen chloride in dioxane (5 mL, 20.00 mmol). The reaction mixture was heated at 70° C. for 3 hours and then cooled to ambient temperature. Diethyl ether (5 mL) was added and the resulting solid was collected by filtration and washed with heptane. The solid was purified by reverse phase HPLC (C18, CH$_3$CN/water (0.1% trifluoroacetic acid), 10-100%) to provide the title compound as the trifluoroacetic acid salt (0.035 g, 70% yield). $^1$H NMR (300 MHz, DMSO-$d_6$) δ 10.96 (d, J=5.5 Hz, 1H), 9.43 (s, 1H), 7.72 (d, J=2.4 Hz, 1H), 7.68 (dd, J=8.6, 2.4 Hz, 1H), 7.55 (s, 1H), 7.36 (d, J=8.9 Hz, 1H), 6.92 (dd, J=7.0, 5.8 Hz, 1H), 6.39-6.35 (m, 1H), 4.52 (m, 1H), 4.11 (s, 3H), 3.28-3.06 (m, 4H), 2.76 (s, 3H), 2.74 (s, 3H), 2.23 (d, J=10.1 Hz, 2H), 2.03 (d, J=11.1 Hz, 2H), 1.73-1.65 (m, 4H), 1.65-1.34 (m, 4H). MS (ESI+) m/z 499.1 (M+H)$^+$.

Example 145

3-{5-fluoro-2-[(4-fluorophenyl)amino]pyridin-3-yl}-1-methyl-1,6-dihydro-7H-pyrrolo[2,3-c]pyridin-7-one

Example 145A 5-fluoro-3-(7-methoxy-1-methyl-1H-pyrrolo[2,3-c]pyridin-3-yl)pyridin-2-amine 3-Bromo-5-fluoropyridin-2-amine (0.25 g, 1.309 mmol), Example 59A (0.377 g, 1.309 mmol), tris(dibenzylideneacetone)dipalladium (0) (0.036 g, 0.039 mmol), 1,3,5,7-tetramethyl-6-phenyl-2,4,8-trioxa-6-phosphaadamantane (0.038 g, 0.131 mmol) and sodium carbonate (0.486 g, 4.58 mmol) were combined and sparged with argon for 15 minutes. Meanwhile a solution of 4:1 dioxane/water (9 mL) was sparged with nitrogen for 15 minutes and transferred by syringe into the reaction vessel under argon. The mixture was stirred for 4 hours at 60° C., cooled and partitioned into water and ethyl acetate. The organic layer was washed with water, saturated aqueous sodium chloride, dried over anhydrous sodium sulfate, treated with 3-mercaptopropyl functionalized silica for 30 minutes, filtered and concentrated. Purification by chromatography (silica gel, 0-3% methanol in dichloromethane) afforded the title compound (0.23 g, 64%).

Example 145B 5-fluoro-N-(4-fluorophenyl)-3-(7-methoxy-1-methyl-1H-pyrrolo[2,3-c]pyridin-3-yl)pyridin-2-amine 1-bromo-4-fluorobenzene (0.129 g, 0.735 mmol), Example 145A (0.1 g, 0.367 mmol), diacetoxypalladium (3.30 mg, 0.015 mmol), dicyclohexyl(2',4',6'-triisopropyl-[1,1'-biphenyl]-2-yl)phosphine (0.014 g, 0.029 mmol) and cesium carbonate (0.239 g, 0.735 mmol) were combined in tert-butanol (0.360 mL)/toluene (1.80 mL) and heated by microwave at 150° C. for 40 minutes. The mixture was cooled and partitioned between ethyl acetate and water. The organic layer was washed with saturated aqueous sodium chloride, dried over anhydrous sodium sulfate, treated with 3-mercaptopropyl functionalized silica for 30 minutes, filtered and concentrated. Purification by chromatography (silica gel, 0-40% ethyl acetate in heptanes) afforded the title compound (0.097 g, 72%).

Example 145C

3-{5-fluoro-2-[(4-fluorophenyl)amino]pyridin-3-yl}-1-methyl-1,6-dihydro-7H-pyrrolo[2,3-c]pyridin-7-one Example 145B (0.097 g, 0.265 mmol) and 4M hydrogen chloride in dioxane (5 mL, 20.00 mmol) were heated at 90° C. for 4 hours, cooled and concentrated. Purification of the residue by trituration in diethyl ether afforded the title compound (0.11 g, 99%). $^1$H NMR (300 MHz, DMSO-$d_6$) δ 10.98 (d, J=5.43 Hz, 1H) 8.07 (d, J=2.71 Hz, 1H) 7.80 (s, 1H) 7.61 (s, 1H) 7.44-7.56 (m, 3H) 7.00-7.08 (m, 2H) 6.84-6.90 (m, 1H) 6.26 (d, J=5.76 Hz, 1H) 4.12 (s, 3H). MS (ESI+) m/z 353 (M+H)$^+$.

Example 146

3-[5-amino-2-(2,4-difluorophenoxy)phenyl]-1-methyl-1,6-dihydro-7H-pyrrolo[2,3-c]pyridin-7-one

Example 146A 3-(2-(2,4-difluorophenoxy)-5-nitrophenyl)-1-methyl-1H-pyrrolo[2,3-c]pyridin-7(6H)-one A solution of Example 2C (1.133 g, 2.75 mmol) in dioxane (35 mL) was treated with 4 N HCl in dioxane (35 mL, 140 mmol) and stirred at 70° C. overnight. The solution was cooled, diluted with 200 mL ethyl acetate, then washed with 200 mL of 1:1 saturated aqueous sodium chloride/sodium bicarbonate and dried over anhydrous sodium sulfate. Filtration and solvent removal provided 1.085 g of the product as a yellow solid.

Example 146B 3-(5-amino-2-(2,4-difluorophenoxy)phenyl)-1-methyl-1H-pyrrolo[2,3-c]pyridin-7(6H)-one Example 146B was prepared according to the procedure used for the preparation of Example 2D, substituting Example 146A for Example 2C. $^1$H NMR (300 MHz, DMSO-$d_6$) δ ppm 10.88 (d, J=5.0 Hz, 1H), 7.36 (s, 1H), 7.29 (m, 1H), 6.93-6.79 (m, 2H), 6.76-6.68 (m, 3H), 6.56-6.46 (m, 2H), 5.04 (s, 2H), 4.03 (s, 3H). MS (ESI+) m/z 368.2 (M+H)$^+$.

Example 147

N-[4-(2,4-difluorophenoxy)-3-(1-methyl-7-oxo-6,7-dihydro-1H-pyrrolo[2,3-c]pyridin-3-yl)phenyl]-4-methylpentanamide A solution of Example 146B and diisopropylethyl amine (0.15 M and 0.44 M in N,N-dimethylacetamide, respectively, 275 μL, 0.04 mmol Example 146 (1.0 equivalent) and 0.12 mmol diisopropylethyl amine (3.0 equivalents)), 0-(7-azabenzotriazol-1-yl)-N,N,N',N'-tetramethyluronium hexafluorophosphate (0.17 M in N,N-dimethylacetamide, 275 μL, 0.048 mmol, 1.2 equivalents), and 4-methylpentanoic acid (0.41 M in N,N-dimethylacetamide, 122 μL, 0.048 mmol, 1.2 eq) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the solution was loaded directly into an injection loop and purified by preparative HPLC on a Phenomenex Luna C8(2) 5 μm 100 Å AXIA column (50 mm×21.2 mm), eluting with a gradient of acetonitrile (A) and 0.1% ammonium acetate in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-$d_6$) δ 7.85 (d, J=2.6 Hz, 1H), 7.51 (s, 1H), 7.46-7.32 (m, 2H), 7.08-6.97 (m, 2H), 6.95 (d, J=7.0 Hz, 1H), 6.85 (d, J=8.7 Hz, 1H), 6.63 (d, J=7.0 Hz, 1H), 4.07 (s, 3H), 2.32 (t, J=7.5 Hz, 2H), 1.61-1.46 (m, 3H), 0.90 (d, J=6.2 Hz, 6H). MS (ESI+) m/z 466.1 (M+H)$^+$.

Example 148

2,5-dichloro-N-[4-(2,4-difluorophenoxy)-3-(1-methyl-7-oxo-6,7-dihydro-1H-pyrrolo[2,3-c]pyridin-3-yl)phenyl]benzamide Example 148 was prepared according to the procedure used for the preparation of Example 147, substituting 2,5-dichlorobenzoic acid for 4-methylpentanoic acid. $^1$H NMR (400 MHz, DMSO-$d_6$) δ 7.94 (d, J=2.6 Hz, 1H), 7.71 (dd, J=2.1, 0.8 Hz, 1H), 7.65-7.54 (m, 4H), 7.39 (ddd, J=11.2, 8.6, 2.8 Hz, 1H), 7.15-7.00 (m, 2H), 6.96 (d, J=7.0 Hz, 1H), 6.91 (d, J=8.8 Hz, 1H), 6.66 (d, J=7.0 Hz, 1H), 4.09 (s, 3H). MS (ESI+) m/z 539.9 (M+H)$^+$.

Example 149

N-[4-(2,4-difluorophenoxy)-3-(1-methyl-7-oxo-6,7-dihydro-1H-pyrrolo[2,3-c]pyridin-3-yl)phenyl]-2-(2-methoxyphenyl)acetamide Example 149 was prepared according to the procedure used for the preparation of Example 147, substituting -(2-methoxyphenyl)acetic acid for 4-methylpentanoic acid. $^1$H NMR (400 MHz, DMSO-$d_6$) δ 7.88 (d, J=2.6 Hz, 1H), 7.52 (s, 1H), 7.43 (dd, J=8.8, 2.6 Hz, 1H), 7.36 (ddd, J=11.2, 8.5, 2.8 Hz, 1H), 7.30-7.19 (m, 2H), 7.09-6.95 (m, 3H), 6.97-6.87 (m, 2H), 6.85 (d, J=8.7 Hz, 1H), 6.62 (d, J=7.0 Hz, 1H), 4.07 (s, 3H), 3.86 (m, 2H), 3.77 (s, 3H). MS (ESI+) m/z 516.1 (M+H)$^+$.

Example 150

N-[4-(2,4-difluorophenoxy)-3-(1-methyl-7-oxo-6,7-dihydro-1H-pyrrolo[2,3-c]pyridin-3-yl)phenyl]pyridine-2-carboxamide Example 150 was prepared according to the procedure used for the preparation of Example 147, substituting pyridine-2-carboxylic acid for 4-methylpentanoic acid. $^1$H NMR (400 MHz, DMSO-d$_6$) δ 8.76 (ddd, J=4.7, 1.7, 0.9 Hz, 1H), 8.20-8.12 (m, 2H), 8.08 (td, J=7.6, 1.7 Hz, 1H), 7.74 (dd, J=8.8, 2.6 Hz, 1H), 7.69 (ddd, J=7.5, 4.7, 1.3 Hz, 1H), 7.57 (s, 1H), 7.39 (ddd, J=11.2, 8.6, 2.8 Hz, 1H), 7.16-7.00 (m, 2H), 6.97 (d, J=7.0 Hz, 1H), 6.90 (d, J=8.8 Hz, 1H), 6.74 (d, J=7.0 Hz, 1H), 4.10 (s, 3H). MS (ESI+) m/z 473.1 (M+H)$^+$.

Example 151

N-[4-(2,4-difluorophenoxy)-3-(1-methyl-7-oxo-6,7-dihydro-1H-pyrrolo[2,3-c]pyridin-3-yl)phenyl]-5-methylpyrazine-2-carboxamide Example 151 was prepared according to the procedure used for the preparation of Example 147, substituting 5-methylpyrazine-2-carboxylic acid for 4-methylpentanoic acid. $^1$H NMR (400 MHz, DMSO-d$_6$) δ 9.16 (d, J=1.4 Hz, 1H), 8.70 (d, J=1.4 Hz, 1H), 8.12 (d, J=2.6 Hz, 1H), 7.73 (dd, J=8.8, 2.6 Hz, 1H), 7.57 (s, 1H), 7.39 (ddd, J=11.2, 8.6, 2.8 Hz, 1H), 7.17-7.00 (m, 2H), 6.97 (d, J=7.0 Hz, 1H), 6.89 (d, J=8.8 Hz, 1H), 6.74 (d, J=7.0 Hz, 1H), 4.09 (s, 3H), 2.64 (s, 3H). MS (ESI+) m/z 487.8 (M+H)$^+$.

Example 152

N-[4-(2,4-difluorophenoxy)-3-(1-methyl-7-oxo-6,7-dihydro-1H-pyrrolo[2,3-c]pyridin-3-yl)phenyl]-3-phenylpropanamide Example 152 was prepared according to the procedure used for the preparation of Example 147, substituting 3-phenylpropionic acid for 4-methylpentanoic acid. $^1$H NMR (400 MHz, DMSO-d$_6$) δ 7.83 (d, J=2.6 Hz, 1H), 7.51 (s, 1H), 7.44-7.16 (m, 7H), 7.08-6.97 (m, 2H), 6.95 (d, J=7.0 Hz, 1H), 6.84 (d, J=8.7 Hz, 1H), 6.62 (d, J=7.0 Hz, 1H), 4.07 (s, 3H), 2.93 (t, J=7.6 Hz, 2H), 2.64 (t, J=7.6 Hz, 2H). MS (ESI+) m/z 500.1 (M+H)$^+$.

Example 153

N-[4-(2,4-difluorophenoxy)-3-(1-methyl-7-oxo-6,7-dihydro-1H-pyrrolo[2,3-c]pyridin-3-yl)phenyl]-4-phenoxybutanamide Example 153 was prepared according to the procedure used for the preparation of Example 147, substituting 4-phenoxybutanoic acid for 4-methylpentanoic acid. $^1$H NMR (400 MHz, DMSO-d$_6$) δ 7.85 (d, J=2.6 Hz, 1H), 7.51 (s, 1H), 7.48-7.31 (m, 2H), 7.32-7.25 (m, 2H), 7.10-6.88 (m, 6H), 6.85 (d, J=8.7 Hz, 1H), 6.63 (d, J=7.0 Hz, 1H), 4.07 (s, 3H), 4.02 (t, J=6.2 Hz, 2H), 2.51 (m, 2H), 2.05 (m, 2H). MS (ESI+) m/z 530.1 (M+H)$^+$.

Example 154

N-[4-(2,4-difluorophenoxy)-3-(1-methyl-7-oxo-6,7-dihydro-1H-pyrrolo[2,3-c]pyridin-3-yl)phenyl]-2-(3-phenoxyphenyl)acetamide Example 154 was prepared according to the procedure used for the preparation of Example 147, substituting 3-phenoxyphenylacetic acid for 4-methylpentanoic acid. $^1$H NMR (400 MHz, DMSO-d$_6$) δ 7.84 (d, J=2.6 Hz, 1H), 7.51 (s, 1H), 7.46-7.31 (m, 5H), 7.18-7.09 (m, 2H), 7.09-6.97 (m, 5H), 6.94 (d, J=7.0 Hz, 1H), 6.92-6.82 (m, 2H), 6.61 (d, J=7.0 Hz, 1H), 4.07 (s, 3H), 3.64 (s, 2H). MS (ESI+) m/z 578.0 (M+H)$^+$.

Example 155

4-(acetylamino)-N-[4-(2,4-difluorophenoxy)-3-(1-methyl-7-oxo-6,7-dihydro-1H-pyrrolo[2,3-c]pyridin-3-yl)phenyl]benzamide Example 155 was prepared according to the procedure used for the preparation of Example 147, substituting 4-(acetylamino)benzoic acid for 4-methylpentanoic acid. $^1$H NMR (400 MHz, DMSO-d$_6$) δ 8.01 (m, 1H), 7.95 (m, 2H), 7.71 (m, 2H), 7.63 (m, 1H), 7.56 (s, 1H), 7.45-7.31 (m, 1H), 7.13-7.01 (m, 2H), 6.96 (d, J=7.0 Hz, 1H), 6.89 (m, 1H), 6.70 (d, J=7.0 Hz, 1H), 4.09 (s, 3H), 3.00 (s, 3H). MS (ESI+) m/z 529.0 (M+H)$^+$.

Example 156

N-[4-(2,4-difluorophenoxy)-3-(1-methyl-7-oxo-6,7-dihydro-1H-pyrrolo[2,3-c]pyridin-3-yl)phenyl]-4-(phenoxymethyl)benzamide Example 156 was prepared according to the procedure used for the preparation of Example 147, substituting 4-(phenoxymethyl)benzoic acid for 4-methylpentanoic acid. $^1$H NMR (400 MHz, DMSO-d$_6$) δ 8.02 (d, J=2.6 Hz, 1H), 8.01-7.94 (m, 2H), 7.67-7.50 (m, 4H), 7.38 (ddd, J=11.2, 8.6, 2.7 Hz, 1H), 7.35-7.27 (m, 2H), 7.19-6.99 (m, 4H), 7.01-6.93 (m, 2H), 6.90 (d, J=8.8 Hz, 1H), 6.70 (d, J=7.0 Hz, 1H), 5.22 (bds, 2H), 4.09 (s, 3H). MS (ESI+) m/z 578.0 (M+H)$^+$.

Example 157

N-[4-(2,4-difluorophenoxy)-3-(1-methyl-7-oxo-6,7-dihydro-1H-pyrrolo[2,3-c]pyridin-3-yl)phenyl]-2-oxo-1-phenylpyrrolidine-3-carboxamide Example 157 was prepared according to the procedure used for the preparation of Example 147, substituting 2-oxo-1-phenylpyrrolidine-3-carboxylic acid for 4-methylpentanoic acid. $^1$H NMR (400 MHz, DMSO-d$_6$) δ 7.93 (d, J=2.6 Hz, 1H), 7.69-7.63 (m, 2H), 7.54 (s, 1H), 7.48 (dd, J=8.8, 2.6 Hz, 1H), 7.46-7.32 (m, 3H), 7.23-7.16 (m, 1H), 7.12-6.98 (m, 2H), 6.95 (d, J=7.0 Hz, 1H), 6.89 (d, J=8.8 Hz, 1H), 6.64 (d, J=7.0 Hz, 1H), 4.08 (s, 3H), 3.92 (m, 2H), 2.40 (m, 2H). MS (ESI+) m/z 555.0 (M+H)$^+$.

Example 158

2-(1,2-benzoxazol-3-yl)-N-[4-(2,4-difluorophenoxy)-3-(1-methyl-7-oxo-6,7-dihydro-1H-pyrrolo[2,3-c]pyridin-3-yl)phenyl]acetamide Example 158 was prepared according to the procedure used for the preparation of Example 147, substituting 2-(1,2-benzoxazol-3-yl)acetic acid for 4-methylpentanoic acid. $^1$H NMR (400 MHz, DMSO-d$_6$) δ 7.91 (d, J=8.0 Hz, 1H), 7.86 (d, J=2.6 Hz, 1H), 7.77-7.64 (m, 2H), 7.52 (s, 1H), 7.48-7.32 (m, 3H), 7.11-6.98 (m, 2H), 6.93 (d, J=7.0 Hz, 1H), 6.87 (d, J=8.8 Hz, 1H), 6.60 (d, J=7.0 Hz, 1H), 4.17 (d, J=6.9 Hz, 2H), 4.07 (s, 3H). MS (ESI+) m/z 527.0 (M+H)$^+$.

Example 159

2-(5-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide Example 159 was prepared according to the procedure used for the preparation of Example 147, substituting (5-chloro-2-fluorophenyl)acetic acid for 4-methylpentanoic acid. $^1$H NMR (400 MHz, DMSO-$d_6$) δ 7.87 (d, J=2.6 Hz, 1H), 7.54-7.29 (m, 5H), 7.19 (td, J=8.5, 3.1 Hz, 1H), 7.10-6.97 (m, 2H), 6.94 (d, J=7.0 Hz, 1H), 6.86 (d, J=8.8 Hz, 1H), 6.61 (d, J=7.0 Hz, 1H), 4.07 (s, 3H), 3.86 (m, 2H). MS (ESI+) m/z 538.0 (M+H)$^+$.

Example 160

2-(4-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide Example 160 was prepared according to the procedure used for the preparation of Example 147, substituting 2-(4-chloro-2-fluorophenyl)acetic acid for 4-methylpentanoic acid. $^1$H NMR (400 MHz, DMSO-$d_6$) δ 7.86 (d, J=2.6 Hz, 1H), 7.52 (s, 1H), 7.47-7.30 (m, 4H), 7.28 (dd, J=8.1, 2.1 Hz, 1H), 7.10-6.97 (m, 2H), 6.94 (d, J=7.0 Hz, 1H), 6.86 (d, J=8.8 Hz, 1H), 6.61 (d, J=7.0 Hz, 1H), 4.07 (s, 3H), 3.86 (m, 2H). MS (ESI+) m/z 538.0 (M+H)$^+$.

Example 161

N-[4-(2,4-difluorophenoxy)-3-(1-methyl-7-oxo-6,7-dihydro-1H-pyrrolo[2,3-c]pyridin-3-yl)phenyl]-2-(6-methylpyridin-3-yl)acetamide Example 161 was prepared according to the procedure used for the preparation of Example 147, substituting 2-(6-methylpyridin-3-yl)acetic acid for 4-methylpentanoic acid. $^1$H NMR (400 MHz, DMSO-$d_6$) δ 8.38 (d, J=2.3 Hz, 1H), 7.86 (d, J=2.6 Hz, 1H), 7.65 (dd, J=7.9, 2.4 Hz, 1H), 7.51 (s, 1H), 7.46-7.31 (m, 2H), 7.25 (d, J=7.9 Hz, 1H), 7.09-6.97 (m, 2H), 6.94 (d, J=7.0 Hz, 1H), 6.85 (d, J=8.8 Hz, 1H), 6.61 (d, J=7.0 Hz, 1H), 4.07 (s, 3H), 3.66 (m, 2H), 2.45 (s, 3H). MS (ESI+) m/z 501.0 (M+H)$^+$.

Example 162

N-[4-(2,4-difluorophenoxy)-3-(1-methyl-7-oxo-6,7-dihydro-1H-pyrrolo[2,3-c]pyridin-3-yl)phenyl]-2-(3,4-dihydro-2H-chromen-6-yl)acetamide Example 162 was prepared according to the procedure used for the preparation of Example 147, substituting 2-(3,4-dihydro-2H-chromen-6-yl)acetic acid for 4-methylpentanoic acid. $^1$H NMR (400 MHz, DMSO-$d_6$) δ 7.87 (d, J=2.6 Hz, 1H), 7.51 (s, 1H), 7.43 (dd, J=8.8, 2.6 Hz, 1H), 7.40-7.31 (m, 1H), 7.08-6.96 (m, 4H), 6.94 (d, J=7.0 Hz, 1H), 6.85 (d, J=8.8 Hz, 1H), 6.71-6.59 (m, 2H), 4.10 (t, J=4.9 Hz, 2H), 4.07 (s, 3H), 3.50 (s, 2H), 2.71 (m, 2H), 1.96-1.83 (m, 2H). MS (ESI+) m/z 542.1 (M+H)$^+$.

Example 163

N-[4-(2,4-difluorophenoxy)-3-(1-methyl-7-oxo-6,7-dihydro-1H-pyrrolo[2,3-c]pyridin-3-yl)phenyl]-2-(2-methyl-1,3-thiazol-5-yl)acetamide Example 163 was prepared according to the procedure used for the preparation of Example 147, substituting 2-(2-methyl-1,3-thiazol-5-yl)acetic acid for 4-methylpentanoic acid. $^1$H NMR (400 MHz, DMSO-$d_6$) δ 7.84 (d, J=2.7 Hz, 1H), 7.52 (s, 1H), 7.47 (s, 1H), 7.42 (dd, J=8.8, 2.6 Hz, 1H), 7.37 (ddd, J=11.1, 8.8, 2.8 Hz, 1H), 7.04 (ddd, J=8.0, 7.0, 4.2 Hz, 2H), 6.95 (d, J=7.0 Hz, 1H), 6.86 (d, J=8.8 Hz, 1H), 6.61 (d, J=7.0 Hz, 1H), 4.08 (s, 3H), 3.88 (s, 2H), 2.61 (s, 3H). MS (ESI+) m/z 507.0 (M+H)$^+$.

Example 164

N-[4-(2,4-difluorophenoxy)-3-(1-methyl-7-oxo-6,7-dihydro-1H-pyrrolo[2,3-c]pyridin-3-yl)phenyl]-2-(1,5-dimethyl-1H-pyrazol-3-yl)acetamide Example 164 was prepared according to the procedure used for the preparation of Example 147, substituting 2-(1,5-dimethyl-1H-pyrazol-3-yl)acetic acid for 4-methylpentanoic acid. $^1$H NMR (400 MHz, DMSO-$d_6$) δ 7.87 (d, J=2.6 Hz, 1H), 7.52 (s, 1H), 7.43 (dd, J=8.8, 2.6 Hz, 1H), 7.41-7.31 (m, 1H), 7.30-6.72 (m, 4H), 6.63 (d, J=7.0 Hz, 1H), 5.98 (s, 1H), 4.07 (s, 3H), 3.65 (s, 3H), 3.51 (s, 2H), 2.21 (s, 3H). MS (ESI+) m/z 503.7 (M+H)$^+$.

Example 165

N-[4-(2,4-difluorophenoxy)-3-(1-methyl-7-oxo-6,7-dihydro-1H-pyrrolo[2,3-c]pyridin-3-yl)phenyl]-2-[4-(2-fluorophenyl)-1H-pyrazol-1-yl]acetamide Example 165 was prepared according to the procedure used for the preparation of Example 147, substituting 2-[4-(2-fluorophenyl)-1H-pyrazol-1-yl]acetic acid for 4-methylpentanoic acid. $^1$H NMR (400 MHz, DMSO-$d_6$) δ 7.94-7.85 (m, 3H), 7.53 (s, 1H), 7.46-7.31 (m, 3H), 7.32-7.22 (m, 2H), 7.12-6.98 (m, 2H), 6.94 (d, J=7.0 Hz, 1H), 6.88 (d, J=8.8 Hz, 1H), 6.70 (dd, J=3.8, 2.3 Hz, 1H), 6.62 (d, J=7.0 Hz, 1H), 5.11 (s, 2H), 4.07 (s, 3H). MS (ESI+) m/z 570.0 (M+H)$^+$.

Example 166 methyl (2E)-3-[(4-fluorophenyl){2-(1-methyl-7-oxo-6,7-dihydro-1H-pyrrolo[2,3-c]pyridin-3-yl)-4-[(methylsulfonyl)methyl]phenyl}amino]prop-2-enoate Example 121C (34 mg, 0.080 mmol) and methyl 3,3-dimethoxypropanoate (0.113 mL, 0.800 mmol) were combined in acetic acid (0.5 mL). The reaction mixture was heated at 90° C. for 6 hours, cooled, and concentrated. The residue was partitioned with ethyl acetate and saturated aqueous sodium bicarbonate. The organic layer was washed with saturated aqueous sodium chloride, dried with anhydrous sodium sulfate, filtered, and concentrated. The residue was purified by reverse phase HPLC (C8, methanol/water (10 mM ammonium acetate), 10-100%) to provide the title compound (14 mg, 34%). $^1$H NMR (300 MHz, DMSO-$d_6$) δ ppm 10.90 (d, J=4.07 Hz, 1H) 7.91 (d, J=13.22 Hz, 1H) 7.63 (d, J=1.70 Hz, 1H) 7.42-7.56 (m, 2H) 6.97-7.08 (m, 3H) 6.77-6.90 (m, 3H) 6.32 (d, J=6.78 Hz, 1H) 4.63 (s, 2H) 4.58 (d, J=13.22 Hz, 1H) 3.97 (s, 3H) 3.54 (s, 3H) 2.99 (s, 3H). MS (ESI+) m/z 510 (M+H)$^+$.

Example 167

4-({[4-(2,4-difluorophenoxy)-3-(1-methyl-7-oxo-6,7-dihydro-1H-pyrrolo[2,3-c]pyridin-3-yl)phenyl]amino}methyl)benzonitrile A solution of Example 146B (0.163 M in N,N-dimethylacetamide, 253 μL, 0.041 mmol, 1.0 equivalent), acetic acid (4.3

M in methanol, 187 μL, 0.82 mmol, 20 equivalents), NaBH$_3$CN (0.32 M in methanol, 187 μL, 0.061 mmol, 1.5 equivalents) and 4-cyanobenzaldehyde (0.4 M in N,N-dimethylacetamide, 153 μL, 0.061 mmol, 1.5 equivalents) were mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 50° C., and passed through the reactor at 180 μL min$^{-1}$ (10 minute residence time). Upon exiting the reactor, the solution was loaded directly into an injection loop and purified by preparative HPLC on a Phenomenex Luna C8(2) 5 μm 100 Å AXIA column (50 mm×21.2 mm), eluting with a gradient of acetonitrile (A) and 0.1% ammonium acetate in water (B) at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to provide the title compound. $^1$H NMR (400 MHz, DMSO-d$_6$) δ 7.81 (m, 1H), 7.59 (d, J=8.0 Hz, 2H), 7.36 (s, 1H), 7.27 (m, 1H), 6.90 (m, 1H), 6.81-6.71 (m, 3H), 6.60 (d, J=2.8 Hz, 1H), 6.55 (dd, J=8.7, 2.9 Hz, 1H), 6.19 (d, J=7.0 Hz, 1H), 4.40 (bds, 2H), 4.01 (s, 3H). MS (ESI+) m/z 483.0 (M+H)$^+$.

Example 168

3-[2-(2,4-difluorophenoxy)-5-{[3-(4-methoxyphenoxy)benzyl]amino}phenyl]-1-methyl-1,6-dihydro-7H-pyrrolo[2,3-c]pyridin-7-one Example 168 was prepared according to the procedure used for the preparation of Example 167, substituting 3-(4-methoxyphenoxy)benzaldehyde for 4-cyanobenzaldehyde. $^1$H NMR (400 MHz, DMSO-d$_6$) δ 7.38-7.23 (m, 3H), 7.11 (d, J=7.7 Hz, 1H), 6.98-6.87 (m, 6H), 6.83-6.70 (m, 4H), 6.61 (d, J=2.8 Hz, 1H), 6.54 (dd, J=8.7, 2.8 Hz, 1H), 6.20 (d, J=7.0 Hz, 1H), 4.27 (bs, 2H), 4.01 (s, 3H), 3.74 (s, 3H). MS (ESI+) m/z 580.0 (M+H)$^+$.

Example 169

3-[2-(2,4-difluorophenoxy)-5-{[(3-methylpyridin-2-yl)methyl]amino}phenyl]-1-methyl-1,6-dihydro-7H-pyrrolo[2,3-c]pyridin-7-one Example 169 was prepared according to the procedure used for the preparation of Example 167, substituting 3-methylpyridin-2-carboxaldehyde for 4-cyanobenzaldehyde. $^1$H NMR (400 MHz, DMSO-d$_6$) δ 8.37 (dd, J=4.9, 1.6 Hz, 1H), 7.65-7.58 (m, 1H), 7.40 (s, 1H), 7.31-7.21 (m, 2H), 6.91-6.84 (m, 3H), 6.85-6.64 (m, 3H), 6.50 (d, J=7.0 Hz, 1H), 4.36 (bs, 2H), 4.03 (s, 3H), 2.37 (s, 3H). MS (ESI+) m/z 473.1 (M+H)$^+$.

Example 170

3-[5-{[4-(benzyloxy)benzyl]amino}-2-(2,4-difluorophenoxy)phenyl]-1-methyl-1,6-dihydro-7H-pyrrolo[2,3-c]pyridin-7-one Example 170 was prepared according to the procedure used for the preparation of Example 167, substituting 4-(benzyloxy)benzaldehyde for 4-cyanobenzaldehyde. $^1$H NMR (400 MHz, DMSO-d$_6$) δ 7.47-7.41 (m, 2H), 7.43-7.18 (m, 7H), 7.02-6.95 (m, 2H), 6.93-6.84 (m, 1H), 6.82-6.69 (m, 3H), 6.66 (d, J=2.8 Hz, 1H), 6.56 (dd, J=8.7, 2.8 Hz, 1H), 6.28 (d, J=7.0 Hz, 1H), 5.08 (s, 2H), 4.21 (bds, 2H), 4.01 (s, 3H). MS (ESI+) m/z 564.0 (M+H)$^+$.

Example 171

3-[5-{[(5-chloro-3-methyl-1-phenyl-1H-pyrazol-4-yl)methyl]amino}-2-(2,4-difluorophenoxy)phenyl]-1-methyl-1,6-dihydro-7H-pyrrolo[2,3-c]pyridin-7-one Example 171 was prepared according to the procedure used for the preparation of Example 167, substituting 5-chloro-3-methyl-1-phenyl-1H-pyrazol-4-carboxaldehyde for 4-cyanobenzaldehyde. $^1$H NMR (400 MHz, DMSO-d$_6$) δ 7.62-7.34 (m, 6H), 7.27 (ddd, J=11.3, 8.6, 2.8 Hz, 1H), 7.02-6.85 (m, 1H), 6.87-6.72 (m, 4H), 6.64 (dd, J=8.7, 2.8 Hz, 1H), 6.52 (d, J=7.0 Hz, 1H), 4.11 (bds, 2H), 4.03 (s, 3H), 2.29 (s, 3H). MS (ESI+) m/z 572.0 (M+H)$^+$.

Example 172

3-({[4-(2,4-difluorophenoxy)-3-(1-methyl-7-oxo-6,7-dihydro-1H-pyrrolo[2,3-c]pyridin-3-yl)phenyl]amino}methyl)benzonitrile Example 172 was prepared according to the procedure used for the preparation of Example 167, substituting 3-cyanobenzaldehyde for 4-cyanobenzaldehyde. $^1$H NMR (400 MHz, DMSO-d$_6$) δ 7.81 (s, 1H), 7.77-7.70 (m, 2H), 7.58 (t, J=7.7 Hz, 1H), 7.36 (s, 1H), 7.27 (ddd, J=11.3, 8.6, 2.9 Hz, 1H), 6.94-6.85 (m, 1H), 6.83-6.72 (m, 3H), 6.63 (d, J=2.8 Hz, 1H), 6.57 (dd, J=8.7, 2.8 Hz, 1H), 6.18 (d, J=7.0 Hz, 1H), 4.37 (bds, 2H), 4.01 (s, 3H). MS (ESI+) m/z 483.1 (M+H)$^+$.

Example 173

3-{2-(2,4-difluorophenoxy)-5[(4-phenoxybenzyl)amino]phenyl}-1-methyl-1,6-dihydro-7H-pyrrolo[2,3-c]pyridin-7-one Example 173 was prepared according to the procedure used for the preparation of Example 167, substituting 4-(phenoxy)benzaldehyde for 4-cyanobenzaldehyde. $^1$H NMR (400 MHz, DMSO-d$_6$) δ 7.44-7.35 (m, 5H), 7.27 (ddd, J=11.3, 8.6, 2.9 Hz, 1H), 7.14 (t, J=7.4 Hz, 1H), 7.03-6.95 (m, 4H), 6.94-6.71 (m, 4H), 6.67 (d, J=2.8 Hz, 1H), 6.58 (dd, J=8.7, 2.8 Hz, 1H), 6.28 (d, J=7.0 Hz, 1H), 4.28 (bds, 2H), 4.02 (s, 3H). MS (ESI+) m/z 550.1 (M+H)$^+$.

Example 174

3-{2-(2,4-difluorophenoxy)-5-[(3,3-dimethylbutyl)amino]phenyl}-1-methyl-1,6-dihydro-7H-pyrrolo[2,3-c]pyridin-7-one Example 174 was prepared according to the procedure used for the preparation of Example 167, substituting 3,3-dimethylbutanal for 4-cyanobenzaldehyde. $^1$H NMR (400 MHz, DMSO-d$_6$) δ 7.39 (s, 1H), 7.26 (ddd, J=11.4, 8.6, 2.9 Hz, 1H), 6.93-6.66 (m, 5H), 6.59-6.49 (m, 2H), 4.03 (s, 3H), 3.06-2.98 (m, 2H), 1.54-1.46 (m, 2H), 0.94 (s, 9H). MS (ESI+) m/z 452.1 (M+H)$^+$.

Example 175

3-{5-[(2,6-difluorobenzyl)amino]-2-(2,4-difluorophenoxy)phenyl}-1-methyl-1,6-dihydro-7H-pyrrolo[2,3-c]pyridin-7-one Example 175 was prepared according to the procedure used for the preparation of Example 167, substituting 2,6- difluorobenzaldehyde for 4-cyanobenzaldehyde. $^1$H NMR (400 MHz, DMSO-d$_6$) δ 7.45-7.36 (m, 2H), 7.26 (ddd, J=11.3, 8.6, 2.9 Hz, 1H), 7.11 (t, J=7.8 Hz, 2H), 6.92-6.84 (m, 2H), 6.84-6.71 (m, 3H), 6.64 (dd, J=8.7, 2.8 Hz, 1H), 6.49 (d, J=7.0 Hz, 1H), 4.30 (bds, 2H), 4.03 (s, 3H). MS (ESI+) m/z 494.0 (M+H)$^+$.

Example 176

3-{2-(2,4-difluorophenoxy)-5-[(6,7-dihydro-5H-pyrrolo[1,2-a]imidazol-2-ylmethyl)amino]phenyl}-1-methyl-1,6-dihydro-7H-pyrrolo[2,3-c]pyridin-7-one Example 176 was prepared according to the procedure used for the preparation of Example 167, substituting (6,7-dihydro-5H-pyrrolo[1,2-a]imidazol-2-carboxaldehyde for 4-cyanobenzaldehyde. $^1$H NMR (400 MHz, DMSO-d$_6$) δ 7.39 (s, 1H), 7.27 (m, 1H), 7.12 (m, 1H), 6.89 (d, J=7.1 Hz, 1H), 6.84-6.72 (m, 4H), 6.64-6.48 (m, 2H), 4.16 (s, 2H), 4.03 (s, 3H), 3.97 (m, 2H), 2.96 (m, 2H), 2.80 (m, 2H). MS (ESI+) m/z 488.0 (M+H)$^+$.

Example 177

3-[5-{[2-(benzyloxy)-3-methoxybenzyl]amino}-2-(2,4-difluorophenoxy)phenyl]-1-methyl-1,6-dihydro-7H-pyrrolo[2,3-c]pyridin-7-one Example 177 was prepared according to the procedure used for the preparation of Example 167, substituting 2-(benzyloxy)-3-methoxybenzaldehyde for 4-cyanobenzaldehyde. $^1$H NMR (400 MHz, DMSO-d$_6$) δ 7.44-7.20 (m, 7H), 7.10-7.03 (m, 1H), 7.04-6.97 (m, 1H), 6.96-6.85 (m, 2H), 6.74 (m, 3H), 6.57 (d, J=2.8 Hz, 1H), 6.45 (dd, J=8.7, 2.8 Hz, 1H), 6.22 (d, J=7.0 Hz, 1H), 4.98 (s, 2H), 4.17 (bds, 2H), 4.00 (s, 3H), 3.86 (s, 3H). MS (ESI+) m/z 594.0 (M+H)$^+$.

Example 178

2-({[4-(2,4-difluorophenoxy)-3-(1-methyl-7-oxo-6,7-dihydro-1H-pyrrolo[2,3-c]pyridin-3-yl)phenyl]amino}methyl)benzonitrile Example 178 was prepared according to the procedure used for the preparation of Example 167, substituting 2-cyanobenzaldehyde for 4-cyanobenzaldehyde. $^1$H NMR (400 MHz, DMSO-d$_6$) δ 7.85 (dd, J=7.7, 1.3 Hz, 1H), 7.75-7.67 (m, 1H), 7.63 (d, J=7.8 Hz, 1H), 7.53-7.45 (m, 1H), 7.38 (s, 1H), 7.27 (ddd, J=11.3, 8.6, 2.9 Hz, 1H), 6.95-6.86 (m, 1H), 6.84-6.74 (m, 3H), 6.64 (d, J=2.8 Hz, 1H), 6.58 (dd, J=8.7, 2.8 Hz, 1H), 6.23 (d, J=7.0 Hz, 1H), 4.48 (bds, 2H), 4.02 (s, 3H). MS (ESI+) m/z 483.1 (M+H)$^+$.

Example 179

3-{2-(2,4-difluorophenoxy)-5-[(quinolin-4-ylmethyl)amino]phenyl}-1-methyl-1,6-dihydro-7H-pyrrolo[2,3-c]pyridin-7-one Example 179 was prepared according to the procedure used for the preparation of Example 167, substituting quinolin-4-carboxaldehyde for 4-cyanobenzaldehyde. $^1$H NMR (400 MHz, DMSO-d$_6$) δ 8.85 (d, J=4.4 Hz, 1H), 8.28 (d, J=8.4 Hz, 1H), 8.09 (d, J=8.4 Hz, 1H), 7.86-7.78 (m, 1H), 7.68 (t, J=7.9 Hz, 1H), 7.56 (d, J=4.5 Hz, 1H), 7.35 (s, 1H), 7.27 (ddd, J=11.3, 8.6, 2.9 Hz, 1H), 6.95-6.86 (m, 1H), 6.83-6.73 (m, 2H), 6.68-6.55 (m, 3H), 6.15 (d, J=7.0 Hz, 1H), 4.85 (bds, 2H), 3.98 (s, 3H). MS (ESI+) m/z 509.1 (M+H)$^+$.

Example 180

N-[4-(2,4-difluorophenoxy)-3-(1-methyl-7-oxo-6,7-dihydro-1H-pyrrolo[2,3-c]pyridin-3-yl)phenyl]-1-phenylmethanesulfonamide Example 146B (0.056 g, 0.152 mmol), phenylmethanesulfonyl chloride (0.060 g, 0.315 mmol) and triethylamine (0.090 mL, 0.646 mmol) in dichloromethane (1.980 mL) were combined and the solution was stirred at ambient temperature for 18 hours. The mixture was concentrated, then 1 M sodium hydroxide (0.66 mL, 0.660 mmol) and tetrahydrofuran (1.320 mL) were added and the mixture was stirred at ambient temperature for 90 minutes, and then heated to 60° C. for 2 hours. The mixture was cooled and partitioned between 40 mL each of ethyl acetate and saturated aqueous ammonium chloride. The organic phase was dried over anhydrous sodium sulfate, filtered, concentrated, and the residue purified by reverse phase HPLC (C18, CH$_3$CN/water (0.1% trifluoroacetic acid), 10-100%) to provide the title compound. $^1$H NMR (300 MHz, DMSO-d$_6$) δ 10.96 (m, 1H), 9.79 (bds, 1H), 7.50 (s, 1H), 7.44-7.25 (m, 7H), 7.12-6.99 (m, 3H), 6.91 (dd, J=7.0, 5.7 Hz, 1H), 6.85 (d, J=8.7 Hz, 1H), 6.55 (dd, J=7.0, 1.2 Hz, 1H), 4.47 (s, 2H), 4.09 (s, 3H). MS (ESI) 522.1 (M+H)$^+$.

Example 181

1-(2-chloro-5-fluorophenyl)-N-[4-(2,4-difluorophenoxy)-3-(1-methyl-7-oxo-6,7-dihydro-1H-pyrrolo[2,3-c]pyridin-3-yl)phenyl]methanesulfonamide Example 181 was prepared according to the procedure used for the preparation of Example 180, substituting (2-chloro-5-fluorophenyl)methanesulfonyl chloride for phenylmethanesulfonyl chloride. $^1$H NMR (300 MHz, DMSO-d$_6$) δ 10.96 (bds, 1H), 10.09 (s, 1H), 7.54-7.20 (m, 6H), 7.11-6.97 (m, 3H), 6.99-6.81 (m, 2H), 6.54 (dd, J=7.0, 1.2 Hz, 1H), 4.67 (s, 2H), 4.08 (s, 3H). MS (ESI) 574.0 (M+H)$^+$.

Example 182

N-{4-(2,4-difluorophenoxy)-3-[1-methyl-5-(morpholin-4-ylmethyl)-7-oxo-6,7-dihydro-1H-pyrrolo[2,3-c]pyridin-3-yl]phenyl}ethanesulfonamide Example 182A 5-bromo-3-(2-fluoro-5-nitrophenyl)-7-methoxy-1-methyl-1H-pyrrolo[2,3-c]pyridine Example 182A was prepared according to the procedure used for the preparation of Example 91E, substituting (2-fluoro-5-nitrophenyl)boronic acid for Example 91D.

Example 182B 5-bromo-3-(2-(2,4-difluorophenoxy)-5-nitrophenyl)-7-methoxy-1-methyl-1H-pyrrolo[2,3-c]pyridine A mixture of Example 182A (367 mg, 0.965 mmol), 2,4-difluorophenol (111 μl, 1.158 mmol) and cesium carbonate (472 mg, 1.448 mmol) in 8 mL DMSO was heated under nitrogen at 90° C. for 1.5 hours. The mixture was partitioned between water and ethyl acetate (80 mL). The aqueous phase was extracted with ethyl acetate (2×60 mL). The combined organics were washed with water (2×), saturated aqueous sodium chloride, and dried over anhydrous magnesium sulfate, filtered. The filtrate was concentrated and the residue was purified by column chromatography on silica gel with a gradient of 10-70% ethyl acetate in heptanes to give the title compound (331 mg, 0.742 mmol, 77% yield) as a yellow solid.

Example 182C 4-((3-(2-(2,4-difluorophenoxy)-5-nitrophenyl)-7-methoxy-1-methyl-1H-pyrrolo[2,3-c]pyridin-5-yl)methyl)morpholine A mixture of Example 182B (110 mg, 0.224 mmol), potassium trifluoro(morpholinomethyl)borate (55.7 mg, 0.269 mmol), palladium (II) acetate (3.02 mg, 0.013 mmol), dicyclohexyl(2',4',6'-triisopropyl-[1',1'-biphenyl]-2-yl)phosphine (12.83 mg, 0.027 mmol), and $Cs_2CO_3$ (219 mg, 0.673 mmol) in 4 mL dioxane-water (9:1) was heated under nitrogen in Biotage Initiator microwave oven at 150° C. for 45 minutes. Water was added, extracted with ethyl acetate (2×), washed with water (2×), saturated aqueous sodium chloride, and dried over anhydrous magnesium sulfate, filtered. The filtrate was concentrated, and the residue was purified by column chromatography on silica gel with a gradient of 0-8% methanol in dichloromethane to give the title compound (60 mg, 0.118 mmol, 52.4% yield).

Example 182D 4-(2,4-difluorophenoxy)-3-(7-methoxy-1-methyl-5-(morpholinomethyl)-1H-pyrrolo[2,3-c]pyridin-3-yl)aniline A mixture of Example 182C (58 mg, 0.114 mmol), ammonium chloride (6.08 mg, 0.114 mmol), iron (50.8 mg, 0.909 mmol), in 4 mL tetrahydrofuran and 4 mL ethanol and 2 mL water was heated at reflux for 3 hours. The mixture was diluted with ethyl acetate, washed with water and saturated aqueous sodium chloride, dried over anhydrous magnesium sulfate, and filtered. The filtrated was concentrated to give the title compound (54 mg, 0.112 mmol, 99% yield).

Example 182E

N-(4-(2,4-difluorophenoxy)-3-(7-methoxy-1-methyl-5-(morpholinomethyl)-1H-pyrrolo[2,3-c]pyridin-3-yl)phenyl)ethanesulfonamide To a solution of Example 182D (54 mg, 0.112 mmol) in 5 mL dichloromethane was added diisopropylethylamine (58.9 µL, 0.337 mmol) and ethanesulfonyl chloride (26.6 µL, 0.281 mmol). The mixture was stirred at ambient temperature for 16 hours. Another 1.5 equivalents ethanesulfonyl chloride (16 µL) and 2.0 equivalents diisopropylethylamine (39 µL) were added. The mixture was continued to stir overnight. The mixture was concentrated. The residue was taken into dioxane (6 mL) and treated with sodium hydroxide (2810 µL, 2.81 mmol, 1N aqueous solution). The mixture was heated at 60° C. for 1 hour to hydrolyze the bis-sulfonamide to the manosulfonamide. To the reaction mixture, saturated ammonium chloride solution was added, extracted with ethyl acetate (3×), washed with saturated sodium chloride, dried over anhydrous magnesium sulfate, and filtered. The filtrate was concentrated and the residue was purified by column chromatography on silica gel with a gradient of 0-8% methanol in dichloromethane to give the title compound (10 mg, 0.017 mmol, 16% yield).

Example 182F

N-{4-(2,4-difluorophenoxy)-3-[1-methyl-5-(morpholin-4-ylmethyl)-7-oxo-6,7-dihydro-1H-pyrrolo[2,3-c]pyridin-3-yl]phenyl}ethanesulfonamide Example 182E (8 mg, 0.014 mmol) was treated with 2 mL 4M hydrochloric acid dioxane solution and the resulting suspension was heated at 70° C. for 3 hours. Another 2 mL 4N hydrochloric acid dioxane solution was added and continued to stir for another 3 hours. The suspension was concentrated and the residue was triturated in a small amount of diethyl ether to give the title compound as hydrochloric acid salt (6 mg, 10.08 µmol, 72.2% yield). $^1$H NMR (400 MHz, DMSO-$d_6$) δ 11.04 (s, 1H), 9.81 (d, J=10.8 Hz, 1H), 7.58 (s, 1H), 7.44 (dd, J=17.9, 5.4 Hz, 2H), 7.14 (t, J=8.7 Hz, 2H), 7.05 (t, J=8.0 Hz, 1H), 6.86 (d, J=8.7 Hz, 1H), 6.80 (s, 1H), 4.21 (s, 2H), 4.08 (s, 3H), 3.91 (s, 2H), 3.82-3.65 (m, 3H), 3.34 (s, 1H), 3.11 (dd, J=14.4, 7.1 Hz, 3H), 1.23 (t, J=7.2 Hz, 3H). MS (ESI+) m/z 559.0 (M+H)$^+$.

Example 183

N-{4-(2,4-difluorophenoxy)-3-[1-methyl-7-oxo-5-(piperidin-4-yl)-6,7-dihydro-1H-pyrrolo[2,3-c]pyridin-3-yl]phenyl}ethanesulfonamide Example 183A tert-butyl 4-(3-(2-(2,4-difluorophenoxy)-5-nitrophenyl)-7-methoxy-1-methyl-1H-pyrrolo[2,3-c]pyridin-5-yl)-5,6-dihydropyridine-1(2H)-carboxylate A mixture of Example 182B (238 mg, 0.485 mmol), tert-butyl 4-(4,4,5,5-tetramethyl-1,3,2-dioxaborolan-2-yl)-5,6-dihydropyridine-1(2H)-carboxylate (150 mg, 0.485 mmol), phenylallylchloro[1,3-bis(diisopropylphenyl)-2-imidazol-2-ylidene]palladium(II) (31.4 mg, 0.048 mmol) and potassium phosphate (309 mg, 1.454 mmol) in 9 mL tetrahydrofuran and 3 mL water was heated at 60° C. for 3 hours. Water was added, extracted with ethyl acetate (3×), washed with saturated aqueous sodium chloride, dried over anhydrous magnesium sulfate, and filtered. The filtrate was concentrated and the residue was purified by column chromatography on silica gel with a gradient of 0-50% ethyl acetate in heptanes to give the title compound (212 mg, 0.358 mmol, 73.8% yield) as a yellow solid.

Example 183B tert-butyl 4-(3-(5-amino-2-(2,4-difluorophenoxy)phenyl)-7-methoxy-1-methyl-1H-pyrrolo[2,3-c]pyridin-5-yl)piperidine-1-carboxylate A mixture of Example 183A (200 mg, 0.338 mmol), tetrafluoroethanol (20 mL), and 5% Pd/C (45 mg, 0.188 mmol) in a 50 mL pressure bottle was stirred at ambient temperature for 16 hours under 30 psi of hydrogen and at ambient temperature. The mixture was filtered through a nylon membrane. The filtrate was concentrated to give the title compound (205 mg, 0.363 mmol, 101% yield), which was used without further purification.

Example 183C tert-butyl 4-(3-(2-(2,4-difluorophenoxy)-5-(ethylsulfonamido)phenyl)-7-methoxy-1-methyl-1H-pyrrolo[2,3-c]pyridin-5-yl)piperidine-1-carboxylate To a solution of Example 183B (205 mg, 0.363 mmol) in 10 mL dichloromethane was added N-ethyl-N-isopropylpropan-2-amine (254 µL, 1.452 mmol) and ethanesulfonyl chloride (120 µL, 1.271 mmol). The mixture was stirred at ambient temperature overnight. The mixture was concentrated. The viscous oil residue was taken into dioxane (10 mL) and treated with sodium hydroxide (5446 µL, 5.45 mmol, 1N aqueous solution). The mixture was stirred at ambient temperature for 80 minutes and then quenched with saturated ammonium hydroxide solution, and partitioned between water and ethyl acetate. The aqueous phase was extracted with ethyl acetate (2×). The combined organic phases were washed with saturated aqueous sodium chloride, dried over anhydrous magnesium sulfate, and filtered. The filtrate was concentrated and the residue was purified by column chromatography on silica gel with a gradient of 0-60% ethyl acetate in heptanes to give the title compound (110 mg, 0.167 mmol, 46.1% yield).

Example 183D

N-{4-(2,4-difluorophenoxy)-3-[1-methyl-7-oxo-5-(piperidin-4-yl)-6,7-dihydro-1H-pyrrolo[2,3-c]pyridin-3-yl]phenyl}ethanesulfonamide Example 183C (95 mg, 0.145 mmol) was treated with hydrochloric acid (2 mL, 4M dioxane solution) and the resulting suspension was heated at 70° C. for 3 hours. Another 2 mL of 4N hydrochloric acid solution was added and continued to stir for another 3 hours. The reaction mixture was concentrated and the residue was triturated with diethyl ether to give the title compound as hydrochloric acid salt (65 mg, 0.097 mmol). $^1$H NMR (500 MHz, DMSO-$d_6$) δ 10.97 (d, J=8.7 Hz, 1H), 9.83 (s, 1H), 8.97 (d, J=10.3 Hz, 1H), 8.70 (d, J=11.6 Hz, 1H), 7.51 (s, 1H), 7.44 (d, J=2.7 Hz, 1H), 7.41 (dd, J=11.2, 2.7 Hz, 1H), 7.13-7.02 (m, 3H), 6.86 (d, J=8.7 Hz, 1H), 6.29 (d, J=8.9 Hz, 1H), 4.06 (s, 3H), 3.34 (s, 2H), 3.12 (q, J=7.3 Hz, 2H), 2.91 (q, J=12.1 Hz, 2H), 2.70 (t, J=11.9 Hz, 1H), 2.06 (d, J=13.2 Hz, 2H), 1.71 (dd, J=22.5, 12.6 Hz, 2H), 1.24 (t, J=7.3 Hz, 3H). MS (ESI+) m/z 543.2 (M+H)$^+$.

Example 184

N-[6-(2,4-difluorophenoxy)-5-(1-methyl-7-oxo-6,7-dihydro-1H-pyrrolo[2,3-c]pyridin-3-yl)pyridin-3-yl]ethanesulfonamide

Example 184A 3-bromo-2-(2,4-difluorophenoxy)-5-nitropyridine

A mixture of 3-bromo-2-chloro-5-nitropyridine (0.237 g, 1 mmol), 2,4-difluorophenol (0.13 g, 1 mmol) and cesium carbonate (0.326 g, 1 mmol) in dimethyl sulfoxide (2 mL) was reacted in a Biotage microwave reactor at 80° C. for 30 minutes. The reaction mixture was partitioned between ethyl acetate and water, washed with saturated aqueous sodium chloride, dried over anhydrous magnesium sulfate, filtered and concentrated. The residue was purified by flash chromatography (silica gel, 0-20% ethyl acetate in heptanes) to provide 0.312 g (94%) of the title compound.

Example 184B 3-(2-(2,4-difluorophenoxy)-5-nitropyridin-3-yl)-7-methoxy-1-methyl-1H-pyrrolo[2,3-c]pyridine Example 59A (0.086 g, 0.3 mmol), Example 184A (0.119 g, 0.36 mmol), tris(dibenzylideneacetone)palladium(0) (0.0082 g, 0.009 mmol), 1,3,5,7-tetramethyl-8-phenyl-2,4,6-trioxa-8-phosphaadamantane (0.0088 g, 0.030 mmol) and sodium carbonate (0.137 g, 1.29 mmol) were combined and sparged with nitrogen for 30 minutes. To this were added nitrogen-sparged 1,4-dioxane (1.5 mL) and water (0.375 mL) via syringe. The reaction mixture was stirred at 60° C. for 4 hours, cooled to ambient temperature and slurried in water. The solid was collected by filtration and then triturated in methanol. The resulting solid was dissolved in ethyl acetate, treated with 3-mercaptopropyl-functionalized silica gel for 20 minutes, dried over anhydrous magnesium sulfate, filtered through a plug of Celite, concentrated and dried in a vacuum oven at 60° C. to give 0.097 g (78%) of the title compound.

Example 184C 6-(2,4-difluorophenoxy)-5-(7-methoxy-1-methyl-1H-pyrrolo[2,3-c]pyridin-3-yl)pyridin-3-amine Example 184B (0.095 g, 0.23 mmol) in a mixture of tetrahydrofuran (1 mL), ethanol (0.5 mL) and water (0.25 mL) was treated with zinc dust (0.226 g, 3.46 mmol) and ammonium chloride (0.123 g, 2.304 mmol) and stirred for 30 minutes. The solids were removed by filtration through a plug of Celite. The filtrate was concentrated and the solid was slurried in water, collected by filtration, and dried in a vacuum oven to give 0.07 g (79%) of the title compound.

Example 184D 3-(5-amino-2-(2,4-difluorophenoxy)pyridin-3-yl)-1-methyl-1H-pyrrolo[2,3-c]pyridin-7(6H)-one Example 184C (0.0673 g, 0.176 mmol) in 1,4-dioxane (1.7 mL) was treated with hydrogen chloride solution (4 M in 1,4-dioxane) (0.44 mL, 1.76 mmol), heated at 80° C. for 9 hours, cooled to ambient temperature and concentrated to dryness to give 0.078 g (100%) of the title compound as the di-HCl salt.

Example 184E

N-(6-(2,4-difluorophenoxy)-5-(1-methyl-7-oxo-6,7-dihydro-1H-pyrrolo[2,3-c]pyridin-3-yl)pyridin-3-yl)ethanesulfonamide Example 184D (0.078 g, 0.176 mmol) in tetrahydrofuran (3 mL) was treated sequentially with N-ethyl-N-isopropylpropan-2-amine (0.154 mL, 0.88 mmol) and ethanesulfonyl chloride (0.05 mL, 0.528 mmol) and stirred at ambient temperature overnight. The reaction mixture was concentrated, dissolved in dichloromethane (1 mL), treated with N-ethyl-N-isopropylpropan-2-amine (0.154 mL, 0.88 mmol) and ethanesulfonyl chloride (0.1 mL, 1.056 mmol) and stirred at ambient temperature for 4 hours. The reaction mixture was then concentrated and the residue was taken up in 1,4-dioxane (1 mL), treated with sodium hydroxide solution (4 M aqueous) (0.5 mL, 2 mmol) and heated at 70° C. for 2 hours. Additional sodium hydroxide solution (4 M aqueous) (1 mL, 4 mmol) was added and heating was continued for 2 hours at 80° C. The reaction mixture was cooled to ambient temperature, neutralized with hydrochloric acid solution (2 M aqueous), partitioned between ethyl acetate and water, washed with saturated aqueous sodium chloride, dried over anhydrous magnesium sulfate, filtered, and concentrated. The residue was purified by flash chromatography (silica gel, 0-8% methanol in dichloromethane) to provide the title compound as an impure mixture. The material was further purified by reverse phase HPLC (C18, acetonitrile/water (0.1% trifluoroacetic acid), 10-90%) to give 0.0272 g (31%) of the title compound as the trifluoroacetic acid salt. $^1$H NMR (400 MHz, DMSO-$d_6$) δ 11.04 (d, J=5.49 Hz, 1H), 9.85 (s, 1H), 7.85 (d, J=2.75 Hz, 1H), 7.81 (d, J=2.75 Hz, 1H), 7.76 (s, 1H), 7.43 (m, 2H), 7.13 (m, 1H), 6.97 (m, 1H), 6.60 (d, J=7.02 Hz, 1H), 4.13 (s, 3H), 3.13 (q, J=7.32 Hz, 2H), 1.23 (t, J=7.32 Hz, 3H). MS (ESI+) m/z 461.1 (M+H)$^+$.

Example 185

N-[3-{5-[1-(cyclopropylcarbonyl)piperidin-4-yl]-1-methyl-7-oxo-6,7-dihydro-1H-pyrrolo[2,3-c]pyridin-3-yl}-4-(2,4-difluorophenoxy)phenyl]ethanesulfonamide Example 183D (hydrochloric acid salt) (32 mg, 0.055 mmol) was suspended in 1 mL dimethylformamide, treated with cyclopropanecarboxylic acid (5.23 mg, 0.061 mmol), 1H-benzo[d][1,2,3]triazol-1-ol hydrate (10.16 mg, 0.066 mmol), $N^1$-((ethylimino)methylene)-$N^3$,$N^3$-dimethylpropane-1,3-diamine hydrochloride (12.71 mg, 0.066 mmol) and triethylamine (23.11 μL, 0.166 mmol). The mixture was stirred at ambient temperature for 2 hours. The mixture was concentrated. To the oil residue was added water. The precipitate was collected via filtration, and the solid collected was dried in vacuum, and then triturated in small amount of diethyl ether to give the title compound (22 mg, 0.036 mmol, 65.2% yield). $^1$H NMR (400 MHz, DMSO-$d_6$) δ 10.93 (bs, 1H), 9.79 (s, 1H), 7.52-7.18 (m, 2H), 7.14-6.95 (m, 3H), 6.86 (d, J=8.7 Hz, 1H), 6.32 (s, 1H), 4.55-4.21 (m, 2H), 4.05 (s, 3H), 3.10 (q, J=7.3 Hz, 2H), 2.40-1.62 (m, 3H), 1.64-1.34 (m, 2H), 1.23 (t, J=7.3 Hz, 3H), 0.84-0.63 (m, 4H). MS (ESI+) m/z=611.1 (M+H)$^+$.

Example 186

N-[4-(2,4-difluorophenoxy)-3-{5-[1-(ethylsulfonyl)piperidin-4-yl]-1-methyl-7-oxo-6,7-dihydro-1H-pyrrolo[2,3-c]pyridin-3-yl}phenyl]ethanesulfonamide A suspension of Example 183D (hydrochloric acid salt) (24 mg, 0.041 mmol) in 1 mL dimethylformamide was treated with triethylamine (17.33 μL, 0.124 mmol) and ethanesulfonyl chloride (4.40 μL, 0.050 mmol) at 0° C. The mixture was stirred at 0° C. for 4 hours and then concentrated. To the oil residue was added water. The resulting solid was collected via filtration, dried in vacuum, and then triturated in small amount of diethyl ether to give the title compound (14 mg, 0.022 mmol, 53.2% yield). $^1$H NMR (400 MHz, DMSO-$d_6$) δ 10.94 (bs, 1H), 9.80 (s, 1H), 7.50 (s, 1H), 7.47-7.36 (m, 2H), 7.14-6.98 (m, 3H), 6.86 (d, J=8.7 Hz, 1H), 6.34 (s, 1H), 4.05 (s, 2H), 3.74-3.66 (m, 2H), 3.17-3.00 (m, 4H), 2.88-2.77 (m, 2H), 1.98-1.86 (m, 2H), 1.67-1.48 (m, 2H), 1.29-1.14 (m, 6H). MS (ESI+) m/z=635.1 (M+H)$^+$.

Example 187

3-{2-(2,4-difluorophenoxy)-5-[(ethylsulfonyl)amino]phenyl}-N-[3-(1H-imidazol-1-yl)propyl]-1-methyl-7-oxo-6,7-dihydro-1H-pyrrolo[2,3-c]pyridine-5-carboxamide Example 187A 5-bromo-7-chloro-1-methyl-1H-pyrrolo[2,3-c]pyridine Sodium hydride (60% dispersion in oil, 1.45 g, 36.3 mmol) was added portionwise to a 0° C. solution of 5-bromo-7-chloro-1H-pyrrolo[2,3-c]pyridine (CAS 1198096-48-8) (4.2 g, 18.14 mmol) and tetrahydrofuran (42 mL). After 15 minutes at 0° C. iodomethane (1.7 mL, 27.2 mmol) was added. The reaction mixture was stirred at 0° C. for 30 minutes and at ambient temperature for 2 hours. The reaction mixture was cooled to 0° C. and 30 mL saturated aqueous ammonium chloride solution was added, followed by addition of saturated aqueous sodium chloride. The mixture was extracted with ethyl acetate. The organic extract was washed with saturated aqueous sodium chloride, dried (anhydrous sodium sulfate), filtered, and concentrated to afford 5 g yellow solid. The crude product was purified by flash chromatography (silica gel, 2-20% ethyl acetate in heptanes) to provide 3.7 g (84%) of the title compound.

Example 187B 5-bromo-3-iodo-7-methoxy-1-methyl-1H-pyrrolo[2,3-c]pyridine

A solution of Example 187A (3.24 g, 13.44 mmol) and dimethylformamide (37 mL) was cooled to 0° C. After the addition of 1-iodopyrrolidine-2,5-dione (3.6 g, 16.00 mmol), the reaction mixture was stirred at ambient temperature for 3 hours. The solution was cooled to 0° C. and 60 mL water was added followed by aqueous sodium bisulfate (60 mL, 10%) solution. The mixture was stirred for 1 hour at ambient temperature. Solid was collected by filtration, rinsed with water and was dried under vacuum to provide 4.9 g (99%) of the title compound.

Example 187C 5-bromo-3-(2-chloro-5-nitrophenyl)-7-methoxy-1-methyl-1H-pyrrolo[2,3-c]pyridine A nitrogen degassed solution of Example 187B (1.0 g, 2.72 mmol), (2-chloro-5-nitrophenyl)boronic acid (0.549 g, 2.72 mmol), 1,3,5,7-tetramethyl-8-phenyl-2,4,6-trioxa-8-phosphaadamantane (40 mg, 0.137 mmol), tris(dibenzylideneacetone)dipalladium(0) (64 mg, 0.070 mmol), dioxane (10 mL) and water (3.2 mL) was stirred at 60° C. for 2.5 hours. The reaction mixture was cooled to ambient temperature, and was extracted with 150 mL of a solution of chloroform containing 25% isopropyl alcohol. The organic extract was washed with water, saturated aqueous sodium chloride, then 2 more times with water. The organic layer (containing suspended solid) was concentrated to afford a yellow solid which was dissolved in 200 mL of warm chloroform containing 30% isopropyl alcohol, and was treated with 2 g mercaptopropyl functionalized silica gel. The mixture was filtered through Celite while warm. The filtrate was concentrated to provide 0.98 g (91%) of the title compound.

Example 187D methyl 3-(5-amino-2-(2,4-difluorophenoxy)phenyl)-7-methoxy-1-methyl-1H-pyrrolo[2,3-c]pyridine-5-carboxylate A solution of Example 187C (750 mg, 1.530 mmol) in methanol (10 mL) was added to [1,1'-bis(diphenylphosphino)ferrocene]dichloropalladium(II) (56.0 mg, 0.076 mmol) and triethylamine (0.426 mL, 3.06 mmol) in a 50 mL pressure bottle. The mixture was pressurized with carbon monoxide (60 psi), and was stirred for 16 hours at 100° C. After cooling to ambient temperature, the suspension (catalyst not filtered) was concentrated to afford 1.25 g of a black semi-solid which was dissolved in dichloromethane and was filtered through Celite. Solvent was concentrated and the residue was purified by flash chromatography (silica gel, 7-75% ethyl acetate in heptanes) to provide 340 mg (51%) of the title compound.

Example 187E 3-(2-(2,4-difluorophenoxy)-5-(ethylsulfonamido)phenyl)-7-methoxy-1-methyl-1H-pyrrolo[2,3-c]pyridine-5-carboxylic acid Ethanesulfonyl chloride (0.22 mL, 2.322 mmol) was added dropwise to a 0° C. solution of Example 187D (340 mg, 0.774 mmol), triethylamine (0.45 mL, 3.23 mmol) and dichloromethane (8 mL). The reaction mixture was stirred at ambient temperature for overnight. Sodium hydroxide solution (2.7 mL 10%) was added to the reaction mixture. The solution was stirred at 85° C. for 1.5 hours. The reaction mixture was cooled to ambient temperature and saturated aqueous ammonium chloride was added, followed by the addition of 1N HCl. The pH of the mixture was about 3. The solution was extracted with ethyl acetate. The extract was washed with water, saturated aqueous sodium chloride, dried (anhydrous magnesium sulfate), filtered, and concentrated to afford 440 mg brown oil. The reaction mixture was then stirred at 95° C. for 2 hours with 9 mL dioxane and aqueous sodium hydroxide (2.8 mL, 10%). The reaction mixture was cooled to ambient temperature, and water was added. The solution was acidified with 1N HCl to pH3 and was extracted with ethyl acetate. The extract was washed with water, saturated aqueous sodium chloride, dried (anhydrous magnesium sulfate), filtered, and concentrated to provide 380 mg (95%) of the title compound.

Example 187F 3-(2-(2,4-difluorophenoxy)-5-(ethylsulfonamido)phenyl)-1-methyl-7-oxo-6,7-dihydro-1H-pyrrolo[2,3-c]pyridine-5-carboxylic acid A solution of Example 187E (335 mg, 0.647 mmol), 4M hydrogen chloride in dioxane (2.0 mL, 8.00 mmol) and dioxane (10 mL) was stirred at 75° C. for 4 hours. The reaction mixture was cooled to ambient temperature and was concentrated to dryness. The residue was dried (in-vacuo) to provide 315 mg (97%) of the title compound.

Example 187G

3-{2-(2,4-difluorophenoxy)-5-[(ethylsulfonyl)amino]phenyl}-N-[3-(1H-imidazol-1-yl)propyl]-1-methyl-7-oxo-6,7-dihydro-1H-pyrrolo[2,3-c]pyridine-5-carboxamide Example 187F (15 mg, 0.03 mmole) was dissolved in dimethylformamide (1.0 mL) and carbonyldiimidazole (6 mg, 0.04 mmol) was added. The reaction mixture was placed on a shaker at ambient temperature for 4 hours. To this mixture was then added a solution of 3-(1H-imidazol-1-yl)propan-1-amine (5.0 mg, 0.04 mmol) and diisopropylethylamine (0.075 mL, 10% in dimethylformamide). The reaction mixture was placed on a shaker at ambient temperature overnight. The reaction mixture was filtered and was purified by reverse phase HPLC (Phenomenex Luna C8(2) 5 µm 100 Å AXIA column (30 mm×75 mm) A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A). Samples were injected in 1.5 mL DMSO:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export, to provide the title compound. $^1$H NMR (400 MHz, DMSO-d$_6$) δ 9.05 (t, J=1.5 Hz, 1H), 7.76 (t, J=1.7 Hz, 1H), 7.66 (t, J=1.6 Hz, 1H), 7.61 (s, 1H), 7.42-7.29 (m, 3H), 7.24-7.09 (m, 2H), 7.04 (tdd, J=9.4, 3.0, 1.4 Hz, 1H), 6.90 (d, J=8.7 Hz, 1H), 4.25 (t, J=6.9 Hz, 2H), 4.11 (s, 3H), 3.26 (t, J=6.6 Hz, 2H), 3.12 (q, J=7.3 Hz, 2H), 2.07 (p, J=6.8 Hz, 2H), 1.24 (t, J=7.3 Hz, 3H). MS (APCI) m/z 611.1 (M+H)$^+$.

Example 188

3-{2-(2,4-difluorophenoxy)-5-[(ethylsulfonyl)amino]phenyl}-N-[2-(dimethylamino)ethyl]-1-methyl-7-oxo-6,7-dihydro-1H-pyrrolo[2,3-c]pyridine-5-carboxamide Example 188 was prepared according to the procedure used for the preparation of Example 187G, substituting N$^1$,N$^1$-dimethylethane-1,2-diamine for 3-(1H-imidazol-1-yl)propan-1-amine $^1$H NMR (400 MHz, DMSO-d$_6$) δ 7.62 (s, 1H), 7.41-7.33 (m, 2H), 7.31 (s, 1H), 7.18 (dd, J=8.9, 2.6 Hz, 1H), 7.16-7.10 (m, 1H), 7.09-7.01 (m, 1H), 6.90 (d, J=8.7 Hz, 1H), 4.11 (s, 3H), 3.60 (t, J=5.9 Hz, 2H), 3.25 (t, J=6.0 Hz, 2H), 3.12 (q, J=7.3 Hz, 2H), 2.85 (s, 6H), 1.24 (t, J=7.3 Hz, 3H). MS (APCI) m/z 574.0 (M+H)$^+$.

Example 189

N-(cyanomethyl)-3-{2-(2,4-difluorophenoxy)-5-[(ethylsulfonyl)amino]phenyl}-1-methyl-7-oxo-6,7-dihydro-1H-pyrrolo[2,3-c]pyridine-5-carboxamide Example 189 was prepared according to the procedure used for the preparation of Example 187G, substituting 2-aminoacetonitrile for 3-(1H-imidazol-1-yl)propan-1-amine $^1$H NMR (400 MHz, DMSO-$d_6$) δ 7.61 (s, 1H), 7.40-7.35 (m, 2H), 7.35-7.29 (m, 1H), 7.20 (dd, J=8.8, 2.7 Hz, 1H), 7.13 (td, J=9.2, 5.5 Hz, 1H), 7.03 (tdd, J=9.0, 3.0, 1.4 Hz, 1H), 6.92 (d, J=8.8 Hz, 1H), 4.31 (s, 2H), 4.11 (s, 3H), 3.12 (q, J=7.4 Hz, 2H), 1.25 (t, J=7.3 Hz, 3H). MS (APCI) m/z 542.0 (M+H)$^+$.

Example 190

3-{2-(2,4-difluorophenoxy)-5-[(ethylsulfonyl)amino]phenyl}-N-(3-hydroxypropyl)-1-methyl-7-oxo-6,7-dihydro-1H-pyrrolo[2,3-c]pyridine-5-carboxamide Example 190 was prepared according to the procedure used for the preparation of Example 187G, substituting 3-aminopropan-1-ol for 3-(1H-imidazol-1-yl)propan-1-amine $^1$H NMR (400 MHz, DMSO-$d_6$) δ 7.59 (s, 1H), 7.40-7.31 (m, 3H), 7.17 (td, J=8.7, 3.1 Hz, 2H), 7.05 (tdd, J=9.3, 2.9, 1.5 Hz, 1H), 6.89 (d, J=8.8 Hz, 1H), 4.11 (s, 3H), 3.46 (t, J=6.3 Hz, 2H), 3.30 (t, J=7.1 Hz, 2H), 3.13 (q, J=7.4 Hz, 2H), 1.68 (p, J=6.7 Hz, 2H), 1.25 (t, J=7.3 Hz, 3H). MS (APCI) m/z 561.0 (M+H)$^+$.

Example 191

N-{4-(2,4-difluorophenoxy)-3-[1-methyl-5-(morpholin-4-ylcarbonyl)-7-oxo-6,7-dihydro-1H-pyrrolo[2,3-c]pyridin-3-yl]phenyl}ethanesulfonamide Example 191 was prepared according to the procedure used for the preparation of Example 187G, substituting morpholine for 3-(1H-imidazol-1-yl)propan-1-amine $^1$H NMR (400 MHz, DMSO-$d_6$) δ 7.61 (s, 1H), 7.43-7.32 (m, 2H), 7.18-6.98 (m, 3H), 6.65 (s, 1H), 4.09 (s, 3H), 3.66-3.54 (m, 4H), 3.49 (d, J=5.5 Hz, 4H), 3.10 (q, J=7.3 Hz, 2H), 1.24 (t, J=7.3 Hz, 3H). MS (APCI) m/z 573.0 (M+H)$^+$.

Example 192

3-{2-(2,4-difluorophenoxy)-5-[(ethylsulfonyl)amino]phenyl}-1-methyl-7-oxo-N-(pyridin-3-ylmethyl)-6,7-dihydro-1H-pyrrolo[2,3-c]pyridine-5-carboxamide Example 192 was prepared according to the procedure used for the preparation of Example 187G, substituting pyridin-3-ylmethanamine for 1,3-diamine for 3-(1H-imidazol-1-yl)propan-1-amine $^1$H NMR (400 MHz, DMSO-$d_6$) δ 8.79 (d, J=2.0 Hz, 1H), 8.77-8.69 (m, 1H), 8.37 (dt, J=8.2, 1.7 Hz, 1H), 7.92 (dd, J=8.1, 5.5 Hz, 1H), 7.61 (s, 1H), 7.40 (s, 1H), 7.37 (d, J=2.8 Hz, 1H), 7.36-7.31 (m, 1H), 7.17 (dd, J=8.8, 2.7 Hz, 1H), 7.12 (td, J=9.2, 5.5 Hz, 1H), 7.02 (tdd, J=9.2, 3.0, 1.4 Hz, 1H), 6.90 (d, J=8.8 Hz, 1H), 4.62 (s, 2H), 4.11 (s, 3H), 3.10 (q, J=7.3 Hz, 2H), 1.22 (t, J=7.3 Hz, 3H). MS (APCI) m/z 594.0 (M+H)$^+$.

Example 193

N-{4-(2,4-difluorophenoxy)-3-[1-methyl-7-oxo-5-(pyrrolidin-1-ylcarbonyl)-6,7-dihydro-1H-pyrrolo[2,3-c]pyridin-3-yl]phenyl}ethanesulfonamide Example 193 was prepared according to the procedure used for the preparation of Example 187G, substituting pyrrolidine for 3-(1H-imidazol-1-yl)propan-1-amine $^1$H NMR (400 MHz, DMSO-$d_6$) δ 7.62 (s, 1H), 7.44-7.30 (m, 2H), 7.14 (dd, J=8.8, 2.6 Hz, 1H), 7.11 (dd, J=9.1, 5.5 Hz, 1H), 7.04 (tdd, J=9.2, 3.0, 1.2 Hz, 1H), 6.88 (d, J=8.8 Hz, 1H), 6.85 (s, 1H), 4.10 (s, 3H), 3.10 (q, J=7.4 Hz, 2H), 1.84 (s, 4H), 1.23 (t, J=7.3 Hz, 3H). MS (APCI) m/z 557.0 (M+H)$^+$.

Example 194

N-[4-(2,4-difluorophenoxy)-3-{5-[(4-hydroxypiperidin-1-yl)carbonyl]-1-methyl-7-oxo-6,7-dihydro-1H-pyrrolo[2,3-c]pyridin-3-yl]phenyl}ethanesulfonamide Example 194 was prepared according to the procedure used for the preparation of Example 187G, substituting piperidin-4-ol for 3-(1H-imidazol-1-yl)propan-1-amine $^1$H NMR (400 MHz, DMSO-$d_6$) δ 7.60 (s, 1H), 7.43-7.32 (m, 2H), 7.16-7.11 (m, 1H), 7.09 (dd, J=9.0, 5.6 Hz, 1H), 7.07-6.99 (m, 1H), 6.87 (d, J=8.8 Hz, 1H), 6.59 (s, 1H), 4.09 (s, 3H), 3.18 (s, 4H), 3.10 (q, J=7.3 Hz, 2H), 1.72 (s, 2H), 1.37 (s, 2H), 1.23 (t, J=7.3 Hz, 4H). MS (APCI) m/z 587.1 (M+H)$^+$.

Example 195

N-(cyclopentylmethyl)-3-{2-(2,4-difluorophenoxy)-5-[(ethylsulfonyl)amino]phenyl}-1-methyl-7-oxo-6,7-dihydro-1H-pyrrolo[2,3-c]pyridine-5-carboxamide Example 195 was prepared according to the procedure used for the preparation of Example 187G, substituting cyclopentylmethanamine for 1,3-diamine for 3-(1H-imidazol-1-yl)propan-1-amine $^1$H NMR (400 MHz, DMSO-$d_6$) δ 7.59 (s, 1H), 7.43-7.30 (m, 3H), 7.24-7.13 (m, 2H), 7.03 (tdd, J=9.2, 3.0, 1.6 Hz, 1H), 6.88 (d, J=8.8 Hz, 1H), 4.11 (s, 3H), 3.21-3.15 (m, 2H), 3.12 (q, J=7.3 Hz, 2H), 2.11 (p, J=7.4 Hz, 1H), 1.67 (dq, J=12.9, 7.1 Hz, 2H), 1.57 (ddt, J=10.6, 8.3, 4.1 Hz, 2H), 1.51 (dq, J=8.0, 5.4, 4.2 Hz, 2H), 1.23 (q, J=7.3 Hz, 5H). MS (APCI) m/z 585.0 (M+H)$^+$.

Example 196

3-{2-(2,4-difluorophenoxy)-5-[(ethylsulfonyl)amino]phenyl}-1-methyl-N-[2-(morpholin-4-yl)ethyl]-7-oxo-6,7-dihydro-1H-pyrrolo[2,3-c]pyridine-5-carboxamide Example 196 was prepared according to the procedure used for the preparation of Example 187G, substituting 2-morpholinoethanamine for 3-(1H-imidazol-1-yl)propan-1-amine $^1$H NMR (400 MHz, DMSO-$d_6$) δ 7.62 (s, 1H), 7.42-7.35 (m, 2H), 7.33 (d, J=3.1 Hz, 1H), 7.18 (dd, J=8.8, 2.7 Hz, 1H), 7.15-7.09 (m, 1H), 7.09-7.00 (m, 1H), 6.91 (d, J=8.8 Hz, 1H), 4.11 (s, 3H), 3.98 (d, J=16.8 Hz, 2H), 3.68 (s, 2H), 3.63 (t, J=6.2 Hz, 2H), 3.52 (s, 2H), 3.30 (t, J=6.2 Hz, 2H), 3.18 (s, 2H), 3.13 (p, J=7.3, 6.6 Hz, 5H), 1.24 (t, J=7.3 Hz, 3H). MS (APCI) m/z 616.2 (M+H)$^+$.

Example 197

3-{2-(2,4-difluorophenoxy)-5-[(ethylsulfonyl)amino]phenyl}-1-methyl-N-[2-(4-methylpiperazin-1-yl)ethyl]-7-oxo-6,7-dihydro-1H-pyrrolo[2,3-c]pyridine-5-carboxamide Example 197 was prepared according to the procedure used for the preparation of Example 187G, substituting 2-(4-methylpiperazin-1-yl)ethanamine for 3-(1H-imidazol-1-yl)propan-1-amine $^1$H NMR (400 MHz, DMSO-$d_6$) δ 7.62 (s, 1H), 7.38 (d, J=2.5 Hz, 1H), 7.36 (t, J=2.7 Hz, 1H), 7.34 (s, 1H), 7.18 (dd, J=8.8, 2.7 Hz, 1H), 7.13 (td, J=9.2, 5.6 Hz, 1H), 6.91 (d, J=8.7 Hz, 1H), 4.11 (s, 3H), 3.96 (s, 1H), 3.55 (t, J=6.3 Hz, 4H), 3.29 (d, J=59.7 Hz, 6H), 3.12 (q, J=7.3 Hz, 2H), 3.06 (t, J=6.3 Hz, 2H), 2.85 (s, 3H), 1.24 (t, J=7.3 Hz, 3H). MS (APCI) m/z 629.1 (M+H)$^+$.

Example 198

3-{2-(2,4-difluorophenoxy)-5-[(ethylsulfonyl)amino]phenyl}-1-methyl-7-oxo-N-[2-(piperidin-1-yl)ethyl]-6,7-dihydro-1H-pyrrolo[2,3-c]pyridine-5-carboxamide Example 198 was prepared according to the procedure used for the preparation of Example 187G, substituting 2-(piperidin-1-yl)ethanamine for 3-(1H-imidazol-1-yl)propan-1-amine $^1$H NMR (400 MHz, DMSO-d$_6$) δ 7.62 (s, 1H), 7.38 (dd, J=4.4, 2.9 Hz, 1H), 7.37-7.33 (m, 1H), 7.32 (s, 1H), 7.21-7.08 (m, 2H), 7.05 (tdd, J=8.9, 2.9, 1.3 Hz, 1H), 6.91 (d, J=8.7 Hz, 1H), 4.11 (s, 3H), 3.62 (t, J=6.3 Hz, 2H), 3.52 (d, J=12.2 Hz, 2H), 3.21 (t, J=6.3 Hz, 2H), 3.12 (q, J=7.3 Hz, 2H), 2.93 (td, J=12.2, 11.7, 3.0 Hz, 2H), 1.85 (d, J=14.4 Hz, 2H), 1.66 (dt, J=26.6, 13.8 Hz, 3H), 1.50-1.33 (m, 1H), 1.24 (t, J=7.3 Hz, 3H). MS (APCI) m/z 614.1 (M+H)$^+$.

Example 199

3-{2-(2,4-difluorophenoxy)-5-[(ethylsulfonyl)amino]phenyl}-1-methyl-7-oxo-N-(tetrahydrofuran-3-ylmethyl)-6,7-dihydro-1H-pyrrolo[2,3-c]pyridine-5-carboxamide Example 199 was prepared according to the procedure used for the preparation of Example 187G, substituting (tetrahydrofuran-3-yl)methanamine for 3-(1H-imidazol-1-yl)propan-1-amine $^1$H NMR (400 MHz, DMSO-d$_6$) δ 7.60 (s, 1H), 7.40-7.32 (m, 3H), 7.20-7.12 (m, 2H), 7.08-6.98 (m, 1H), 6.89 (d, J=8.8 Hz, 1H), 4.11 (s, 3H), 3.79-3.73 (m, 1H), 3.70-3.66 (m, 1H), 3.66-3.59 (m, 1H), 3.45 (dd, J=8.6, 5.3 Hz, 1H), 3.24 (dd, J=7.4, 5.3 Hz, 2H), 3.12 (q, J=7.3 Hz, 2H), 2.46 (p, J=6.5 Hz, 1H), 1.95 (dtd, J=13.5, 8.0, 5.7 Hz, 1H), 1.58 (dq, J=13.1, 6.7 Hz, 1H), 1.24 (t, J=7.3 Hz, 3H). MS (APCI) m/z 587.0 (M+H)$^+$.

Example 200

3-{2-(2,4-difluorophenoxy)-5-[(ethylsulfonyl)amino]phenyl}-N,1-dimethyl-7-oxo-6,7-dihydro-1H-pyrrolo[2,3-c]pyridine-5-carboxamide Example 200 was prepared according to the procedure used for the preparation of Example 187G, substituting methanamine for 3-(1H-imidazol-1-yl)propan-1-amine $^1$H NMR (400 MHz, DMSO-d$_6$) δ 7.59 (s, 1H), 7.39-7.34 (m, 2H), 7.32 (s, 1H), 7.19 (dd, J=8.8, 2.7 Hz, 1H), 7.13 (td, J=9.2, 5.6 Hz, 1H), 7.04 (tdd, J=9.2, 2.9, 1.3 Hz, 1H), 6.91 (d, J=8.8 Hz, 1H), 4.10 (s, 3H), 3.12 (q, J=7.3 Hz, 2H), 2.78 (s, 3H), 1.24 (t, J=7.3 Hz, 3H). MS (APCI) m/z 517.0 (M+H)$^+$.

Example 201

3-{2-(2,4-difluorophenoxy)-5-[(ethylsulfonyl)amino]phenyl}-N-(furan-3-ylmethyl)-1-methyl-7-oxo-6,7-dihydro-1H-pyrrolo[2,3-c]pyridine-5-carboxamide Example 201 was prepared according to the procedure used for the preparation of Example 187G, substituting furan-3-ylmethanamine for 3-(1H-imidazol-1-yl)propan-1-amine $^1$H NMR (400 MHz, DMSO-d$_6$) δ 7.60 (d, J=3.7 Hz, 3H), 7.38 (s, 1H), 7.38-7.30 (m, 2H), 7.17 (dd, J=8.9, 2.7 Hz, 1H), 7.15-7.09 (m, 1H), 7.01 (tdd, J=9.1, 2.8, 1.4 Hz, 1H), 6.88 (d, J=8.8 Hz, 1H), 6.50-6.44 (m, 1H), 4.29 (s, 2H), 4.10 (s, 3H), 3.10 (q, J=7.3 Hz, 2H), 1.22 (t, J=7.3 Hz, 3H). MS (APCI) m/z 583.0 (M+H)$^+$.

Example 202

3-{3-cyclopropyl-2-[(2,4-difluorophenyl)amino]-5-[(methylsulfonyl)methyl]phenyl}-1-methyl-1,6-dihydro-7H-pyrrolo[2,3-c]pyridin-7-one Example 202A 1-bromo-4-((methylsulfonyl)methyl)benzene A 250 mL round-bottomed flask was charged with 4-bromobenzyl bromide (5 g, 20 mmol) and N,N-dimethylformamide (10.81 mL). Sodium methanesulfinate (3.06 g, 30 mmol) was added. The reaction mixture was stirred at 65° C. for 1 hour. The reaction mixture was cooled to ambient temperature and diluted with water. The resulting suspension was stirred for 10 minutes and filtered. The solid was rinsed with water and dried under vacuum to provide the title compound (4.75 g, 95% yield).

Example 202B 2,4-difluoro-N-(4-((methylsulfonyl)methyl)phenyl)aniline

A 100-mL microwave tube was charged with 2,4-difluoroaniline (1.235 mL, 12.26 mmol), Example 202A (3.05 g, 12.26 mmol), diacetoxypalladium (0.055 g, 0.245 mmol), dicyclohexyl(2',4',6'-triisopropyl-[1',1'-biphenyl]-2-yl)phosphine (0.234 g, 0.49 mmol), cesium carbonate (5.59 g, 17.16 mmol), toluene (40.9 mL) and tert-butanol (8.17 mL). The tube was sealed, and the reaction mixture was heated in a Milestone Ethos microwave, 5 minute ramp to 150° C., then 10 minutes fixed hold time. The reaction mixture was filtered through a 10 g Celite SPE column and rinsed with ethyl acetate. The filtrate was concentrated. The residue was purified by flash chromatography (20-100% ethyl acetate in heptanes) to provide 3.44 g (94%) of the title compound.

Example 202C 2-bromo-N-(2,4-difluorophenyl)-4-((methylsulfonyl)methyl)aniline

A 500 mL round-bottomed flask was charged with Example 202B (3.44 g, 11.57 mmol) and acetic acid (116 mL). The reaction mixture was placed into a water bath. N-bromosuccinimide (2.06 g, 11.57 mmol) was added in 2 portions 10 minutes apart. The reaction mixture was stirred at ambient temperature for 1.5 hours. The reaction mixture was quenched with aqueous sodium thiosulfate solution (200 mL, 10%) and diluted with water. The reaction mixture was extracted twice with ethyl acetate. The combined organic layers were washed twice with sodium hydroxide solution (2 M aqueous) (until the pH of the aqueous was >7) and once with saturated aqueous sodium chloride solution, dried over anhydrous magnesium sulfate, filtered, and concentrated. The residue was taken up into ethyl acetate, then treated with heptanes. The resulting slurry was stirred for 30 minutes and filtered to provide 3.82 g (88% yield) of the title compound.

Example 202D 2-cyclopropyl-N-(2,4-difluorophenyl)-4-((methylsulfonyl)methyl)aniline A 5-mL microwave vial was charged with Example 202C (0.2287 g, 0.608 mmol), cyclopropylboronic acid (0.209 g, 2.432 mmol), cesium carbonate (0.99 g, 3.04 mmol) and dichloropalladium (II) bistriphenylphosphine (0.021 g, 0.03 mmol). The tube was sealed, and the mixture was sparged with nitrogen for 30 minutes. Degassed 1,4-dioxane (2.53 mL) and water (0.507 mL) were added. The reaction mixture was heated at 100° C. overnight. The reaction mixture was partitioned between ethyl acetate and water. The organic layer was washed with saturated aqueous sodium chloride solution, dried over anhydrous magnesium sulfate, filtered, and concentrated. The residue was purified by flash chromatography (10-70% ethyl acetate in heptanes) to provide 0.143 g (70%) of the title compound.

Example 202E 2-bromo-6-cyclopropyl-N-(2,4-difluorophenyl)-4-((methylsulfonyl)methyl)aniline Example 202E (0.1114 g, 63%) was prepared according to the procedure used for the preparation of Example 202C, substituting Example 202D for Example 202B.

Example 202F 2-cyclopropyl-N-(2,4-difluorophenyl)-6-(7-methoxy-1-methyl-1H-pyrrolo[2,3-c]pyridin-3-yl)-4-((methylsulfonyl)methyl)aniline Example 59A (0.066 g, 0.228 mmol), Example 202E (0.1 g, 0.24 mmol), tris(dibenzylideneacetone)dipalladium(0) (0.00627 g, 0.00685 mmol), 1,3,5,7-tetramethyl-8-phenyl-2,4,6-trioxa-8-phosphaadamantane (0.00667 g, 0.023 mmol) and sodium carbonate (0.104 g, 0.982 mmol) were combined and sparged with nitrogen for 30 minutes. To this were added nitrogen-sparged 1,4-dioxane (1.1 mL) and water (0.275 mL) via syringe. The reaction mixture was stirred at 60° C. for 5 hours. The reaction mixture was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite, and concentrated. The residue was purified by flash chromatography (silica gel, 0-10% ethyl acetate in dichloromethane) to give 0.0941 g (83%) of the title compound.

Example 202G 3-(3-cyclopropyl-2-((2,4-difluorophenyl)amino)-5-((methylsulfonyl)methyl)phenyl)-1-methyl-1H-pyrrolo[2,3-c]pyridin-7(6H)-one Example 202F (0.094 g, 0.189 mmol) in methanol (2 mL) was treated with hydrogen chloride solution (4 M in 1,4-dioxane, 0.945 mL, 3.78 mmol) and heated at 90° C. for 3.67 hours. The reaction mixture was cooled to room temperature and concentrated. The residue was purified by flash chromatography (silica gel, 0-6% methanol in dichloromethane) to give 0.100 g (>100%) of the title compound. Approximately one-third of the material was further purified by reverse phase HPLC (C18, acetonitrile/water (0.1% trifluoroacetic acid), 10-70%) to provide 0.031 g (33.9%) of the title compound. $^1$H NMR (400 MHz, DMSO-$d_6$) δ 10.86 (d, J=5.49 Hz, 1H), 7.30 (d, J=1.83 Hz, 1H), 7.26 (s, 1H), 7.04 (m, 2H), 6.95 (d, J=1.53 Hz, 1H), 6.81 (m, 1H), 6.64 (m, 1H), 6.43 (d, J=7.02 Hz, 1H), 6.15 (m, 1H), 4.47 (s, 2H), 3.98 (s, 3H), 2.92 (s, 3H), 1.99 (m, 1H), 0.84 (m, 2H), 0.60 (m, 2H). MS (ESI+) m/z 484.1 (M+H)$^+$.

Example 203

1-methyl-3-{5-[(methylsulfonyl)methyl]-2-(pyridin-2-ylamino)phenyl}-1,6-dihydro-7H-pyrrolo[2,3-c]pyridin-7-one

Example 203A

N-(2-(7-methoxy-1-methyl-1H-pyrrolo[2,3-c]pyridin-3-yl)-4-((methylsulfonyl)methyl)phenyl)pyridin-2-amine Example 121A (0.05 g, 0.145 mmol), 2-bromopyridine (0.028 mL, 0.29 mmol), diacetoxypalladium (0.0016 g, 0.00724 mmol), dicyclohexyl(2',4',6'-triisopropyl-[1,1'-biphenyl]-2-yl)phosphine (0.0069 g, 0.014 mmol), and cesium carbonate (0.094 g, 0.29 mmol) were combined in a 5-mL microwave vial. Toluene (1.2 mL) and tert-butanol (0.3 mL) were added. The vial was capped and the mixture was reacted at 150° C. for 30 minutes in a Biotage microwave reactor. Additional 2-bromopyridine (0.028 mL, 0.29 mmol), diacetoxypalladium (0.0016 g, 0.00724 mmol) and dicyclohexyl(2',4',6'-triisopropyl-[1,1'-biphenyl]-2-yl)phosphine (0.0069 g, 0.014 mmol) were added and the mixture was reacted in a Biotage microwave reactor for another 40 minutes at 150° C. The reaction mixture was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite and concentrated. The residue was purified by flash chromatography (silica gel, 0-90% ethyl acetate in dichloromethane) to give 0.04 g (65.4%) of the title compound.

Example 203B 1-methyl-3-(5-((methylsulfonyl)methyl)-2-(pyridin-2-ylamino)phenyl)-1H-pyrrolo[2,3-c]pyridin-7(6H)-one A mixture of Example 203A (0.062 g, 0.147 mmol) in methanol (1 mL) was treated with hydrogen chloride solution (4 M in 1,4-dioxane, 1 mL, 4 mmol) and heated at 75° C. for 2.5 hours. Additional hydrogen chloride solution (4 M in 1,4-dioxane, 1 mL, 4 mmol) was added and heating was continued for another 3.5 hours. The reaction mixture was then concentrated and the residue was purified by preparative HPLC on a Phenomenex Luna C8(2) 5 µm 100 Å AXIA column (30 mm×75 mm) A gradient of 20-100% acetonitrile (A) and 10 mM ammonium acetate in water (B) was used, at a flow rate of 50 mL/minute (0-0.5 minutes 20% A, 0.5-7.0 minutes linear gradient 20-95% A, 7.0-10.0 minutes 100% A, 10.0-12.0 minutes linear gradient 100-20% A to give the title compound. $^1$H NMR (400 MHz, DMSO-$d_6$) δ 10.89 (d, J=5.19 Hz, 1H), 8.08 (m, 1H), 7.98 (d, J=8.24 Hz, 1H), 7.89 (s, 1H), 7.47 (m, 1H), 7.42 (s, 1H), 7.34 (d, J=2.14 Hz, 1H), 7.27 (dd, J=8.24, 2.14 Hz, 1H), 6.79 (dd, J=6.71, 5.80 Hz, 1H), 6.76 (d, J=8.24 Hz, 1H), 6.70 (m, 1H), 6.25 (d, J=6.71 Hz, 1H), 4.45 (s, 2H), 4.09 (s, 3H), 2.93 (s, 3H). MS (ESI+) m/z 409.1 (M+H)$^+$.

Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623) (100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl) acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno [3,2-f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis(246 S, Z)-4-(4-chlorophenyl)-2,3,9-trimethyl-6H-thieno[3,2-f][1,2,4]triazolo[4,3-a][1,4]diazepin-6-yl)acetamide) bis(2,2,2-trifluoroacetate) (3.0 mg, 1.5%); ESI-MS m/z=913.2 [(M+H)$^+$]; 911.0 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl) acetamide(2,2,2-trifluoro acetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via an approximately 3-fold serial dilution from one of the following:
Assay method A: 250 µM-4.2 nM
Assay method B: 0.47 mM to 7.8 nM
Assay method C: 500 µM-8.5 nM
Assay method D: 2.5 mM-800 nM
Assay method E: 0.047 mM to 0.78 nM or 5-fold serial dilution from Assay method D For Assay methods A, C, and D: Compounds were then diluted 6:100 in assay buffer (20 mM Sodium Phosphate, pH 6.0, 50 mM NaCl, 1 mM Ethylenediaminetetraacetic acid, 0.01% Triton X-100, 1 mM DL-Dithiothreitol) to yield 3× working solutions. Six microliters (µL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution were added to the assay plate to reach a final volume of 18 µL.

For Assay methods B and E: Compound dilutions were added directly into white, low-volume assay plates (Perkin Elmer Proxiplate 384 Plus #6008280) using a Labcyte Echo in conjunction with Labcyte Access and Thermo Multidrop CombinL robotics. Compounds were then suspended in eight microliters (µL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B, C, D, and E contains 2% DMSO, 8 nM His-tagged bromodomain, 1 nM Europium-conjugated anti-His-tag antibody and 100 nM or 30 nM probe (for BDI or BDII, respectively) and compound concentration in the range of: 5 µM-85 pM for method A, 9.19 µM 150 pM for method B, 10 µM-169 pM for method C, 50 µM-16 nM for method D, and 0.92 µM-15 pM for method E.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37° C. and an atmosphere of 5% $CO_2$. For compound testing, MX-1 cells were plated in 96-well black bottom plates at a density of 5000 cells/well in 90 μL of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Example # | TR-FRET Protocol | TR-FRET Binding Ki BRD4 (BDI_K57-E168) (μM) | TR-FRET Binding Ki BRD4 (BDII_E352-M457) (μM) | Cellular proliferation $EC_{50}$ (μM) |
| --- | --- | --- | --- | --- |
| 1 | A | 0.085 | 0.313 | 0.584 |
| 2 | B | 0.0062 | 0.013 | 0.038 |
| 3 | A | 0.026 | 0.043 | 0.161 |
| 4 | A | 0.0059 | 0.0072 | 0.056 |
| 5 | C | 0.010 | 0.029 | 0.067 |
| 6 | C | 0.0028 | 0.057 | 0.036 |
| 7 | C | 0.0040 | 0.016 | 0.093 |
| 8 | C | 0.0016 | 0.0064 | 0.033 |
| 9 | C | 0.012 | 0.029 | 0.128 |
| 10 | C | 0.0180 | 0.142 | 0.225 |
| 11 | C | 0.0089 | 0.031 | 0.037 |
| 12 | C | 0.684 | 1.17 | NA |
| 13 | C | 0.173 | 0.213 | 0.136 |
| 14 | C | 0.073 | 1.34 | 0.506 |
| 15 | C | 0.0033 | 0.012 | 0.021 |
| 16 | D | 0.0021 | 0.027 | 0.059 |
| 17 | A | 0.034 | 0.038 | 0.107 |
| 18 | A | 0.012 | 0.021 | 0.068 |
| 19 | C | 0.016 | 0.080 | 0.176 |
| 20 | C | 0.018 | 0.165 | 0.181 |
| 21 | C | 0.438 | 0.721 | NA |
| 22 | C | 0.015 | 0.120 | 0.384 |
| 23 | C | 0.013 | 0.117 | 0.256 |
| 24 | C | 0.017 | 0.089 | 0.231 |
| 25 | E | 0.014 | 0.060 | 0.08 |
| 26 | C | 0.0070 | 0.060 | 0.123 |
| 27 | C | 0.0080 | 0.032 | 0.176 |
| 28 | C | 0.0093 | 0.053 | 0.129 |
| 29 | C | 0.012 | 0.089 | 0.191 |
| 30 | C | 0.045 | 0.312 | >3 |
| 31 | C | 0.021 | 0.087 | 0.398 |
| 32 | C | 0.0061 | 0.011 | 0.127 |
| 33 | C | 0.034 | 0.274 | 0.716 |
| 34 | C | 0.0016 | 0.029 | 0.095 |
| 35 | C | 0.042 | 0.111 | NA |
| 36 | C | 0.146 | 0.515 | NA |
| 37 | C | 0.052 | 0.099 | NA |
| 38 | C | 0.090 | 0.435 | NA |
| 39 | C | 0.063 | 0.051 | NA |
| 40 | C | 0.023 | 0.064 | 0.087 |
| 41 | C | 0.063 | 0.406 | 0.403 |
| 42 | C | 0.013 | 0.079 | 0.221 |
| 43 | C | 2.58 | 2.54 | NA |
| 44 | C | 0.014 | 0.089 | 0.136 |
| 45 | C | 0.037 | 0.070 | 0.279 |
| 46 | C | 0.205 | 1.09 | 0.479 |
| 47 | B | 0.033 | 0.124 | NA |
| 48 | C | 0.014 | 0.040 | 0.114 |
| 49 | C | 0.013 | 0.024 | 0.052 |
| 50 | C | 1.71 | >4.44 | NA |
| 51 | C | 0.047 | 0.062 | 0.201 |
| 52 | C | 0.0046 | 0.0071 | 0.02 |
| 53 | C | 0.0032 | 0.0066 | 0.039 |
| 54 | C | 0.0034 | 0.026 | 0.021 |
| 55 | C | 0.0042 | 0.0099 | 0.029 |
| 56 | B | 0.013 | 0.018 | 0.036 |
| 57 | B | 0.014 | 0.037 | 0.066 |
| 58 | B | 0.072 | 0.088 | 0.057 |
| 59 | B | 0.606 | 0.600 | NA |
| 60 | B | 0.016 | 0.0062 | 0.037 |
| 61 | C | 0.018 | 0.043 | 0.125 |
| 62 | C | 0.357 | 0.291 | NA |
| 63 | C | 0.074 | 0.066 | 0.187 |
| 64 | B | 0.036 | 0.057 | 0.084 |
| 65 | B | 0.416 | 2.64 | NA |
| 66 | B | 0.219 | 0.741 | NA |
| 67 | B | 0.045 | 1.38 | >3 |
| 68 | B | 0.103 | 0.124 | 0.038 |
| 69 | B | 0.773 | 2.29 | NA |
| 70 | B | 0.613 | 1.66 | NA |
| 71 | B | 0.197 | 0.285 | 0.255 |
| 72 | B | 0.492 | 0.967 | NA |
| 73 | B | 0.043 | 0.021 | 0.194 |
| 74 | B | >2.38 | 0.388 | NA |
| 75 | B | 0.131 | 0.042 | NA |
| 76 | B | 0.077 | 0.064 | NA |
| 77 | B | 0.062 | 0.139 | NA |
| 78 | B | 0.020 | 0.073 | 0.088 |
| 79 | B | 0.150 | 0.084 | NA |
| 80 | B | 0.056 | 0.053 | NA |
| 81 | B | 0.081 | 0.100 | NA |
| 82 | B | 0.066 | 0.049 | NA |
| 83 | B | 0.043 | 0.046 | 0.10 |
| 84 | B | 0.055 | 0.025 | NA |
| 85 | B | 0.044 | 0.017 | NA |
| 86 | B | 0.697 | 0.764 | NA |
| 87 | B | 1.52 | 0.565 | NA |
| 88 | B | 0.287 | 0.739 | NA |
| 89 | B | >2.38 | 1.22 | NA |
| 90 | B | 0.054 | 0.039 | 0.096 |
| 91 | B | 0.0054 | 0.0095 | 0.008 |
| 92 | B | 0.0017 | 0.0018 | 0.008 |
| 93 | B | 0.484 | 0.619 | NA |
| 94 | B | 0.168 | 1.87 | NA |
| 95 | B | 0.0042 | 0.0021 | 0.008 |

TABLE 1-continued

| Example # | TR-FRET Protocol | TR-FRET Binding Ki BRD4 (BDI_K57-E168) (μM) | TR-FRET Binding Ki BRD4 (BDII_E352-M457) (μM) | Cellular proliferation EC$_{50}$ (μM) |
|---|---|---|---|---|
| 96 | B | 0.0069 | 0.011 | 0.015 |
| 97 | B | 0.158 | 0.081 | 0.398 |
| 98 | B | 0.992 | 2.03 | NA |
| 99 | B | >2.38 | 2.43 | NA |
| 100 | B | 0.0041 | 0.0048 | 0.009 |
| 101 | B | 0.0022 | 0.0025 | 0.005 |
| 102 | B | 0.095 | 0.081 | 0.739 |
| 103 | B | 0.0084 | 0.0049 | 0.089 |
| 104 | B | 0.072 | 0.107 | >3 |
| 105 | B | 0.528 | 0.329 | 0.806 |
| 106 | B | 0.031 | 0.067 | 0.338 |
| 107 | B | >2.38 | 0.407 | NA |
| 108 | B | 0.093 | 0.181 | 0.46 |
| 109 | B | 0.057 | 0.067 | 0.268 |
| 110 | B | 0.061 | 0.215 | 0.136 |
| 111 | B | 0.908 | 0.337 | 0.713 |
| 112 | B | 1.05 | 1.05 | NA |
| 113 | B | 0.583 | 0.506 | 1.63 |
| 114 | B | 1.41 | 1.20 | >3 |
| 115 | B | 1.35 | 1.33 | 1.42 |
| 116 | B | 0.093 | 0.145 | 0.578 |
| 117 | B | 0.776 | 0.750 | NA |
| 118 | B | 0.776 | 0.382 | 1.51 |
| 119 | B | 0.599 | 0.478 | >3 |
| 120 | B | 0.077 | 0.208 | 0.306 |
| 121 | B | 0.012 | 0.079 | 0.04 |
| 122 | B | 0.025 | 0.055 | 0.044 |
| 123 | B | 0.130 | 0.428 | NA |
| 124 | B | 0.127 | 0.104 | NA |
| 125 | B | 0.069 | 0.092 | 0.267 |
| 126 | B | 0.0083 | 0.0057 | 0.0819 |
| 127 | B | 0.619 | 0.476 | 0.947 |
| 128 | B | 1.49 | 0.654 | >3 |
| 129 | B | 1.14 | 1.19 | NA |
| 130 | B | 0.247 | 1.15 | >3 |
| 131 | B | 0.281 | 1.25 | 1.4 |
| 132 | B | 0.249 | 1.24 | 0.658 |
| 133 | B | 0.049 | 2.68 | 1.68 |
| 134 | B | 0.103 | 0.518 | 0.456 |
| 135 | B | 0.027 | 0.109 | 0.388 |
| 136 | B | 1.09 | 1.32 | NA |
| 137 | B | 0.106 | 0.374 | 0.872 |
| 138 | B | 1.15 | >4 | NA |
| 139 | B | 0.129 | 0.525 | >3 |
| 140 | B | 0.490 | 0.817 | 1.82 |
| 141 | B | 0.064 | 0.495 | 0.98 |
| 142 | B | 0.87 | 2.31 | NA |
| 143 | B | 0.446 | 1.68 | NA |
| 144 | E | 0.0082 | 0.107 | 0.0731 |
| 145 | E | 0.174 | 0.296 | NA |
| 146 | B | 0.0253 | 0.0901 | NA |
| 147 | B | 0.0594 | 0.134 | NA |
| 148 | E | 0.0651 | 0.150 | 0.17 |
| 149 | E | 0.0416 | 0.054 | NA |
| 150 | E | 0.0220 | 0.145 | NA |
| 151 | E | 0.0161 | 0.032 | 0.20 |
| 152 | B | 0.141 | 0.0953 | NA |
| 153 | B | 0.321 | 0.293 | NA |
| 154 | B | 1.76 | 0.828 | 1.59 |
| 155 | E | 0.0278 | 0.163 | 0.31 |
| 156 | E | 0.598 | >0.92 | NA |
| 157 | E | 0.118 | 0.333 | NA |
| 158 | B | 0.0764 | 0.153 | NA |
| 159 | B | 0.0624 | 0.0596 | NA |
| 160 | B | 0.101 | >0.408 | NA |
| 161 | B | >0.238 | 0.0791 | NA |
| 162 | B | 0.146 | 0.183 | NA |
| 163 | B | 0.024 | 0.0813 | NA |
| 164 | B | 0.011 | 0.073 | NA |
| 165 | B | 0.214 | 0.105 | NA |
| 166 | B | 0.109 | 0.047 | NA |
| 167 | B | 0.0328 | 0.156 | 0.338 |
| 168 | B | 0.386 | 1.2 | NA |
| 169 | E | 0.0265 | 0.107 | 0.132 |
| 170 | B | 0.216 | 1.10 | 1.02 |
| 171 | B | 0.176 | 0.384 | 0.198 |
| 172 | E | 0.071 | 0.226 | NA |
| 173 | B | 0.214 | 0.781 | NA |
| 174 | E | 0.0575 | 0.215 | NA |
| 175 | E | 0.0691 | 0.285 | NA |
| 176 | E | 0.0423 | 0.101 | 0.289 |
| 177 | E | 0.133 | 0.248 | >3.0 |
| 178 | E | 0.0308 | 0.239 | 0.233 |
| 179 | E | 0.0699 | 0.231 | NA |
| 180 | E | 0.0349 | 0.0593 | >1.0 |
| 181 | E | 0.0658 | 0.128 | >1.0 |
| 182 | E | 0.0292 | 0.0999 | NA |
| 183 | E | 0.00263 | 0.0134 | 0.356 |
| 184 | E | 0.00531 | 0.00472 | 0.309 |
| 185 | E | 0.00429 | 0.00794 | 0.0614 |
| 186 | E | 0.00038 | 0.00082 | 0.0134 |
| 187 | E | 0.00121 | 0.00202 | 0.0647 |
| 188 | E | 0.00142 | 0.0135 | 0.0299 |
| 189 | E | 0.00195 | 0.00882 | 0.0779 |
| 190 | E | 0.00201 | 0.00385 | 0.082 |
| 191 | E | 0.00763 | 0.0546 | NA |
| 192 | E | 0.00090 | 0.0013 | 0.0107 |
| 193 | E | 0.0043 | 0.0413 | 0.111 |
| 194 | E | 0.0105 | 0.0685 | NA |
| 195 | E | 0.0104 | 0.0127 | 0.162 |
| 196 | E | 0.00166 | 0.00964 | 0.0309 |
| 197 | E | 0.00205 | 0.00423 | 0.0676 |
| 198 | E | 0.00318 | 0.0109 | NA |
| 199 | E | 0.00363 | 0.0065 | 0.0368 |
| 200 | E | 0.00324 | 0.00456 | 0.0436 |
| 201 | E | 0.00347 | 0.0114 | NA |
| 202 | E | 0.00582 | 0.0163 | 0.0983 |
| 203 | E | 0.0138 | 0.0439 | 0.118 |

NA = Not Determined

LPS (Lipopolysaccharide) Induced IL-6 Production Mouse Assay

Compounds of the Examples listed in Table 2 were assayed for their ability to inhibit LPS (lipopolysaccharide) induced IL-6 (Interleukin-6) production in mice. Fox Chase SCID® female mice (Charles Rivers Labs, 5 per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 2 all exhibited a p value less than 0.05.

TABLE 2

| Inhibition of LPS induced IL-6 production | |
|---|---|
| Compound of Example # | % inhibition at 3 mg/kg |
| 2 | 27 |
| 4 | 40 |
| 11 | 66 |
| 15 | 44 |
| 16 | 69 |
| 17 | 49 |
| 25 | 62 |
| 32 | 33 |
| 52 | 77 |
| 53 | 74 |
| 60 | 62 |

Xenograft Tumor Growth Inhibition Assay

The effect of compounds of the examples to inhibit the growth of OPM-2 xenograft tumors implanted in mice was evaluated. A suspension of cancer cells ($5 \times 10^6$ per 0.1 mL) prepared in RPMI culture medium (Invitrogen, Carlsbad, Calif.) was diluted 1:1 with a solution of Matrigel™ (BD Biosciences, Franklin Lakes, N.J.) and inoculated subcutaneously into the right hind flank of female SCID-beige (Charles River Labs) mice. Randomization into treatment and vehicle control groups (10/group) occurred when the mean tumor volume reached approximately 250 mm$^3$ Compounds were formulated in 10% EtOH, 30% PEG 400, 60% Phosol 53 MCT. Administration of compound or vehicle was initiated on the day following randomization and continued for 21 days. Tumors were measured twice a week throughout the treatment period using a pair of calipers and tumor volumes were calculated according to the formula $V=L\times W^2/2$ (V: volume, mm$^3$; L: length, mm; W: width, m) Tumor growth inhibition (TGI) was calculated based on the mean tumor volume measured on the first day that the mean volume of the vehicle group exceeded 2000 mm$^3$ according to the formula:

% TGI=100−mean tumor volume of treatment group/
mean tumor volume of control group×100.

Results are shown in Table 3.

TABLE 3

| OPM-2 human multiple myeloma cancer xenograft model | | | | |
|---|---|---|---|---|
| Compound of Example # | Dose (mg/kg) | route, regimen | % TGI[a] | % removed from study[b] |
| 17 | 10 | PO, QDx21 | 60*** | 10 |
| 17 | 30 | PO, QDx21 | 64*** | 10 |
| 52 | 1 | PO, QDx21 | 13 | 0 |
| 52 | 3 | PO, QDx21 | 16 | 10 |

[a]The p values (as indicated by asterisks) are derived from Student's T test comparison of treatment group vs. control group.
*p < 0.05,
**p < 0.01,
***p < 0.001.
[b]Percentage of treatment group that were removed from study due to morbidity or weight loss in excess of 20%.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:
1. A compound of formula (I) or a pharmaceutically acceptable salt thereof,

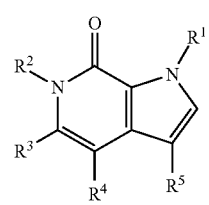

(I)

wherein
$R^1$ is H, $C_1$-$C_3$ alkyl, or $C_1$-$C_3$ haloalkyl;
$R^2$ is H, $C_1$-$C_3$ alkyl, or $C_1$-$C_3$ haloalkyl;
$R^3$ is H, $C_1$-$C_6$ alkyl, $C_2$-$C_6$ alkenyl, $C_2$-$C_6$ alkynyl, halogen, —$OR^{3a}$, —$NR^{3b}R^{3c}$, —$N(R^{3b})C(O)R^{3d}$, —$N(R^{3b})C(O)NR^{3b}R^{3c}$, —$N(R^{3b})S(O)_2NR^{3b}R^{3c}$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of halogen, $G^1$, —$OR^{3a}$, and —$NR^{3b}R^{3c}$;
$R^{3a}$, $R^{3b}$, and $R^{3c}$, at each occurrence, are each independently H, $C_1$-$C_6$ alkyl, $C_1$-$C_6$ haloalkyl, $G^1$, —($C_1$-$C_6$ alkylenyl)-$G^1$, —($C_1$-$C_6$ alkylenyl)-CN, —($C_1$-$C_6$ alkylenyl)-$OR^{z1}$, or —($C_1$-$C_6$ alkylenyl)-$NR^{z3}R^{z4}$;
$R^{3d}$, at each occurrence, is independently $C_1$-$C_6$ alkyl, $C_1$-$C_6$ haloalkyl, $G^1$, or —($C_1$-$C_6$ alkylenyl)-$G^1$;
$G^1$, at each occurrence, is independently aryl, heteroaryl, heterocycle, cycloalkyl, or cycloalkenyl; and each $G^1$ is optionally substituted with 1, 2, 3, 4, or 5 $R^{1g}$ groups;
$R^4$ is H, $C_1$-$C_6$ alkyl, halogen, or $C_1$-$C_6$ haloalkyl;
$R^5$ is phenyl or pyridinyl; each of which is substituted with 1, 2, or 3 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^2$, —$OR^a$, —$OC(O)R^b$, —$OC(O)NR^cR^d$, —$SR^a$, —$S(O)_2R^a$, —$S(O)_2NR'R^d$, —$C(O)R^a$, —$C(O)OR^a$, —$C(O)NR^cR^d$, —$NR^cR^d$, —$N(R^e)C(O)R^b$, —$N(R^e)S(O)_2R^b$, —$N(R^e)C(O)O(R^b)$, —$N(R^e)C(O)NR^cR^d$, —$N(R^e)S(O)_2NR'R^d$, —($C_1$-$C_6$ alkylenyl)-$G^2$, —($C_1$-$C_6$ alkylenyl)-$OR^a$, —($C_1$-$C_6$ alkylenyl)-$OC(O)R^b$, —($C_1$-$C_6$ alkylenyl)-$OC(O)NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, —($C_1$-$C_6$ alkylenyl)-$N(R^e)S(O)_2NR^cR^d$, and —($C_1$-$C_6$ alkylenyl)-CN;
$R^a$, $R^c$, $R^d$, and $R^e$, at each occurrence, are each independently H, $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;
$R^b$, at each occurrence, is independently $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{Y1}$, —$S(O)_2NR^{y3}R^{y4}$, and $G^2$;

$G^2$, at each occurrence, are each independently aryl, heteroaryl, heterocycle, cycloalkyl, or cycloalkenyl; and each $G^2$ group is optionally substituted with 1, 2, 3, 4, or 5 $R^{2g}$ groups;

$R^{1g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)(C_3$-$C_6$ cycloalkyl), —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —$(C_1$-$C_6$ alkylenyl)-$OR^{z1}$, —$(C_1$-$C_6$ alkylenyl)-$OC(O)R^{z2}$, —$(C_1$-$C_6$alkylenyl)-$OC(O)NR^{z3}R^{z4}$, —$(C_1$-$C_6$ alkylenyl)-$S(O)_2R^{z1}$, —$(C_1$-$C_6$ alkylenyl)-$S(O)_2NR^{z3}R^{z4}$, —$(C_1$-$C_6$ alkylenyl)-$C(O)R^{z1}$, —$(C_1$-$C_6$ alkylenyl)-$C(O)OR^{z1}$, —$(C_1$-$C_6$ alkylenyl)-$C(O)NR^{z3}R^{z4}$, —$(C_1$-$C_6$ alkylenyl)-$NR^{z3}R^{z4}$, —$(C_1$-$C_6$ alkylenyl)-$N(R^{z3})C(O)R^{z2}$, —$(C_1$-$C_6$ alkylenyl)-$N(R^{z3})S(O)_2R^{z2}$, —$(C_1$-$C_6$ alkylenyl)-$N(R^{z3})C(O)O(R^{z2})$, —$(C_1$-$C_6$ alkylenyl)-$N(R^{z3})C(O)NR^{z3}R^{z4}$, —$(C_1$-$C_6$ alkylenyl)-$N(R^{z3})S(O)_2NR^{z3}R^{z4}$, —$(C_1$-$C_6$ alkylenyl)-CN, or —O(phenyl); wherein the phenyl moiety and the $C_3$-$C_6$ cycloalkyl moiety are each optionally substituted with 1, 2, 3, or 4 substituents independently selected from the group consisting of $C_1$-$C_6$ alkyl, halogen, $C_1$-$C_6$ haloalkyl, —OH, —O(alkyl), —O(haloalkyl), CN, and $NO_2$;

$R^{2g}$, at each occurrence, is independently $C_1$-$C_6$ alkyl, $C_2$-$C_6$ alkenyl, $C_2$-$C_6$ alkynyl, halogen, $C_1$-$C_6$ haloalkyl, oxo, —CN, $NO_2$, —$OR^1$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, —$N(R^{y3})S(O)_2NR^{y3}R^{y4}$, $G^{2b}$, —$(C_1$-$C_6$ alkylenyl)-$OR^1$, —$(C_1$-$C_6$ alkylenyl)-$OC(O)R^{y2}$, —$(C_1$-$C_6$ alkylenyl)-$OC(O)NR^{y3}R^{y4}$, —$(C_1$-$C_6$ alkylenyl)-$S(O)_2R^{y1}$, —$(C_1$-$C_6$ alkylenyl)-$S(O)_2NR^{y3}R^{y4}$, —$(C_1$-$C_6$ alkylenyl)-$C(O)R^{y1}$, —$(C_1$-$C_6$ alkylenyl)-$C(O)OR^{y1}$, —$(C_1$-$C_6$ alkylenyl)-$C(O)NR^{y3}R^{y4}$, —$(C_1$-$C_6$ alkylenyl)-$NR^{y3}R^{y4}$, —$(C_1$-$C_6$ alkylenyl)-$N(R^{y3})C(O)R^{y2}$, —$(C_1$-$C_6$ alkylenyl)-$N(R^{y3})S(O)_2R^{y2}$, —$(C_1$-$C_6$ alkylenyl)-$N(R^{y3})C(O)O(R^{y2})$, —$(C_1$-$C_6$ alkylenyl)-$N(R^{y3})C(O)NR^{y3}R^{y4}$, —$(C_1$-$C_6$ alkylenyl)-$N(R^{y3})S(O)_2NR^{y3}R^{y4}$, —$(C_1$-$C_6$ alkylenyl)-CN, or —$(C_1$-$C_6$ alkylenyl)-$G^{2b}$;

$R^{y1}$, $R^{y3}$, and $R^{y4}$, at each occurrence, are each independently H, $C_1$-$C_6$ alkyl, $C_1$-$C_6$ haloalkyl, $G^{2b}$, or —$(C_1$-$C_6$ alkylenyl)-$G^{2b}$;

$R^{y2}$, at each occurrence, is independently $C_1$-$C_6$ alkyl, $C_1$-$C_6$ haloalkyl, $G^{2b}$, or —$(C_1$-$C_6$ alkylenyl)-$G^{2b}$;

$G^{2b}$, at each occurrence, is independently aryl, heteroaryl, cycloalkyl, cycloalkenyl, or heterocycle; and each $G^{2b}$ group is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —$(C_1$-$C_6$ alkylenyl)-$OR^{z1}$, —$(C_1$-$C_6$ alkylenyl)-$OC(O)R^{z2}$, —$(C_1$-$C_6$ alkylenyl)-$OC(O)NR^{z3}R^{z4}$, —$(C_1$-$C_6$ alkylenyl)-$S(O)_2R^{z1}$, —$(C_1$-$C_6$ alkylenyl)-$S(O)_2NR^{z3}R^{z4}$, —$(C_1$-$C_6$ alkylenyl)-$C(O)R^{z1}$, —$(C_1$-$C_6$ alkylenyl)-$C(O)OR^{z1}$, —$(C_1$-$C_6$ alkylenyl)-$C(O)NR^{z3}R^{z4}$, —$(C_1$-$C_6$ alkylenyl)-$NR^{z3}R^{z4}$, —$(C_1$-$C_6$ alkylenyl)-$N(R^{z3})C(O)R^{z2}$, —$(C_1$-$C_6$ alkylenyl)-$N(R^{z3})S(O)_2R^{z2}$, —$(C_1$-$C_6$ alkylenyl)-$N(R^{z3})C(O)O(R^{z2})$, —$(C_1$-$C_6$ alkylenyl)-$N(R^{z3})C(O)NR^{z3}R^{z4}$, —$(C_1$-$C_6$ alkylenyl)-$N(R^{z3})S(O)_2NR^{z3}R^{z4}$, and —$(C_1$-$C_6$ alkylenyl)-CN;

$R^{z1}$, $R^{z3}$, and $R^{z4}$, at each occurrence, are each independently H, $C_1$-$C_6$ alkyl, or $C_1$-$C_6$ haloalkyl; and $R^{z2}$, at each occurrence, is independently $C_1$-$C_6$ alkyl or $C_1$-$C_6$ haloalkyl.

2. The compound of claim 1, or a pharmaceutically acceptable salt thereof, wherein
$R^1$ is $C_1$-$C_3$ alkyl.

3. The compound of claim 2, or a pharmaceutically acceptable salt thereof, wherein
$R^2$ is H or $C_1$-$C_3$ alkyl.

4. The compound of claim 3, or a pharmaceutically acceptable salt thereof, wherein $R^3$ is H, $C_1$-$C_6$ alkyl, $C_2$-$C_6$ alkenyl, halogen, —$C(O)R^{3a}$, —$C(O)OR^{3a}$, —$C(O)NR^{3b}R^{3c}$, or $G^1$; wherein the $C_1$-$C_6$ alkyl and the $C_2$-$C_6$ alkenyl are each independently unsubstituted or substituted with 1 or 2 substituents independently selected from the group consisting of halogen, $G^1$, —$OR^{3a}$, and —$NR^{3b}R^{3c}$.

5. The compound of claim 3, or a pharmaceutically acceptable salt thereof, wherein $R^3$ is H, $C_1$-$C_3$ alkyl, $C_2$-$C_4$ alkenyl, halogen, or $G^1$; wherein the $C_1$-$C_3$ alkyl and the $C_2$-$C_4$ alkenyl are each independently unsubstituted or substituted with 1 or 2 substituents independently selected from the group consisting of halogen, —OH, —$O(C_1$-$C_3$ alkyl), —$NH_2$, —N(H)($C_1$-$C_3$ alkyl), or —$N(C_1$-$C_3$ alkyl)$_2$.

6. The compound of claim 3, or a pharmaceutically acceptable salt thereof, wherein $R^3$ is H, halogen, unsubstituted $C_1$-$C_3$ alkyl, optionally substituted phenyl, optionally substituted 1,2-oxazolyl, or $C_2$-$C_4$ alkenyl which is substituted with 2 substituents independently selected from the group consisting of halogen and —OH; and $R^5$ is phenyl or pyridinyl, each of which is substituted with 1, 2, or 3 substituents independently selected from the group consisting of $C_1$-$C_3$ alkyl, halogen, $C_1$-$C_3$ haloalkyl, —CN, $NO_2$, $G^2$, —$OR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)S(O)_2R^b$, —$(C_1$-$C_3$ alkylenyl)-$G^2$ wherein $G^2$ is optionally substituted heterocycle, —$(C_1$-$C_3$ alkylenyl)-$S(O)_2R^a$, —$(C_1$-$C_3$ alkylenyl)-$S(O)_2NR^cR^d$, —$(C_1$-$C_3$ alkylenyl)-$NR^cR^d$, and —$(C_1$-$C_3$ alkylenyl)-$N(R^e)S(O)_2R^b$.

7. The compound of claim 3, or a pharmaceutically acceptable salt thereof, wherein $R^1$ is $C_1$-$C_3$ alkyl; $R^2$ is H or $C_1$-$C_3$ alkyl; $R^3$ is H, unsubstituted $C_1$-$C_3$ alkyl, or halogen; $R^4$ is H, $C_1$-$C_3$ alkyl, or halogen; and $R^5$ is phenyl or pyridinyl; each of which is substituted with 1, 2, or 3 substituents, wherein one substituent is selected from the group consisting of —$OR^a$ and —$NR^cR^d$, and the other optional substituents are selected from the group consisting of $C_1$-$C_3$ alkyl, halogen, $C_1$-$C_3$ haloalkyl, —$S(O)_2R^a$, —$S(O)_2NR^cR^d$, —$N(R^e)S(O)_2R^b$, —$(C_1$-$C_3$ alkylenyl)-$G^2$ wherein $G^2$ is optionally substituted heterocycle, —$(C_1$-$C_3$ alkylenyl)-$S(O)_2R^a$, —$(C_1$-$C_3$ alkylenyl)-$S(O)_2NR^cR^d$, —$(C_1$-$C_3$ alkylenyl)-$NR^cR^d$, and —$(C_1$-$C_3$ alkylenyl)-$N(R^e)S(O)_2R^b$.

8. The compound of claim 1, or a pharmaceutically acceptable salt thereof, wherein $R^5$ is represented by the following formula:

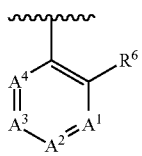

wherein
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is $C(R^7)$, $A^2$ is N, $A^3$ is $C(R^9)$, and $A^4$ is $C(R^{10})$; or
$A^1$ is $C(R^7)$, $A^2$ is $C(R^8)$, $A^3$ is N, and $A^4$ is $C(R^{10})$; or
$A^1$ is $C(R^7)$, $A^2$ is $C(R^8)$, $A^3$ is $C(R^9)$, and $A^4$ is N;
$R^6$ is halogen, —$OR^a$, or —$NR^cR^d$;
$R^7$ is H;
$R^{10}$ is H;
$R^8$ is H, halogen, —$OR^a$, —$NR^cR^d$, —$C(O)R^a$, —$C(O)NR^cR^d$, $G^2$, —$(C_1\text{-}C_6$ alkylenyl)-$G^2$, or —$(C_1\text{-}C_6$ alkylenyl)-$NR^cR^d$;
$R^9$ is H, halogen, —CN, $C_1\text{-}C_6$ haloalkyl, —$N(R^e)S(O)_2R^b$, —$S(O)_2R^a$, —$S(O)_2NR^cR^d$, —$(C_1\text{-}C_6$ alkylenyl)-$G^2$ wherein $G^2$ is optionally substituted heterocycle, —$(C_1\text{-}C_6$ alkylenyl)-$S(O)_2R^a$, —$(C_1\text{-}C_6$ alkylenyl)-$S(O)_2NR^cR^d$, —$(C_1\text{-}C_6$ alkylenyl)-$NR^cR^d$, or —$(C_1\text{-}C_6$ alkylenyl)-$N(R^e)S(O)_2R^b$;
$R^a$, $R^c$, $R^d$, and $R^e$, at each occurrence, are each independently H, $C_2\text{-}C_6$ alkenyl, $C_2\text{-}C_6$ alkynyl, $C_1\text{-}C_6$ haloalkyl, $G^2$, or $C_1\text{-}C_6$ alkyl wherein the $C_1\text{-}C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;
$R^b$, at each occurrence, is independently $C_2\text{-}C_6$ alkenyl, $C_2\text{-}C_6$ alkynyl, $C_1\text{-}C_6$ haloalkyl, $G^2$, or $C_1\text{-}C_6$ alkyl wherein the $C_1\text{-}C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;
$G^2$, at each occurrence, are each independently aryl, heteroaryl, heterocycle, cycloalkyl, or cycloalkenyl; and each $G^2$ group is optionally substituted with 1, 2, 3, 4, or 5 $R^{2g}$ groups;
$R^{2g}$, at each occurrence, is independently $C_1\text{-}C_6$ alkyl, $C_2\text{-}C_6$ alkenyl, $C_2\text{-}C_6$ alkynyl, halogen, $C_1\text{-}C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, —$N(R^{y3})S(O)_2NR^{y3}R^{y4}$, $G^{2b}$, —$(C_1\text{-}C_6$ alkylenyl)-$OR^1$, —$(C_1\text{-}C_6$ alkylenyl)-$OC(O)R^{y2}$, —$(C_1\text{-}C_6$ alkylenyl)-$OC(O)NR^{y3}R^{y4}$, —$(C_1\text{-}C_6$ alkylenyl)-$S(O)_2R^{y1}$, —$(C_1\text{-}C_6$ alkylenyl)-$S(O)_2NR^{y3}R^{y4}$, —$(C_1\text{-}C_6$ alkylenyl)-$C(O)R^{y1}$, —$(C_1\text{-}C_6$ alkylenyl)-$C(O)OR^{y1}$, —$(C_1\text{-}C_6$ alkylenyl)-$C(O)NR^{y3}R^{y4}$, —$(C_1\text{-}C_6$ alkylenyl)-$NR^{y3}R^{y4}$, —$(C_1\text{-}C_6$ alkylenyl)-$N(R^{y3})C(O)R^{y2}$, —$(C_1\text{-}C_6$ alkylenyl)-$N(R^{y3})S(O)_2R^{y2}$, —$(C_1\text{-}C_6$ alkylenyl)-$N(R^{y3})C(O)O(R^{y2})$, —$(C_1\text{-}C_6$ alkylenyl)-$N(R^{y3})C(O)NR^{y3}R^{y4}$, —$(C_1\text{-}C_6$ alkylenyl)-$N(R^{y3})S(O)_2NR^{y3}R^{y4}$, —$(C_1\text{-}C_6$ alkylenyl)-CN, or —$(C_1\text{-}C_6$ alkylenyl)-$G^{2b}$;
$R^{y1}$, $R^{y3}$, and $R^{y4}$, at each occurrence, are each independently H, $C_1\text{-}C_6$ alkyl, $C_1\text{-}C_6$ haloalkyl, $G^{2b}$, or —$(C_1\text{-}C_6$ alkylenyl)-$G^{2b}$;
$R^{y2}$, at each occurrence, is independently $C_1\text{-}C_6$ alkyl, $C_1\text{-}C_6$ haloalkyl, $G^{2b}$, or —$(C_1\text{-}C_6$ alkylenyl)-$G^{2b}$;

$G^{2b}$, at each occurrence, is independently aryl, heteroaryl, cycloalkyl, cycloalkenyl, or heterocycle; and each $G^{2b}$ group is optionally substituted with 1, 2, 3, 4, or 5 substituents independently selected from the group consisting of $C_1\text{-}C_6$ alkyl, $C_2\text{-}C_6$ alkenyl, $C_2\text{-}C_6$ alkynyl, halogen, $C_1\text{-}C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(RZ^3)C(O)NR^{z3}R^{z4}$, —$N(R^{z3})S(O)_2NR^{z3}R^{z4}$, —$(C_1\text{-}C_6$ alkylenyl)-$OR^{z1}$, —$(C_1\text{-}C_6$ alkylenyl)-$OC(O)R^{z2}$, —$(C_1\text{-}C_6$ alkylenyl)-$OC(O)NR^{z3}R^{z4}$, —$(C_1\text{-}C_6$ alkylenyl)-$S(O)_2R^{z1}$, —$(C_1\text{-}C_6$ alkylenyl)-$S(O)_2NR^{z3}R^{z4}$, —$(C_1\text{-}C_6$ alkylenyl)-$C(O)R^{z1}$, —$(C_1\text{-}C_6$ alkylenyl)-$C(O)OR^{z1}$, —$(C_1\text{-}C_6$ alkylenyl)-$C(O)NR^{z3}R^{z4}$, —$(C_1\text{-}C_6$ alkylenyl)-$NR^{z3}R^{z4}$, —$(C_1\text{-}C_6$ alkylenyl)-$N(R^{z3})C(O)R^{z2}$, —$(C_1\text{-}C_6$ alkylenyl)-$N(R^{z3})S(O)_2R^{z2}$, —$(C_1\text{-}C_6$ alkylenyl)-$N(R^{z3})C(O)O(R^{z2})$, —$(C_1\text{-}C_6$ alkylenyl)-$N(R^{z3})C(O)NR^{z3}R^{z4}$, —$(C_1\text{-}C_6$ alkylenyl)-$N(R^{z3})S(O)_2NR^{z3}R^{z4}$, and —$(C_1\text{-}C_6$ alkylenyl)-CN;

$R^{z1}$, $R^{z3}$, and $R^{z4}$, at each occurrence, are each independently H, $C_1\text{-}C_6$ alkyl, or $C_1\text{-}C_6$ haloalkyl; and $R^{z2}$, at each occurrence, is independently $C_1\text{-}C_6$ alkyl or $C_1\text{-}C_6$ haloalkyl.

9. The compound of claim 8, or a pharmaceutically acceptable salt thereof, wherein
$R^1$ is methyl; and
$R^2$ is H or methyl.

10. The compound of claim 9, or a pharmaceutically acceptable salt thereof, wherein
$R^2$ is H;
$R^3$ is H, unsubstituted $C_1\text{-}C_3$ alkyl, or halogen; and
$R^4$ is H, $C_1\text{-}C_3$ alkyl, or halogen.

11. The compound of claim 10, or a pharmaceutically acceptable salt thereof wherein
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$.

12. The compound of claim 11, or a pharmaceutically acceptable salt thereof wherein
$R^8$ is H or halogen.

13. The compound of claim 12, or a pharmaceutically acceptable salt thereof wherein
$R^6$ is —$OR^a$ or —$NR^cR^d$, wherein
$R^a$ and $R^d$ are each independently $C_1\text{-}C_6$ haloalkyl, $G^2$, or $C_1\text{-}C_6$ alkyl wherein the $C_1\text{-}C_6$ alkyl is optionally substituted with one $G^2$ group; and
$R^c$ is H or unsubstituted $C_1\text{-}C_6$ alkyl; and
$R^9$ is —$N(R^e)S(O)_2R^b$, —$S(O)_2R^a$, —$S(O)_2NR^cR^d$, —$(C_1\text{-}C_6$ alkylenyl)-$G^2$ wherein $G^2$ is optionally substituted heterocycle, —$(C_1\text{-}C_6$ alkylenyl)-$S(O)_2R^a$, —$(C_1\text{-}C_6$ alkylenyl)-$S(O)_2NR^cR^d$, —$(C_1\text{-}C_6$ alkylenyl)-$NR^cR^d$, or —$(C_1\text{-}C_6$ alkylenyl)-$N(R^e)S(O)_2R^b$.

14. The compound of claim 12, or a pharmaceutically acceptable salt thereof wherein
$R^6$ is —$OR^a$ or —$NR^cR^d$, wherein
$R^a$ and $R^d$ are each independently $C_1\text{-}C_6$ haloalkyl or unsubstituted $C_1\text{-}C_6$ alkyl; and
$R^c$ is H or unsubstituted $C_1\text{-}C_3$ alkyl; and
$R^9$ is —$S(O)_2R^a$ or —$(CH_2)$—$SO_2R^a$, wherein $R^a$, at each occurrence, is independently unsubstituted $C_1\text{-}C_3$ alkyl.

15. The compound of claim 12, or a pharmaceutically acceptable salt thereof wherein
$R^6$ is —$OR^a$ or —$NR^cR^d$, wherein
$R^a$ is $G^2$ or $C_1\text{-}C_3$ alkyl wherein the $C_1\text{-}C_3$ alkyl is substituted with one $G^2$ group; and $G^2$ is aryl, $C_4\text{-}C_6$ heterocycle, $C_3$-$C_6$ cycloalkyl, $C_5$-$C_6$ heteroaryl, or adamantyl, each of which is optionally substituted;
$R^c$ is H or unsubstituted $C_1$-$C_3$ alkyl; and
$R^d$ is optionally substituted phenyl or $C_1$-$C_3$ alkyl wherein the $C_1$-$C_3$ alkyl is substituted with one $G^2$ group; and $G^2$ is phenyl, $C_3$-$C_6$ cycloalkyl, or bicyclo[2.2.1]heptyl, each of which is optionally substituted; and
$R^9$ is —N($R^e$)S(O)$_2R^b$, —S(O)$_2R^a$, —S(O)$_2$N$R^cR^d$, —($C_1$-$C_3$ alkylenyl)-$G^2$ wherein $G^2$ is optionally substituted $C_4$-$C_6$ heterocycle; —($C_1$-$C_3$ alkylenyl)-S(O)$_2R^a$, —($C_1$-$C_3$ alkylenyl)-S(O)$_2$N$R^cR^d$, —($C_1$-$C_3$ alkylenyl)-N$R^cR^d$, or —($C_1$-$C_3$ alkylenyl)-N($R^e$)S(O)$_2R^b$; wherein
$R^a$ and $R^b$ are each independently $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted;
$R^e$ and $R^c$ are each independently H or unsubstituted $C_1$-$C_3$ alkyl; and
$R^d$ is H, $C_1$-$C_6$ haloalkyl, $G^2$, or $C_1$-$C_6$ alkyl wherein the $C_1$-$C_6$ alkyl is optionally substituted with one $G^2$ group, and $G^2$ is phenyl, $C_3$-$C_6$ cycloalkyl, $C_5$-$C_6$ heteroaryl, or $C_4$-$C_6$ heterocycle, each of which is optionally substituted.

16. The compound of claim 12, or a pharmaceutically acceptable salt thereof wherein
$R^6$ is —O$R^a$; wherein
$R^a$ is $G^2$, and
$G^2$ is optionally substituted phenyl or optionally substituted $C_3$-$C_6$ cycloalkyl; and
$R^9$ is —N($R^e$)S(O)$_2R^b$, —S(O)$_2R^a$, —($C_1$-$C_3$ alkylenyl)-S(O)$_2R^a$, —($C_1$-$C_3$ alkylenyl)-S(O)$_2$N$R^cR^d$, or —($C_1$-$C_3$ alkylenyl)-N($R^e$)S(O)$_2R^b$; wherein
$R^a$ is unsubstituted $C_1$-$C_3$ alkyl or optionally substituted $C_4$-$C_6$ heterocycle,
$R^b$ is unsubstituted $C_1$-$C_3$ alkyl or optionally substituted benzyl;
$R^c$ is H or unsubstituted $C_1$-$C_3$ alkyl;
$R^d$ is H or unsubstituted $C_1$-$C_3$ alkyl; and
$R^e$ is H.

17. The compound of claim 12, or a pharmaceutically acceptable salt thereof wherein
$R^3$ is H;
$R^4$ is H;
$R^6$ is —O$R^a$; wherein
$R^a$ is $G^2$, and
$G^2$ is phenyl substituted with 1 or 2 halogen; and
$R^9$ is —N($R^e$)S(O)$_2R^b$, —S(O)$_2R^a$, or —(CH$_2$)—S(O)$_2R^a$, wherein
$R^a$ and $R^b$ are each independently unsubstituted $C_1$-$C_3$ alkyl, and
$R^e$ is H.

18. The compound of claim 12, or a pharmaceutically acceptable salt thereof, wherein
$R^6$ is —N$R^cR^d$, wherein
$R^c$ is H or unsubstituted $C_1$-$C_3$ alkyl; and
$R^d$ is optionally substituted phenyl or $C_1$-$C_3$ alkyl wherein the $C_1$-$C_3$ alkyl is substituted with one $G^2$ group, wherein $G^2$ is optionally substituted $C_3$-$C_6$ cycloalkyl, and
$R^9$ is —N($R^e$)S(O)$_2R^b$, —S(O)$_2R^a$, —($C_1$-$C_3$ alkylenyl)-S(O)$_2R^a$, —($C_1$-$C_3$ alkylenyl)-S(O)$_2$N$R^cR^d$, or —($C_1$-$C_3$ alkylenyl)-N($R^e$)S(O)$_2R^b$; wherein
$R^a$ is unsubstituted $C_1$-$C_3$ alkyl or optionally substituted $C_4$-$C_6$ heterocycle,
$R^b$ is unsubstituted $C_1$-$C_3$ alkyl or optionally substituted benzyl;
$R^c$ is H or unsubstituted $C_1$-$C_3$ alkyl;
$R^d$ is H or unsubstituted $C_1$-$C_3$ alkyl; and
$R^e$ is H.

19. The compound of claim 12, or a pharmaceutically acceptable salt thereof, wherein
$R^3$ is H,
$R^4$ is H,
$R^6$ is —N$R^cR^d$, wherein
$R^c$ is H or methyl; and
$R^d$ is phenyl substituted with 1 or 2 halogen, or $R^d$ is $C_1$-$C_3$ alkyl wherein the $C_1$-$C_3$ alkyl is substituted with one $G^2$ group, and $G^2$ is optionally substituted cyclopropyl, and
$R^9$ is —(CH$_2$)—S(O)$_2R^a$; wherein $R^a$ is unsubstituted $C_1$-$C_3$ alkyl.

20. The compound of claim 1 or a pharmaceutically acceptable salt thereof, wherein the compound is selected from the group consisting of:
1-methyl-3-(2-phenoxyphenyl)-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)phenyl]methanesulfonamide;
N-[4-(2,4-difluorophenoxy)-3-(1-methyl-7-oxo-6,7-dihydro-1H-pyrrolo[2,3-c]pyridin-3-yl)phenyl]propane-2-sulfonamide;
N-[4-(2,4-difluorophenoxy)-3-(1-methyl-7-oxo-6,7-dihydro-1H-pyrrolo[2,3-c]pyridin-3-yl)phenyl]ethanesulfonamide;
N-[4-(4-chlorophenoxy)-3-(1-methyl-7-oxo-6,7-dihydro-1H-pyrrolo[2,3-c]pyridin-3-yl)phenyl]ethanesulfonamide;
N-{4-[(trans-4-methoxycyclohexyl)oxy]-3-(1-methyl-7-oxo-6,7-dihydro-1H-pyrrolo[2,3-c]pyridin-3-yl)phenyl}ethanesulfonamide;
N-[3-(1-methyl-7-oxo-6,7-dihydro-1H-pyrrolo[2,3-c]pyridin-3-yl)-4-(tetrahydro-2H-pyran-4-yloxy)phenyl]ethanesulfonamide;
N-{4-[(4,4-difluorocyclohexyl)oxy]-3-(1-methyl-7-oxo-6,7-dihydro-1H-pyrrolo[2,3-c]pyridin-3-yl)phenyl}ethanesulfonamide;
N-{4-[(cis-4-methoxycyclohexyl)oxy]-3-(1-methyl-7-oxo-6,7-dihydro-1H-pyrrolo[2,3-c]pyridin-3-yl)phenyl}ethanesulfonamide;
N-[3-(1-methyl-7-oxo-6,7-dihydro-1H-pyrrolo[2,3-c]pyridin-3-yl)-4-(oxetan-3-yloxy)phenyl]ethanesulfonamide;
N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide;
N-[2-(2,4-difluorophenoxy)-4-fluoro-5-(1-methyl-7-oxo-6,7-dihydro-1H-pyrrolo[2,3-c]pyridin-3-yl)phenyl]methanesulfonamide;
N-[2,4-bis(2,4-difluorophenoxy)-5-(1-methyl-7-oxo-6,7-dihydro-1H-pyrrolo[2,3-c]pyridin-3-yl)phenyl]methanesulfonamide;
N-[4-(cyclopropylmethoxy)-2-methyl-3-(1-methyl-7-oxo-6,7-dihydro-1H-pyrrolo[2,3-c]pyridin-3-yl)phenyl]ethanesulfonamide;
N-[4-(4-fluorophenoxy)-3-(1-methyl-7-oxo-6,7-dihydro-1H-pyrrolo[2,3-c]pyridin-3-yl)phenyl]ethanesulfonamide;
N-[4-(4-cyanophenoxy)-3-(1-methyl-7-oxo-6,7-dihydro-1H-pyrrolo[2,3-c]pyridin-3-yl)phenyl]methanesulfonamide;

3-[2-(2,4-difluorophenoxy)-5-(methylsulfonyl)phenyl]-1-methyl-1,6-dihydro-7H-pyrrolo[2,3-c]pyridin-7-one;
1-methyl-3-[5-(methylsulfonyl)-2-phenoxyphenyl]-1,6-dihydro-7H-pyrrolo[2,3-c]pyridin-7-one;
3-[2-(3,4-difluorophenoxy)-5-(methylsulfonyl)phenyl]-1-methyl-1,6-dihydro-7H-pyrrolo[2,3-c]pyridin-7-one;
3-[2-methoxy-5-(methylsulfonyl)phenyl]-1-methyl-1,6-dihydro-7H-pyrrolo[2,3-c]pyridin-7-one;
3-[2-(cyclopropylmethoxy)-5-(methylsulfonyl)phenyl]-1-methyl-1,6-dihydro-7H-pyrrolo[2,3-c]pyridin-7-one;
1-methyl-3-[5-(methylsulfonyl)-2-(tetrahydrofuran-3-yloxy)phenyl]-1,6-dihydro-7H-pyrrolo[2,3-c]pyridin-7-one;
1-methyl-3-[5-(methylsulfonyl)-2-(tetrahydrofuran-3-ylmethoxy)phenyl]-1,6-dihydro-7H-pyrrolo[2,3-c]pyridin-7-one;
1-methyl-3-[5-(methylsulfonyl)-2-(tetrahydro-2H-pyran-4-yloxy)phenyl]-1,6-dihydro-7H-pyrrolo[2,3-c]pyridin-7-one;
3-{2-[(4,4-difluorocyclohexyl)oxy]-5-(methylsulfonyl)phenyl}-1-methyl-1,6-dihydro-7H-pyrrolo[2,3-c]pyridin-7-one;
1-methyl-3-[5-(methylsulfonyl)-2-(tetrahydro-2H-pyran-3-yloxy)phenyl]-1,6-dihydro-7H-pyrrolo[2,3-c]pyridin-7-one;
3-[2-(2,2-dimethylpropoxy)-5-(methylsulfonyl)phenyl]-1-methyl-1,6-dihydro-7H-pyrrolo[2,3-c]pyridin-7-one;
3-[2-(cyclobutylmethoxy)-5-(methylsulfonyl)phenyl]-1-methyl-1,6-dihydro-7H-pyrrolo[2,3-c]pyridin-7-one;
1-methyl-3-{2-[(1-methylcyclopropyl)methoxy]-5-(methylsulfonyl)phenyl}-1,6-dihydro-7H-pyrrolo[2,3-c]pyridin-7-one;
1-methyl-3-[5-(methylsulfonyl)-2-(oxetan-3-ylmethoxy)phenyl]-1,6-dihydro-7H-pyrrolo[2,3-c]pyridin-7-one;
1-methyl-3-[5-(methylsulfonyl)-2-(tetrahydro-2H-pyran-4-ylmethoxy)phenyl]-1,6-dihydro-7H-pyrrolo[2,3-c]pyridin-7-one;
3-[2-(2-cyclopropylethoxy)-5-(methylsulfonyl)phenyl]-1-methyl-1,6-dihydro-7H-pyrrolo[2,3-c]pyridin-7-one;
3-{2-[(cis-4-hydroxycyclohexyl)oxy]-5-(methylsulfonyl)phenyl}-1-methyl-1,6-dihydro-7H-pyrrolo[2,3-c]pyridin-7-one;
3-{2-[(trans-4-hydroxycyclohexyl)oxy]-5-(methylsulfonyl)phenyl}-1-methyl-1,6-dihydro-7H-pyrrolo[2,3-c]pyridin-7-one;
3-[2-(2-cyclopentylethoxy)-5-(methylsulfonyl)phenyl]-1-methyl-1,6-dihydro-7H-pyrrolo[2,3-c]pyridin-7-one;
3-[2-(2-cyclohexylethoxy)-5-(methylsulfonyl)phenyl]-1-methyl-1,6-dihydro-7H-pyrrolo[2,3-c]pyridin-7-one;
1-methyl-3-[5-(methylsulfonyl)-2-(2-phenylethoxy)phenyl]-1,6-dihydro-7H-pyrrolo[2,3-c]pyridin-7-one;
3-[2-(2,3-dihydro-1H-inden-2-yloxy)-5-(methylsulfonyl)phenyl]-1-methyl-1,6-dihydro-7H-pyrrolo[2,3-c]pyridin-7-one;
1-methyl-3-{5-(methylsulfonyl)-2-[2-(thiophen-2-yl)ethoxy]phenyl}-1,6-dihydro-7H-pyrrolo[2,3-c]pyridin-7-one;
3-[2-(3,3-dimethylbutoxy)-5-(methylsulfonyl)phenyl]-1-methyl-1,6-dihydro-7H-pyrrolo[2,3-c]pyridin-7-one;
3-{2-[(4,4-difluorocyclohexyl)methoxy]-5-(methylsulfonyl)phenyl}-1-methyl-1,6-dihydro-7H-pyrrolo[2,3-c]pyridin-7-one;
3-{2-[(2,2-difluorocyclopropyl)methoxy]-5-(methylsulfonyl)phenyl}-1-methyl-1,6-dihydro-7H-pyrrolo[2,3-c]pyridin-7-one;
3-{2-[(2,2-difluorocyclopropyl)methoxy]-5-(methylsulfonyl)phenyl}-1,6-dimethyl-1,6-dihydro-7H-pyrrolo[2,3-c]pyridin-7-one;
3-{2-[(cyclopropylmethyl)amino]-5-(methylsulfonyl)phenyl}-1-methyl-1,6-dihydro-7H-pyrrolo[2,3-c]pyridin-7-one;
3-{2-[(cyclopropylmethyl)(methyl)amino]-5-(methylsulfonyl)phenyl}-1-methyl-1,6-dihydro-7H-pyrrolo[2,3-c]pyridin-7-one;
4-({[2-(1-methyl-7-oxo-6,7-dihydro-1H-pyrrolo[2,3-c]pyridin-3-yl)-4-(methylsulfonyl)phenyl]amino}methyl)benzonitrile;
3-{2-[(cyclohexylmethyl)amino]-5-(methylsulfonyl)phenyl}-1-methyl-1,6-dihydro-7H-pyrrolo[2,3-c]pyridin-7-one;
3-[2-(4-chlorophenoxy)-5-(ethylsulfonyl)phenyl]-1-methyl-1,6-dihydro-7H-pyrrolo[2,3-c]pyridin-7-one;
3-[2-(2,4-difluorophenoxy)-5-(ethylsulfonyl)phenyl]-1-methyl-1,6-dihydro-7H-pyrrolo[2,3-c]pyridin-7-one;
3-[2-(cyclopropylmethoxy)-6-methylphenyl]-1-methyl-1,6-dihydro-7H-pyrrolo[2,3-c]pyridin-7-one;
4-(2,4-difluorophenoxy)-3-(1-methyl-7-oxo-6,7-dihydro-1H-pyrrolo[2,3-c]pyridin-3-yl)benzenesulfonamide;
3-{2-(2,4-difluorophenoxy)-5-[(methylsulfonyl)methyl]phenyl}-1-methyl-1,6-dihydro-7H-pyrrolo[2,3-c]pyridin-7-one;
3-{2-(2,4-difluorophenoxy)-5-[(ethylsulfonyl)methyl]phenyl}-1-methyl-1,6-dihydro-7H-pyrrolo[2,3-c]pyridin-7-one;
3-{2-(2,4-difluorophenoxy)-5-[2-(ethylsulfonyl)propan-2-yl]phenyl}-1-methyl-1,6-dihydro-7H-pyrrolo[2,3-c]pyridin-7-one;
3-{2-(2,4-difluorophenoxy)-5-[1-(ethylsulfonyl)ethyl]phenyl}-1-methyl-1,6-dihydro-7H-pyrrolo[2,3-c]pyridin-7-one;
3-{2-(2,4-difluorophenoxy)-5-[(1R)-1-(ethylsulfonyl)ethyl]phenyl}-1-methyl-1,6-dihydro-7H-pyrrolo[2,3-c]pyridin-7-one;
3-{2-(2,4-difluorophenoxy)-5-[(1S)-1-(ethylsulfonyl)ethyl]phenyl}-1-methyl-1,6-dihydro-7H-pyrrolo[2,3-c]pyridin-7-one;
3-{2-(2,4-difluorophenoxy)-5-[(phenylsulfonyl)methyl]phenyl}-1-methyl-1,6-dihydro-7H-pyrrolo[2,3-c]pyridin-7-one;
3-[2-(2,4-difluorophenoxy)-5-(ethylsulfonyl)pyridin-3-yl]-1-methyl-1,6-dihydro-7H-pyrrolo[2,3-c]pyridin-7-one;
3-{2-(2,4-difluorophenoxy)-5-[(methylsulfonyl)methyl]pyridin-3-yl}-1-methyl-1,6-dihydro-7H-pyrrolo[2,3-c]pyridin-7-one;
3-[2-(4-fluorophenoxy)-5-(methylsulfonyl)phenyl]-1-methyl-1,6-dihydro-7H-pyrrolo[2,3-c]pyridin-7-one;
3-[2-(4-tert-butylphenoxy)-5-(methylsulfonyl)phenyl]-1-methyl-1,6-dihydro-7H-pyrrolo[2,3-c]pyridin-7-one;
1-methyl-3-[5-(methylsulfonyl)-2-(naphthalen-2-yloxy)phenyl]-1,6-dihydro-7H-pyrrolo[2,3-c]pyridin-7-one;
1-methyl-3-[5-(methylsulfonyl)-2-(2,2,3,3,3-pentafluoropropoxy)phenyl]-1,6-dihydro-7H-pyrrolo[2,3-c]pyridin-7-one;
1-methyl-3-[5-(methylsulfonyl)-2-{2-[tricyclo[3.3.1.1$^{3,7}$]dec-1-yl]ethoxy}phenyl]-1,6-dihydro-7H-pyrrolo[2,3-c]pyridin-7-one;
3-[2-(3-cyclopentylpropoxy)-5-(methylsulfonyl)phenyl]-1-methyl-1,6-dihydro-7H-pyrrolo[2,3-c]pyridin-7-one;
3-{2-[(1-acetylpiperidin-4-yl)oxy]-5-(methylsulfonyl)phenyl}-1-methyl-1,6-dihydro-7H-pyrrolo[2,3-c]pyridin-7-one;

3-{2-[(cyclopentylmethyl)amino]-5-(methylsulfonyl)phenyl}-1-methyl-1,6-dihydro-7H-pyrrolo[2,3-c]pyridin-7-one;

1-methyl-3-{5-(methylsulfonyl)-2-[(2,2,2-trifluoroethyl)amino]phenyl}-1,6-dihydro-7H-pyrrolo[2,3-c]pyridin-7-one;

3-{2-[(2,2,3,3,4,4,4-heptafluorobutyl)amino]-5-(methylsulfonyl)phenyl}-1-methyl-1,6-dihydro-7H-pyrrolo[2,3-c]pyridin-7-one;

3-[2-{[(1S,4R)-bicyclo[2.2.1]hept-2-ylmethyl]amino}-5-(methylsulfonyl)phenyl]-1-methyl-1,6-dihydro-7H-pyrrolo[2,3-c]pyridin-7-one;

3-{2-[(2-cyclopentylethyl)amino]-5-(methylsulfonyl)phenyl}-1-methyl-1,6-dihydro-7H-pyrrolo[2,3-c]pyridin-7-one;

3-[2-(2-chloro-4-methylphenoxy)-5-(ethylsulfonyl)phenyl]-1-methyl-1,6-dihydro-7H-pyrrolo[2,3-c]pyridin-7-one;

3-[5-(ethylsulfonyl)-2-(pyridin-4-yloxy)phenyl]-1-methyl-1,6-dihydro-7H-pyrrolo[2,3-c]pyridin-7-one;

3-{2-[(4,6-dimethylpyridin-3-yl)oxy]-5-(ethylsulfonyl)phenyl}-1-methyl-1,6-dihydro-7H-pyrrolo[2,3-c]pyridin-7-one;

3-[2-(3,4-dichlorophenoxy)-5-(ethylsulfonyl)phenyl]-1-methyl-1,6-dihydro-7H-pyrrolo[2,3-c]pyridin-7-one;

3-{5-(ethylsulfonyl)-2-[4-(trifluoromethyl)phenoxy]phenyl}-1-methyl-1,6-dihydro-7H-pyrrolo[2,3-c]pyridin-7-one;

4-[4-(ethylsulfonyl)-2-[1-methyl-7-oxo-6,7-dihydro-1H-pyrrolo[2,3-c]pyridin-3-yl]phenoxy]benzonitrile;

3-[2-(4-chloro-3-ethylphenoxy)-5-(ethylsulfonyl)phenyl]-1-methyl-1,6-dihydro-7H-pyrrolo[2,3-c]pyridin-7-one;

4-[4-(ethylsulfonyl)-2-[1-methyl-7-oxo-6,7-dihydro-1H-pyrrolo[2,3-c]pyridin-3-yl]phenoxy]-3-methoxybenzonitrile;

3-[5-(ethylsulfonyl)-2-(pyridin-3-yloxy)phenyl]-1-methyl-1,6-dihydro-7H-pyrrolo[2,3-c]pyridin-7-one;

3-[2-(2,4-dichlorophenoxy)-5-(ethylsulfonyl)phenyl]-1-methyl-1,6-dihydro-7H-pyrrolo[2,3-c]pyridin-7-one;

2-[4-(ethylsulfonyl)-2-[1-methyl-7-oxo-6,7-dihydro-1H-pyrrolo[2,3-c]pyridin-3-yl]phenoxy]benzonitrile;

3-[2-(2,3-dichlorophenoxy)-5-(ethylsulfonyl)phenyl]-1-methyl-1,6-dihydro-7H-pyrrolo[2,3-c]pyridin-7-one;

3-[2-(2-chloro-4-methoxyphenoxy)-5-(ethylsulfonyl)phenyl]-1-methyl-1,6-dihydro-7H-pyrrolo[2,3-c]pyridin-7-one;

3-{5-(ethylsulfonyl)-2-[(6-methylpyrazin-2-yl)oxy]phenyl}-1-methyl-1,6-dihydro-7H-pyrrolo[2,3-c]pyridin-7-one;

3-[5-(ethylsulfonyl)-2-(pyridazin-4-yloxy)phenyl]-1-methyl-1,6-dihydro-7H-pyrrolo[2,3-c]pyridin-7-one;

3-[5-(ethylsulfonyl)-2-(pyrimidin-5-yloxy)phenyl]-1-methyl-1,6-dihydro-7H-pyrrolo[2,3-c]pyridin-7-one;

3-{5-(ethylsulfonyl)-2-[(3-methylpyrazin-2-yl)oxy]phenyl}-1-methyl-1,6-dihydro-7H-pyrrolo[2,3-c]pyridin-7-one;

3-{5-(ethylsulfonyl)-2-[(1,3,5-trimethyl-1H-pyrazol-4-yl)oxy]phenyl}-1-methyl-1,6-dihydro-7H-pyrrolo[2,3-c]pyridin-7-one;

5-chloro-3-{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one;

3,5-bis {2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-(3,5-dimethyl-1,2-oxazol-4-yl)-1-methyl-1,6-dihydro-7H-pyrrolo[2,3-c]pyridin-7-one;

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]methanesulfonamide;

3-[2-(cyclopropylmethoxy)-5-(2,3-dihydro-1H-indol-1-ylsulfonyl)phenyl]-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]-N-methyl-methanesulfonamide;

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide;

N-cyclohexyl-1-[4-(2,4-difluorophenoxy)-3-(1-methyl-7-oxo-6,7-dihydro-1H-pyrrolo[2,3-c]pyridin-3-yl)phenyl]methanesulfonamide;

3-{2-(2,4-difluorophenoxy)-5-[(piperidin-1-ylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]-N-(1,3-thiazol-2-yl)methanesulfonamide;

3-[2-(2,4-difluorophenoxy)-5-(piperazin-1-ylmethyl)phenyl]-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)benzyl]ethanesulfonamide;

4-chloro-3-[2-(2,4-difluorophenoxy)-5-(methylsulfonyl)phenyl]-1-methyl-1,6-dihydro-7H-pyrrolo[2,3-c]pyridin-7-one;

4-chloro-3-[2-(2-cyclopropylethoxy)-5-(methylsulfonyl)phenyl]-1-methyl-1,6-dihydro-7H-pyrrolo[2,3-c]pyridin-7-one;

3-{2-[(cyclopropylmethyl)amino]-5-[(methylsulfonyl)methyl]phenyl}-1-methyl-1,6-dihydro-7H-pyrrolo[2,3-c]pyridin-7-one;

3-{5-[(4-aminopiperidin-1-yl)methyl]-2-(2,4-difluorophenoxy)phenyl}-1-methyl-1,6-dihydro-7H-pyrrolo[2,3-c]pyridin-7-one;

3-{2-(2,4-difluorophenoxy)-5-[(piperidin-4-ylamino)methyl]phenyl}-1-methyl-1,6-dihydro-7H-pyrrolo[2,3-c]pyridin-7-one;

3-{2-(2,4-difluorophenoxy)-5-{[4-(dimethylamino)piperidin-1-yl]methyl}phenyl]-1-methyl-1,6-dihydro-7H-pyrrolo[2,3-c]pyridin-7-one;

3-{2-(2,4-difluorophenoxy)-5-{[(3,3-dimethylbutyl)amino]methyl}phenyl]-1-methyl-1,6-dihydro-7H-pyrrolo[2,3-c]pyridin-7-one;

3-{2-(2,4-difluorophenoxy)-5-[(4-methoxypiperidin-1-yl)methyl]phenyl]-1-methyl-1,6-dihydro-7H-pyrrolo[2,3-c]pyridin-7-one;

3-{2-(2,4-difluorophenoxy)-5-[(4-methylpiperazin-1-yl)methyl]phenyl]-1-methyl-1,6-dihydro-7H-pyrrolo[2,3-c]pyridin-7-one;

3-[2-(2,4-difluorophenoxy)-5-{[(3-methylbutyl)amino]methyl}phenyl]-1-methyl-1,6-dihydro-7H-pyrrolo[2,3-c]pyridin-7-one;

3-[5-{[(cyclopropylmethyl)amino]methyl}-2-(2,4-difluorophenoxy)phenyl]-1-methyl-1,6-dihydro-7H-pyrrolo[2,3-c]pyridin-7-one;
3-[2-(2,4-difluorophenoxy)-5-{[(1H-imidazol-4-ylmethyl)amino]methyl}phenyl]-1-methyl-1,6-dihydro-7H-pyrrolo[2,3-c]pyridin-7-one;
3-[5-(chloromethyl)-2-(2,4-difluorophenoxy)phenyl]-1-methyl-1,6-dihydro-7H-pyrrolo[2,3-c]pyridin-7-one;
3-{2-[(4-fluorophenyl)amino]-5-[(methylsulfonyl)methyl]phenyl}-1-methyl-1,6-dihydro-7H-pyrrolo[2,3-c]pyridin-7-one;
3-{2-[(2,4-difluorophenyl)amino]-5-[(methylsulfonyl)methyl]phenyl}-1-methyl-1,6-dihydro-7H-pyrrolo[2,3-c]pyridin-7-one;
3-[2-(2,4-difluorophenoxy)-5-(methylsulfonyl)phenyl]-1,4-dimethyl-1,6-dihydro-7H-pyrrolo[2,3-c]pyridin-7-one;
3-[2-(2-cyclopropylethoxy)-5-(methylsulfonyl)phenyl]-1,4-dimethyl-1,6-dihydro-7H-pyrrolo[2,3-c]pyridin-7-one;
3-{2-(cyclopropylmethoxy)-5-[(3,3-difluoroazetidin-1-yl)sulfonyl]phenyl}-1-methyl-1,6-dihydro-7H-pyrrolo[2,3-c]pyridin-7-one;
5-[(1 Z)-2-chloro-4-hydroxybut-1-en-1-yl]-3-[2-(2,4-difluorophenoxy)-5-(ethylsulfonyl)phenyl]-1-methyl-1,6-dihydro-7H-pyrrolo[2,3-c]pyridin-7-one;
3-[2-(2,4-difluorophenoxy)-5-{[(furan-3-ylmethyl)amino]methyl}phenyl]-1-methyl-1,6-dihydro-7H-pyrrolo[2,3-c]pyridin-7-one;
3-[5-{[(2-cyclopentylethyl)amino]methyl}-2-(2,4-difluorophenoxy)phenyl]-1-methyl-1,6-dihydro-7H-pyrrolo[2,3-c]pyridin-7-one;
3-[2-(2,4-difluorophenoxy)-5-{[4-(trifluoromethyl)piperidin-1-yl]methyl}phenyl]-1-methyl-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)benzyl]-2-methoxybenzenesulfonamide;
1-(4-chlorophenyl)-N-[4-(2,4-difluorophenoxy)-3-(1-methyl-7-oxo-6,7-dihydro-1H-pyrrolo[2,3-c]pyridin-3-yl)benzyl]methanesulfonamide;
N-[4-(2,4-difluorophenoxy)-3-(1-methyl-7-oxo-6,7-dihydro-1H-pyrrolo[2,3-c]pyridin-3-yl)benzyl]-1-(4-methylphenyl)methanesulfonamide;
N-[4-(2,4-difluorophenoxy)-3-(1-methyl-7-oxo-6,7-dihydro-1H-pyrrolo[2,3-c]pyridin-3-yl)benzyl]-1-[4-(trifluoromethyl)phenyl]methanesulfonamide;
1-(4-cyanophenyl)-N-[4-(2,4-difluorophenoxy)-3-(1-methyl-7-oxo-6,7-dihydro-1H-pyrrolo[2,3-c]pyridin-3-yl)benzyl]methanesulfonamide;
N-[4-(2,4-difluorophenoxy)-3-(1-methyl-7-oxo-6,7-dihydro-1H-pyrrolo[2,3-c]pyridin-3-yl)benzyl]-2,2,2-trifluoroethanesulfonamide;
3-[5-(aminomethyl)-2-(2,4-difluorophenoxy)phenyl]-1-methyl-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)benzyl]cyclopentanesulfonamide;
2,5-dichloro-N-[4-(2,4-difluorophenoxy)-3-(1-methyl-7-oxo-6,7-dihydro-1H-pyrrolo[2,3-c]pyridin-3-yl)benzyl]thiophene-3-sulfonamide;
N-[4-(2,4-difluorophenoxy)-3-(1-methyl-7-oxo-6,7-dihydro-1H-pyrrolo[2,3-c]pyridin-3-yl)benzyl]-5-methyl-1,2-oxazole-4-sulfonamide;
N-[4-(2,4-difluorophenoxy)-3-(1-methyl-7-oxo-6,7-dihydro-1H-pyrrolo[2,3-c]pyridin-3-yl)benzyl]-3,5-dimethyl-1,2-oxazole-4-sulfonamide;
N-[4-(2,4-difluorophenoxy)-3-(1-methyl-7-oxo-6,7-dihydro-1H-pyrrolo[2,3-c]pyridin-3-yl)benzyl]benzenesulfonamide;
3-{2-[(cyclopropylmethyl)amino]phenyl}-1-methyl-1,6-dihydro-7H-pyrrolo[2,3-c]pyridin-7-one;
3-{2-chloro-5-[(methylsulfonyl)methyl]pyridin-3-yl}-1-methyl-1,6-dihydro-7H-pyrrolo[2,3-c]pyridin-7-one;
3-[2-{[trans-4-(dimethylamino)cyclohexyl]oxy}-5-(pyrrolidin-1-ylsulfonyl)phenyl]-1-methyl-1,6-dihydro-7H-pyrrolo[2,3-c]pyridin-7-one;
3-{5-fluoro-2-[(4-fluorophenyl)amino]pyridin-3-yl}-1-methyl-1,6-dihydro-7H-pyrrolo[2,3-c]pyridin-7-one;
3-[5-amino-2-(2,4-difluorophenoxy)phenyl]-1-methyl-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)phenyl]-4-methylpentanamide;
2,5-dichloro-N-[4-(2,4-difluorophenoxy)-3-(1-methyl-7-oxo-6,7-dihydro-1H-pyrrolo[2,3-c]pyridin-3-yl)phenyl]benzamide;
N-[4-(2,4-difluorophenoxy)-3-(1-methyl-7-oxo-6,7-dihydro-1H-pyrrolo[2,3-c]pyridin-3-yl)phenyl]-2-(2-methoxyphenyl)acetamide;
N-[4-(2,4-difluorophenoxy)-3-(1-methyl-7-oxo-6,7-dihydro-1H-pyrrolo[2,3-c]pyridin-3-yl)phenyl]pyridine-2-carboxamide;
N-[4-(2,4-difluorophenoxy)-3-(1-methyl-7-oxo-6,7-dihydro-1H-pyrrolo[2,3-c]pyridin-3-yl)phenyl]-5-methylpyrazine-2-carboxamide;
N-[4-(2,4-difluorophenoxy)-3-(1-methyl-7-oxo-6,7-dihydro-1H-pyrrolo[2,3-c]pyridin-3-yl)phenyl]-3-phenylpropanamide;
N-[4-(2,4-difluorophenoxy)-3-(1-methyl-7-oxo-6,7-dihydro-1H-pyrrolo[2,3-c]pyridin-3-yl)phenyl]-4-phenoxybutanamide;
N-[4-(2,4-difluorophenoxy)-3-(1-methyl-7-oxo-6,7-dihydro-1H-pyrrolo[2,3-c]pyridin-3-yl)phenyl]-2-(3-phenoxyphenyl)acetamide;
4-(acetylamino)-N-[4-(2,4-difluorophenoxy)-3-(1-methyl-7-oxo-6,7-dihydro-1H-pyrrolo[2,3-c]pyridin-3-yl)phenyl]benzamide;
N-[4-(2,4-difluorophenoxy)-3-(1-methyl-7-oxo-6,7-dihydro-1H-pyrrolo[2,3-c]pyridin-3-yl)phenyl]-4-(phenoxymethyl)benzamide;
N-[4-(2,4-difluorophenoxy)-3-(1-methyl-7-oxo-6,7-dihydro-1H-pyrrolo[2,3-c]pyridin-3-yl)phenyl]-2-oxo-1-phenylpyrrolidine-3-carboxamide;
2-(1,2-benzoxazol-3-yl)-N-[4-(2,4-difluorophenoxy)-3-(1-methyl-7-oxo-6,7-dihydro-1H-pyrrolo[2,3-c]pyridin-3-yl)phenyl]acetamide;
2-(5-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide;
2-(4-chloro-2-fluorophenyl)-N-[4-(2,4-difluorophenoxy)-3-(1-methyl-7-oxo-6,7-dihydro-1H-pyrrolo[2,3-c]pyridin-3-yl)phenyl]acetamide;
N-[4-(2,4-difluorophenoxy)-3-(1-methyl-7-oxo-6,7-dihydro-1H-pyrrolo[2,3-c]pyridin-3-yl)phenyl]-2-(6-methylpyridin-3-yl)acetamide;
N-[4-(2,4-difluorophenoxy)-3-(1-methyl-7-oxo-6,7-dihydro-1H-pyrrolo[2,3-c]pyridin-3-yl)phenyl]-2-(3,4-dihydro-2H-chromen-6-yl)acetamide;
N-[4-(2,4-difluorophenoxy)-3-(1-methyl-7-oxo-6,7-dihydro-1H-pyrrolo[2,3-c]pyridin-3-yl)phenyl]-2-(2-methyl-1,3-thiazol-5-yl)acetamide;

N-[4-(2,4-difluorophenoxy)-3-(1-methyl-7-oxo-6,7-dihydro-1H-pyrrolo[2,3-c]pyridin-3-yl)phenyl]-2-(1,5-dimethyl-1H-pyrazol-3-yl)acetamide;
N-[4-(2,4-difluorophenoxy)-3-(1-methyl-7-oxo-6,7-dihydro-1H-pyrrolo[2,3-c]pyridin-3-yl)phenyl]-2-[4-(2-fluorophenyl)-1H-pyrazol-1-yl]acetamide;
methyl (2E)-3-[(4-fluorophenyl){2-(1-methyl-7-oxo-6,7-dihydro-1H-pyrrolo[2,3-c]pyridin-3-yl)-4-[(methylsulfonyl)methyl]phenyl}amino]prop-2-enoate;
4-({[4-(2,4-difluorophenoxy)-3-(1-methyl-7-oxo-6,7-dihydro-1H-pyrrolo[2,3-c]pyridin-3-yl)phenyl]amino}methyl)benzonitrile;
3-[2-(2,4-difluorophenoxy)-5-{[3-(4-methoxyphenoxy)benzyl]amino}phenyl]-1-methyl-1,6-dihydro-7H-pyrrolo[2,3-c]pyridin-7-one;
3-[2-(2,4-difluorophenoxy)-5-{[(3-methylpyridin-2-yl)methyl]amino}phenyl]-1-methyl-1,6-dihydro-7H-pyrrolo[2,3-c]pyridin-7-one;
3-[5-{[4-(benzyloxy)benzyl]amino}-2-(2,4-difluorophenoxy)phenyl]-1-methyl-1,6-dihydro-7H-pyrrolo[2,3-c]pyridin-7-one;
3-[5-{[(5-chloro-3-methyl-1-phenyl-1H-pyrazol-4-yl)methyl]amino}-2-(2,4-difluorophenoxy)phenyl]-1-methyl-1,6-dihydro-7H-pyrrolo[2,3-c]pyridin-7-one;
3-({[4-(2,4-difluorophenoxy)-3-(1-methyl-7-oxo-6,7-dihydro-1H-pyrrolo[2,3-c]pyridin-3-yl)phenyl]amino}methyl)benzonitrile;
3-{2-(2,4-difluorophenoxy)-5-[(4-phenoxybenzyl)amino]phenyl}-1-methyl-1,6-dihydro-7H-pyrrolo[2,3-c]pyridin-7-one;
3-{2-(2,4-difluorophenoxy)-5-[(3,3-dimethylbutyl)amino]phenyl}-1-methyl-1,6-dihydro-7H-pyrrolo[2,3-c]pyridin-7-one;
3-{5-[(2,6-difluorobenzyl)amino]-2-(2,4-difluorophenoxy)phenyl}-1-methyl-1,6-dihydro-7H-pyrrolo[2,3-c]pyridin-7-one;
3-{2-(2,4-difluorophenoxy)-5-[(6,7-dihydro-5H-pyrrolo[1,2-a]imidazol-2-ylmethyl)amino]phenyl}-1-methyl-1,6-dihydro-7H-pyrrolo[2,3-c]pyridin-7-one;
3-[5-{[2-(benzyloxy)-3-methoxybenzyl]amino}-2-(2,4-difluorophenoxy)phenyl]-1-methyl-1,6-dihydro-7H-pyrrolo[2,3-c]pyridin-7-one;
2-({[4-(2,4-difluorophenoxy)-3-(1-methyl-7-oxo-6,7-dihydro-1H-pyrrolo[2,3-c]pyridin-3-yl)phenyl]amino}methyl)benzonitrile;
3-{2-(2,4-difluorophenoxy)-5-[(quinolin-4-ylmethyl)amino]phenyl}-1-methyl-1,6-dihydro-7H-pyrrolo[2,3-c]pyridin-7-one;
N-[4-(2,4-difluorophenoxy)-3-(1-methyl-7-oxo-6,7-dihydro-1H-pyrrolo[2,3-c]pyridin-3-yl)phenyl]-1-phenylmethanesulfonamide;
1-(2-chloro-5-fluorophenyl)-N-[4-(2,4-difluorophenoxy)-3-(1-methyl-7-oxo-6,7-dihydro-1H-pyrrolo[2,3-c]pyridin-3-yl)phenyl]methanesulfonamide;
N-{4-(2,4-difluorophenoxy)-3-[1-methyl-5-(morpholin-4-ylmethyl)-7-oxo-6,7-dihydro-1H-pyrrolo[2,3-c]pyridin-3-yl]phenyl}ethanesulfonamide;
N-{4-(2,4-difluorophenoxy)-3-[1-methyl-7-oxo-5-(piperidin-4-yl)-6,7-dihydro-1H-pyrrolo[2,3-c]pyridin-3-yl]phenyl}ethanesulfonamide;
N-[6-(2,4-difluorophenoxy)-5-(1-methyl-7-oxo-6,7-dihydro-1H-pyrrolo[2,3-c]pyridin-3-yl)pyridin-3-yl]ethanesulfonamide;
N-[3-{5-[1-(cyclopropylcarbonyl)piperidin-4-yl]-1-methyl-7-oxo-6,7-dihydro-1H-pyrrolo[2,3-c]pyridin-3-yl}-4-(2,4-difluorophenoxy)phenyl]ethanesulfonamide;
N-[4-(2,4-difluorophenoxy)-3-{5-[1-(ethylsulfonyl)piperidin-4-yl]-1-methyl-7-oxo-6,7-dihydro-1H-pyrrolo[2,3-c]pyridin-3-yl}phenyl]ethanesulfonamide;
3-{2-(2,4-difluorophenoxy)-5-[(ethylsulfonyl)amino]phenyl}-N-[3-(1H-imidazol-1-yl)propyl]-1-methyl-7-oxo-6,7-dihydro-1H-pyrrolo[2,3-c]pyridine-5-carboxamide;
3-{2-(2,4-difluorophenoxy)-5-[(ethylsulfonyl)amino]phenyl}-N-[2-(dimethylamino)ethyl]-1-methyl-7-oxo-6,7-dihydro-1H-pyrrolo[2,3-c]pyridine-5-carboxamide;
N-(cyanomethyl)-3-{2-(2,4-difluorophenoxy)-5-[(ethylsulfonyl)amino]phenyl}-1-methyl-7-oxo-6,7-dihydro-1H-pyrrolo[2,3-c]pyridine-5-carboxamide;
3-{2-(2,4-difluorophenoxy)-5-[(ethylsulfonyl)amino]phenyl}-N-(3-hydroxypropyl)-1-methyl-7-oxo-6,7-dihydro-1H-pyrrolo[2,3-c]pyridine-5-carboxamide;
N-{4-(2,4-difluorophenoxy)-3-[1-methyl-5-(morpholin-4-ylcarbonyl)-7-oxo-6,7-dihydro-1H-pyrrolo[2,3-c]pyridin-3-yl]phenyl}ethanesulfonamide;
3-{2-(2,4-difluorophenoxy)-5-[(ethylsulfonyl)amino]phenyl}-1-methyl-7-oxo-N-(pyridin-3-ylmethyl)-6,7-dihydro-1H-pyrrolo[2,3-c]pyridine-5-carboxamide;
N-{4-(2,4-difluorophenoxy)-3-[1-methyl-7-oxo-5-(pyrrolidin-1-ylcarbonyl)-6,7-dihydro-1H-pyrrolo[2,3-c]pyridin-3-yl]phenyl}ethanesulfonamide;
N-[4-(2,4-difluorophenoxy)-3-{5-[(4-hydroxypiperidin-1-yl)carbonyl]-1-methyl-7-oxo-6,7-dihydro-1H-pyrrolo[2,3-c]pyridin-3-yl}phenyl]ethanesulfonamide;
N-(cyclopentylmethyl)-3-{2-(2,4-difluorophenoxy)-5-[(ethylsulfonyl)amino]phenyl}-1-methyl-7-oxo-6,7-dihydro-1H-pyrrolo[2,3-c]pyridine-5-carboxamide;
3-{2-(2,4-difluorophenoxy)-5-[(ethylsulfonyl)amino]phenyl}-1-methyl-N-[2-(morpholin-4-yl)ethyl]-7-oxo-6,7-dihydro-1H-pyrrolo[2,3-c]pyridine-5-carboxamide;
3-{2-(2,4-difluorophenoxy)-5-[(ethylsulfonyl)amino]phenyl}-1-methyl-N-[2-(4-methylpiperazin-1-yl)ethyl]-7-oxo-6,7-dihydro-1H-pyrrolo[2,3-c]pyridine-5-carboxamide;
3-{2-(2,4-difluorophenoxy)-5-[(ethylsulfonyl)amino]phenyl}-1-methyl-7-oxo-N-[2-(piperidin-1-yl)ethyl]-6,7-dihydro-1H-pyrrolo[2,3-c]pyridine-5-carboxamide;
3-{2-(2,4-difluorophenoxy)-5-[(ethylsulfonyl)amino]phenyl}-1-methyl-7-oxo-N-(tetrahydrofuran-3-ylmethyl)-6,7-dihydro-1H-pyrrolo[2,3-c]pyridine-5-carboxamide;
3-{2-(2,4-difluorophenoxy)-5-[(ethylsulfonyl)amino]phenyl}-N, 1-dimethyl-7-oxo-6,7-dihydro-1H-pyrrolo[2,3-c]pyridine-5-carboxamide;
3-{2-(2,4-difluorophenoxy)-5-[(ethylsulfonyl)amino]phenyl}-N-(furan-3-ylmethyl)-1-methyl-7-oxo-6,7-dihydro-1H-pyrrolo[2,3-c]pyridine-5-carboxamide;
3-{3-cyclopropyl-2-[(2,4-difluorophenyl)amino]-5-[(methylsulfonyl)methyl]phenyl}-1-methyl-1,6-dihydro-7H-pyrrolo[2,3-c]pyridin-7-one; and
1-methyl-3-{5-[(methylsulfonyl)methyl]-2-(pyridin-2-ylamino)phenyl}-1,6-dihydro-7H-pyrrolo[2,3-c]pyridin-7-one.

21. The compound of claim 9 or a pharmaceutically acceptable salt wherein
$R^2$ is H;
$R^3$ is —C(O)$R^{3a}$, —C(O)N$R^{3b}R^{3c}$, $C_4$-$C_6$ heterocycle, or $C_1$-$C_3$ alkyl which is substituted with $C_4$-$C_6$ heterocycle; wherein each of the $C_4$-$C_6$ heterocycle moieties is optionally substituted with 1, 2, 3, 4, or 5 $R^{1g}$;

$R^{3a}$ is $C_4$-$C_6$ heterocycle which is optionally substituted with 1, 2, 3, 4, or 5 $R^{1g}$;

$R^{3b}$ is H or $C_1$-$C_6$ alkyl;

$R^{3c}$ is H, $C_1$-$C_6$ alkyl, —($C_1$-$C_6$ alkylenyl)-$OR^{z1}$, —($C_1$-$C_6$ alkylenyl)-$NR^{z3}R^{z4}$, —($C_1$-$C_6$ alkylenyl)-CN, or —($C_1$-$C_6$ alkylenyl)-$G^1$; wherein $G^1$ is $C_4$-$C_6$ heterocycle, $C_5$-$C_6$ heteroaryl, $C_3$-$C_6$ cycloalkyl, or phenyl; each of which is optionally substituted with 1, 2, 3, 4, or 5 $R^{1g}$;

$R^6$ is —$OR^a$ or —$NR^cR^d$; wherein
  $R^a$ and $R^d$ are each independently $G^2$ or $C_1$-$C_6$ alkyl substituted with a $G^2$ group;
  wherein $G^2$ is phenyl, $C_3$-$C_6$ cycloalkyl, $C_4$-$C_6$ heterocycle, or $C_5$-$C_6$ heteroaryl;
  each of which is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{Y3})C(O)O(R^{y2})$, —$N(R^{y3})C(O)NR^{y3}R^{y4}$, and —$N(R^{y3})S(O)_2NR^{y3}R^{y4}$;

$R^c$ is hydrogen or unsubstituted $C_1$-$C_6$ alkyl;

$R^{y1}$, $R^{y3}$, and $R^{y4}$, at each occurrence, are each independently H, $C_1$-$C_6$ alkyl, or $C_1$-$C_6$ haloalkyl; and $R^{y2}$, at each occurrence, is independently $C_1$-$C_6$ alkyl or $C_1$-$C_6$ haloalkyl; and $R^9$ is H, halogen, —CN, $C_1$-$C_6$ haloalkyl, —$N(R^e)S(O)_2R^b$, —$S(O)_2R^a$, —$S(O)_2NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$NR^cR^d$, or —($C_1$-$C_6$ alkylenyl)-N($R^e$)$S(O)_2R^b$; wherein $R^c$, $R^d$, and $R^e$, at each occurrence, are each independently H or unsubstituted $C_1$-$C_6$ alkyl; and $R^a$ and $R^b$, at each occurrence, is independently $C_1$-$C_6$ haloalkyl, or unsubstituted $C_1$-$C_6$ alkyl.

22. The compound of claim 21 or a pharmaceutically acceptable salt wherein $R^3$ is —$C(O)R^{3a}$ or —$C(O)NR^{3b}R^{3c}$;

$A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$;

$R^6$ is —$OR^a$ or —$NR^cR^d$; wherein
  $R^a$ and $R^d$ are each independently phenyl, pyridinyl, or $C_1$-$C_3$ alkyl substituted with a $C_3$-$C_6$ cycloalkyl; wherein the phenyl, pyridinyl, and the $C_3$-$C_6$ cycloalkyl are optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, and —$N(R^{y3})S(O)_2NR^{y3}R^{y4}$;

$R^c$ is hydrogen or unsubstituted $C_1$-$C_3$ alkyl;

$R^{y1}$, $R^{y3}$, and $R^{y4}$, at each occurrence, are each independently H, $C_1$-$C_6$ alkyl, or $C_1$-$C_6$ haloalkyl; and $R^{y2}$, at each occurrence, is independently $C_1$-$C_6$ alkyl or $C_1$-$C_6$ haloalkyl;

$R^8$ is H or halogen; and $R^9$ is —$N(R^e)S(O)_2R^b$ or —($C_1$-$C_6$ alkylenyl)-$S(O)_2R^a$; wherein $R^e$ is H or unsubstituted $C_1$-$C_3$ alkyl; and $R^a$ and $R^b$, are independently $C_1$-$C_3$ alkyl.

23. A compound of formula (I) or a pharmaceutically acceptable salt thereof,

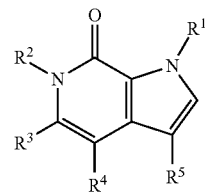

(I)

wherein $R^1$ is H, $C_1$-$C_3$ alkyl, or $C_1$-$C_3$ haloalkyl;

$R^2$ is H, $C_1$-$C_3$ alkyl, or $C_1$-$C_3$ haloalkyl;

$R^3$ is H, $C_1$-$C_6$ alkyl, $C_2$-$C_6$ alkenyl, $C_2$-$C_6$ alkynyl, halogen, —$OR^{3a}$, —$NR^{3b}R^{3c}$, —$N(R^{3b})C(O)R^{3d}$, —$N(R^{3b})C(O)NR^{3b}R^{3c}$, —$N(R^{3b})S(O)_2NR^{3b}R^{3c}$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of halogen, $G^1$, —$OR^{3a}$, and —$NR^{3b}R^{3c}$;

$R^{3a}$, $R^{3b}$, and $R^{3c}$, at each occurrence, are each independently H, $C_1$-$C_6$ alkyl, $C_1$-$C_6$ haloalkyl, $G^1$, or —($C_1$-$C_6$ alkylenyl)-$G^1$;

$R^{3d}$, at each occurrence, is independently $C_1$-$C_6$ alkyl, $C_1$-$C_6$ haloalkyl, $G^1$, or —($C_1$-$C_6$ alkylenyl)-$G^1$;

$G^1$, at each occurrence, is independently aryl, heteroaryl, heterocycle, cycloalkyl, or cycloalkenyl; and each $G^1$ is optionally substituted with 1, 2, 3, 4, or 5 $R^{1g}$ groups;

$R^4$ is H, $C_1$-$C_6$ alkyl, halogen, or $C_1$-$C_6$ haloalkyl;

$R^5$ is phenyl or pyridinyl; each of which is substituted with 1, 2, or 3 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^2$, —$OR^a$, —$OC(O)R^b$, —$OC(O)NR^cR^d$, —$SR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)C(O)R^b$, —$N(R^e)S(O)_2R^b$, —$N(R^e)C(O)O(R^b)$, —$N(R^e)C(O)NR^cR^d$, —$N(R^e)S(O)_2NR^cR^d$, —($C_1$-$C_6$ alkylenyl)-$G^2$, —($C_1$-$C_6$ alkylenyl)-$OR^a$, —($C_1$-$C_6$ alkylenyl)-$OC(O)R^b$, —($C_1$-$C_6$ alkylenyl)-$OC(O)NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, —($C_1$-$C_6$ alkylenyl)-$N(R^e)S(O)_2NR^cR^d$, and —($C_1$-$C_6$ alkylenyl)-CN;

$R^a$, $R^c$, $R^d$, and $R^e$, at each occurrence, are each independently H, $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;

$R^b$, at each occurrence, is independently $C_2$-$C_6$ alkenyl, $C_2$-$C_6$ alkynyl, $C_1$-$C_6$ haloalkyl, $G^2$, or $C_1$-$C_6$ alkyl wherein the $C_1$-$C_6$ alkyl is optionally substituted with one substituent selected from the group consisting of —$OR^{y1}$, —$NR^{y3}R^{y4}$, —$C(O)OR^{y1}$, —$C(O)NR^{y3}R^{y4}$, —$S(O)_2R^{y1}$, —$S(O)_2NR^{y3}R^{y4}$, and $G^2$;

G², at each occurrence, are each independently aryl, heteroaryl, heterocycle, cycloalkyl, or cycloalkenyl; and each G² group is optionally substituted with 1, 2, 3, 4, or 5 R²ᵍ groups;

R¹ᵍ, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, NO₂, —OR$^{z1}$, —OC(O)R$^{z2}$, —OC(O)NR$^{z3}$R$^{z4}$, —SR$^{z1}$, —S(O)₂R$^{z1}$, —S(O)₂NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)₂R$^{z2}$, —N(R$^{z3}$)C(O)O(R$^{z2}$), —N(R$^{z3}$)C(O)NR$^{z3}$R$^{z4}$, —N(R$^{z3}$)S(O)₂NR$^{z3}$R$^{z4}$, —($C_1$-$C_6$ alkylenyl)-OR$^{z1}$, —($C_1$-$C_6$ alkylenyl)-OC(O)R$^{z2}$, —($C_1$-$C_6$ alkylenyl)-OC(O)NR$^{z3}$R$^{z4}$, —($C_1$-$C_6$ alkylenyl)-S(O)₂R$^{z1}$, —($C_1$-$C_6$ alkylenyl)-S(O)₂NR$^{z3}$R$^{z4}$, —($C_1$-$C_6$ alkylenyl)-C(O)R$^{z1}$, —($C_1$-$C_6$ alkylenyl)-C(O)OR$^{z1}$, —($C_1$-$C_6$ alkylenyl)-C(O)NR$^{z3}$R$^{z4}$, —($C_1$-$C_6$ alkylenyl)-NR$^{z3}$R$^{z4}$, —($C_1$-$C_6$ alkylenyl)-N(R$^{z3}$)C(O)R$^{z2}$, —($C_1$-$C_6$ alkylenyl)-N(R$^{z3}$)S(O)₂R$^{z2}$, —($C_1$-$C_6$ alkylenyl)-N(R$^{z3}$)C(O)O(R$^{z2}$), —($C_1$-$C_6$ alkylenyl)-N(R$^{z3}$)C(O)NR$^{z3}$R$^{z4}$, —($C_1$-$C_6$ alkylenyl)-N(R$^{z3}$)S(O)₂NR$^{z3}$R$^{z4}$, —($C_1$-$C_6$ alkylenyl)-CN, or —O(phenyl) wherein the phenyl moiety is optionally substituted with 1, 2, 3, or 4 substituents independently selected from the group consisting of $C_1$-$C_6$ alkyl, halogen, $C_1$-$C_6$ haloalkyl, —OH, —O(alkyl), —O(haloalkyl), CN, and NO₂;

R²ᵍ, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, NO₂, —OR$^{y1}$, —OC(O)R$^{y2}$, —OC(O)NR$^{y3}$R$^{y4}$, —SR$^{y1}$, —S(O)₂R$^{y1}$, —S(O)₂NR$^{y3}$R$^{y4}$, —C(O)R$^{y1}$, —C(O)OR$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)₂R$^{y2}$, —N(R$^{y3}$)C(O)O(R$^{y2}$), —N(R$^{y3}$)C(O)NR$^{y3}$R$^{y4}$, —N(R$^{y3}$)S(O)₂NR$^{y3}$R$^{y4}$, G$^{2b}$, —($C_1$-$C_6$ alkylenyl)-OR¹, —($C_1$-$C_6$ alkylenyl)-OC(O)R$^{y2}$, —($C_1$-$C_6$ alkylenyl)-OC(O)NR$^{y3}$R$^{y4}$, —($C_1$-$C_6$ alkylenyl)-S(O)₂R$^{y1}$, —($C_1$-$C_6$ alkylenyl)-S(O)₂NR$^{y3}$R$^{y4}$, —($C_1$-$C_6$ alkylenyl)-C(O)R$^{y1}$, —($C_1$-$C_6$ alkylenyl)-C(O)OR$^{y1}$, —($C_1$-$C_6$ alkylenyl)-C(O)NR$^{y3}$R$^{y4}$, —($C_1$-$C_6$ alkylenyl)-NR$^{y3}$R$^{y4}$, —($C_1$-$C_6$ alkylenyl)-N(R$^{y3}$)C(O)R$^{y2}$, —($C_1$-$C_6$ alkylenyl)-N(R$^{y3}$)S(O)₂R$^{y2}$, —($C_1$-$C_6$ alkylenyl)-N(R$^{y3}$)C(O)O(R$^{y2}$), —($C_1$-$C_6$ alkylenyl)-N(R$^{y3}$)C(O)NR$^{y3}$R$^{y4}$, —($C_1$-$C_6$ alkylenyl)-N(R$^{y3}$)S(O)₂NR$^{y3}$R$^{y4}$, —($C_1$-$C_6$ alkylenyl)-CN, or —($C_1$-$C_6$ alkylenyl)-G$^{2b}$;

R$^{y1}$, R$^{y3}$, and R$^{y4}$, at each occurrence, are each independently H, $C_1$-$C_6$ alkyl, $C_1$-$C_6$ haloalkyl, G$^{2b}$, or —($C_1$-$C_6$ alkylenyl)-G$^{2b}$;

R$^{y2}$, at each occurrence, is independently $C_1$-$C_6$ alkyl, $C_1$-$C_6$ haloalkyl, G$^{2b}$, or —($C_1$-$C_6$ alkylenyl)-G$^{2b}$;

G$^{2b}$, at each occurrence, is independently aryl, heteroaryl, cycloalkyl, cycloalkenyl, or heterocycle; and each G$^{2b}$ group is optionally substituted with 1, 2, 3, 4, or 5 substituents independently selected from the group consisting of $C_1$-$C_6$ alkyl, $C_2$-$C_6$ alkenyl, $C_2$-$C_6$ alkynyl, halogen, $C_1$-$C_6$ haloalkyl, —CN, NO₂, —OR$^{z1}$, —OC(O)R$^{z2}$, —OC(O)NR$^{z3}$R$^{z4}$, —SR$^{z1}$, —S(O)₂R$^{z1}$, —S(O)₂NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)₂R$^{z2}$, —N(R$^{z3}$)C(O)O(R$^{z2}$), —N(R$^{z3}$)C(O)NR$^{z3}$R$^{z4}$, —N(R$^{z3}$)S(O)₂NR$^{z3}$R$^{z4}$, —($C_1$-$C_6$ alkylenyl)-OR$^{z1}$, —($C_1$-$C_6$ alkylenyl)-OC(O)R$^{z2}$, —($C_1$-$C_6$ alkylenyl)-OC(O) NR$^{z3}$R$^{z4}$, —($C_1$-$C_6$ alkylenyl)-S(O)₂R$^{z1}$, —($C_1$-$C_6$ alkylenyl)-S(O)₂NR$^{z3}$R$^{z4}$, —($C_1$-$C_6$ alkylenyl)-C(O)R$^{z1}$, —($C_1$-$C_6$ alkylenyl)-C(O)OR$^{z1}$, —($C_1$-$C_6$ alkylenyl)-C(O) NR$^{z3}$R$^{z4}$, —($C_1$-$C_6$ alkylenyl)-NR$^{z3}$R$^{z4}$, —($C_1$-$C_6$ alkylenyl)-N(R$^{z3}$)C(O)R$^{z2}$, —($C_1$-$C_6$ alkylenyl)-N(R$^{z3}$)S(O)₂R$^{z2}$, —($C_1$-$C_6$ alkylenyl)-N(R$^{z3}$)C(O)O(R$^{z2}$), —($C_1$-$C_6$ alkylenyl)-N(R$^{z3}$)C(O)NR$^{z3}$R$^{z4}$, —($C_1$-$C_6$ alkylenyl)-N(R$^{z3}$)S(O)₂NR$^{z3}$R$^{z4}$, and —($C_1$-$C_6$ alkylenyl)-CN;

R$^{z1}$, R$^{z3}$, and R$^{z4}$, at each occurrence, are each independently H, $C_1$-$C_6$ alkyl, or $C_1$-$C_6$ haloalkyl; and R$^{z2}$, at each occurrence, is independently $C_1$-$C_6$ alkyl or $C_1$-$C_6$ haloalkyl.

24. A compound of claim 1 or a pharmaceutically acceptable salt thereof, wherein the compound is selected from the group consisting of:

3-[2-(2,4-difluorophenoxy)-5-(methylsulfonyl)phenyl]-1-methyl-1,6-dihydro-7H-pyrrolo[2,3-c]pyridin-7-one;

3-{2-(2,4-difluorophenoxy)-5-[(methylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]pyridin-3-yl}-1-methyl-1,6-dihydro-7H-pyrrolo[2,3-c]pyridin-7-one;

N-[4-(2,4-difluorophenoxy)-3-(1-methyl-7-oxo-6,7-dihydro-1H-pyrrolo[2,3-c]pyridin-3-yl)phenyl]ethanesulfonamide;

1-[4-(2,4-difluorophenoxy)-3-(1-methyl-7-oxo-6,7-dihydro-1H-pyrrolo[2,3-c]pyridin-3-yl)phenyl]methanesulfonamide;

N-[4-(2,4-difluorophenoxy)-3-{5-[1-(ethylsulfonyl)piperidin-4-yl]-1-methyl-7-oxo-6,7-dihydro-1H-pyrrolo[2,3-c]pyridin-3-yl}phenyl]ethanesulfonamide;

1-[4-(2,4-difluorophenoxy)-3-(1-methyl-7-oxo-6,7-dihydro-1H-pyrrolo[2,3-c]pyridin-3-yl)phenyl]-N,N-dimethylmethanesulfonamide;

3-{2-(2,4-difluorophenoxy)-5-[(ethylsulfonyl)amino]phenyl}-1-methyl-7-oxo-N-(pyridin-3-ylmethyl)-6,7-dihydro-1H-pyrrolo[2,3-c]pyridine-5-carboxamide;

3-{2-(2,4-difluorophenoxy)-5-[(morpholin-4-ylsulfonyl)methyl]phenyl}-1-methyl-1,6-dihydro-7H-pyrrolo[2,3-c]pyridin-7-one;

3-{2-(2,4-difluorophenoxy)-5-[(methylsulfonyl)methyl]phenyl}-5-ethyl-1-methyl-1,6-dihydro-7H-pyrrolo[2,3-c]pyridin-7-one;

5-chloro-3-{2-(2,4-difluorophenoxy)-5-[(methylsulfonyl)methyl]phenyl}-1-methyl-1,6-dihydro-7H-pyrrolo[2,3-c]pyridin-7-one;

1-[4-(2,4-difluorophenoxy)-3-(1-methyl-7-oxo-6,7-dihydro-1H-pyrrolo[2,3-c]pyridin-3-yl)phenyl]-N-methylmethanesulfonamide;

N-{4-[(4,4-difluorocyclohexyl)oxy]-3-(1-methyl-7-oxo-6,7-dihydro-1H-pyrrolo[2,3-c]pyridin-3-yl)phenyl}ethanesulfonamide;

N-[4-(2,4-difluorophenoxy)-2-fluoro-5-(1-methyl-7-oxo-6,7-dihydro-1H-pyrrolo[2,3-c]pyridin-3-yl)phenyl]methanesulfonamide;

3-{2-[(2,4-difluorophenyl)amino]-5-[(methylsulfonyl)methyl]phenyl}-1-methyl-1,6-dihydro-7H-pyrrolo[2,3-c]pyridin-7-one;

3-{2-[(4,4-difluorocyclohexyl)oxy]-5-(methylsulfonyl)phenyl}-1-methyl-1,6-dihydro-7H-pyrrolo[2,3-c]pyridin-7-one; and 3-{2-[(cyclopropylmethyl)amino]-5-[(methylsulfonyl)methyl]phenyl}-1-methyl-1,6-dihydro-7H-pyrrolo[2,3-c]pyridin-7-one.

25. A pharmaceutical composition comprising a therapeutically effective amount of a compound of formula (I) according to claim 1, or a pharmaceutically acceptable salt thereof, and a pharmaceutically acceptable carrier.

* * * * *